US011618785B2

(12) United States Patent
Takahashi et al.

(10) Patent No.: US 11,618,785 B2
(45) Date of Patent: Apr. 4, 2023

(54) ANTI-CD3 ANTIBODY AND MOLECULES COMPRISING THE ANTIBODY

(71) Applicant: Daiichi Sankyo Company, Limited, Tokyo (JP)

(72) Inventors: Tohru Takahashi, Tokyo (JP); Chigusa Yoshimura, Tokyo (JP); Shiho Kozuma, Tokyo (JP); Kensuke Nakamura, Tokyo (JP); Chikako Suzuki, Tokyo (JP); Junya Ichikawa, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 274 days.

(21) Appl. No.: 16/472,346

(22) PCT Filed: Dec. 21, 2017

(86) PCT No.: PCT/JP2017/046006
§ 371 (c)(1),
(2) Date: Jun. 21, 2019

(87) PCT Pub. No.: WO2018/117237
PCT Pub. Date: Jun. 28, 2018

(65) Prior Publication Data

US 2019/0359712 A1 Nov. 28, 2019

(30) Foreign Application Priority Data

Dec. 22, 2016 (JP) ............................ JP2016-249148

(51) Int. Cl.
*C07K 16/28* (2006.01)
*C07K 16/30* (2006.01)
*C07K 16/32* (2006.01)
*C12N 15/85* (2006.01)

(52) U.S. Cl.
CPC .......... *C07K 16/2809* (2013.01); *C07K 16/30* (2013.01); *C07K 16/32* (2013.01); *C12N 15/85* (2013.01); *C07K 2317/53* (2013.01); *C12N 2015/8518* (2013.01)

(58) Field of Classification Search
None
See application file for complete search history.

(56) References Cited

U.S. PATENT DOCUMENTS 7,465,445 B2 12/2008 Tezuka et al.
7,998,478 B2 8/2011 Tezuka et al.
8,236,308 B2 8/2012 Kischel et al.
9,315,578 B2 4/2016 Kumagai et al.
2007/0071675 A1 3/2007 Wu et al.
2009/0252683 A1 10/2009 Kischel et al.
2011/0275787 A1 11/2011 Kufer et al.
2013/0129729 A1 5/2013 Kischel et al.
2014/0099318 A1 4/2014 Huang et al.
2016/0280787 A1 9/2016 Igawa et al.
2017/0137519 A1 5/2017 Huang et al.

FOREIGN PATENT DOCUMENTS

JP 2009-511521 A 3/2009
JP 2014-517844 A 7/2014
RU 2203682 C2 5/2003
WO WO-01/15732 A1 3/2001
WO WO-01/77342 A1 10/2001
WO WO 2007/108152 A1 9/2007
WO WO 2008/119567 A2 10/2008
WO WO 2012/162067 A2 11/2012
WO WO 2015/026892 A1 2/2015
WO WO 2015/181098 A1 12/2015
WO WO 2016/076345 A1 5/2016
WO WO 2016/116626 A1 7/2016

OTHER PUBLICATIONS

Vajdos et al. (J Mol Biol. Jul. 5, 2002;320(2):415-28). (Year: 2002).*
Bedouelle et al. (FEBS J. Jan. 2006;273(1):34-46). (Year: 2006).*
Brown et al. (J Immunol. May 1, 1996;156(9):3285-91). (Year: 1996).*
Colman (Research in Immunology, 145:33-36, 1994). (Year: 1994).*
Damschroder et al., Mol Immunol. Aug. 2004;41(10):985-1000. (Year: 2004).*
Meyer et al. (British Journal of Haematology, 2018, 180, 808-820). (Year: 2018).*
Mariuzza, R.A., "The Structural Basis of Antigen-Antibody Recognition," Ann. Rev. Biophys. Biophys. Chem., 1987, 16:139-159.
Office Action and Search Report dated Mar. 5, 2021 in RU 2019122411, with English translations.
Roitt et al., "Immunology," Moscow, "Mir," 2000, 110-111.
Rudikoff et al., "Single amino acid substitution altering antigen-binding specificity," Proc. Natl. Acad. Sci. USA, Mar. 1982, 79:1979-1983.
Arnett et al., "Crystal structure of a human CD3-ε/δ mega dimer in complex with a UCHT1 single-chain antibody fragment," PNAS, Nov. 16, 2004, 101 (46): 16268-16273.
Katz et al., "Studying protein-protein interactions using peptide arrays," Chem. Soc. Rev., 2011, 40:2131-2145.
Kjer-Nielsen et al., "Crystal structure of the human T cell receptor CD3εγ heterodimer complexed to the therapeutic mAb OKT3," PNAS, May 18, 2004, 101(20):7675-7680.

(Continued)

*Primary Examiner* — Zachary S Skelding
(74) *Attorney, Agent, or Firm* — Foley & Lardner LLP

(57) ABSTRACT

The present invention provides a novel antibody binding to human CD3, and a molecule having antigen binding activity that includes the antibody.

The present invention provides a novel antibody binding to human CD3, a molecule having antigen binding activity that includes the antibody, and a pharmaceutical composition having cytotoxic activity that includes the antibody or the molecule as an active ingredient.

41 Claims, 85 Drawing Sheets

Specification includes a Sequence Listing.

(56) References Cited

OTHER PUBLICATIONS

International Search Report dated Jan. 30, 2018, in PCT/JP2017/046006.

Abramowicz et al., "Release of tumor necrosis factor, interleukin-2, and gamma-interferon in serum after injection of OKT3 monoclonal antibody in kidney transplant recipients," Transplantation, 1989, 47(4):606-608.

Conrad et al., "TCR and CD3 Antibody Cross-Reactivity in 44 Species," Cytometry A., 2007, 71(11):925-933.

Cosimi et al., "Treatment of acute renal allograft rejection with OKT3 monoclonal antibody," Transplantation, 1981, 32(6):535-539.

Fong et al., "High expression of TROP2 correlates with poor prognosis in pancreatic cancer," Br. J. Cancer, 2008, 99(8):1290-1295.

Fong et al., "TROP2: a novel prognostic marker in squamous cell carcinoma of the oral cavity," Mod. Pathol., 2008, 21(2):186-191.

George et al., "Redirection of T cell-mediated cytotoxicity by a recombinant single-chain Fv molecule," J. Immunol., 1994, 152(4):1802-1811.

Gilbert et al., "Treatment of Refractory Cardiac Allograft Rejection with OKT3 Monoclonal Antibody," Am.J.Med., Feb. 1987, 82:202-206.

Lum et al., "Targeting T Cells with Bispecific Antibodies for Cancer Therapy," BioDrugs, 2011, 25(6):365-379.

Meuer et al., "T cell receptor triggering induces responsiveness to interleukin 1 and interleukin 2 but does not lead to T cell proliferation," Eur. J. Immunol., 1986, 136:4106-4112.

Muhlmann et al., "TROP2 expression as prognostic marker for gastric carcinoma," J. Clin. Pathol., 2009, 62(2):152-158.

NHP Reagent Resource, Mass Biologies, UMass Medical School, Commercial Reagent Clones, http://www.nhpreagents.org/NHP/clonelist.aspx?ID=77, 1 page, date unknown.

Ning et al., "TROP2 expression and its correlation with tumor proliferation and angiogenesis in human gliomas," Neurol. Sci., 2013, 34(10):1745-1750.

Ohmachi et al., "Clinical Significance of TROP2 Expression in Colorectal Cancer," Clin. Cancer Res., May 15, 2006, 12 (10), 3057-3063.

Salmeron et al., "A conformational epitope expressed upon association of CD3-epsilon with either CD3-delta or CD3-gamma is the main target for recognition by anti-CD3 monoclonal antibodies," J. Immunol., 1991, 147, 3047-3052.

Sandusky et al., "Use of Monoclonal Antibodies to Human Lymphocytes to Identify Lymphocyte Subsets in Lymph Nodes of the Rhesus Monkey and the Dog," J. Med. Primatol., 1986, 15:441-451.

Thistlethwaite et al., "Monitoring and complications of monoclonal therapy, Complications and Monitoring of OKT3 Therapy," Am. J. Kidney Dis., 1988, 11(2):112-119.

Thistlethwaite et al., "OKT3 treatment of steroid-resistant renal allograft rejection," Transplantation, 1987, 43(2):176-184.

Toussaint et al., "Possible nephrotoxicity of the prophylactic use of OKT3 monoclonal antibody after cadaveric renal transplantation," Transplantation, 1989, 48(3):524-526.

Uda et al., CD3 polymorphism in cynomolgus monkeys (*Macaca fascicularis*), J.Med.Primatol., 2001, 30:141-147.

Woodie et al., "Humanized OKT3 antibodies: successful transfer of immune modulating properties and idiotype expression," J. Immunol., 1992, 148(9):2756-2763.

Yankelevich et al., "Anti-CD3 × Anti-GD2 Bispecific Antibody Redirects T-Cell Cytolytic Activity to Neuroblastoma Targets," Pediatr. Blood Cancer, Dec. 15, 2012, 59(7):1198-1205.

Office Action dated Aug. 6, 2021 in RU 2019122411, with English translation.

Pan et al., "Blocking Neuropilin-1 Function Has an Additive Effect with Anti-VEGF to Inhibit Tumor Growth," Cancer Cell, Jan. 2007, 11:53-67.

Singer et al., Geny i genomy, Moscow, Mir, 1998, 1:63-64.

Office Action dated Nov. 2, 2022 in CN 2017800797171, with English translation.

* cited by examiner

[Figure 1]

SEQ ID NO: 1 Amino acid sequence of human CD3ε

MQSGTHWRVLGLCLLSVGVWGQDGNEEMGGITQTPYKVSISGTTVILTCPQ
YPGSEILWQHNDKNIGGDEDDKNIGSDEDHLSLKEFSELEQSGYYVCYPRG
SKPEDANFYLYLRARVCENCMEMDVMSVATIVIVDICITGGLLLLVYYWSK
NRKAKAKPVTRGAGAGGRQRGQNKERPPPVPNPDYEPIRKGQRDLYSGLNQ
RRI (NCBI Reference Sequence: NP_000724.1)

[Figure 2]

SEQ ID NO: 2 Amino acid sequence of human CD3δ

MEHSTFLSGLVLATLLSQVSPFKIPIEELEDRVFVNCNTSITWVEGTVGTL
LSDITRLDLGKRILDPRGIYRCNGTDIYKDKESTVQVHYRMCQSCVELDPA
TVAGIIVTDVIATLLLALGVFCFAGHETGRLSGAADTQALLRNDQVYQPLR
DRDDAQYSHLGGNWARNK (NCBI Reference Sequence: NP_000723.1)

[Figure 3]

SEQ ID NO: 4 Nucleotide sequence encoding a human CD3εγ single-chain antigen

ATGAGAGGATCGCATCACCATCACCATCACGGATCCCAGAGCATTAAAGGT
AATCACCTGGTGAAAGTGTATGACTATCAAGAAGATGGTAGCGTTCTGCTG
ACCTGTGATGCAGAAGCAAAAAACATTACCTGGTTCAAAGACGGCAAAATG
ATTGGTTTTCTGACCGAAGATAAAAAAAAATGGAATCTGGGCAGCAATGCA
AAAGATCCGCGTGGTATGTATCAGTGTAAAGGTAGCCAGAATAAAAGCAAA
CCGCTGCAGGTTTATTATCGTATGGGTAGCGCAGATGATGCAAAAAAAGAT
GCAGCCAAAAAAGACGACGCGAAAAAAGATGATGCTAAAAAAGACGGTTCC
GATGGCAATGAAGAAATGGGTGGTATTACCCAGACCCCGTATAAAGTTAGC
ATTAGCGGCACCACCGTTATTCTGACCTGTCCGCAGTATCCGGGTAGCGAA
ATTCTGTGGCAGCATAACGATAAAAACATTGGCGGTGATGAGGACGACAAA
AATATCGGTAGTGATGAAGATCATCTGAGCCTGAAAGAATTCAGCGAACTG
GAACAGAGCGGTTATTATGTTTGTTATCCTCGTGGTAGCAAACCGGAAGAT
GCAAACTTTTATCTGTATCTGCGTGCACGTGTTGGGAAGCTTAAT

His tag (1-36), Human CD3εγ single-chain antigen (37-660), Linker (280-357)

[Figure 4]

SEQ ID NO: 5 Amino acid sequence of His-scCD3 antigen

MRGSHHHHHHGSQSIKGNHLVKVYDYQEDGSVLLTCDAEAKNITWFKDGKM
IGFLTEDKKKWNLGSNAKDPRGMYQCKGSQNKSKPLQVYYRMGSADDAKKD
AAKKDDAKKDDAKKDGSDGNEEMGGITQTPYKVSISGTTVILTCPQYPGSE
ILWQHNDKNIGGDEDDKNIGSDEDHLSLKEFSELEQSGYYVCYPRGSKPED
ANFYLYLRARVGKLN

His tag (1-12), Human CD3εγ single-chain antigen (13-220), Linker (94-119)

[Figure 5]

SEQ ID NO: 50 Sense primer Nhe-polyC-S for heavy chain gene amplification

5'-GCTAGCGCTACCGGACTCAGATCCCCCCCCCCCCCDN-3'

[Figure 6]

SEQ ID NO: 51 First antisense primer rIgγ-AS1 for heavy chain gene amplification

5'-TCACTGAGCTGGTGAGAGTGTAGAGCCC-3'

[Figure 7]

SEQ ID NO: 52 Second antisense primer rIgγ-AS2 for heavy chain gene amplification

5'-TCACCGAGCTGCTGAGGGTGTAGAGCCC-3'

[Figure 8]

SEQ ID NO: 53 Sense primer Nhe-polyC-S2 for light chain gene amplification

5'-GCTAGCGCTACCGGACTCAGATCCCCCCCCCCCCCDN-3'

[Figure 9]

SEQ ID NO: 54 First antisense primer rIgL-AS1 for light chain gene amplification

5'-TTCCACATCACTCGGGTAGAAATCAG-3'

[Figure 10]

SEQ ID NO: 55 Second antisense primer rIgL-AS2 for light chain gene amplification

5'-TAACACCAGGGTAGAAATCTGTCACCAT-3'

[Figure 11]

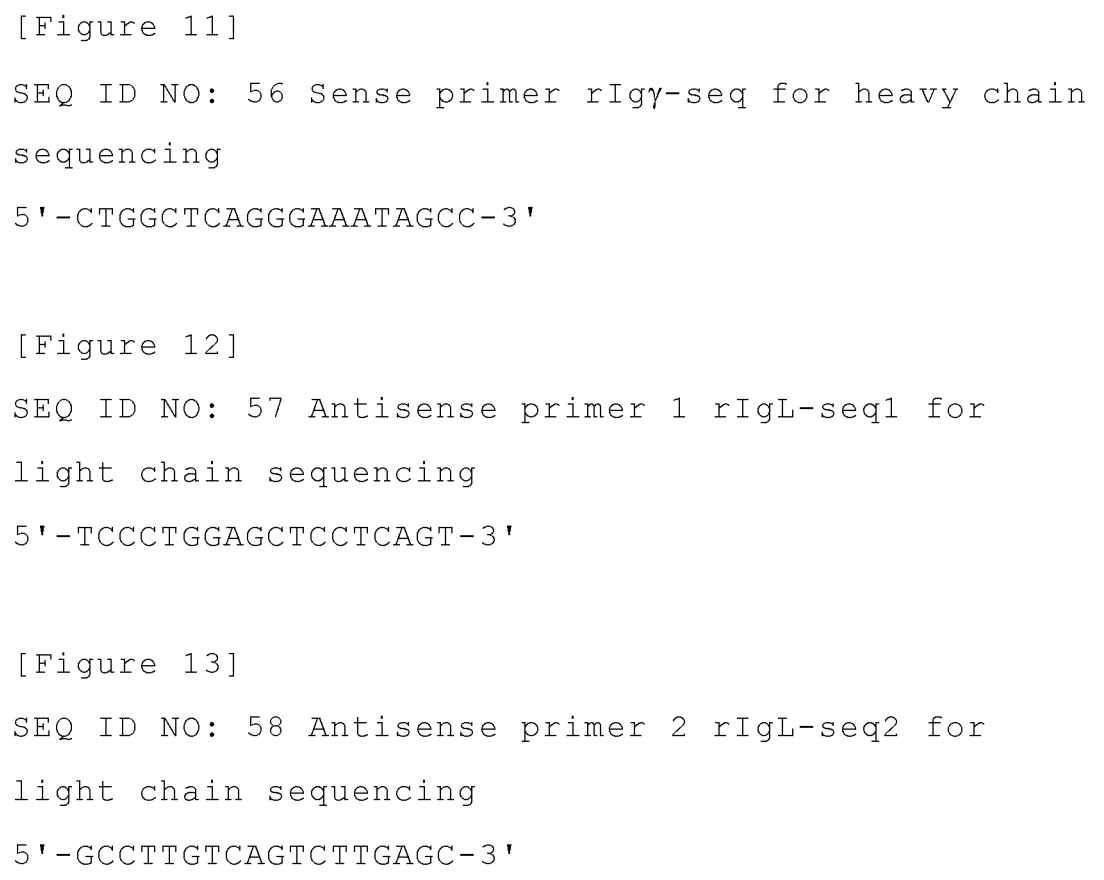

SEQ ID NO: 56 Sense primer rIgγ-seq for heavy chain sequencing

5'-CTGGCTCAGGGAAATAGCC-3'

[Figure 12]

SEQ ID NO: 57 Antisense primer 1 rIgL-seq1 for light chain sequencing

5'-TCCCTGGAGCTCCTCAGT-3'

[Figure 13]

SEQ ID NO: 58 Antisense primer 2 rIgL-seq2 for light chain sequencing

5'-GCCTTGTCAGTCTTGAGC-3'

[Figure 14]

SEQ ID NO: 6 Nucleotide sequence encoding the heavy chain variable region of C3-147

GAGGTGCAGTTGGTGGAGTCTGGGGGAGGCCTGGTGCAGCCTGGAAGGGCC
CTGAAACTCTCCTGTGTAGTCTCTGGAGTCACATTCAATTACTACGGGATG
AGCTGGATCCGCCAGGCTCCAGGGAAGGGGCTGGAGTGGGTTGCATCCATT
ACTAATTCTGGTGGTAGAATTTACTATCCAGACTCTGTGAAGGGCCGATTC
ACTATCTCCAGAGAAAATACACAAAAGACCCTATACCTACAAATGAACAGT
CTGAGGTCTGAGGACACGGCCACTTATTACTGTACTCTCGATGGTCGCGAT
GGTTGGGTTGCTTACTGGGGCCAAGGCACTCTGGTCACTGTCTCTTCA

[Figure 15]

SEQ ID NO: 7 Amino acid sequence of the heavy chain variable region of C3-147

EVQLVESGGGLVQPGRALKLSCVVSGVTFNYYGMSWIRQAPGKGLEWVASI
TNSGGRIYYPDSVKGRFTISRENTQKTLYLQMNSLRSEDTATYYCTLDGRD
GWVAYWGQGTLVTVSS

[Figure 16]

SEQ ID NO: 8 Nucleotide sequence encoding the light chain variable region of C3-147

CAGTTTGTGCTTACTCAGCCAAACTCTGTGTCTACGAATCTCGGAACCACA
GTCGAACTGTCTTGCAAGCGCAACACTGGGAACATTGGAAGCAATTATGTG
AACTGGTACCAGCAGCATGAGGGAAGATCTCCCACCACTATTATTTATAGG
GATGATAAGAGACCAGATGGAGTTTCTGACAGGTTCTCTGGGTCCATTGAC
AGATCTTCCAAGTCAGCCCTCCTGACAATCAATAATGTGCAGACTGAAGAT
GAAGCTGACTACTTCTGTCAGTCTTACAGTAGTGGTTTTATTTTCGGCGGT
GGAACCAAGCTCACTGTCCTA

[Figure 17]

SEQ ID NO: 9 Amino acid sequence of the light chain variable region of C3-147

QFVLTQPNSVSTNLGTTVELSCKRNTGNIGSNYVNWYQQHEGRSPTTIIYR
DDKRPDGVSDRFSGSIDRSSKSALLTINNVQTEDEADYFCQSYSSGFIFGG
GTKLTVL

[Figure 18]

SEQ ID NO: 10 G4S linker sense

GTCACTGTCTCTTCAGGTGGAGGCGGTTCAGGCGGAGGTGGCAGCGGCGGT
GGCGGGAGTCAGTTTGTGCTTACT

[Figure 19]

SEQ ID NO: 11 G4S linker antisense

AGTAAGCACAAACTGACTCCCGCCACCGCCGCTGCCACCTCCGCCTGAACC

GCCTCCACCTGAAGAGACAGTGAC

[Figure 20]

SEQ ID NO: 14 Nucleotide sequence encoding C3E-7000

ATGAAACACCTGTGGTTCTTCCTCCTGCTGGTGGCAGCTCCCAGATGGGTG
CTGAGCGAGGTGCAGTTGGTGGAGTCTGGGGGAGGCCTGGTGCAGCCTGGA
AGGGCCCTGAAACTCTCCTGTGTAGTCTCTGGAGTCACATTCAATTACTAC
GGGATGAGCTGGATCCGCCAGGCTCCAGGGAAGGGGCTGGAGTGGGTTGCA
TCCATTACTAATTCTGGTGGTAGAATTTACTATCCAGACTCTGTGAAGGGC
CGATTCACTATCTCCAGAGAAAATACACAAAAGACCCTATACCTACAAATG
AACAGTCTGAGGTCTGAGGACACGGCCACTTATTACTGTACTCTCGATGGT
CGCGATGGTTGGGTTGCTTACTGGGGCCAAGGCACTCTGGTCACTGTCTCT
TCAGGTGGAGGCGGTTCAGGCGGAGGTGGCAGCGGCGGTGGCGGGAGTCAG
TTTGTGCTTACTCAGCCAAACTCTGTGTCTACGAATCTCGGAACCACAGTC
GAACTGTCTTGCAAGCGCAACACTGGGAACATTGGAAGCAATTATGTGAAC
TGGTACCAGCAGCATGAGGGAAGATCTCCCACCACTATTATTTATAGGGAT
GATAAGAGACCAGATGGAGTTTCTGACAGGTTCTCTGGGTCCATTGACAGA
TCTTCCAAGTCAGCCCTCCTGACAATCAATAATGTGCAGACTGAAGATGAA
GCTGACTACTTCTGTCAGTCTTACAGTAGTGGTTTTATTTTCGGCGGTGGA
ACCAAGCTCACTGTCCTAGGCGCGTCTGCGGCCGCAGGATCCGGTGGTGAT
TACAAAGATGATGACGATAAAGGTGCAGCGGCGCATCACCATCATCACCAC

Signal sequence (1-57), C3E-7000(58-867), FLAG-His tag (784-867)

[Figure 21]

SEQ ID NO: 15 Amino acid sequence in C3E-7000

EVQLVESGGGLVQPGRALKLSCVVSGVTFNYYGMSWIRQAPGKGLEWVASI
TNSGGRIYYPDSVKGRFTISRENTQKTLYLQMNSLRSEDTATYYCTLDGRD
GWVAYWGQGTLVTVSSGGGGSGGGGSGGGGSQFVLTQPNSVSTNLGTTVEL
SCKRNTGNIGSNYVNWYQQHEGRSPTTIIYRDDKRPDGVSDRFSGSIDRSS
KSALLTINNVQTEDEADYFCQSYSSGFIFGGGTKLTVLGASAAAGSGGDYK
DDDDKGAAAHHHHHH

C3E-7000(1-270), FLAG-His tag (243-270)

[Figure 22]

SEQ ID NO: 16 Amino acid sequence of the heavy chain variable region of C3E-7034

EVQLVESGGGLVQPGGSLRLSCAASGVTFNYYGMSWIRQAPGKGLEWVASI
TNSGGRIYYPDSVKGRFTISRENTQKTLYLQMNSLRAEDTAVYYCTLDGRD
GWVAYWGQGTLVTVSS

[Figure 23]

SEQ ID NO: 17 Amino acid sequence of the light chain variable region of C3E-7034

NFMLTQPHSVSESPGKTVTISCKRNTGNIGSNYVNWYQQHEGSSPTTIIYR
DDKRPDGVSDRFSGSIDRSSKSASLTISNLKTEDEADYFCQSYSSGFIFGG
GTKLTVL

[Figure 24]

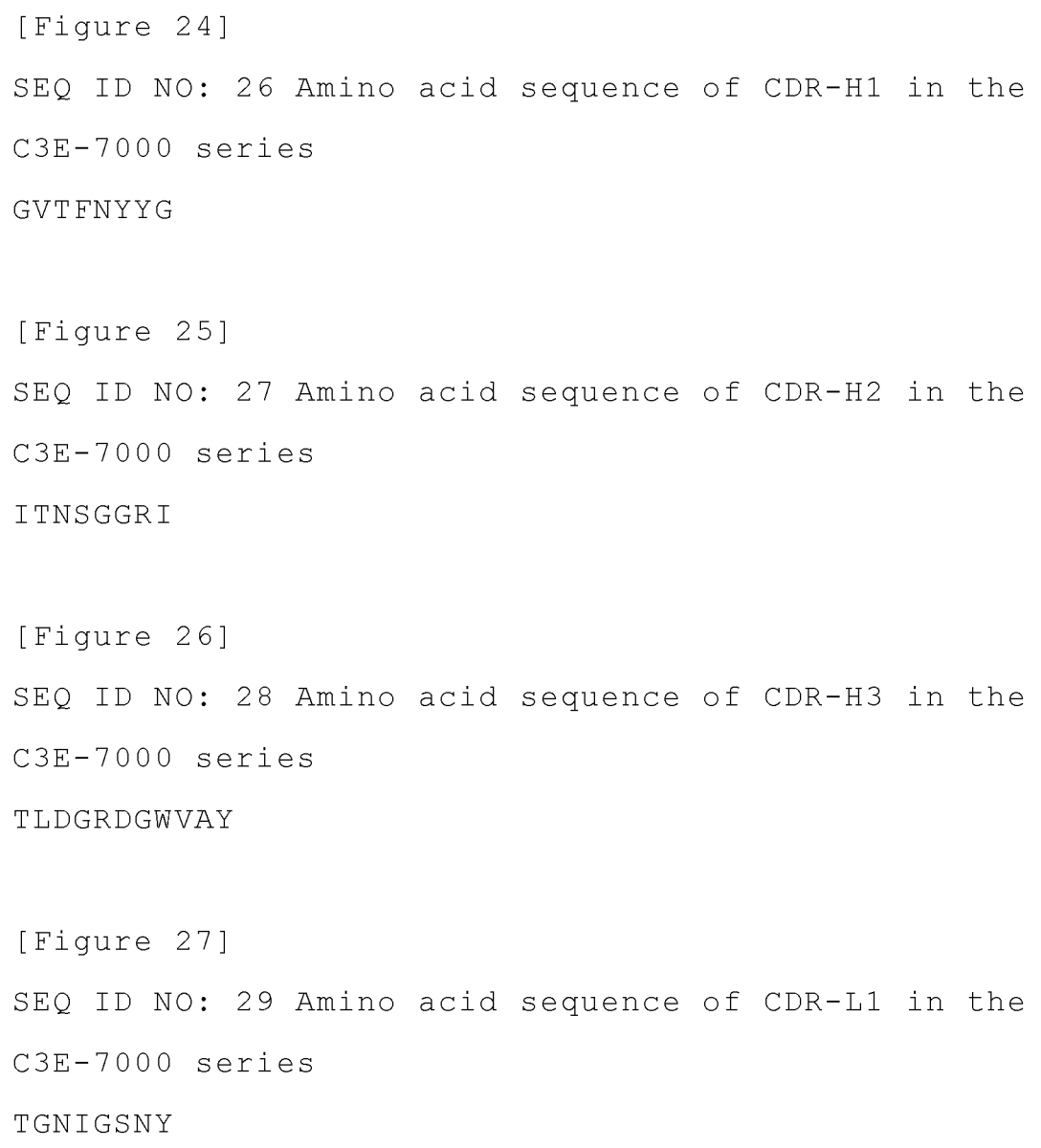

SEQ ID NO: 26 Amino acid sequence of CDR-H1 in the C3E-7000 series

GVTFNYYG

[Figure 25]

SEQ ID NO: 27 Amino acid sequence of CDR-H2 in the C3E-7000 series

ITNSGGRI

[Figure 26]

SEQ ID NO: 28 Amino acid sequence of CDR-H3 in the C3E-7000 series

TLDGRDGWVAY

[Figure 27]

SEQ ID NO: 29 Amino acid sequence of CDR-L1 in the C3E-7000 series

TGNIGSNY

[Figure 28]

SEQ ID NO: 30 Amino acid sequence of CDR-L2 in the C3E-7000 series

RDD

[Figure 29]

SEQ ID NO: 31 Amino acid sequence of CDR-L3 in the C3E-7000 series

QSYSSGFI

[Figure 30]

SEQ ID NO: 20 Amino acid sequence of the light chain variable region of C3E-7035

QAVLTQPSSVSGVPGQRVTISCKRNTGNIGSNYVNWYQQLPGTAPKLLIYR
DDKRPSGVPDRFSGSKSGTSASLAITGFQAEDEADYYCQSYSSGFIFGGGT
KLTVL

[Figure 31]

SEQ ID NO: 22 (C3E_7035 AA) Amino acid sequence of C3E-7035

GEVQLVESGGGLVQPGGSLRLSCAASGVTFNYYGMSWIRQAPGKGLEWVAS
ITNSGGRIYYPDSVKGRFTISRENTQKTLYLQMNSLRAEDTAVYYCTLDGR
DGWVAYWGQGTLVTVSSGGGGSGGGGSGGGGSMAQAVLTQPSSVSGVPGQR
VTISCKRNTGNIGSNYVNWYQQLPGTAPKLLIYRDDKRPSGVPDRFSGSKS
GTSASLAITGFQAEDEADYYCQSYSSGFIFGGGTKLTVLGAAAGAGGDYKD
DDDKGAAAHHHHHH

C3E-7035(1-269), FLAG-His tag (244-269)

[Figure 32]

SEQ ID NO: 23 Amino acid sequence of the light chain variable region of C3E-7036

NFMLTQPSSVSGVPGQRVTISCTGNTGNIGSNYVNWYQQLPGTAPKLLIYR
DDKRPSGVPDRFSGSKSGTSASLAITGFQAEDEADYYCQSYSSGFIFGGGT
KLTVL

[Figure 33]

SEQ ID NO: 25 Amino acid sequence of C3E-7036

GEVQLVESGGGLVQPGGSLRLSCAASGVTFNYYGMSWIRQAPGKGLEWVAS
ITNSGGRIYYPDSVKGRFTISRENTQKTLYLQMNSLRAEDTAVYYCTLDGR
DGWVAYWGQGTLVTVSSGGGGSGGGGSGGGGSNFMLTQPSSVSGVPGQRVT
ISCTGNTGNIGSNYVNWYQQLPGTAPKLLIYRDDKRPSGVPDRFSGSKSGT
SASLAITGFQAEDEADYYCQSYSSGFIFGGGTKLTVLGAAAGAGGDYKDDD
DKGAAAHHHHHH

C3E-7036(1-267), FLAG-His tag (242-267)

[Figure 34]

SEQ ID NO: 18 Nucleotide sequence encoding C3E-7034

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTAATTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
AACTTTATGCTGACCCAGCCCCACAGTGTGTCAGAGAGCCCTGGCAAGACT
GTCACCATCTCTTGTAAAAGGAACACCGGAAATATTGGCAGTAACTACGTG
AATTGGTATCAGCAGCATGAAGGGTCTAGTCCAACCACAATCATCTACCGG
GACGATAAGAGACCCGACGGGGTGTCCGATCGATTCTCCGGATCTATCGAC
CGGTCAAGCAAGAGTGCTTCACTGACCATTAGCAATCTGAAAACAGAGGAC
GAAGCAGATTACTTTTGCCAGTCCTATTCCTCTGGCTTCATCTTTGGAGGC
GGGACTAAACTGACCGTGCTGGGCGCGGCCGCAGGTGCAGGTGGTGATTAC
AAAGATGATGACGATAAAGGTGCAGCGGCGCATCACCATCATCACCAC

Signal sequence (1-57), C3E-7034(58-864), FLAG-His tag (787-864)

[Figure 35]

SEQ ID NO: 21 Nucleotide sequence encoding C3E-7035

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTAATTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
ATGGCCCAGGCTGTGCTCACTCAGCCGTCCTCTGTTTCTGGCGTACCTGGC
CAACGGGTGACCATTAGCTGTAAAAGGAATACCGGGAATATCGGGTCTAAC
TACGTGAACTGGTATCAGCAGCTTCCAGGGACAGCTCCCAAGTTGCTGATC
TATCGCGACGACAAAAGACCCTCAGGGGTCCCTGACCGATTTAGTGGCAGC
AAAAGCGGTACTTCCGCTTCCCTGGCGATAACCGGCTTTCAGGCCGAAGAT
GAGGCAGACTACTATTGCCAGTCATATTCCAGCGGCTTCATCTTCGGAGGC
GGAACTAAGCTGACAGTGCTGGGCGCGGCCGCAGGTGCAGGTGGTGATTAC
AAAGATGATGACGATAAAGGTGCAGCGGCGCATCACCATCATCACCAC

Signal sequence (1-57), C3E-7035(58-864), FLAG-His tag (787-864)

[Figure 36]

SEQ ID NO: 24 Nucleotide sequence encoding C3E-7036

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTAATTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
AACTTTATGCTCACTCAGCCGTCCTCTGTTTCTGGCGTACCTGGCCAACGG
GTGACCATTAGCTGTACGGGTAATACCGGGAATATCGGGTCTAACTACGTG
AACTGGTATCAGCAGCTTCCAGGGACAGCTCCCAAGTTGCTGATCTATCGC
GACGACAAAAGACCCTCAGGGGTCCCTGACCGATTTAGTGGCAGCAAAAGC
GGTACTTCCGCTTCCCTGGCGATAACCGGCTTTCAGGCCGAAGATGAGGCA
GACTACTATTGCCAGTCATATTCCAGCGGCTTCATCTTCGGAGGCGGAACT
AAGCTGACAGTGTTGGGTGCGGCCGCAGGTGCAGGTGGTGATTACAAAGAT
GATGACGATAAAGGTGCAGCGGCGCATCACCATCATCACCAC

Signal sequence (1-57), C3E-7036(58-858), FLAG-His tag (781-858)

[Figure 37]

SEQ ID NO: 3 Amino acid sequence of human CD3γ

MEQGKGLAVLILAIILLQGTLAQSIKGNHLVKVYDYQEDGSVLLTCDAEAK
NITWFKDGKMIGFLTEDKKKWNLGSNAKDPRGMYQCKGSQNKSKPLQVYYR
MCQNCIELNAATISGFLFAEIVSIFVLAVGVYFIAGQDGVRQSRASDKQTL
LPNDQLYQPLKDREDDQYSHLQGNQLRRN (uniprotID_P09693)

[Figure 38]

SEQ ID NO: 19 Amino acid sequence of C3E-7034

GEVQLVESGGGLVQPGGSLRLSCAASGVTFNYYGMSWIRQAPGKGLEWVAS
ITNSGGRIYYPDSVKGRFTISRENTQKTLYLQMNSLRAEDTAVYYCTLDGR
DGWVAYWGQGTLVTVSSGGGGSGGGGSGGGGSNFMLTQPHSVSESPGKTVT
ISCKRNTGNIGSNYVNWYQQHEGSSPTTIIYRDDKRPDGVSDRFSGSIDRS
SKSASLTISNLKTEDEADYFCQSYSSGFIFGGGTKLTVLGAAAGAGGDYKD
DDDKGAAAHHHHHH

C3E-7034(2-269), FLAG-His tag (244-269)

[Figure 39]
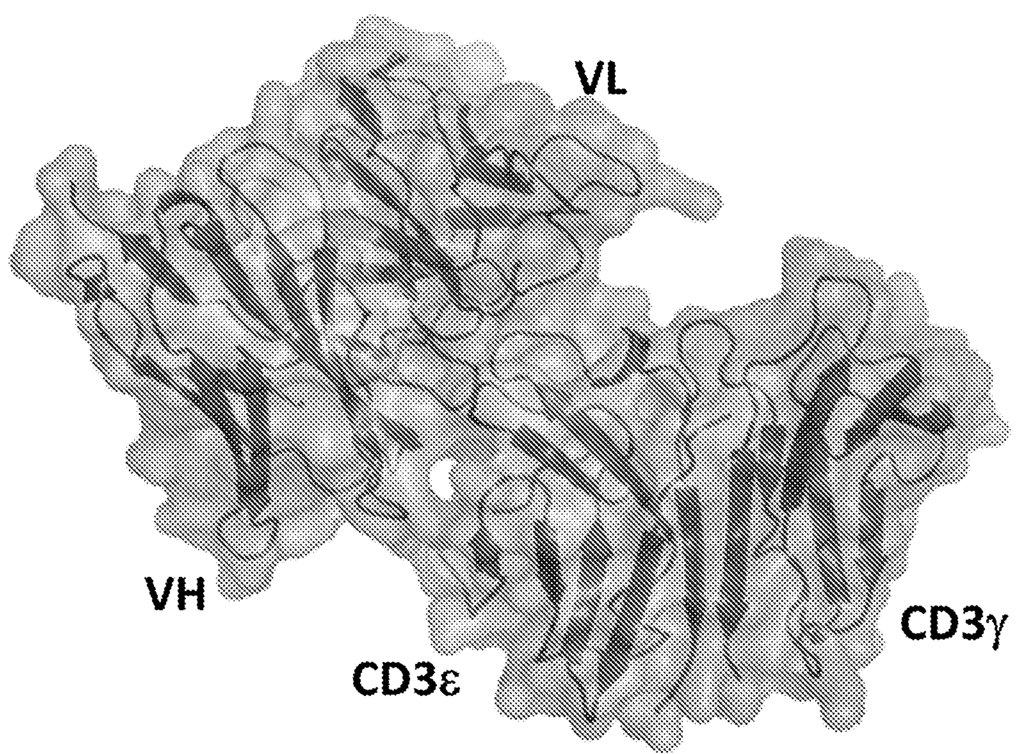

[Figure 40]
A
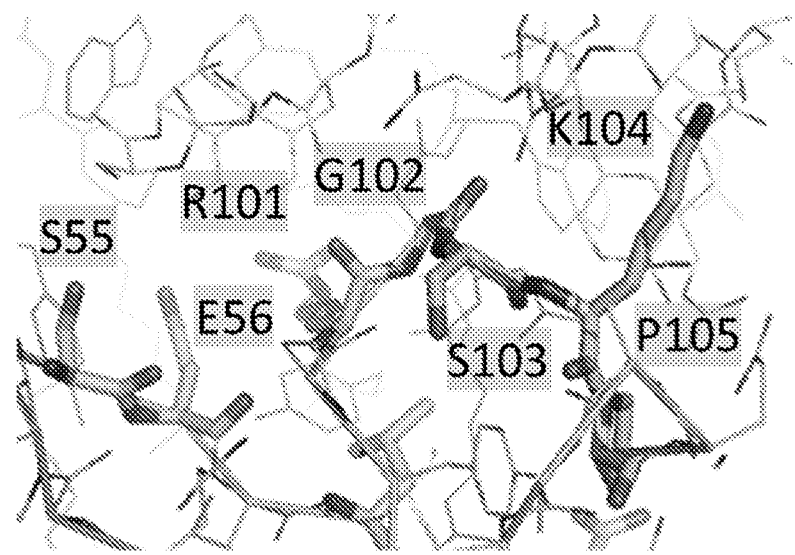
B
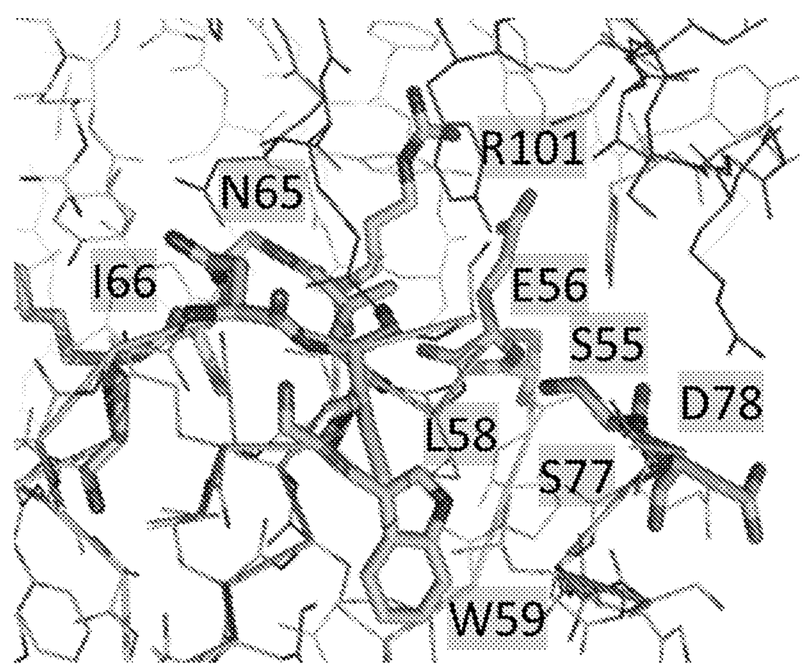

[Figure 41]

huCD3ε

*MQSGTHWRVLGLCLLSVGVWGQ*DGNEEMGGITQTPYKVSISGTTVILTCPQ
YPGSEILWQHNDKNIGGDEDDKNIGSDEDHLSLKEFSELEQSGYYVCYPRG
SKPEDANFYLYLRARVCENCMEMDVMSVATIVIVDICITGGLLLLVYYWSK
NRKAKAKPVTRGAGAGGRQRGQNKERPPPVPNPDYEPIRKGQRDLYSGLNQ
RRI

[Figure 42]

SEQ ID NO: 36 Amino acid sequence of the heavy chain variable region of OKT3

QVQLQQSGAELARPGASVKMSCKASGYTFTRYTMHWVKQRPGQGLEWIGYI
NPSRGYTNYNQKFKDKATLTTDKSSSTAYMQLSSLTSEDSAVYYCARYYDD
HYCLDYWGQGTTLTVSS

[Figure 43]

SEQ ID NO: 38 Amino acid sequence of the heavy chain variable region of C3E-3007

QVQLVQSGAESKKPGASVKVSCKASGYTFTRYTMHWVRQAPGQGLEWMGYI
NPSRGYTNYNQKFKDRVTITADKSTSTAYMELSSLRSEDTAVYYCARYYDD
HYCLDYWGQGTLVTVSS

[Figure 44]

SEQ ID NO: 37 Amino acid sequence of the light chain variable region of OKT3

QIVLTQSPAIMSASPGEKVTMTCSASSSVSYMNWYQQKSGTSPKRWIYDTS
KLASGVPAHFRGSGSGTSYSLTISGMEAEDAATYYCQQWSSNPFTFGSGTK
LEIK

[Figure 45]

SEQ ID NO: 39 Amino acid sequence of light chain variable region of C3E-3007

QIQMTQSPSSLAVSLGERATITCSASSSVSYMNWYQQKPGKAPKRWIYDTS
KLASGVPDRFSGSGSGTDFTLTISSLQAEDVATYYCQQWSSNPFTFGQGTK
VEIK

[Figure 46]

SEQ ID NO: 34 Nucleotide sequence encoding C3E-3007

ATGAAGCACCTGTGGTTCTTTCTGCTGCTGGTGGCCGCTCCCAGATGGGTG
CTGTCTCAGGTGCAGCTGGTGCAGTCTGGCGCCGAGAGCAAAAAGCCTGGC
GCCTCCGTGAAGGTGTCCTGCAAGGCCAGCGGCTACACCTTTACCCGGTAC
ACCATGCACTGGGTGCGCCAGGCACCTGGACAGGGCCTGGAATGGATGGGC
TACATCAACCCCAGCCGGGGCTACACCAACTACAACCAGAAATTCAAGGAC
CGCGTGACCATCACCGCCGACAAGAGCACCAGCACCGCCTACATGGAACTG
AGCAGCCTGCGGAGCGAGGACACCGCCGTGTACTACTGTGCCCGGTACTAC
GACGACCACTACTGCCTGGACTACTGGGGCCAGGGCACACTCGTGACCGTG
TCTAGTGGTGGAGGCGGTTCAGGCGGAGGTGGCAGCGGCGGTGGCGGGAGT
CAGATCCAGATGACCCAGAGCCCTAGCAGCCTGGCCGTGTCTCTGGGAGAG
AGAGCCACCATCACCTGTAGCGCCAGCAGCAGCGTGTCCTACATGAACTGG
TATCAGCAGAAGCCCGGCAAGGCCCCCAAGCGGTGGATCTACGATACCAGC
AAGCTGGCCTCCGGCGTGCCCGATAGATTTTCTGGCAGCGGCTCCGGCACC
GACTTCACCCTGACAATCAGCTCCCTGCAGGCCGAGGACGTGGCCACCTAC
TACTGTCAGCAGTGGTCCAGCAACCCCTTCACCTTCGGCCAGGGCACCAAG
GTGGAAATCAAGCGGGGCGCGTCTGCGGCCGCAGGTAGCGGTGGTGATTAC
AAAGATGATGACGATAAAGGTGCAGCGGCGCATCACCATCATCACCAC

Signal sequence (1-57), C3E-3007 (58-864), FLAG-His tag (778-864)

[Figure 47]

SEQ ID NO: 35 Amino acid sequence of C3E-3007

QVQLVQSGAESKKPGASVKVSCKASGYTFTRYTMHWVRQAPGQGLEWMGYI

NPSRGYTNYNQKFKDRVTITADKSTSTAYMELSSLRSEDTAVYYCARYYDD

HYCLDYWGQGTLVTVSSGGGGSGGGGSGGGGSQIQMTQSPSSLAVSLGERA

TITCSASSSVSYMNWYQQKPGKAPKRWIYDTSKLASGVPDRFSGSGSGTDF

TLTISSLQAEDVATYYCQQWSSNPFTFGQGTKVEIKRGASAAAGSGGDYKD

DDDKGAAAHHHHHH

C3E-3007 (1-269), FLAG-His tag (242-269)

[Figure 48]
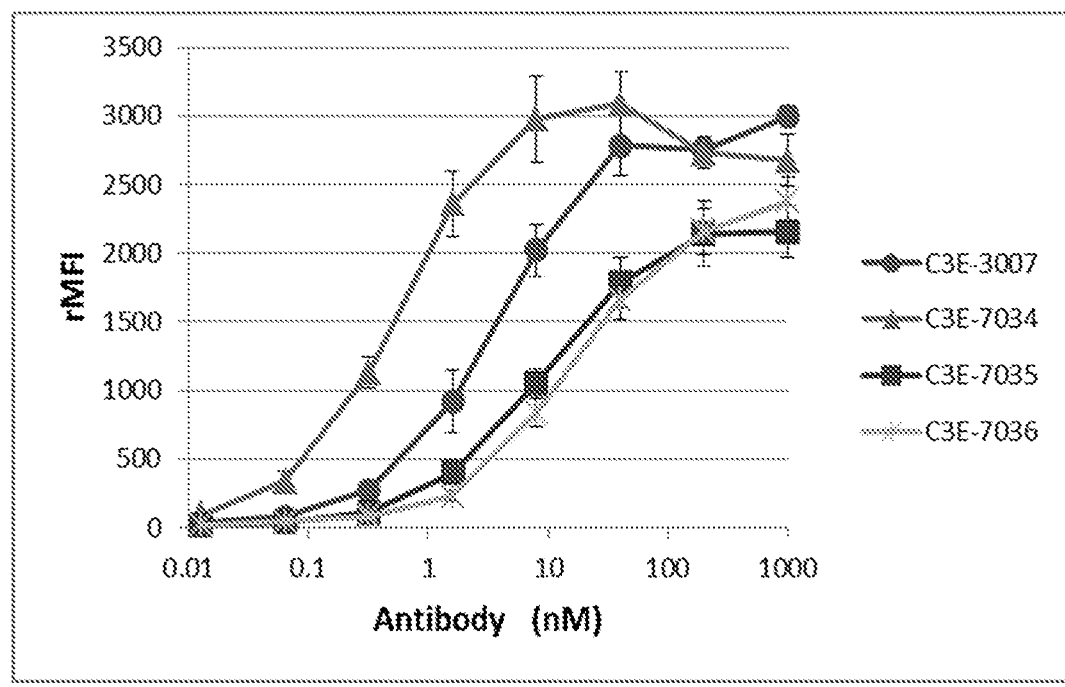
[Figure 49]
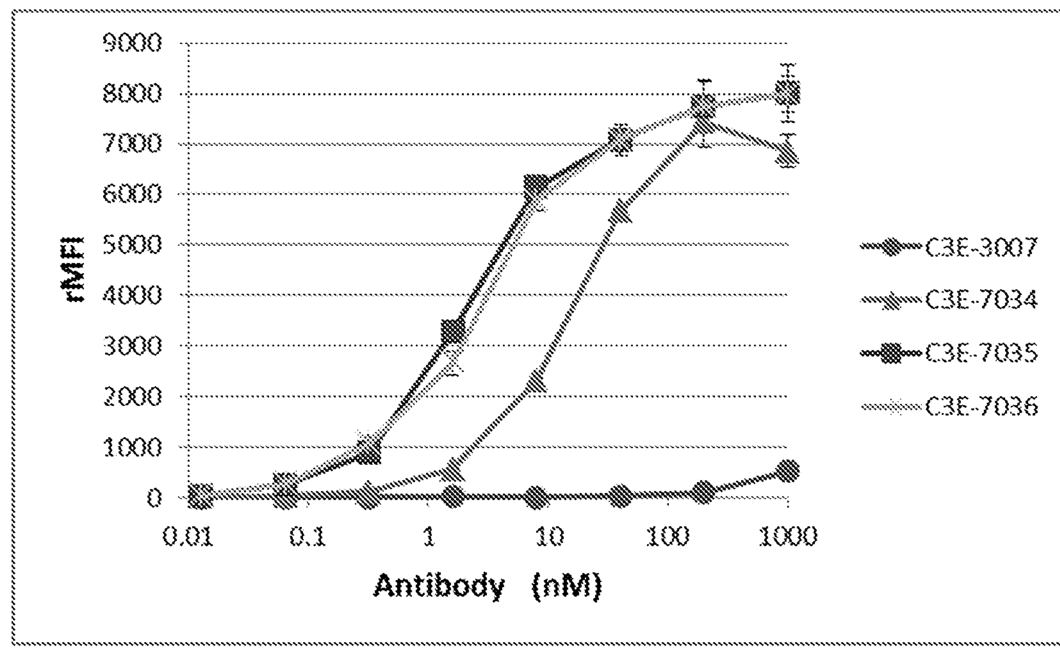

[Figure 50]
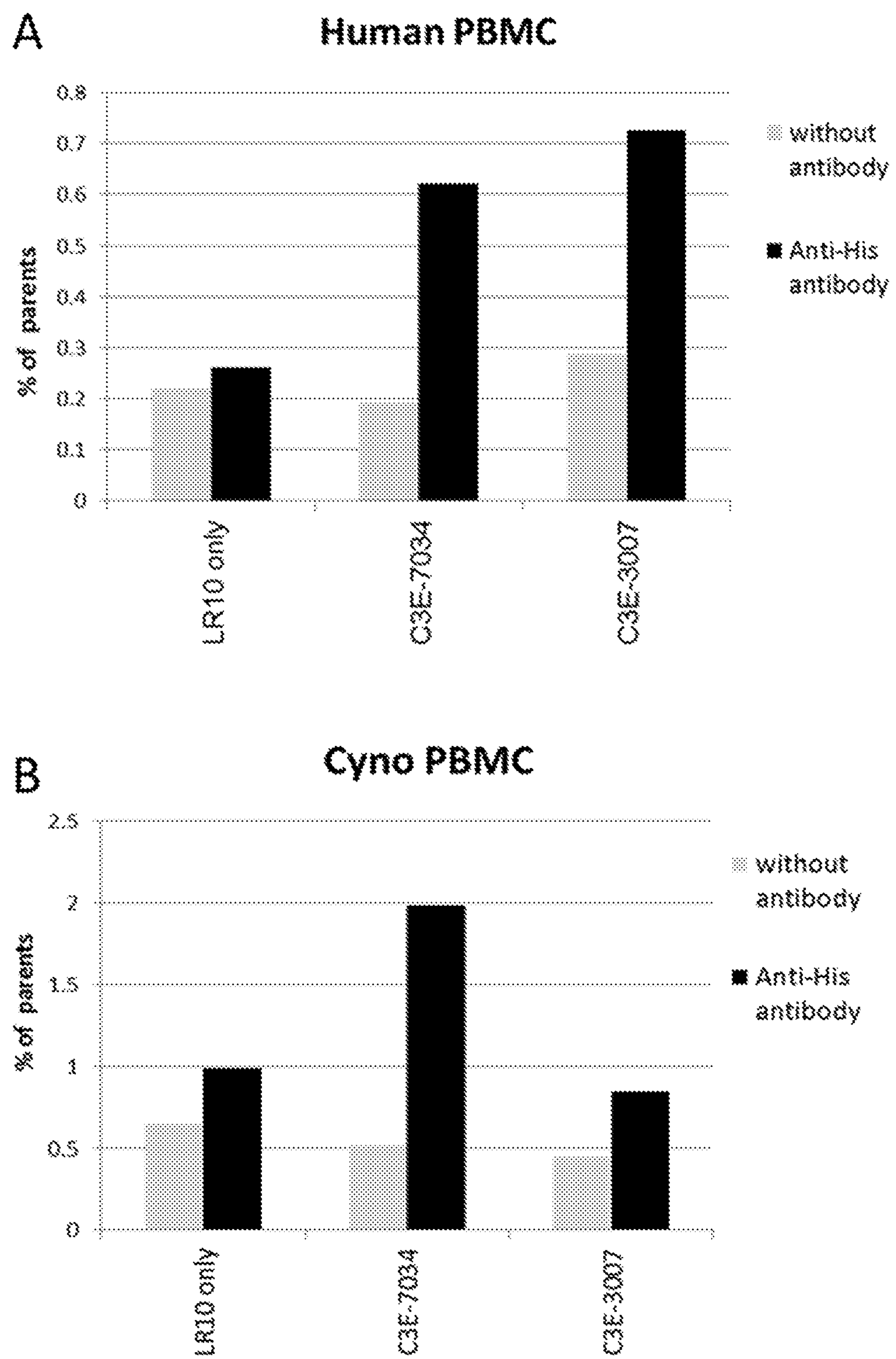

[Figure 51]

SEQ ID NO: 41 Amino acid sequence of HT1-11 scFv

QVQLVQSGAEVKKPGASVKVSCKASGYTFTTAGMQWVRQAPGQGLEWMGWI
NTHSGVPKYAEDFKGRVTISADTSTSTAYLQLSSLKSEDTAVYYCARSGFG
SSYWYFDVWGQGTLVTVSSGGGGSGGGGSGGGGSDIQMTQSPSSLSASVGD
RVTITCKASQDVSTAVAWYQQKPGKAPKLLIYSASYRYTGVPSRFSGSGSG
TDFTLTISSLQPEDFAVYYCQQHYITPLTFGQGTKLEIKRTGAAAHHHHHH

HT1-11 scFv (1-255), His tag (246-255)

[Figure 52]

SEQ ID NO: 40 Nucleotide sequence encoding HT1-11 scFv

ATGAAGCACCTGTGGTTCTTTCTGCTGCTGGTGGCCGCTCCCAGATGGGTG
CTGTCTCAGGTGCAGCTGGTGCAGTCTGGCGCCGAAGTGAAGAAACCAGGC
GCCAGCGTGAAGGTGTCCTGCAAGGCCAGCGGCTACACCTTTACCACCGCC
GGCATGCAGTGGGTGCGCCAGGCTCCTGGACAGGGCCTGGAATGGATGGGC
TGGATCAACACCCACAGCGGCGTGCCCAAATACGCCGAGGACTTCAAGGGC
AGAGTGACCATCAGCGCCGACACCAGCACCTCCACAGCCTACCTGCAGCTG
AGCAGCCTGAAGTCCGAGGACACCGCCGTGTACTACTGCGCCAGAAGCGGC
TTCGGCAGCAGCTACTGGTACTTCGACGTGTGGGGCCAGGGCACCCTCGTG
ACAGTGTCTAGCGGAGGCGGAGGATCTGGCGGCGGAGGAAGTGGCGGAGGG
GGATCCGATATCCAGATGACCCAGAGCCCCAGCAGCCTGTCTGCCAGCGTG
GGCGACAGAGTGACAATTACATGCAAGGCCTCCCAGGACGTGTCCACAGCC
GTGGCCTGGTATCAGCAGAAGCCTGGCAAGGCCCCCAAGCTGCTGATCTAC
AGCGCCAGCTACCGGTACACCGGCGTGCCAAGCAGATTTTCCGGCAGCGGC
TCCGGCACCGACTTCACCCTGACAATCAGCTCCCTGCAGCCCGAGGATTTC
GCCGTGTATTATTGCCAGCAGCACTACATCACCCCCCTGACCTTCGGCCAG
GGGACCAAGCTGGAAATCAAGAGAACAGGCGCCGCTGCCCACCACCACCAT
CACCAT

Signal sequence (1-57), HT1-11 scFv (58-822), His tag (792-822)

[Figure 53]
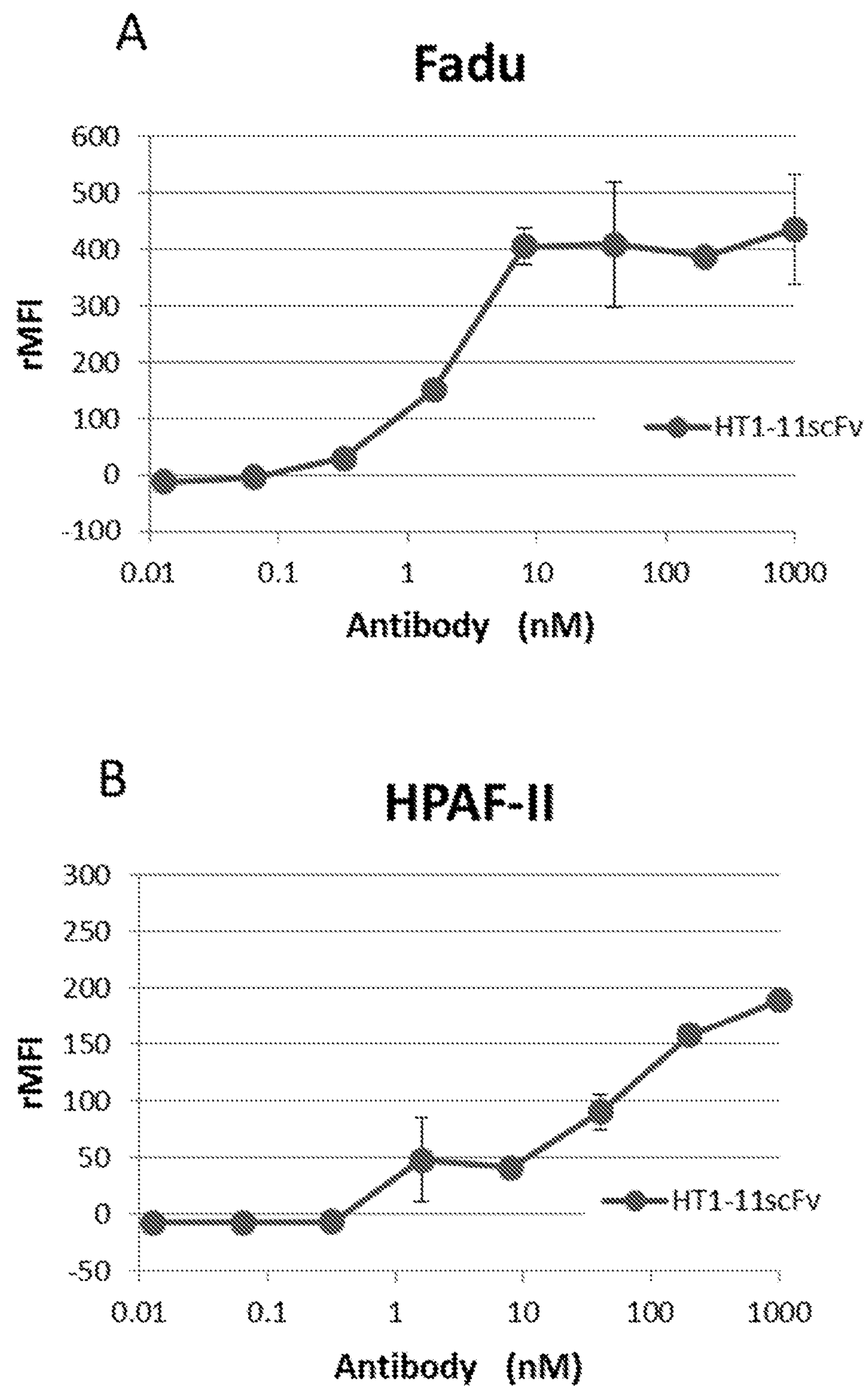

[Figure 54]
SEQ ID NO: 42 ORF nucleotide sequence encoding T2C-0001

ATGAAACACCTGTGGTTCTTCCTCCTGCTGGTGGCAGCTCCCAGATG
GGTGCTGAGCGGACAGGTGCAGCTGGTGCAGTCTGGCGCCGAAGTGA
AGAAACCAGGCGCCAGCGTGAAGGTGTCCTGCAAGGCCAGCGGCTAC
ACCTTTACCACCGCCGGCATGCAGTGGGTGCGCCAGGCTCCTGGACA
GGGCCTGGAATGGATGGGCTGGATCAACACCCACAGCGGCGTGCCCA
AATACGCCGAGGACTTCAAGGGCAGAGTGACCATCAGCGCCGACACC
AGCACCTCCACAGCCTACCTGCAGCTGAGCAGCCTGAAGTCCGAGGA
CACCGCCGTGTACTACTGCGCCAGAAGCGGCTTCGGCAGCAGCTACT
GGTACTTCGACGTGTGGGGCCAGGGCACCCTCGTGACAGTGTCTAGC
GGAGGCGGAGGATCTGGCGGCGGAGGAAGTGGCGGAGGGGGATCCGA
TATCCAGATGACCCAGAGCCCCAGCAGCCTGTCTGCCAGCGTGGGCG
ACAGAGTGACAATTACATGCAAGGCCTCCCAGGACGTGTCCACAGCC
GTGGCCTGGTATCAGCAGAAGCCTGGCAAGGCCCCCAAGCTGCTGAT
CTACAGCGCCAGCTACCGGTACACCGGCGTGCCAAGCAGATTTTCCG
GCAGCGGCTCCGGCACCGACTTCACCCTGACAATCAGCTCCCTGCAG
CCCGAGGATTTCGCCGTGTATTATTGCCAGCAGCACTACATCACCCC
CCTGACCTTCGGCCAGGGGACCAAGCTGGAAATCAAGAGAACAGGGG
GAGGCGGTTCAGAAGTGCAGCTGGTGGAATCCGGGGGGGGCCTGGTG
CAGCCTGGGGGGAGCCTGAGACTGAGTTGTGCCGCCTCTGGGGTGAC
ATTTAACTACTATGGCATGTCTTGGATCCGCCAGGCACCTGGAAAGG
GCCTGGAGTGGGTGGCCAGCATCACTAATTCCGGCGGGCGAATCTAC
TATCCCGACAGCGTCAAGGGCAGGTTCACAATTTCCCGCGAGAACAC
ACAGAAAACTCTGTACCTGCAGATGAATAGCCTGAGAGCCGAAGATA
CAGCTGTGTACTATTGCACTCTGGACGGCAGGGATGGGTGGGTCGCC
TATTGGGGGCAGGGAACCCTGGTGACAGTCAGCTCCGGAGGAGGAGG
ATCTGGCGGAGGAGGCAGTGGGGGAGGCGGGTCAAACTTTATGCTGA
CCCAGCCCCACAGTGTGTCAGAGAGCCCTGGCAAGACTGTCACCATC
TCTTGTAAAAGGAACACCGGAAATATTGGCAGTAACTACGTGAATTG
GTATCAGCAGCATGAAGGGTCTAGTCCAACCACAATCATCTACCGGG
ACGATAAGAGACCCGACGGGGTGTCCGATCGATTCTCCGGATCTATC
GACCGGTCAAGCAAGAGTGCTTCACTGACCATTAGCAATCTGAAAAC
AGAGGACGAAGCAGATTACTTTTGCCAGTCCTATTCCTCTGGCTTCA
TCTTTGGAGGCGGGACTAAACTGACCGTGCTGGGCGCGGCCGCAGGT
GCAGGTGGTGATTACAAAGATGATGACGATAAAGGTGCAGCGGCGCA
TCACCATCATCACCAC

Signal sequence (1-57), Bispecific antibody (58-1536), FLAG-His tag (1537-1614)

[Figure 55]

SEQ ID NO: 44 ORF nucleotide sequence encoding T2C-0003

ATGAAACACCTGTGGTTCTTCCTCCTGCTGGTGGCAGCTCCCAGATG
GGTGCTGAGCGGACAGGTGCAGCTGGTGCAGTCTGGCGCCGAAGTGA
AGAAACCAGGCGCCAGCGTGAAGGTGTCCTGCAAGGCCAGCGGCTAC
ACCTTTACCACCGCCGGCATGCAGTGGGTGCGCCAGGCTCCTGGACA
GGGCCTGGAATGGATGGGCTGGATCAACACCCACAGCGGCGTGCCCA
AATACGCCGAGGACTTCAAGGGCAGAGTGACCATCAGCGCCGACACC
AGCACCTCCACAGCCTACCTGCAGCTGAGCAGCCTGAAGTCCGAGGA
CACCGCCGTGTACTACTGCGCCAGAAGCGGCTTCGGCAGCAGCTACT
GGTACTTCGACGTGTGGGGCCAGGGCACCCTCGTGACAGTGTCTAGC
GGAGGCGGAGGATCTGGCGGCGGAGGAAGTGGCGGAGGGGGATCCGA
TATCCAGATGACCCAGAGCCCCAGCAGCCTGTCTGCCAGCGTGGGCG
ACAGAGTGACAATTACATGCAAGGCCTCCCAGGACGTGTCCACAGCC
GTGGCCTGGTATCAGCAGAAGCCTGGCAAGGCCCCCAAGCTGCTGAT
CTACAGCGCCAGCTACCGGTACACCGGCGTGCCAAGCAGATTTTCCG
GCAGCGGCTCCGGCACCGACTTCACCCTGACAATCAGCTCCCTGCAG
CCCGAGGATTTCGCCGTGTATTATTGCCAGCAGCACTACATCACCCC
CCTGACCTTCGGCCAGGGGACCAAGCTGGAAATCAAGAGAACAGGGG
GAGGCGGTTCAGAAGTGCAGCTGGTGGAATCCGGCGGAGGCCTGGTC
CAGCCTGGCGGCAGCCTGAAACTGAGCTGCGCCGCCAGCGGCTTCAC
CTTCAACAAATACGCCATGAACTGGGTCCGCCAGGCTCCTGGAAAGG
GACTCGAGTGGGTGGCCCGGATCAGAAGCAAGTACAACAACTACGCC
ACCTACTACGCCGACAGCGTGAAGGACCGGTTCACCATCAGCCGGGA
CGACAGCAAGAACACCGCCTACCTGCAGATGAACAACCTGAAAACCG
AGGACACAGCCGTGTACTACTGCGTGCGGCACGGCAACTTCGGCAAC
AGCTACATCAGCTACTGGGCCTATTGGGGACAGGGAACACTCGTGAC
AGTGTCCAGTGGCGGAGGCGGCAGTGGTGGGGGAGGAAGCGGAGGTG
GCGGATCTCAGACCGTGGTCACCCAGGAACCCAGCCTGACAGTCAGC
CCTGGAGGCACCGTGACCCTGACCTGTGGAAGCAGCACAGGCGCCGT
GACCAGCGGCTACTACCCCAACTGGGTGCAGCAGAAGCCCGGCCAGG
CTCCTAGAGGCCTGATCGGCGGCACCAAGTTTCTGGCCCCTGGCACC
CCTGCCCGGTTCTCTGGATCTCTGCTGGGCGGCAAGGCCGCCCTGAC
ACTGAGCGGAGTGCAGCCCGAGGACGAGGCCGAGTACTACTGTGCCC
TGTGGTACAGCAACAGATGGGTGTTCGGCGGAGGGACCAAGCTGACC
GTGCTGGGCAGCGGCGCGTCTGCGGCCGCAGGTAGCGGTGGTGATTA
CAAAGATGATGACGATAAAGGTGCAGCGGCGCATCACCATCATCACC
AC

Signal sequence (1-57), Bispecific antibody (58-1647), FLAG-His tag (1561-1647)

[Figure 56]

SEQ ID NO: 46 ORF nucleotide sequence encoding T2C-0005

ATGAAGCACCTGTGGTTCTTCCTCCTGCTGGTGGCAGCTCCCAGATG
GGTGCTGAGCGGACAGGTGCAGCTGGTGCAGTCTGGCGCCGAAGTGA
AGAAACCAGGCGCCAGCGTGAAGGTGTCCTGCAAGGCCAGCGGCTAC
ACCTTTACCACCGCCGGCATGCAGTGGGTGCGCCAGGCTCCTGGACA
GGGCCTGGAATGGATGGGCTGGATCAACACCCACAGCGGCGTGCCCA
AATACGCCGAGGACTTCAAGGGCAGAGTGACCATCAGCGCCGACACC
AGCACCTCCACAGCCTACCTGCAGCTGAGCAGCCTGAAGTCCGAGGA
CACCGCCGTGTACTACTGCGCCAGAAGCGGCTTCGGCAGCAGCTACT
GGTACTTCGACGTGTGGGGCCAGGGCACCCTCGTGACAGTGTCTAGC
GGAGGCGGAGGATCTGGCGGCGGAGGAAGTGGCGGAGGGGGATCCGA
TATCCAGATGACCCAGAGCCCCAGCAGCCTGTCTGCCAGCGTGGGCG
ACAGAGTGACAATTACATGCAAGGCCTCCCAGGACGTGTCCACAGCC
GTGGCCTGGTATCAGCAGAAGCCTGGCAAGGCCCCCAAGCTGCTGAT
CTACAGCGCCAGCTACCGGTACACCGGCGTGCCAAGCAGATTTTCCG
GCAGCGGCTCCGGCACCGACTTCACCCTGACAATCAGCTCCCTGCAG
CCCGAGGATTTCGCCGTGTATTATTGCCAGCAGCACTACATCACCCC
CCTGACCTTCGGCCAGGGGACCAAGCTGGAAATCAAGAGAACAGGGG
GAGGCGGTTCAGAAGTGCAGCTGGTGGAATCCGGGGGGGGCCTGGTG
CAGCCTGGGGGGAGCCTGAGACTGAGTTGTGCCGCCTCTGGGGTGAC
ATTTAACTACTATGGCATGTCTTGGATCCGCCAGGCACCTGGAAAGG
GCCTGGAGTGGGTGGCCAGCATCACTAATTCCGGCGGGCGAATCTAC
TATCCCGACAGCGTCAAGGGCAGGTTCACAATTTCCCGCGAGAACAC
ACAGAAAACTCTGTACCTGCAGATGAATAGCCTGAGAGCCGAAGATA
CAGCTGTGTACTATTGCACTCTGGACGGCAGGGATGGGTGGGTCGCC
TATTGGGGGCAGGGAACCCTGGTGACAGTCAGCTCCGGAGGAGGAGG
ATCTGGCGGAGGAGGCAGTGGGGGAGGCGGGTCAATGGCCCAGGCTG
TGCTCACTCAGCCGTCCTCTGTTTCTGGCGTACCTGGCCAACGGGTG
ACCATTAGCTGTAAAAGGAATACCGGGAATATCGGGTCTAACTACGT
GAACTGGTATCAGCAGCTTCCAGGGACAGCTCCCAAGTTGCTGATCT
ATCGCGACGACAAAAGACCCTCAGGGGTCCCTGACCGATTTAGTGGC
AGCAAAAGCGGTACTTCCGCTTCCCTGGCGATAACCGGCTTTCAGGC
CGAAGATGAGGCAGACTACTATTGCCAGTCATATTCCAGCGGCTTCA
TCTTCGGAGGCGGAACTAAGCTGACAGTGTTGGGCGCGGCCGCAGGT
GCAGGTGGTGATTACAAAGATGATGACGATAAAGGTGCAGCGGCGCA
TCACCATCATCACCAC

Signal sequence (1-57), Bispecific antibody (58-1536), FLAG-His tag (1537-1614)

[Figure 57]

SEQ ID NO: 48 ORF nucleotide sequence encoding T2C-0006

ATGAAGCACCTGTGGTTCTTCCTCCTGCTGGTGGCAGCTCCCAGATG
GGTGCTGAGCGGACAGGTGCAGCTGGTGCAGTCTGGCGCCGAAGTGA
AGAAACCAGGCGCCAGCGTGAAGGTGTCCTGCAAGGCCAGCGGCTAC
ACCTTTACCACCGCCGGCATGCAGTGGGTGCGCCAGGCTCCTGGACA
GGGCCTGGAATGGATGGGCTGGATCAACACCCACAGCGGCGTGCCCA
AATACGCCGAGGACTTCAAGGGCAGAGTGACCATCAGCGCCGACACC
AGCACCTCCACAGCCTACCTGCAGCTGAGCAGCCTGAAGTCCGAGGA
CACCGCCGTGTACTACTGCGCCAGAAGCGGCTTCGGCAGCAGCTACT
GGTACTTCGACGTGTGGGGCCAGGGCACCCTCGTGACAGTGTCTAGC
GGAGGCGGAGGATCTGGCGGCGGAGGAAGTGGCGGAGGGGGATCCGA
TATCCAGATGACCCAGAGCCCCAGCAGCCTGTCTGCCAGCGTGGGCG
ACAGAGTGACAATTACATGCAAGGCCTCCCAGGACGTGTCCACAGCC
GTGGCCTGGTATCAGCAGAAGCCTGGCAAGGCCCCCAAGCTGCTGAT
CTACAGCGCCAGCTACCGGTACACCGGCGTGCCAAGCAGATTTTCCG
GCAGCGGCTCCGGCACCGACTTCACCCTGACAATCAGCTCCCTGCAG
CCCGAGGATTTCGCCGTGTATTATTGCCAGCAGCACTACATCACCCC
CCTGACCTTCGGCCAGGGGACCAAGCTGGAAATCAAGAGAACAGGGG
GAGGCGGTTCAGAAGTGCAGCTGGTGGAATCCGGGGGGGGCCTGGTG
CAGCCTGGGGGGAGCCTGAGACTGAGTTGTGCCGCCTCTGGGGTGAC
ATTTAACTACTATGGCATGTCTTGGATCCGCCAGGCACCTGGAAAGG
GCCTGGAGTGGGTGGCCAGCATCACTAATTCCGGCGGGCGAATCTAC
TATCCCGACAGCGTCAAGGGCAGGTTCACAATTTCCCGCGAGAACAC
ACAGAAAACTCTGTACCTGCAGATGAATAGCCTGAGAGCCGAAGATA
CAGCTGTGTACTATTGCACTCTGGACGGCAGGGATGGGTGGGTCGCC
TATTGGGGGCAGGGAACCCTGGTGACAGTCAGCTCCGGAGGAGGAGG
ATCTGGCGGAGGAGGCAGTGGGGGAGGCGGGTCAAACTTTATGCTCA
CTCAGCCGTCCTCTGTTTCTGGCGTACCTGGCCAACGGGTGACCATT
AGCTGTACGGGTAATACCGGGAATATCGGGTCTAACTACGTGAACTG
GTATCAGCAGCTTCCAGGGACAGCTCCCAAGTTGCTGATCTATCGCG
ACGACAAAAGACCCTCAGGGGTCCCTGACCGATTTAGTGGCAGCAAA
AGCGGTACTTCCGCTTCCCTGGCGATAACCGGCTTTCAGGCCGAAGA
TGAGGCAGACTACTATTGCCAGTCATATTCCAGCGGCTTCATCTTCG
GAGGCGGAACTAAGCTGACAGTGTTGGGCGCGGCCGCAGGTGCAGGT
GGTGATTACAAAGATGATGACGATAAAGGTGCAGCGGCGCATCACCA
TCATCACCAC

Signal sequence (1-57), Bispecific antibody (58-1530), FLAG-His tag (1531-1608)

[Figure 58]

SEQ ID NO: 43 Amino acid sequence of T2C-0001

GQVQLVQSGAEVKKPGASVKVSCKASGYTFTTAGMQWVRQAPGQGLEWMGW
INTHSGVPKYAEDFKGRVTISADTSTSTAYLQLSSLKSEDTAVYYCARSGF
GSSYWYFDVWGQGTLVTVSSGGGGSGGGGSGGGGSDIQMTQSPSSLSASVG
DRVTITCKASQDVSTAVAWYQQKPGKAPKLLIYSASYRYTGVPSRFSGSGS
GTDFTLTISSLQPEDFAVYYCQQHYITPLTFGQGTKLEIKRTGGGGSEVQL
VESGGGLVQPGGSLRLSCAASGVTFNYYGMSWIRQAPGKGLEWVASITNSG
GRIYYPDSVKGRFTISRENTQKTLYLQMNSLRAEDTAVYYCTLDGRDGWVA
YWGQGTLVTVSSGGGGSGGGGSGGGGSNFMLTQPHSVSESPGKTVTISCKR
NTGNIGSNYVNWYQQHEGSSPTTIIYRDDKRPDGVSDRFSGSIDRSSKSAS
LTISNLKTEDEADYFCQSYSSGFIFGGGTKLTVLGAAAGAGGDYKDDDDKG
AAAHHHHHH

T2C-0001 (2-519), FLAG-His tag (494-519)

[Figure 59]

SEQ ID NO: 45 Amino acid sequence of T2C-0003

GQVQLVQSGAEVKKPGASVKVSCKASGYTFTTAGMQWVRQAPGQGLEWMGW
INTHSGVPKYAEDFKGRVTISADTSTSTAYLQLSSLKSEDTAVYYCARSGF
GSSYWYFDVWGQGTLVTVSSGGGGSGGGGSGGGGSDIQMTQSPSSLSASVG
DRVTITCKASQDVSTAVAWYQQKPGKAPKLLIYSASYRYTGVPSRFSGSGS
GTDFTLTISSLQPEDFAVYYCQQHYITPLTFGQGTKLEIKRTGGGGSEVQL
VESGGGLVQPGGSLKLSCAASGFTFNKYAMNWVRQAPGKGLEWVARIRSKY
NNYATYYADSVKDRFTISRDDSKNTAYLQMNNLKTEDTAVYYCVRHGNFGN
SYISYWAYWGQGTLVTVSSGGGGSGGGGSGGGGSQTVVTQEPSLTVSPGGT
VTLTCGSSTGAVTSGYYPNWVQQKPGQAPRGLIGGTKFLAPGTPARFSGSL
LGGKAALTLSGVQPEDEAEYYCALWYSNRWVFGGGTKLTVLGSGASAAAGS
GGDYKDDDDKGAAAHHHHHH

T2C-0003(2-530), FLAG-His tag (501-530)

[Figure 60]

SEQ ID NO: 47 Amino acid sequence of T2C-0005

GQVQLVQSGAEVKKPGASVKVSCKASGYTFTTAGMQWVRQAPGQGLEWMGW
INTHSGVPKYAEDFKGRVTISADTSTSTAYLQLSSLKSEDTAVYYCARSGF
GSSYWYFDVWGQGTLVTVSSGGGGSGGGGSGGGGSDIQMTQSPSSLSASVG
DRVTITCKASQDVSTAVAWYQQKPGKAPKLLIYSASYRYTGVPSRFSGSGS
GTDFTLTISSLQPEDFAVYYCQQHYITPLTFGQGTKLEIKRTGGGGSEVQL
VESGGGLVQPGGSLRLSCAASGVTFNYYGMSWIRQAPGKGLEWVASITNSG
GRIYYPDSVKGRFTISRENTQKTLYLQMNSLRAEDTAVYYCTLDGRDGWVA
YWGQGTLVTVSSGGGGSGGGGSGGGGSMAQAVLTQPSSVSGVPGQRVTISC
KRNTGNIGSNYVNWYQQLPGTAPKLLIYRDDKRPSGVPDRFSGSKSGTSAS
LAITGFQAEDEADYYCQSYSSGFIFGGGTKLTVLGAAAGAGGDYKDDDDKG
AAAHHHHHH

T2C-0005(2-519), FLAG-His tag (494-519)

[Figure 61]

SEQ ID NO: 49 Amino acid sequence of T2C-0006

GQVQLVQSGAEVKKPGASVKVSCKASGYTFTTAGMQWVRQAPGQGLEWMGW

INTHSGVPKYAEDFKGRVTISADTSTSTAYLQLSSLKSEDTAVYYCARSGF

GSSYWYFDVWGQGTLVTVSSGGGGSGGGGSGGGGSDIQMTQSPSSLSASVG

DRVTITCKASQDVSTAVAWYQQKPGKAPKLLIYSASYRYTGVPSRFSGSGS

GTDFTLTISSLQPEDFAVYYCQQHYITPLTFGQGTKLEIKRTGGGGSEVQL

VESGGGLVQPGGSLRLSCAASGVTFNYYGMSWIRQAPGKGLEWVASITNSG

GRIYYPDSVKGRFTISRENTQKTLYLQMNSLRAEDTAVYYCTLDGRDGWVA

YWGQGTLVTVSSGGGGSGGGGSGGGGSNFMLTQPSSVSGVPGQRVTISCTG

NTGNIGSNYVNWYQQLPGTAPKLLIYRDDKRPSGVPDRFSGSKSGTSASLA

ITGFQAEDEADYYCQSYSSGFIFGGGTKLTVLGAAAGAGGDYKDDDDKGAA

AHHHHHH

T2C-0006(2-517), FLAG-His tag (492-517)

[Figure 62]
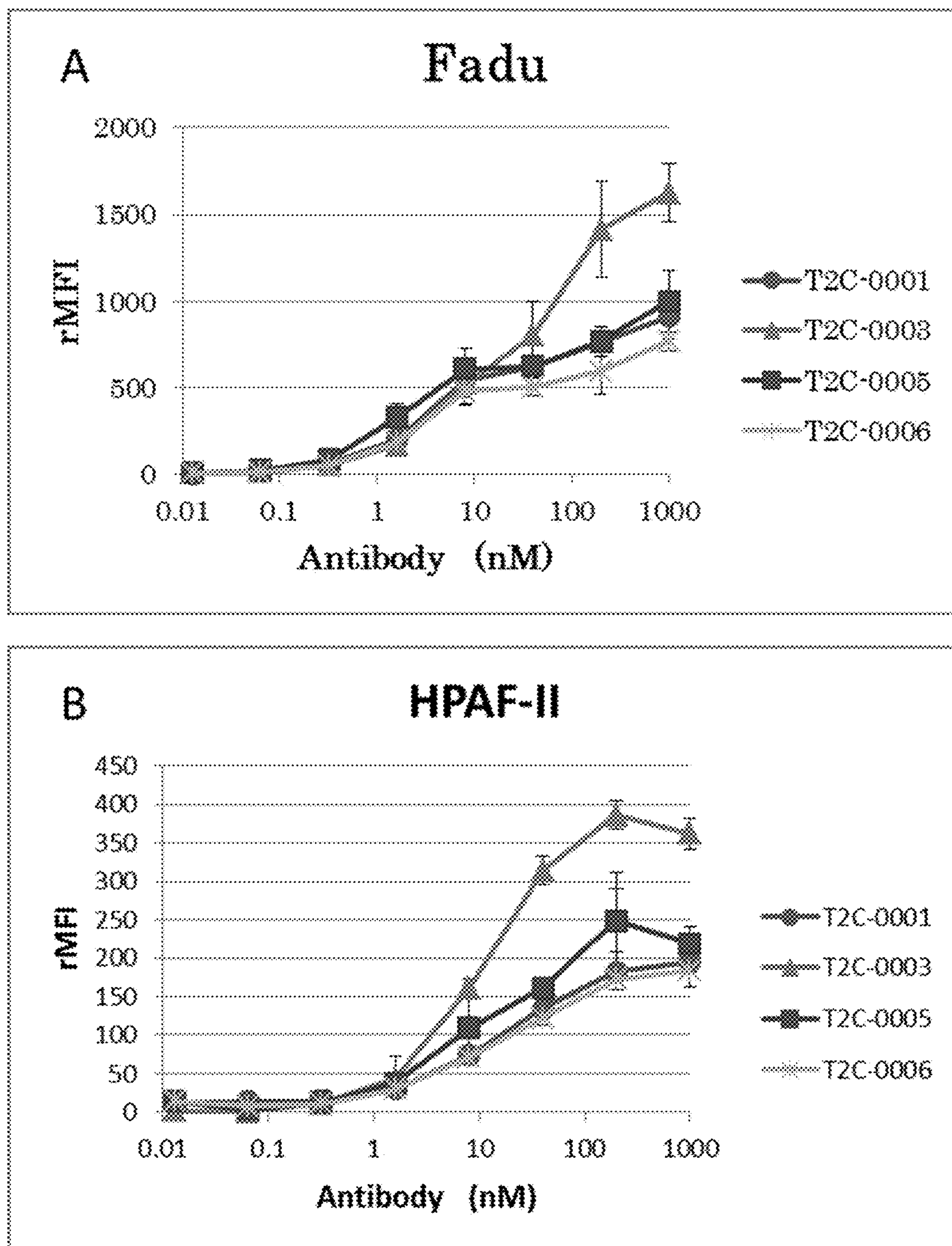

[Figure 63]
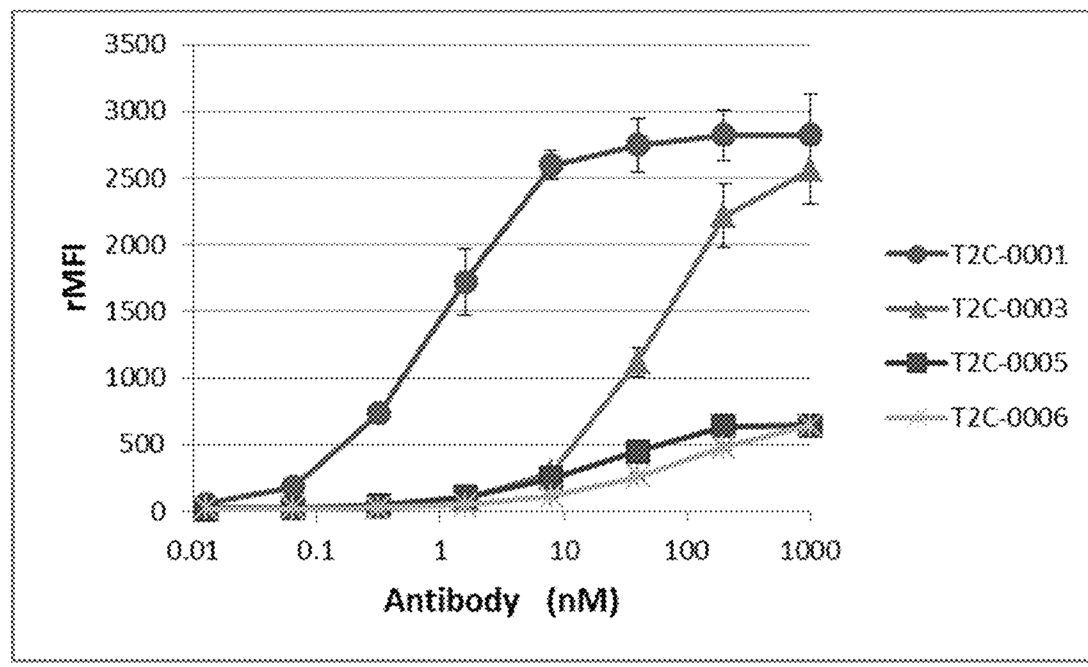
[Figure 64]
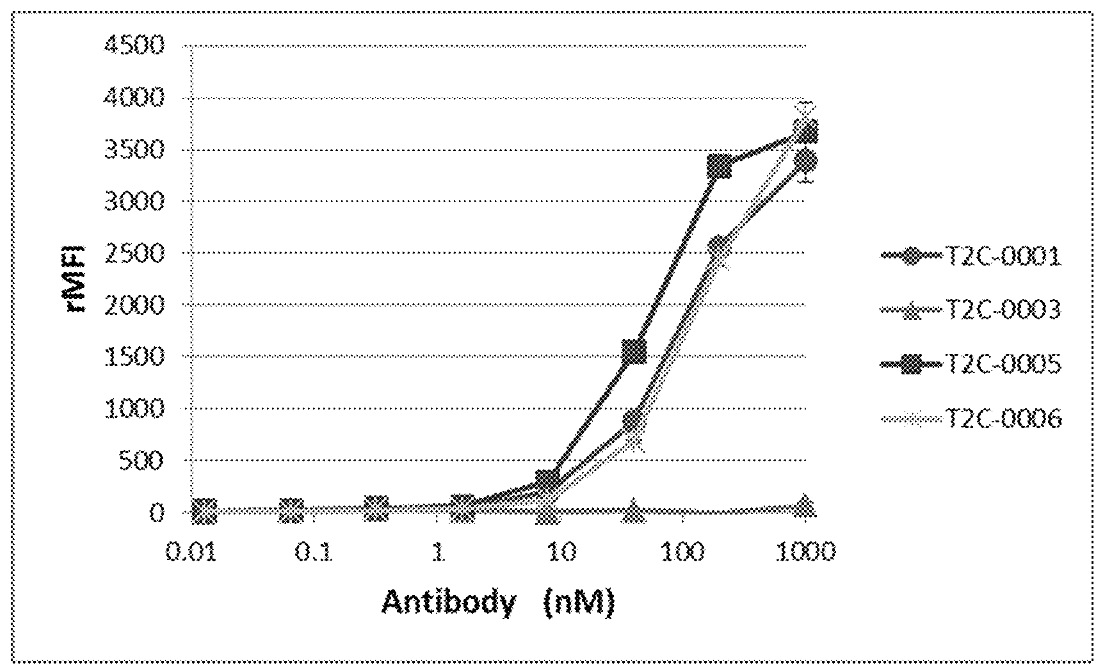

[Figure 65]
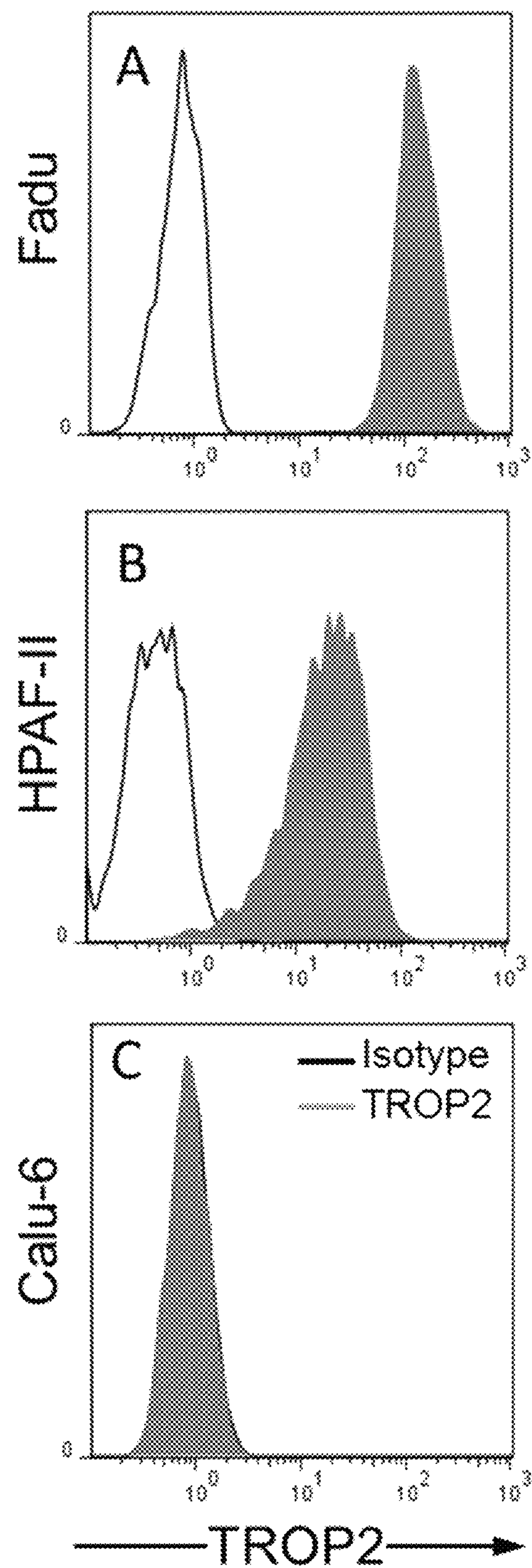

[Figure 66]
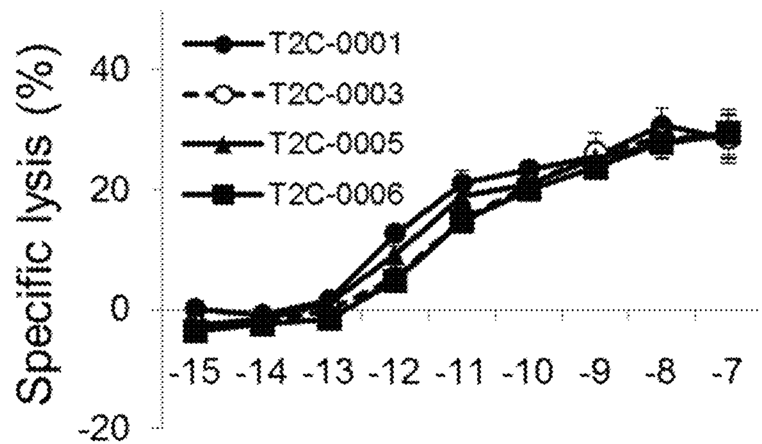
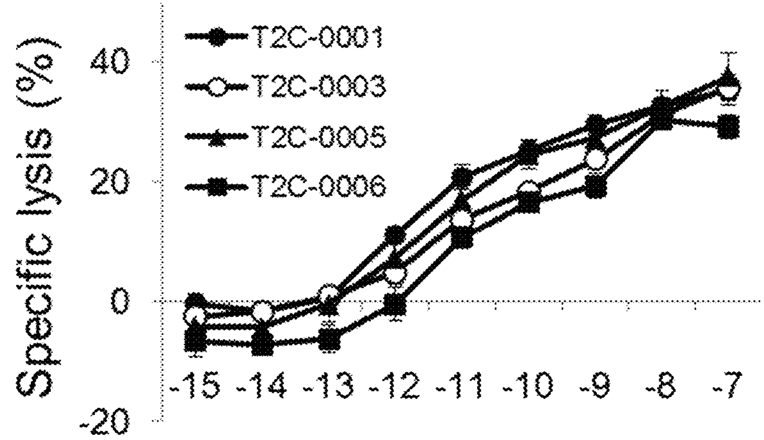
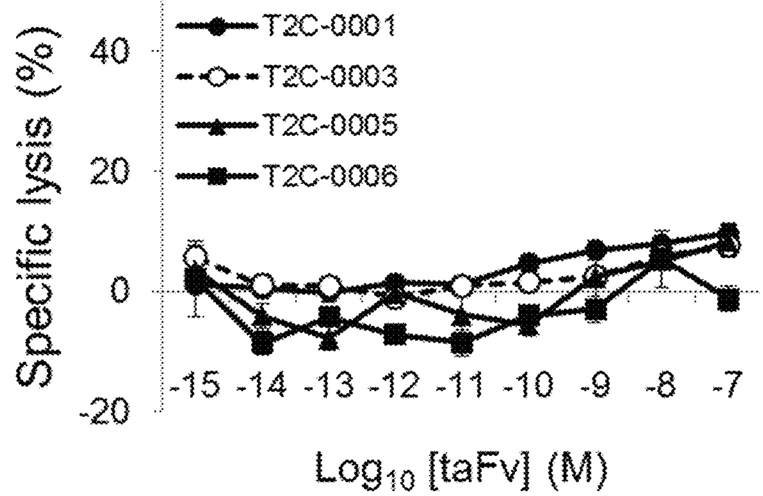

[Figure 67]

SEQ ID NO: 59 Nucleotide sequence encoding C3E-7078

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTAGGTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
AACTTTATGCTGACCCAGCCCCACAGTGTGTCAGAGAGCCCTGGCAAGACT
GTCACCATCTCTTGTAAAAGGAACACCGGAAATATTGGCAGTAACTACGTG
AATTGGTATCAGCAGCATGAAGGGTCTAGTCCAACCACAATCATCTACCGG
GACGATAAGAGACCCGACGGGGTGTCCGATCGATTCTCCGGATCTATCGAC
CGGTCAAGCAAGAGTGCTTCACTGACCATTAGCAATCTGAAAACAGAGGAC
GAAGCAGATTACTTTTGCCAGTCCTATTCCTCTGGCTTCATCTTTGGAGGC
GGGACTAAACTGACCGTGCTGGGCGCGGCCGCAGGTGCAGGTGGTGATTAC
AAAGATGATGACGATAAAGGTGCAGCGGCGCATCACCATCATCACCAC

Signal sequence (1-57), C3E-7078(58-864), FLAG-His tag (787-864)

[Figure 68]

SEQ ID NO: 60 Amino acid sequence of C3E-7078

GEVQLVESGGGLVQPGGSLRLSCAASGVTFNYYGMSWIRQAPGKGLEWVAS
ITRSGGRIYYPDSVKGRFTISRENTQKTLYLQMNSLRAEDTAVYYCTLDGR
DGWVAYWGQGTLVTVSSGGGGSGGGGSGGGGSNFMLTQPHSVSESPGKTVT
ISCKRNTGNIGSNYVNWYQQHEGSSPTTIIYRDDKRPDGVSDRFSGSIDRS
SKSASLTISNLKTEDEADYFCQSYSSGFIFGGGTKLTVLGAAAGAGGDYKD
DDDKGAAAHHHHHH

C3E-7078(1-269), FLAG-His tag (244-269)

[Figure 69]

SEQ ID NO: 61 Nucleotide sequence encoding C3E-7079

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTTCTTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
AACTTTATGCTGACCCAGCCCCACAGTGTGTCAGAGAGCCCTGGCAAGACT
GTCACCATCTCTTGTAAAAGGAACACCGGAAATATTGGCAGTAACTACGTG
AATTGGTATCAGCAGCATGAAGGGTCTAGTCCAACCACAATCATCTACCGG
GACGATAAGAGACCCGACGGGGTGTCCGATCGATTCTCCGGATCTATCGAC
CGGTCAAGCAAGAGTGCTTCACTGACCATTAGCAATCTGAAAACAGAGGAC
GAAGCAGATTACTTTTGCCAGTCCTATTCCTCTGGCTTCATCTTTGGAGGC
GGGACTAAACTGACCGTGCTGGGCGCGGCCGCAGGTGCAGGTGGTGATTAC
AAAGATGATGACGATAAAGGTGCAGCGGCGCATCACCATCATCACCAC

Signal sequence (1-57), C3E-7079(58-864), FLAG-His tag (787-864)

[Figure 70]

SEQ ID NO: 62 Amino acid sequence of C3E-7079

GEVQLVESGGGLVQPGGSLRLSCAASGVTFNYYGMSWIRQAPGKGLEWVAS
ITSSGGRIYYPDSVKGRFTISRENTQKTLYLQMNSLRAEDTAVYYCTLDGR
DGWVAYWGQGTLVTVSSGGGGSGGGGSGGGGSNFMLTQPHSVSESPGKTVT
ISCKRNTGNIGSNYVNWYQQHEGSSPTTIIYRDDKRPDGVSDRFSGSIDRS
SKSASLTISNLKTEDEADYFCQSYSSGFIFGGGTKLTVLGAAAGAGGDYKD
DDDKGAAAHHHHHH

C3E-7079(1-269), FLAG-His tag (244-269)

[Figure 71]

SEQ ID NO: 63 Nucleotide sequence encoding C3E-7085

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTAGGTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
AACTTTATGCTCACTCAGCCGTCCTCTGTTTCTGGCGTACCTGGCCAACGG
GTGACCATTAGCTGTACGGGTAATACCGGGAATATCGGGTCTAACTACGTG
AACTGGTATCAGCAGCTTCCAGGGACAGCTCCCAAGTTGCTGATCTATCGC
GACGACAAAAGACCCTCAGGGGTCCCTGACCGATTTAGTGGCAGCAAAAGC
GGTACTTCCGCTTCCCTGGCGATAACCGGCTTTCAGGCCGAAGATGAGGCA
GACTACTATTGCCAGTCATATTCCAGCGGCTTCATCTTCGGAGGCGGAACT
AAGCTGACAGTGTTGGGCGCGGCCGCAGGTGCAGGTGGTGATTACAAAGAT
GATGACGATAAAGGTGCAGCGGCGCATCACCATCATCACCAC

Signal sequence (1-57), C3E-7085(58-858), FLAG-His tag (787-858)

[Figure 72]

SEQ ID NO: 64 Amino acid sequence of C3E-7085

GEVQLVESGGGLVQPGGSLRLSCAASGVTFNYYGMSWIRQAPGKGLEWVAS
ITRSGGRIYYPDSVKGRFTISRENTQKTLYLQMNSLRAEDTAVYYCTLDGR
DGWVAYWGQGTLVTVSSGGGGSGGGGSGGGGSNFMLTQPSSVSGVPGQRVT
ISCTGNTGNIGSNYVNWYQQLPGTAPKLLIYRDDKRPSGVPDRFSGSKSGT
SASLAITGFQAEDEADYYCQSYSSGFIFGGGTKLTVLGAAAGAGGDYKDDD
DKGAAAHHHHHH

C3E-7085(1-267), FLAG-His tag (242-267)

[Figure 73]

SEQ ID NO: 65 Nucleotide sequence encoding C3E-7086

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTAGGTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
AACTTTATGCTGACCCAGCCCCACAGTGTGTCAGAGAGCCCTGGCAAGACT
GTCACCATCTCTTGTAAAAGGAACACCGGAAATATTGGCAGTAACTACGTG
AATTGGTATCAGCAGCATGAAGGGTCTAGTCCAACCACAATCATCTACCGG
GGCGATAAGAGACCCGACGGGGTGTCCGATCGATTCTCCGGATCTATCGAC
CGGTCAAGCAAGAGTGCTTCACTGACCATTAGCAATCTGAAAACAGAGGAC
GAAGCAGATTACTTTTGCCAGTCCTATTCCTCTGGCTTCATCTTTGGAGGC
GGGACTAAACTGACCGTGCTGGGCGCGGCCGCAGGTGCAGGTGGTGATTAC
AAAGATGATGACGATAAAGGTGCAGCGGCGCATCACCATCATCACCAC

Signal sequence (1-57), C3E-7086(58-864), FLAG-His tag (787-864)

[Figure 74]

SEQ ID NO: 66 Amino acid sequence of C3E-7086

GEVQLVESGGGLVQPGGSLRLSCAASGVTFNYYGMSWIRQAPGKGLEWVAS
ITRSGGRIYYPDSVKGRFTISRENTQKTLYLQMNSLRAEDTAVYYCTLDGR
DGWVAYWGQGTLVTVSSGGGGSGGGGSGGGGSNFMLTQPHSVSESPGKTVT
ISCKRNTGNIGSNYVNWYQQHEGSSPTTIIYRGDKRPDGVSDRFSGSIDRS
SKSASLTISNLKTEDEADYFCQSYSSGFIFGGGTKLTVLGAAAGAGGDYKD
DDDKGAAAHHHHHH

C3E-7086(1-269), FLAG-His tag (244-269)

[Figure 75]

SEQ ID NO: 67 Nucleotide sequence encoding C3E-7087

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTAGGTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
AACTTTATGCTGACCCAGCCCCACAGTGTGTCAGAGAGCCCTGGCAAGACT
GTCACCATCTCTTGTAAAAGGAACACCGGAAATATTGGCAGTAACTACGTG
AATTGGTATCAGCAGCATGAAGGGTCTAGTCCAACCACAATCATCTACCGG
CAGGATAAGAGACCCGACGGGGTGTCCGATCGATTCTCCGGATCTATCGAC
CGGTCAAGCAAGAGTGCTTCACTGACCATTAGCAATCTGAAAACAGAGGAC
GAAGCAGATTACTTTTGCCAGTCCTATTCCTCTGGCTTCATCTTTGGAGGC
GGGACTAAACTGACCGTGCTGGGCGCGGCCGCAGGTGCAGGTGGTGATTAC
AAAGATGATGACGATAAAGGTGCAGCGGCGCATCACCATCATCACCAC

Signal sequence (1-57), C3E-7087(58-864), FLAG-His tag (787-864)

[Figure 76]

SEQ ID NO: 68 Amino acid sequence of C3E-7087

GEVQLVESGGGLVQPGGSLRLSCAASGVTFNYYGMSWIRQAPGKGLEWVAS
ITRSGGRIYYPDSVKGRFTISRENTQKTLYLQMNSLRAEDTAVYYCTLDGR
DGWVAYWGQGTLVTVSSGGGGSGGGGSGGGGSNFMLTQPHSVSESPGKTVT
ISCKRNTGNIGSNYVNWYQQHEGSSPTTIIYRQDKRPDGVSDRFSGSIDRS
SKSASLTISNLKTEDEADYFCQSYSSGFIFGGGTKLTVLGAAAGAGGDYKD
DDDKGAAAHHHHHH

C3E-7087(1-269), FLAG-His tag (244-269)

[Figure 77]

SEQ ID NO: 69 Nucleotide sequence encoding C3E-7088

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTAGGTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
AACTTTATGCTGACCCAGCCCCACAGTGTGTCAGAGAGCCCTGGCAAGACT
GTCACCATCTCTTGTAAAAGGAACACCGGAAATATTGGCAGTAACTACGTG
AATTGGTATCAGCAGCATGAAGGGTCTAGTCCAACCACAATCATCTACCGG
AACGATAAGAGACCCGACGGGGTGTCCGATCGATTCTCCGGATCTATCGAC
CGGTCAAGCAAGAGTGCTTCACTGACCATTAGCAATCTGAAAACAGAGGAC
GAAGCAGATTACTTTTGCCAGTCCTATTCCTCTGGCTTCATCTTTGGAGGC
GGGACTAAACTGACCGTGCTGGGCGCGGCCGCAGGTGCAGGTGGTGATTAC
AAAGATGATGACGATAAAGGTGCAGCGGCGCATCACCATCATCACCAC

Signal sequence (1-57), C3E-7088(58-864), FLAG-His tag (787-864)

[Figure 78]

SEQ ID NO: 70 Amino acid sequence of C3E-7088

GEVQLVESGGGLVQPGGSLRLSCAASGVTFNYYGMSWIRQAPGKGLEWVAS
ITRSGGRIYYPDSVKGRFTISRENTQKTLYLQMNSLRAEDTAVYYCTLDGR
DGWVAYWGQGTLVTVSSGGGGSGGGGSGGGGSNFMLTQPHSVSESPGKTVT
ISCKRNTGNIGSNYVNWYQQHEGSSPTTIIYRNDKRPDGVSDRFSGSIDRS
SKSASLTISNLKTEDEADYFCQSYSSGFIFGGGTKLTVLGAAAGAGGDYKD
DDDKGAAAHHHHHH

C3E-7088(1-269), FLAG-His tag (244-269)

[Figure 79]

SEQ ID NO: 71 Nucleotide sequence encoding C3E-7089

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTAGGTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
AACTTTATGCTGACCCAGCCCCACAGTGTGTCAGAGAGCCCTGGCAAGACT
GTCACCATCTCTTGTAAAAGGAACACCGGAAATATTGGCAGTAACTACGTG
AATTGGTATCAGCAGCATGAAGGGTCTAGTCCAACCACAATCATCTACCGG
AGCGATAAGAGACCCGACGGGGTGTCCGATCGATTCTCCGGATCTATCGAC
CGGTCAAGCAAGAGTGCTTCACTGACCATTAGCAATCTGAAAACAGAGGAC
GAAGCAGATTACTTTTGCCAGTCCTATTCCTCTGGCTTCATCTTTGGAGGC
GGGACTAAACTGACCGTGCTGGGCGCGGCCGCAGGTGCAGGTGGTGATTAC
AAAGATGATGACGATAAAGGTGCAGCGGCGCATCACCATCATCACCAC

Signal sequence (1-57), C3E-7089(58-864), FLAG-His tag (787-864)

[Figure 80]

SEQ ID NO: 72 Amino acid sequence of C3E-7089

GEVQLVESGGGLVQPGGSLRLSCAASGVTFNYYGMSWIRQAPGKGLEWVAS
ITRSGGRIYYPDSVKGRFTISRENTQKTLYLQMNSLRAEDTAVYYCTLDGR
DGWVAYWGQGTLVTVSSGGGGSGGGGSGGGGSNFMLTQPHSVSESPGKTVT
ISCKRNTGNIGSNYVNWYQQHEGSSPTTIIYRSDKRPDGVSDRFSGSIDRS
SKSASLTISNLKTEDEADYFCQSYSSGFIFGGGTKLTVLGAAAGAGGDYKD
DDDKGAAAHHHHHH

C3E-7089(1-269), FLAG-His tag (244-269)

[Figure 81]

SEQ ID NO: 73 Nucleotide sequence encoding C3E-7090

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTAGGTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
AACTTTATGCTGACCCAGCCCCACAGTGTGTCAGAGAGCCCTGGCAAGACT
GTCACCATCTCTTGTAAAAGGAACACCGGAAATATTGGCAGTAACTACGTG
AATTGGTATCAGCAGCATGAAGGGTCTAGTCCAACCACAATCATCTACCGG
GCCGATAAGAGACCCGACGGGGTGTCCGATCGATTCTCCGGATCTATCGAC
CGGTCAAGCAAGAGTGCTTCACTGACCATTAGCAATCTGAAAACAGAGGAC
GAAGCAGATTACTTTTGCCAGTCCTATTCCTCTGGCTTCATCTTTGGAGGC
GGGACTAAACTGACCGTGCTGGGCGCGGCCGCAGGTGCAGGTGGTGATTAC
AAAGATGATGACGATAAAGGTGCAGCGGCGCATCACCATCATCACCAC

Signal sequence (1-57), C3E-7090(58-864), FLAG-His tag (787-864)

[Figure 82]

SEQ ID NO: 74 Amino acid sequence of C3E-7090

GEVQLVESGGGLVQPGGSLRLSCAASGVTFNYYGMSWIRQAPGKGLEWVAS
ITRSGGRIYYPDSVKGRFTISRENTQKTLYLQMNSLRAEDTAVYYCTLDGR
DGWVAYWGQGTLVTVSSGGGGSGGGGSGGGGSNFMLTQPHSVSESPGKTVT
ISCKRNTGNIGSNYVNWYQQHEGSSPTTIIYRADKRPDGVSDRFSGSIDRS
SKSASLTISNLKTEDEADYFCQSYSSGFIFGGGTKLTVLGAAAGAGGDYKD
DDDKGAAAHHHHHH

C3E-7090(1-269), FLAG-His tag (244-269)

[Figure 83]

SEQ ID NO: 75 Nucleotide sequence encoding C3E-7091

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTTCTTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
AACTTTATGCTGACCCAGCCCCACAGTGTGTCAGAGAGCCCTGGCAAGACT
GTCACCATCTCTTGTAAAAGGAACACCGGAAATATTGGCAGTAACTACGTG
AATTGGTATCAGCAGCATGAAGGGTCTAGTCCAACCACAATCATCTACCGG
GGCGATAAGAGACCCGACGGGGTGTCCGATCGATTCTCCGGATCTATCGAC
CGGTCAAGCAAGAGTGCTTCACTGACCATTAGCAATCTGAAAACAGAGGAC
GAAGCAGATTACTTTTGCCAGTCCTATTCCTCTGGCTTCATCTTTGGAGGC
GGGACTAAACTGACCGTGCTGGGCGCGGCCGCAGGTGCAGGTGGTGATTAC
AAAGATGATGACGATAAAGGTGCAGCGGCGCATCACCATCATCACCAC

Signal sequence (1-57), C3E-7091(58-864), FLAG-His tag (787-864)

[Figure 84]

SEQ ID NO: 76 Amino acid sequence of C3E-7091

GEVQLVESGGGLVQPGGSLRLSCAASGVTFNYYGMSWIRQAPGKGLEWVAS
ITSSGGRIYYPDSVKGRFTISRENTQKTLYLQMNSLRAEDTAVYYCTLDGR
DGWVAYWGQGTLVTVSSGGGGSGGGGSGGGGSNFMLTQPHSVSESPGKTVT
ISCKRNTGNIGSNYVNWYQQHEGSSPTTIIYRGDKRPDGVSDRFSGSIDRS
SKSASLTISNLKTEDEADYFCQSYSSGFIFGGGTKLTVLGAAAGAGGDYKD
DDDKGAAAHHHHHH

C3E-7091(1-269), FLAG-His tag (244-269)

[Figure 85]

SEQ ID NO: 77 Nucleotide sequence encoding C3E-7092

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTTCTTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
AACTTTATGCTGACCCAGCCCCACAGTGTGTCAGAGAGCCCTGGCAAGACT
GTCACCATCTCTTGTAAAAGGAACACCGGAAATATTGGCAGTAACTACGTG
AATTGGTATCAGCAGCATGAAGGGTCTAGTCCAACCACAATCATCTACCGG
CAGGATAAGAGACCCGACGGGGTGTCCGATCGATTCTCCGGATCTATCGAC
CGGTCAAGCAAGAGTGCTTCACTGACCATTAGCAATCTGAAAACAGAGGAC
GAAGCAGATTACTTTTGCCAGTCCTATTCCTCTGGCTTCATCTTTGGAGGC
GGGACTAAACTGACCGTGCTGGGCGCGGCCGCAGGTGCAGGTGGTGATTAC
AAAGATGATGACGATAAAGGTGCAGCGGCGCATCACCATCATCACCAC

Signal sequence (1-57), C3E-7092(58-864), FLAG-His tag (787-864)

[Figure 86]

SEQ ID NO: 78 Amino acid sequence of C3E-7092

GEVQLVESGGGLVQPGGSLRLSCAASGVTFNYYGMSWIRQAPGKGLEWVAS
ITSSGGRIYYPDSVKGRFTISRENTQKTLYLQMNSLRAEDTAVYYCTLDGR
DGWVAYWGQGTLVTVSSGGGGSGGGGSGGGGSNFMLTQPHSVSESPGKTVT
ISCKRNTGNIGSNYVNWYQQHEGSSPTTIIYRQDKRPDGVSDRFSGSIDRS
SKSASLTISNLKTEDEADYFCQSYSSGFIFGGGTKLTVLGAAAGAGGDYKD
DDDKGAAAHHHHHH

C3E-7092(1-269), FLAG-His tag (244-269)

[Figure 87]

SEQ ID NO: 79 Nucleotide sequence encoding C3E-7093

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTTCTTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
AACTTTATGCTGACCCAGCCCCACAGTGTGTCAGAGAGCCCTGGCAAGACT
GTCACCATCTCTTGTAAAAGGAACACCGGAAATATTGGCAGTAACTACGTG
AATTGGTATCAGCAGCATGAAGGGTCTAGTCCAACCACAATCATCTACCGG
AACGATAAGAGACCCGACGGGGTGTCCGATCGATTCTCCGGATCTATCGAC
CGGTCAAGCAAGAGTGCTTCACTGACCATTAGCAATCTGAAAACAGAGGAC
GAAGCAGATTACTTTTGCCAGTCCTATTCCTCTGGCTTCATCTTTGGAGGC
GGGACTAAACTGACCGTGCTGGGCGCGGCCGCAGGTGCAGGTGGTGATTAC
AAAGATGATGACGATAAAGGTGCAGCGGCGCATCACCATCATCACCAC

Signal sequence (1-57), C3E-7093(58-864), FLAG-His tag (787-864)

[Figure 88]

SEQ ID NO: 80 Amino acid sequence of C3E-7093

GEVQLVESGGGLVQPGGSLRLSCAASGVTFNYYGMSWIRQAPGKGLEWVAS
ITSSGGRIYYPDSVKGRFTISRENTQKTLYLQMNSLRAEDTAVYYCTLDGR
DGWVAYWGQGTLVTVSSGGGGSGGGGSGGGGSNFMLTQPHSVSESPGKTVT
ISCKRNTGNIGSNYVNWYQQHEGSSPTTIIYRNDKRPDGVSDRFSGSIDRS
SKSASLTISNLKTEDEADYFCQSYSSGFIFGGGTKLTVLGAAAGAGGDYKD
DDDKGAAAHHHHHH

C3E-7093(1-269), FLAG-His tag (244-269)

[Figure 89]

SEQ ID NO: 81Nucleotide sequence encoding C3E-7094

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTTCTTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
AACTTTATGCTGACCCAGCCCCACAGTGTGTCAGAGAGCCCTGGCAAGACT
GTCACCATCTCTTGTAAAAGGAACACCGGAAATATTGGCAGTAACTACGTG
AATTGGTATCAGCAGCATGAAGGGTCTAGTCCAACCACAATCATCTACCGG
AGCGATAAGAGACCCGACGGGGTGTCCGATCGATTCTCCGGATCTATCGAC
CGGTCAAGCAAGAGTGCTTCACTGACCATTAGCAATCTGAAAACAGAGGAC
GAAGCAGATTACTTTTGCCAGTCCTATTCCTCTGGCTTCATCTTTGGAGGC
GGGACTAAACTGACCGTGCTGGGCGCGGCCGCAGGTGCAGGTGGTGATTAC
AAAGATGATGACGATAAAGGTGCAGCGGCGCATCACCATCATCACCAC

Signal sequence (1-57), C3E-7094(58-864), FLAG-His tag (787-864)

[Figure 90]

SEQ ID NO: 82 Amino acid sequence of C3E-7094

GEVQLVESGGGLVQPGGSLRLSCAASGVTFNYYGMSWIRQAPGKGLEWVAS
ITSSGGRIYYPDSVKGRFTISRENTQKTLYLQMNSLRAEDTAVYYCTLDGR
DGWVAYWGQGTLVTVSSGGGGSGGGGSGGGGSNFMLTQPHSVSESPGKTVT
ISCKRNTGNIGSNYVNWYQQHEGSSPTTIIYRSDKRPDGVSDRFSGSIDRS
SKSASLTISNLKTEDEADYFCQSYSSGFIFGGGTKLTVLGAAAGAGGDYKD
DDDKGAAAHHHHHH

C3E-7094(1-269), FLAG-His tag (244-269)

[Figure 91]

SEQ ID NO: 83 Nucleotide sequence encoding C3E-7095

ATGAAACACCTGTGGTTCTTCCTCCTGCTGGTGGCAGCTCCCAGATGGGTG
CTGAGCGGAGAAGTGCAGCTGGTGGAATCCGGGGGGGGCCTGGTGCAGCCT
GGGGGGAGCCTGAGACTGAGTTGTGCCGCCTCTGGGGTGACATTTAACTAC
TATGGCATGTCTTGGATCCGCCAGGCACCTGGAAAGGGCCTGGAGTGGGTG
GCCAGCATCACTTCTTCCGGCGGGCGAATCTACTATCCCGACAGCGTCAAG
GGCAGGTTCACAATTTCCCGCGAGAACACACAGAAAACTCTGTACCTGCAG
ATGAATAGCCTGAGAGCCGAAGATACAGCTGTGTACTATTGCACTCTGGAC
GGCAGGGATGGGTGGGTCGCCTATTGGGGGCAGGGAACCCTGGTGACAGTC
AGCTCCGGAGGAGGAGGATCTGGCGGAGGAGGCAGTGGGGGAGGCGGGTCA
AACTTTATGCTGACCCAGCCCCACAGTGTGTCAGAGAGCCCTGGCAAGACT
GTCACCATCTCTTGTAAAAGGAACACCGGAAATATTGGCAGTAACTACGTG
AATTGGTATCAGCAGCATGAAGGGTCTAGTCCAACCACAATCATCTACCGG
GCCGATAAGAGACCCGACGGGGTGTCCGATCGATTCTCCGGATCTATCGAC
CGGTCAAGCAAGAGTGCTTCACTGACCATTAGCAATCTGAAAACAGAGGAC
GAAGCAGATTACTTTTGCCAGTCCTATTCCTCTGGCTTCATCTTTGGAGGC
GGGACTAAACTGACCGTGCTGGGCGCGGCCGCAGGTGCAGGTGGTGATTAC
AAAGATGATGACGATAAAGGTGCAGCGGCGCATCACCATCATCACCAC

Signal sequence (1-57), C3E-7095(58-864), FLAG-His tag (787-864)

[Figure 92]

SEQ ID NO: 84 Amino acid sequence of C3E-7095

GEVQLVESGGGLVQPGGSLRLSCAASGVTFNYYGMSWIRQAPGKGLE
WVASITSSGGRIYYPDSVKGRFTISRENTQKTLYLQMNSLRAEDTAV
YYCTLDGRDGWVAYWGQGTLVTVSSGGGGSGGGGSGGGGSNFMLTQP
HSVSESPGKTVTISCKRNTGNIGSNYVNWYQQHEGSSPTTIIYRADK
RPDGVSDRFSGSIDRSSKSASLTISNLKTEDEADYFCQSYSSGFIFG
GGTKLTVLGAAAGAGGDYKDDDDKGAAAHHHHHH

C3E-7095(1-269), FLAG-His tag (244-269)

[Figure 93]

SEQ ID NO: 85 HN53R Fw

5’-GTGGCCAGCATCACTAGGTCCGGCGGGCGAATC-3’

[Figure 94]

SEQ ID NO: 86 HN53R Rv

5’-GATTCGCCCGCCGGACCTAGTGATGCTGGCCAC-3’

[Figure 95]

SEQ ID NO: 87 HN53S Rw

5’-GTGGCCAGCATCACTTCTTCCGGCGGGCGAATC-3’

[Figure 96]

SEQ ID NO: 88 HN53S Rv

5’－GATTCGCCCGCCGGAAGAAGTGATGCTGGCCAC-3’

[Figure 97]
SEQ ID NO:89 Nucleotide sequence of AXC-0001

ATGAAACACCTGTGGTTCTTCCTCCTGCTGGTGGCAGCTCCCAGATG
GGTGCTGAGCGGAGAAGTGCAGCTGCAGGAATCTGGCCCTGGCCTCG
TGAAGCCTAGCCAGACCCTGAGCCTGACCTGTACCGTGTCCGGCTAC
AGCATCACCAGCAACTACTGGGGCTGGATCAGAAAGTTCCCCGGCAA
CAAGATGGAATGGATCGGCCACATCACCAACAGCGGCAACACCACCT
ACAACCCCAGCCTGAAGTCCCGGATCAGCATCAGCCGGGACACCAGC
AAGAACCAGTTCTCCCTGAAGCTGTCCAGCGTGACCCCTGCCGATAC
CGCCGTGTACTACTGTGCCAAGGGCGCCTTCGATTACTGGGGCCAGG
GAACCCTCGTGACCGTGTCTAGCGGAGGCGGAGGATCTGGCGGCGGA
GGAAGTGGCGGAGGGGGATCTGATATCCAGATGACCCAGAGCCCCAG
CAGCCTGTCTGCCAGCGTGGGCGACAGAGTGACCATCACCTGTAGAG
CCAGCCAGGACATCGGCAACTACCTGAGCTGGTTCCAGCAGAAAGTG
GGCAAGTCCCCCAGACGGATGATCTACGGCGCCATCAAGCTGGCCGT
GGGCGTGCCAAGCAGATTCAGCGGCAGCAGAAGCGGCAGCGACTACA
CCCTGACCATCAGCTCCCTGCAGCCCGAGGACTTCGCCATCTACTAC
TGCCTGCAGTACATCCAGTTCCCTCTGACCTTCGGCAGCGGCACCAA
GCTGGAAATCAAGAGAACCGGGGGAGGCGGTTCAGAAGTGCAGCTGG
TGGAATCCGGGGGGGGCCTGGTGCAGCCTGGGGGGAGCCTGAGACTG
AGTTGTGCCGCCTCTGGGGTGACATTTAACTACTATGGCATGTCTTG
GATCCGCCAGGCACCTGGAAAGGGCCTGGAGTGGGTGGCCAGCATCA
CTAATTCCGGCGGGCGAATCTACTATCCCGACAGCGTCAAGGGCAGG
TTCACAATTTCCCGCGAGAACACACAGAAAACTCTGTACCTGCAGAT
GAATAGCCTGAGAGCCGAAGATACAGCTGTGTACTATTGCACTCTGG
ACGGCAGGGATGGGTGGGTCGCCTATTGGGGGCAGGGAACCCTGGTG
ACAGTCAGCTCCGGAGGAGGAGGATCTGGCGGAGGAGGCAGTGGGGG
AGGCGGGTCAAACTTTATGCTGACCCAGCCCCACAGTGTGTCAGAGA
GCCCTGGCAAGACTGTCACCATCTCTTGTAAAAGGAACACCGGAAAT
ATTGGCAGTAACTACGTGAATTGGTATCAGCAGCATGAAGGGTCTAG
TCCAACCACAATCATCTACCGGGACGATAAGAGACCCGACGGGGTGT
CCGATCGATTCTCCGGATCTATCGACCGGTCAAGCAAGAGTGCTTCA
CTGACCATTAGCAATCTGAAAACAGAGGACGAAGCAGATTACTTTTG
CCAGTCCTATTCCTCTGGCTTCATCTTTGGAGGCGGGACTAAACTGA
CCGTGCTGGGCGCGGCCGCAGGTGCAGGTGGTGATTACAAAGATGAT
GACGATAAAGGTGCAGCGGCGCATCACCATCATCACCAC

Signal sequence (1-57), AXL-0001(58-1512), FLAG-His tag (1513-1590)

[Figure 98]

SEQ ID NO: 25 Amino acid sequence of AXC-0001

GEVQLQESGPGLVKPSQTLSLTCTVSGYSITSNYWGWIRKFPGNKMEWIGH
ITNSGNTTYNPSLKSRISISRDTSKNQFSLKLSSVTPADTAVYYCAKGAFD
YWGQGTLVTVSSGGGGSGGGGSGGGGSDIQMTQSPSSLSASVGDRVTITCR
ASQDIGNYLSWFQQKVGKSPRRMIYGAIKLAVGVPSRFSGSRSGSDYTLTI
SSLQPEDFAIYYCLQYIQFPLTFGSGTKLEIKRTGGGGSEVQLVESGGGLV
QPGGSLRLSCAASGVTFNYYGMSWIRQAPGKGLEWVASITNSGGRIYYPDS
VKGRFTISRENTQKTLYLQMNSLRAEDTAVYYCTLDGRDGWVAYWGQGTLV
TVSSGGGGSGGGGSGGGGSNFMLTQPHSVSESPGKTVTISCKRNTGNIGSN
YVNWYQQHEGSSPTTIIYRDDKRPDGVSDRFSGSIDRSSKSASLTISNLKT
EDEADYFCQSYSSGFIFGGGTKLTVLGAAAGAGGDYKDDDDKGAAAHHHHH
H

AXC-0001(1-511), FLAG-His tag (486-511)

[Figure 99]

SEQ ID NO: 91 Nucleotide sequence of AXC-0002

ATGAAACACCTGTGGTTCTTCCTCCTGCTGGTGGCAGCTCCCAGATG
GGTGCTGAGCGGAGAAGTGCAGCTGCAGGAATCTGGCCCTGGCCTCG
TGAAGCCTAGCCAGACCCTGAGCCTGACCTGTACCGTGTCCGGCTAC
AGCATCACCAGCAACTACTGGGGCTGGATCAGAAAGTTCCCCGGCAA
CAAGATGGAATGGATCGGCCACATCACCAACAGCGGCAACACCACCT
ACAACCCCAGCCTGAAGTCCCGGATCAGCATCAGCCGGGACACCAGC
AAGAACCAGTTCTCCCTGAAGCTGTCCAGCGTGACCCCTGCCGATAC
CGCCGTGTACTACTGTGCCAAGGGCGCCTTCGATTACTGGGGCCAGG
GAACCCTCGTGACCGTGTCTAGCGGAGGCGGAGGATCTGGCGGCGGA
GGAAGTGGCGGAGGGGGATCTGATATCCAGATGACCCAGAGCCCCAG
CAGCCTGTCTGCCAGCGTGGGCGACAGAGTGACCATCACCTGTAGAG
CCAGCCAGGACATCGGCAACTACCTGAGCTGGTTCCAGCAGAAAGTG
GGCAAGTCCCCCAGACGGATGATCTACGGCGCCATCAAGCTGGCCGT
GGGCGTGCCAAGCAGATTCAGCGGCAGCAGAAGCGGCAGCGACTACA
CCCTGACCATCAGCTCCCTGCAGCCCGAGGACTTCGCCATCTACTAC
TGCCTGCAGTACATCCAGTTCCCTCTGACCTTCGGCAGCGGCACCAA
GCTGGAAATCAAGAGAACCGGGGGAGGCGGTTCAGAAGTGCAGCTGG
TGGAATCCGGGGGGGGCCTGGTGCAGCCTGGGGGGAGCCTGAGACTG
AGTTGTGCCGCCTCTGGGGTGACATTTAACTACTATGGCATGTCTTG
GATCCGCCAGGCACCTGGAAAGGGCCTGGAGTGGGTGGCCAGCATCA
CTAATTCCGGCGGGCGAATCTACTATCCCGACAGCGTCAAGGGCAGG
TTCACAATTTCCCGCGAGAACACACAGAAAACTCTGTACCTGCAGAT
GAATAGCCTGAGAGCCGAAGATACAGCTGTGTACTATTGCACTCTGG
ACGGCAGGGATGGGTGGGTCGCCTATTGGGGGCAGGGAACCCTGGTG
ACAGTCAGCTCCGGAGGAGGAGGATCTGGCGGAGGAGGCAGTGGGGG
AGGCGGGTCAAACTTTATGCTCACTCAGCCGTCCTCTGTTTCTGGCG
TACCTGGCCAACGGGTGACCATTAGCTGTACGGGTAATACCGGGAAT
ATCGGGTCTAACTACGTGAACTGGTATCAGCAGCTTCCAGGGACAGC
TCCCAAGTTGCTGATCTATCGCGACGACAAAAGACCCTCAGGGGTCC
CTGACCGATTTAGTGGCAGCAAAAGCGGTACTTCCGCTTCCCTGGCG
ATAACCGGCTTTCAGGCCGAAGATGAGGCAGACTACTATTGCCAGTC
ATATTCCAGCGGCTTCATCTTCGGAGGCGGAACTAAGCTGACAGTGT
TGGGCGCGGCCGCAGGTGCAGGTGGTGATTACAAAGATGATGACGAT
AAAGGTGCAGCGGCGCATCACCATCATCACCAC

Signal sequence (1-57), AXL-0002(58-1506), FLAG-His tag (1507-1584)

[Figure 100]

SEQ ID NO: 92 Amino acid sequence of AXC-0002

GEVQLQESGPGLVKPSQTLSLTCTVSGYSITSNYWGWIRKFPGNKMEWIGH
ITNSGNTTYNPSLKSRISISRDTSKNQFSLKLSSVTPADTAVYYCAKGAFD
YWGQGTLVTVSSGGGGSGGGGSGGGGSDIQMTQSPSSLSASVGDRVTITCR
ASQDIGNYLSWFQQKVGKSPRRMIYGAIKLAVGVPSRFSGSRSGSDYTLTI
SSLQPEDFAIYYCLQYIQFPLTFGSGTKLEIKRTGGGGSEVQLVESGGGLV
QPGGSLRLSCAASGVTFNYYGMSWIRQAPGKGLEWVASITNSGGRIYYPDS
VKGRFTISRENTQKTLYLQMNSLRAEDTAVYYCTLDGRDGWVAYWGQGTLV
TVSSGGGGSGGGGSGGGGSNFMLTQPSSVSGVPGQRVTISCTGNTGNIGSN
YVNWYQQLPGTAPKLLIYRDDKRPSGVPDRFSGSKSGTSASLAITGFQAED
EADYYCQSYSSGFIFGGGTKLTVLGAAAGAGGDYKDDDDKGAAAHHHHHH

AXC-0002(1-509), FLAG-His tag (484-509)

[Figure 101]
SEQ ID NO: 93 Nucleotide sequence of MGC-0001

ATGAAACACCTGTGGTTCTTCCTCCTGCTGGTGGCAGCTCCCAGATG
GGTGCTGAGCGGACAGGTGCAGCTGGTGCAGTCTGGGGGAGGCTTGG
TCCAGCCTGGAGGGTCCCTGAGACTCTCCTGTGCAGCCTCTGGATTC
ACCTTCAGTGACTACGACATGGACTGGGTCCGCCAGGCTCCAGGGAA
GGGGCTGGAGTGGGTGGCAGTTATATCATCTGATGAAAACACTAAAT
ACTACGCAGACTCCGTGAAGGGCCGATTCACCATCTCCAGAGACAAT
TCCAAGAACACGCTGTATCTGCAAATGAACAGCCTGAGAGCCGAGGA
CACGGCTGTGTATTACTGTGCAACCTATACCAGCACCTGGTATGCCG
TTGACTCCTGGGGCCAGGGAACCCTGGTCACCGTCTCCTCAGGTGGA
GGCGGTTCAGGCGGAGGTGGCAGCGGCGGTGGCGGGAGTGATGTTGT
GATGACTCAGTCTCCACTCTCCCTGCCCGTCACCCCTGGAGAGCCGG
CCTCCATCTCCTGCAGGTCTAGTCAGAGCCTCCTGCATAGTAACGGA
AAGAACTATTTGGATTGGTACCTGCAGAAGCCAGGGCAGTCTCCACA
GCTCCTGATCTATTTGGGTTCTAATCGGGCCTCCGGGGTCCCTGACA
GGTTCAGTGGCAGTGGATCAGGCACAGATTTTACACTGAAGATCAGC
AGAGTGGAGGCTGAGGATGTTGGGGTTTATTACTGCATGCAAACTCT
TCAAACCCCCTACACTTTTGGCCAGGGGACCAAGGTGGAAATCAAAC
GTGGGGGAGGCGGTTCAGAAGTGCAGCTGGTGGAATCCGGGGGGGGC
CTGGTGCAGCCTGGGGGGAGCCTGAGACTGAGTTGTGCCGCCTCTGG
GGTGACATTTAACTACTATGGCATGTCTTGGATCCGCCAGGCACCTG
GAAAGGGCCTGGAGTGGGTGGCCAGCATCACTAATTCCGGCGGGCGA
ATCTACTATCCCGACAGCGTCAAGGGCAGGTTCACAATTTCCCGCGA
GAACACACAGAAAACTCTGTACCTGCAGATGAATAGCCTGAGAGCCG
AAGATACAGCTGTGTACTATTGCACTCTGGACGGCAGGGATGGGTGG
GTCGCCTATTGGGGGCAGGGAACCCTGGTGACAGTCAGCTCCGGAGG
AGGAGGATCTGGCGGAGGAGGCAGTGGGGGAGGCGGGTCAAACTTTA
TGCTGACCCAGCCCCACAGTGTGTCAGAGAGCCCTGGCAAGACTGTC
ACCATCTCTTGTAAAAGGAACACCGGAAATATTGGCAGTAACTACGT
GAATTGGTATCAGCAGCATGAAGGGTCTAGTCCAACCACAATCATCT
ACCGGGACGATAAGAGACCCGACGGGGTGTCCGATCGATTCTCCGGA
TCTATCGACCGGTCAAGCAAGAGTGCTTCACTGACCATTAGCAATCT
GAAAACAGAGGACGAAGCAGATTACTTTTGCCAGTCCTATTCCTCTG
GCTTCATCTTTGGAGGCGGGACTAAACTGACCGTGCTGGGCGCGGCC
GCAGGTGCAGGTGGTGATTACAAAGATGATGACGATAAAGGTGCAGC
GGCGCATCACCATCATCACCAC

Signal sequence (1-57), MGC-0001(58-1542), FLAG-His tag (1543-1620)

[Figure 102]

SEQ ID NO: 94 Amino acid sequence of MGC-0001

GQVQLVQSGGGLVQPGGSLRLSCAASGFTFSDYDMDWVRQAPGKGLEWVAV
ISSDENTKYYADSVKGRFTISRDNSKNTLYLQMNSLRAEDTAVYYCATYTS
TWYAVDSWGQGTLVTVSSGGGGSGGGGSGGGGSDVVMTQSPLSLPVTPGEP
ASISCRSSQSLLHSNGKNYLDWYLQKPGQSPQLLIYLGSNRASGVPDRFSG
SGSGTDFTLKISRVEAEDVGVYYCMQTLQTPYTFGQGTKVEIKRGGGGSEV
QLVESGGGLVQPGGSLRLSCAASGVTFNYYGMSWIRQAPGKGLEWVASITN
SGGRIYYPDSVKGRFTISRENTQKTLYLQMNSLRAEDTAVYYCTLDGRDGW
VAYWGQGTLVTVSSGGGGSGGGGSGGGGSNFMLTQPHSVSESPGKTVTISC
KRNTGNIGSNYVNWYQQHEGSSPTTIIYRDDKRPDGVSDRFSGSIDRSSKS
ASLTISNLKTEDEADYFCQSYSSGFIFGGGTKLTVLGAAAGAGGDYKDDDD
KGAAAHHHHHH

MGC-0001(1-521), FLAG-His tag (496-521)

[Figure 103]
SEQ ID NO: 95 Nucleotide sequence of MGC-0002

ATGAAACACCTGTGGTTCTTCCTCCTGCTGGTGGCAGCTCCCAGATG
GGTGCTGAGCGGACAGGTGCAGCTGGTGCAGTCTGGGGGAGGCTTGG
TCCAGCCTGGAGGGTCCCTGAGACTCTCCTGTGCAGCCTCTGGATTC
ACCTTCAGTGACTACGACATGGACTGGGTCCGCCAGGCTCCAGGGAA
GGGGCTGGAGTGGGTGGCAGTTATATCATCTGATGAAAACACTAAAT
ACTACGCAGACTCCGTGAAGGGCCGATTCACCATCTCCAGAGACAAT
TCCAAGAACACGCTGTATCTGCAAATGAACAGCCTGAGAGCCGAGGA
CACGGCTGTGTATTACTGTGCAACCTATACCAGCACCTGGTATGCCG
TTGACTCCTGGGGCCAGGGAACCCTGGTCACCGTCTCCTCAGGTGGA
GGCGGTTCAGGCGGAGGTGGCAGCGGCGGTGGCGGGAGTGATGTTGT
GATGACTCAGTCTCCACTCTCCCTGCCCGTCACCCCTGGAGAGCCGG
CCTCCATCTCCTGCAGGTCTAGTCAGAGCCTCCTGCATAGTAACGGA
AAGAACTATTTGGATTGGTACCTGCAGAAGCCAGGGCAGTCTCCACA
GCTCCTGATCTATTTGGGTTCTAATCGGGCCTCCGGGGTCCCTGACA
GGTTCAGTGGCAGTGGATCAGGCACAGATTTTACACTGAAGATCAGC
AGAGTGGAGGCTGAGGATGTTGGGGTTTATTACTGCATGCAAACTCT
TCAAACCCCCTACACTTTTGGCCAGGGGACCAAGGTGGAAATCAAAC
GTGGGGGAGGCGGTTCAGAAGTGCAGCTGGTGGAATCCGGGGGGGGC
CTGGTGCAGCCTGGGGGGAGCCTGAGACTGAGTTGTGCCGCCTCTGG
GGTGACATTTAACTACTATGGCATGTCTTGGATCCGCCAGGCACCTG
GAAAGGGCCTGGAGTGGGTGGCCAGCATCACTAATTCCGGCGGGCGA
ATCTACTATCCCGACAGCGTCAAGGGCAGGTTCACAATTTCCCGCGA
GAACACACAGAAAACTCTGTACCTGCAGATGAATAGCCTGAGAGCCG
AAGATACAGCTGTGTACTATTGCACTCTGGACGGCAGGGATGGGTGG
GTCGCCTATTGGGGGCAGGGAACCCTGGTGACAGTCAGCTCCGGAGG
AGGAGGATCTGGCGGAGGAGGCAGTGGGGGAGGCGGGTCAAACTTTA
TGCTCACTCAGCCGTCCTCTGTTTCTGGCGTACCTGGCCAACGGGTG
ACCATTAGCTGTACGGGTAATACCGGGAATATCGGGTCTAACTACGT
GAACTGGTATCAGCAGCTTCCAGGGACAGCTCCCAAGTTGCTGATCT
ATCGCGACGACAAAAGACCCTCAGGGGTCCCTGACCGATTTAGTGGC
AGCAAAAGCGGTACTTCCGCTTCCCTGGCGATAACCGGCTTTCAGGC
CGAAGATGAGGCAGACTACTATTGCCAGTCATATTCCAGCGGCTTCA
TCTTCGGAGGCGGAACTAAGCTGACAGTGTTGGGCGCGGCCGCAGGT
GCAGGTGGTGATTACAAAGATGATGACGATAAAGGTGCAGCGGCGCA
TCACCATCATCACCAC

Signal sequence (1-57), MGC-0002(58-1536), FLAG-His tag (1537-1614)

[Figure 104]

SEQ ID NO: 96 Amino acid sequence of MGC-0002

GQVQLVQSGGGLVQPGGSLRLSCAASGFTFSDYDMDWVRQAPGKGLEWVAV
ISSDENTKYYADSVKGRFTISRDNSKNTLYLQMNSLRAEDTAVYYCATYTS
TWYAVDSWGQGTLVTVSSGGGGSGGGGSGGGGSDVVMTQSPLSLPVTPGEP
ASISCRSSQSLLHSNGKNYLDWYLQKPGQSPQLLIYLGSNRASGVPDRFSG
SGSGTDFTLKISRVEAEDVGVYYCMQTLQTPYTFGQGTKVEIKRGGGGSEV
QLVESGGGLVQPGGSLRLSCAASGVTFNYYGMSWIRQAPGKGLEWVASITN
SGGRIYYPDSVKGRFTISRENTQKTLYLQMNSLRAEDTAVYYCTLDGRDGW
VAYWGQGTLVTVSSGGGGSGGGGSGGGGSNFMLTQPSSVSGVPGQRVTISC
TGNTGNIGSNYVNWYQQLPGTAPKLLIYRDDKRPSGVPDRFSGSKSGTSAS
LAITGFQAEDEADYYCQSYSSGFIFGGGTKLTVLGAAAGAGGDYKDDDDKG
AAAHHHHHH

MGC-0002(1-519), FLAG-His tag (494-519)

[Figure 105]

Primer list

LD52G Fw : CACAATCATCTACCGGGGCGATAAGAGACCCGAC

LD52Q Fw : ACAATCATCTACCGGCAGGATAAGAGACCCGAC

LD52N Fw : ACAATCATCTACCGGAACGATAAGAGACCCGAC

LD52S Fw : CACAATCATCTACCGGAGCGATAAGAGACCCGAC

LD52A Fw : ACAATCATCTACCGGGCCGATAAGAGACCCGAC

LD52G Rv : GTCGGGTCTCTTATCGCCCCGGTAGATGATTGTG

LD52Q Rv : GTCGGGTCTCTTATCCTGCCGGTAGATGATTGT

LD52N Rv : GTCGGGTCTCTTATCGTTCCGGTAGATGATTGT

LD52S Rv : GTCGGGTCTCTTATCGCTCCGGTAGATGATTGTG

LD52A Rv : GTCGGGTCTCTTATCGGCCCGGTAGATGATTGT

[Figure 106-1]
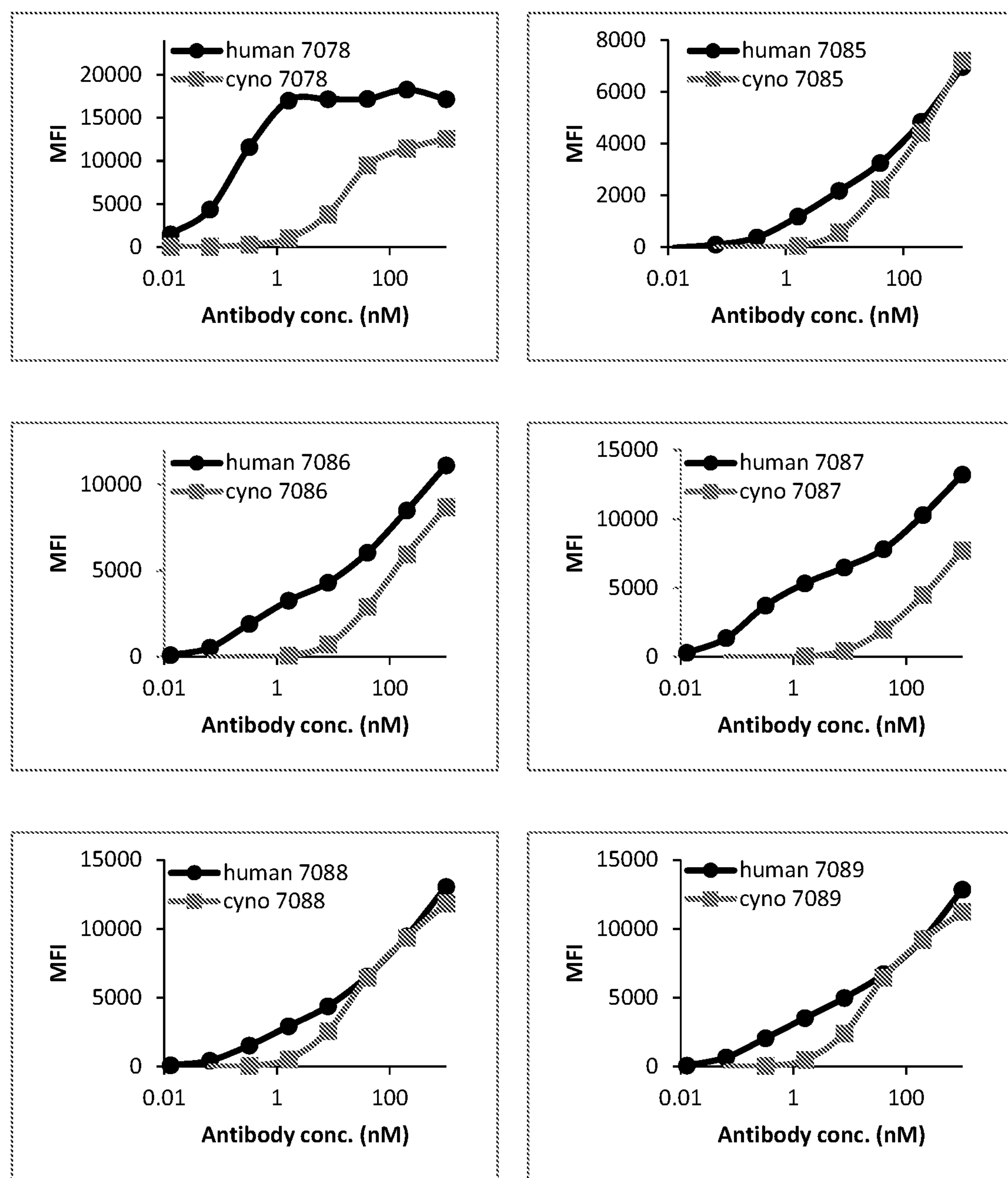

[Figure 106-2]
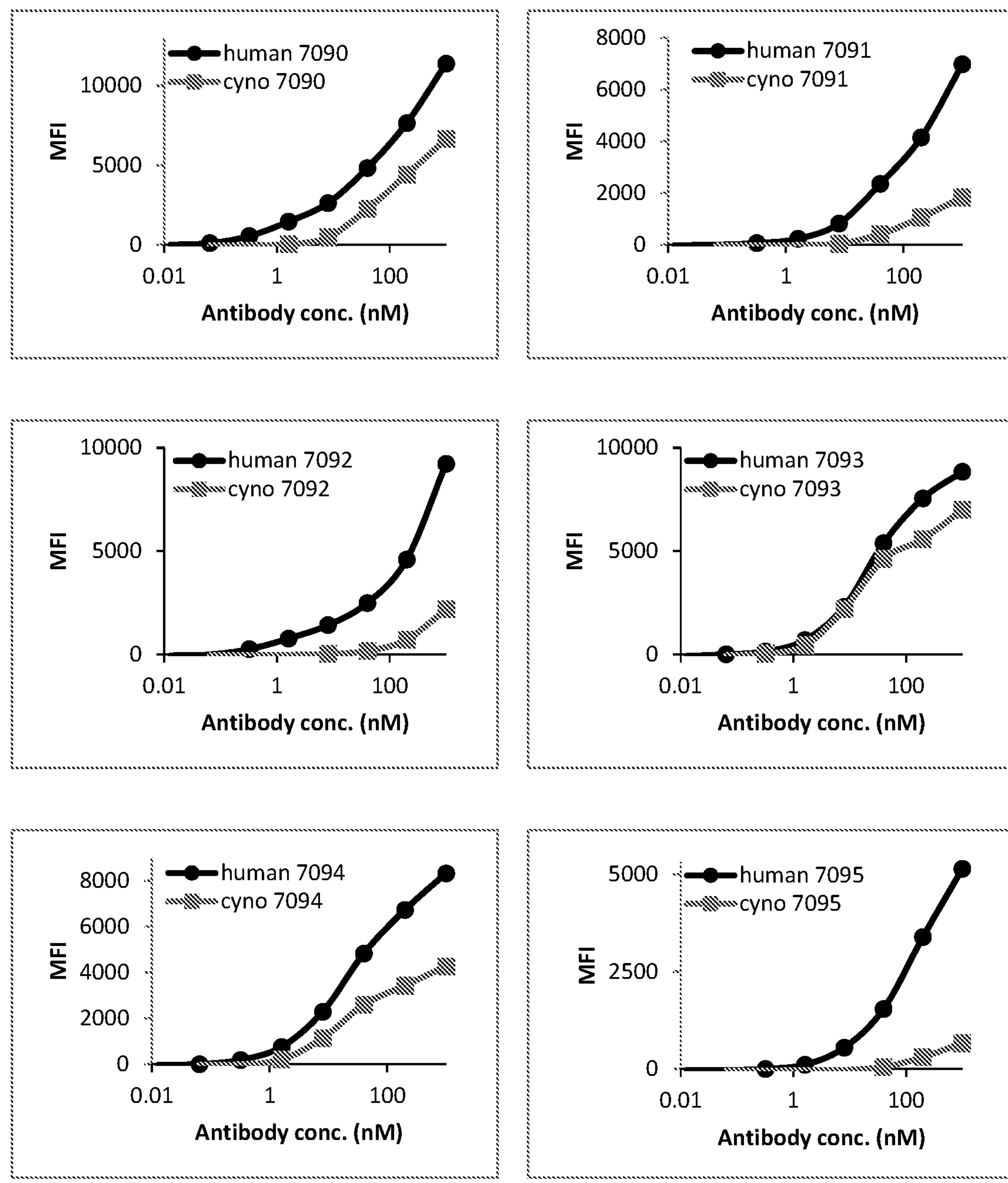

[Figure 107]
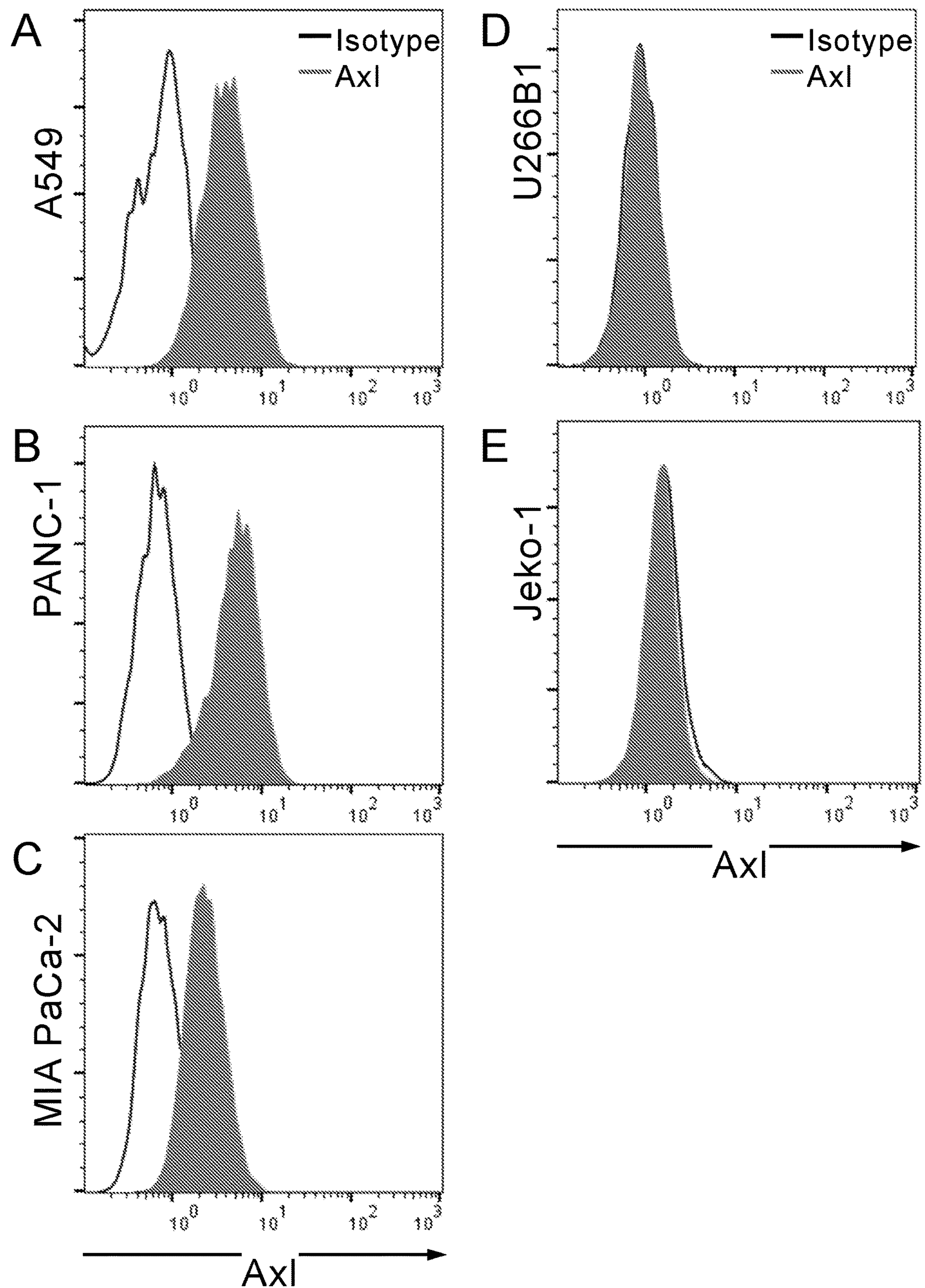

[Figure 108]
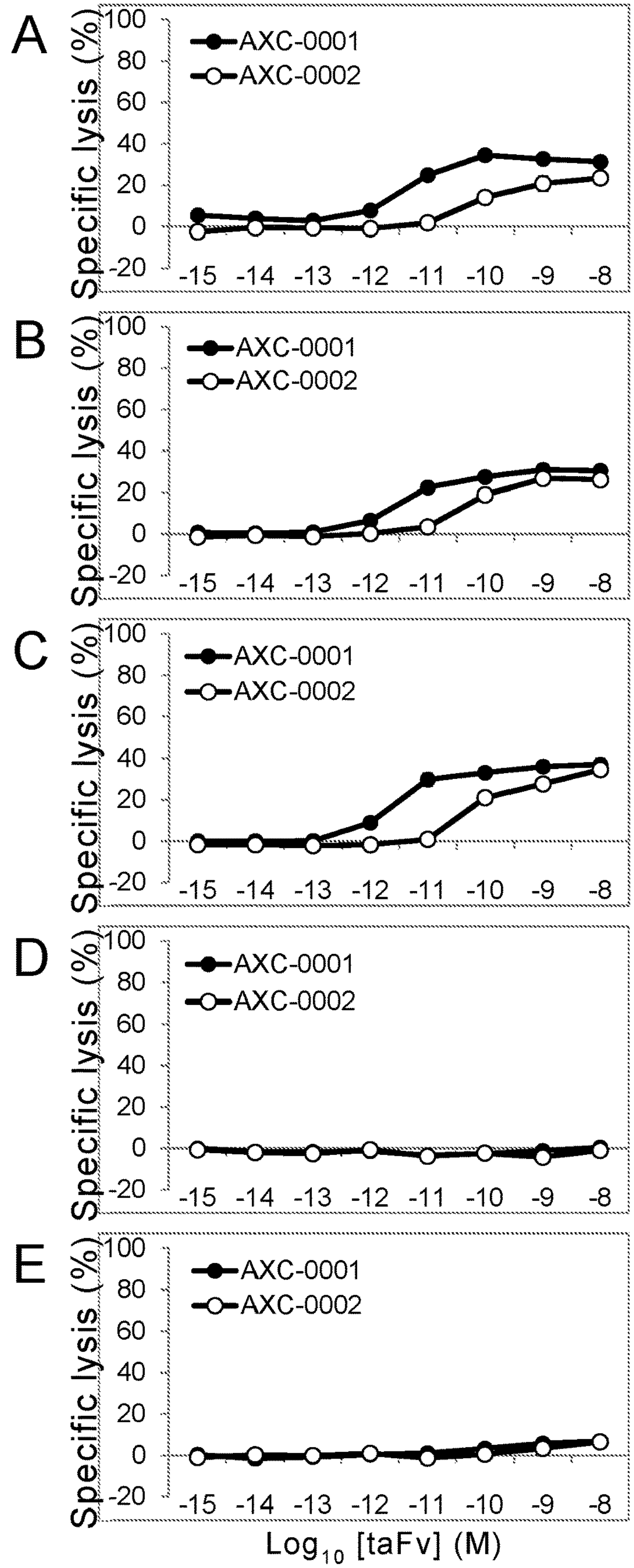

[Figure 109]
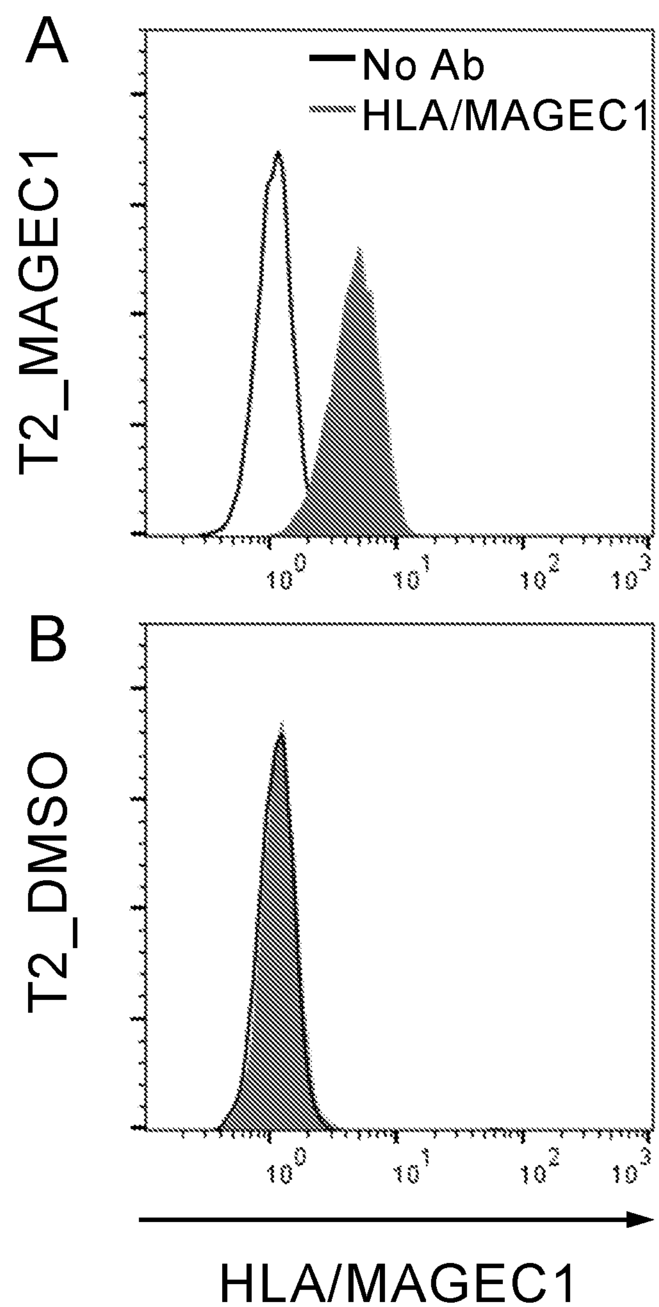

[Figure 110]
A
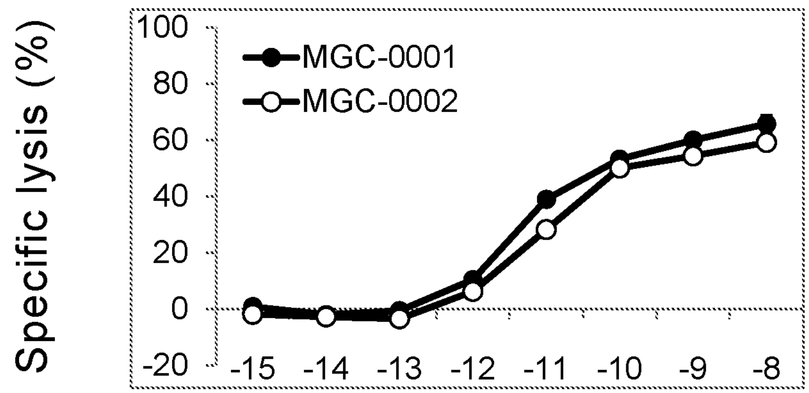
B
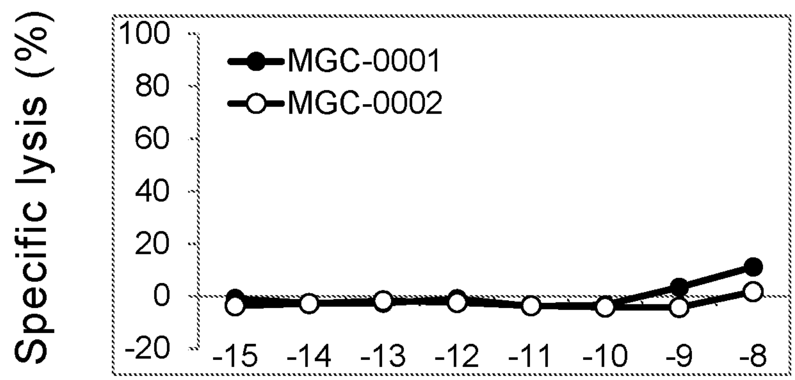

[Figure 111]

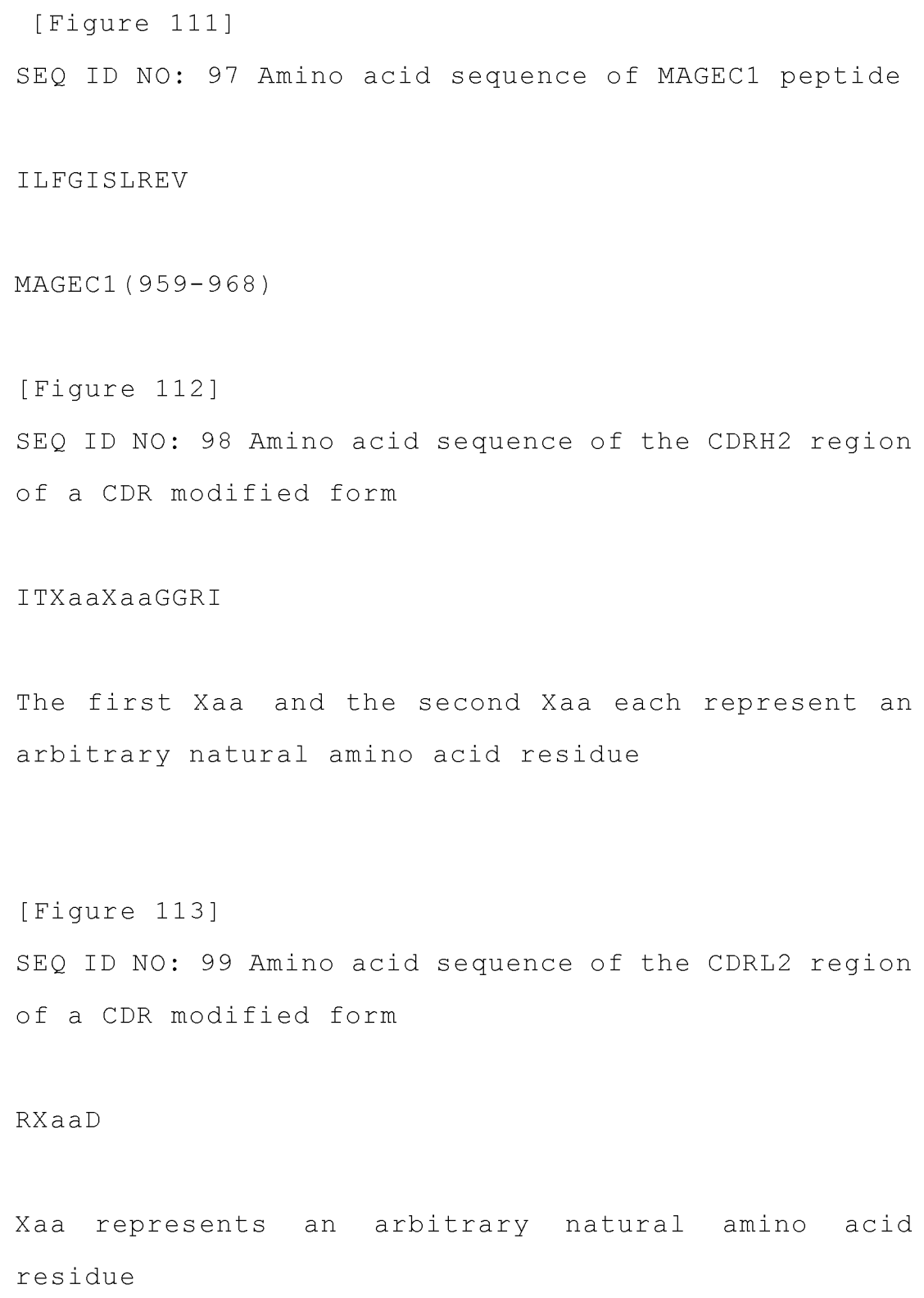

SEQ ID NO: 97 Amino acid sequence of MAGEC1 peptide

ILFGISLREV

MAGEC1(959-968)

[Figure 112]

SEQ ID NO: 98 Amino acid sequence of the CDRH2 region of a CDR modified form

ITXaaXaaGGRI

The first Xaa and the second Xaa each represent an arbitrary natural amino acid residue

[Figure 113]

SEQ ID NO: 99 Amino acid sequence of the CDRL2 region of a CDR modified form

RXaaD

Xaa represents an arbitrary natural amino acid residue

[Figure 114]

SEQ ID NO: 100 Amino acid sequence of the variable region of heavy chain of a CDR modified form of C3E-7034

EVQLVESGGGLVQPGGSLRLSCAASGVTFNYYGMSWIRQAPGKGLEWVASI
TXaaXaaGGRIYYPDSVKGRFTISRENTQKTLYLQMNSLRAEDTAVYYCTL
DGRDGWVAYWGQGTLVTVSS

The first Xaa and the second Xaa each represents an arbitrary natural amino acid residue

[Figure 115]

SEQ ID NO: 101 Amino acid sequence of the variable region of the light chain of a CDR modified form of C3E-7034

NFMLTQPHSVSESPGKTVTISCKRNTGNIGSNYVNWYQQHEGSSPTTIIYR
XaaDKRPDGVSDRFSGSIDRSSKSASLTISNLKTEDEADYFCQSYSSGFIF
GGGTKLTVL

Xaa represents an arbitrary natural amino acid residue

[Figure 116]

SEQ ID NO: 102 Amino acid sequence of the variable region of the light chain of a CDR modified form of C3E-7035

QAVLTQPSSVSGVPGQRVTISCKRNTGNIGSNYVNWYQQLPGTAPKLLIYR
XaaDKRPSGVPDRFSGSKSGTSASLAITGFQAEDEADYYCQSYSSGFIFGG
GTKLTVL

Xaa represents an arbitrary natural amino acid residue

[Figure 117]

SEQ ID NO: 103 amino acid sequence of the variable region of the light chain of a CDR modified form of C3E-7036

NFMLTQPSSVSGVPGQRVTISCTGNTGNIGSNYVNWYQQLPGTAPKLLIYR
XaaDKRPSGVPDRFSGSKSGTSASLAITGFQAEDEADYYCQSYSSGFIFGG
GTKLTVL

Xaa represents an arbitrary natural amino acid residue

ANTI-CD3 ANTIBODY AND MOLECULES COMPRISING THE ANTIBODY

CROSS-REFERENCE TO RELATED APPLICATIONS

This application is the U.S. National Stage of PCT/JP2017.046006, filed Dec. 21, 2017, which claims priority to JP 2016-249148, filed Dec. 22, 2016.

The instant application contains a Sequence Listing which has been submitted in ASCII format via EFS-WEB and is hereby incorporated by reference in its entirety. Said ASCII copy, created on Jun. 20, 2019, is named sequence.txt and is 157,785 bytes.

TECHNICAL FIELD

The present invention relates to a novel antibody which binds to human CD3 and binds to cynomolgus monkey CD3, and to molecules comprising the antibody.

BACKGROUND ART

1) Anti-CD3 monoclonal antibodies, as with any other monoclonal antibody, function by precise recognition of their target molecules. Each anti-CD3 antibody recognizes only a single epitope on the target CD3 molecule. Among monoclonal antibodies specific for a CD3 complex, OKT3 is most widely used and best characterized.

2) OKT3 is a mouse-derived anti-human CD3 monoclonal antibody (Non-Patent Document 1). Anti-CD3 monoclonal antibodies have been administered in a procedure to prevent transplanted organs from being rejected. The antibodies bind to TCR complexes on human T cells and suppress their activation and proliferation. This treatment has been used for a long time in order to prevent the homograft rejection of an organ (Non-Patent Documents 2 through 4). OKT3 is the first anti-CD3 antibody to be used in such a procedure. OKT3 has a strong immunosuppressive effect, whereas its clinical use is hampered due to severe adverse reactions associated with its immunogenicity and mitogenic potential (Non-Patent Documents 5 to 8).

3) OKT3 induces T cell activation and cytokine production in vitro and releases large amounts of cytokines in vivo resulting in cytokine syndrome (Non-Patent Document 5). This is because OKT3 is a bivalent IgG molecule, and thus crosslinks T cells and Fcγ receptor-expressing cells, consequently causing T cell activation (Non-Patent Document 8). In addition, OKT3 is a mouse antibody and is therefore known to cause heterophilic antibodies such as Human Anti-Mouse Antibodies (HAMA) through long-term administration (Non-Patent Document 7). Reports on the application of anti-CD3 antibodies treatment and their adverse reactions are summarized below (Patent Document 1).

4) In order to solve these problems, scFv-formatted OKT3 (Non-Patent Document 9) and humanized OKT3 (Non-Patent Document 10) have been created. A bispecific antibody combining a single chain of OKT3 with a single chain of an antibody against a target antigen expressed on the surface of a cancer cell has been reported in another example of an application of OKT3 (Patent Document 2 and Non-Patent Document 11).

5) Multispecific antibodies comprising the anti-CD3 antibodies described in the prior art are expected to have significant therapeutic potential in the treatment of malignant diseases. For example, TROP2 is known to be overexpressed in various types of epithelial tumors (Non-Patent Documents 12 to 16). An expressed bispecific antibody which genetically links a human TROP2-specific antibody to an antigen-binding fragment of an anti-CD3 antibody has not yet been reported.

6) OKT3 reacts with chimpanzee CD3, but does not react with CD3 derived from other primates such as cynomolgus monkeys (Non-Patent Document 17). Likewise, anti-CD3 monoclonal antibody UCHT-1 also reacts with chimpanzee-derived CD3, but does not react with cynomolgus monkey-derived CD3 (Non-Patent Document 18). On the other hand, some monoclonal antibodies have been found that recognize cynomolgus monkey antigens, but do not recognize their human counterparts. One example from this group is FN-18, which is a monoclonal antibody directed towards cynomolgus monkey-derived CD3 (Non-Patent Document 19).

7) The limitation of OKT3 and the series of modified OKT3 antibodies is their specificity to human CD3. This limitation may constitute a considerable barrier to the development of therapeutic drugs for treating human diseases. This is because candidate drugs for development need to be subjected to preclinical trials to obtain marketing approval, and it is desirable to conduct such preclinical trials on animals, particularly higher primates such as cynomolgus monkeys. Thus, in the case of candidate drugs containing anti-CD3 antibodies, it is very desirable to use an anti-CD3 antibody able to bind both to human CD3 and to cynomolgus monkey CD3.

8) The cross-reactive antibody binding to both of human CD3 and cynomolgus monkey CD3 has been reported in Patent Documents 3 and 4 and Non-Patent Document 20. Also, a bispecific antibody in which a single chain of such an anti-CD3 antibody is bound with a single chain of an antibody against a target antigen expressed on cancer cell surface has been reported (Patent Document 5 and Non-Patent Document 21). However, in order to be able to apply multispecific antibodies or multispecific molecules to highly diverse applicable cancer targets, there is demand for an anti-CD3 antibody which binds to epitopes other than those mentioned above and binds to both human and cynomolgus monkey CD3.

PRIOR ART

Patent Documents

[Patent Document 1] International Publication No. WO2012/162067

[Patent Document 2] International Publication No. WO2007/108152A1

[Patent Document 3] U.S. Pat. No. 8,236,308B2

[Patent Document 4] International Publication No. WO2008/119567A1

[Patent Document 5] International Publication No. WO2015/026892A1

Non-Patent Document

[Non-Patent Document 1] Salmeron A. et al., J. Immunol. (1991) 147, 3047-3052

[Non-Patent Document 2] Cosmi A B. et al., Transplantation (1981) 32, 535-539

[Non-Patent Document 3] Gilbert E M. et al., Am. J. Med. (1987) 82, 202-206

[Non-Patent Document 4] Thistlethwaite J R. et al., Transplanation (1987) 43, 176-184

[Non-Patent Document 5] Abramowicz D. et al., Transplanation (1989) 47, 606-608

[Non-Patent Document 6] Toussaint D. et al., Transplanation (1989) 48, 524-526

[Non-Patent Document 7] Thistlethwaite, J R. et al., Am. J. Kidney Dis. (1988) 11, 112-119

[Non-Patent Document 8] Meuer, S C. et al., Eur. J. Immunol. (1986) 136, 4106-4112

[Non-Patent Document 9] George A J. et al., J. Immunol. (1994) 152 (4), 1802-11

[Non-Patent Document 10] Woodle E S. et al., J Immunol. (1992) 148 (9), 2756-63

[Non-Patent Document 11] Yankelevich M. et al., Pediatr. Blood Cancer (2012) 59 (7), 1198-1205

[Non-Patent Document 12] Ohmachi T. et al., Clin. Cancer Res. (2006) 12 (10), 3057-3063.

[Non-Patent Document 13] Muhlmann G., et al., J. Clin. Pathol. (2009) 62 (2), 152-158

[Non-Patent Document 14] Fong D., et al., Br. J. Cancer (2000) 99 (8), 1290-1295.

[Non-Patent Document 15] Fong D. et al., Mod. Pathol. (2000) 21 (2) (2000), 186-191

[Non-Patent Document 16] Ning S., et al., Neurol. Sci. (2013) 34 (10), 1745-1750

[Non-Patent Document 17] Sandusky et al., J. Med. Primatol. (1986) 15, 441-451

[Non-Patent Document 18]http://www.nhpreagents.org/NHP/clonelist.aspx?ID=77

[Non-Patent Document 19] Uda et al., J. Med. Primatol. (2001) 30, 141-147

[Non-Patent Document 20] Conrad M L. et al., Cytometry A. (2007) 71 (11), 925-33

[Non-Patent Document 21] Lum L G. et al., BioDrugs (2011) 25 (6), 365-379.

SUMMARY OF THE INVENTION

Problem to be Solved by the Invention

An object of the present invention is to provide a novel antibody or an antigen-binding fragment of the antibody (hereinafter, also referred to as an antibody, etc.) which binds to human CD3 and to cynomolgus monkey CD3, a molecule comprising the antibody, etc. and further comprising 1 or 2 or more additional antibodies or antigen-binding fragments of the antibodies, the molecule being multispecific, and a pharmaceutical composition having cytotoxic activity, etc. which includes the antibody, etc. or the molecule as an active ingredient.

Means for Solving the Problem

The present inventors have conducted extensive research to achieve this object and have realized the present invention by developing a novel anti-CD3 antibody and a molecule comprising this antibody.

Specifically, the present invention encompasses the following aspects:

(1) An antibody or an antigen-binding fragment of the antibody, characterized in that:

a heavy chain sequence comprises

CDRH1 comprising the amino acid sequence represented by SEQ ID NO: 26,

CDRH2 comprising the amino acid sequence represented by SEQ ID NO: 98, and

CDRH3 comprising the amino acid sequence represented by SEQ ID NO: 28;

a light chain sequence comprises

CDRL1 comprising the amino acid sequence represented by SEQ ID NO: 29,

CDRL2 comprising the amino acid sequence represented by SEQ ID NO: 99, and

CDRL3 comprising the amino acid sequence represented by SEQ ID NO: 31; and the antibody or antigen-binding fragment binds to human CD3 and to cynomolgus monkey CD3.

(2) An antibody or antigen-binding fragment of an antibody according to (1), wherein in CDRH2 the first Xaa is selected from a group consisting of A, E, G, H, I, L, T, V, R, and S, and the second Xaa is S, or the first Xaa is N, and the second Xaa is selected from a group consisting of E, R, F, Y, L, V, I, K, and T, in CDRL2, Xaa is selected from a group consisting of Q, A, G, S, N, and D, and the antibody or antigen-binding fragment binds to human CD3 and to cynomolgus monkey CD3.

(3) An antibody or antigen-binding fragment of an antibody according to (1) or (2), wherein in CDRH2, the first Xaa is selected from a group consisting of R and S, and the second Xaa is S, in CDRL2, Xaa is selected from a group consisting of Q, A, G, S, N, and D, and the antibody or antigen-binding fragment binds to human CD3 and to cynomolgus monkey CD3.

(4) An antibody or antigen-binding fragment of an antibody according to (1), wherein the heavy chain sequence comprises a variable region having CDRH1, CDRH2, and CDRH3, CDRH1 consisting of an amino acid sequence represented by SEQ ID NO: 26, CDRH2 consisting of an amino acid sequence represented by SEQ ID NO: 27, and CDRH3 consisting of an amino acid sequence represented by SEQ ID NO: 28;

the light chain sequence comprises a variable region having CDRL1, CDRL2, and CDRL3, CDRL1 consisting of an amino acid sequence represented by SEQ ID NO: 29, CDRL2 consisting of an amino acid sequence represented by SEQ ID NO: 30, and CDRL3 consisting of an amino acid sequence represented by SEQ ID NO: 31; and the antibody or antigen-binding fragment binds to human CD3 and to cynomolgus monkey CD3.

(5) An antibody or antigen-binding fragment of an antibody according to any one of (1) to (4), wherein the heavy chain variable region sequence comprises an amino acid sequence represented by SEQ ID NO: 100.

(6) An antibody or antigen-binding fragment thereof according to (5), wherein in the amino acid sequence represented by SEQ ID NO: 100, the first Xaa is selected from a group consisting of A, E, G, H, I, L, T, V, R, and S, and the second Xaa is S, or the first Xaa is N, and the second Xaa is selected from a group consisting of E, R, F, Y, L, V, I, K, and T.

(7) An antibody or antigen-binding fragment thereof according to (5), wherein in the amino acid sequence represented by SEQ ID NO: 100, the first Xaa is selected from a group consisting of R and S, and the second Xaa is S.

(8) An antibody or antigen-binding fragment thereof according to any one of (1) to (7), wherein the light chain variable region comprises an amino acid sequence represented by any one of SEQ ID NOs: 101, 102, and 103.

(9) An antibody or antigen-binding fragment thereof according to (8), wherein in the amino acid sequence represented by any one of SEQ ID NOs: 101, 102, and 103, Xaa is selected from a group consisting of Q, A, G, S, N, and D.

(10) An antibody or antigen-binding fragment of an antibody according to (5), wherein the heavy chain variable region sequence comprises an amino acid sequence represented by SEQ ID NO: 16.

(11) An antibody or antigen-binding fragment of an antibody according to (8), wherein the light chain variable region sequence comprises an amino acid sequence represented by any one of SEQ ID NOs: 17, 20, and 23.

(12) An antibody or binding fragment thereof according to (1) or (2), wherein the antibody or antibody binding fragment comprises a heavy chain variable region comprising an amino acid sequence represented by SEQ ID NO: 100 and a light chain variable region comprising an amino acid sequence represented by any one of SEQ ID NOs: 101, 102, and 103, wherein in the amino acid sequence represented by SEQ ID NO: 100, the first Xaa is selected from a group consisting of A, E, G, H, I, L, T, V, R, and S, and the second Xaa is S, or the first Xaa is N, and the second Xaa is selected from a group consisting of E, R, F, Y, L, V, I, K, and T, and in the amino acid sequence represented by any one of SEQ ID NOs: 101, 102, and 103, Xaa is selected from a group consisting of Q, A, G, S, N, and D.

(13) An antibody or binding fragment thereof according to (12), wherein in SEQ ID NO: 100 the first Xaa is selected from a group consisting of R and S, and the second Xaa is S, and in the amino acid sequence represented by any one of SEQ ID NOs: 101, 102, and 103, Xaa is selected from a group consisting of Q, A, G, S, N, and D.

(14) An antibody or antigen-binding fragment of an antibody comprising a heavy chain variable region comprising the 2nd through 119th amino acid residues of SEQ ID NO: 60 and a light chain variable region comprising the 135th through 243rd amino acid residues of SEQ ID NO: 60, an antibody or antigen-binding fragment of the antibody comprising a heavy chain variable region comprising the 2nd through 119th amino acid residues of SEQ ID NO: 64 and a light chain variable region comprising the 135th through 241st amino acid residues of SEQ ID NO: 64, an antibody or antigen-binding fragment of the antibody comprising a heavy chain variable region comprising the 2nd through 119th amino acid residues of SEQ ID NO: 66 and a light chain variable region comprising the 135th through 243rd amino acid residues of SEQ ID NO: 66, an antibody or antigen-binding fragment of the antibody comprising a heavy chain variable region comprising the 2nd through 119th amino acid residues of SEQ ID NO: 68 and a light chain variable region comprising the 135th through 243rd amino acid residues of SEQ ID NO: 68, an antibody or antigen-binding fragment of the antibody comprising a heavy chain variable region comprising the 2nd through 119th amino acid residues of SEQ ID NO: 70 and a light chain variable region comprising the 135th through 243rd amino acid residues of SEQ ID NO: 70, an antibody or antigen-binding fragment of the antibody comprising a heavy chain variable region comprising the 2nd through 119th amino acid residues of SEQ ID NO: 72 and a light chain variable region comprising the 135th through 243rd amino acid residues of SEQ ID NO: 72, an antibody or antigen-binding fragment of the antibody comprising a heavy chain variable region comprising the 2nd through 119th amino acid residues of SEQ ID NO: 74 and a light chain variable region comprising the 135th through 243rd amino acid residues of SEQ ID NO: 74, an antibody or antigen-binding fragment of the antibody comprising a heavy chain variable region comprising the 2nd through 119th amino acid residues of SEQ ID NO: 76 and a light chain variable region comprising the 135th through 243rd amino acid residues of SEQ ID NO: 76, an antibody or antigen-binding fragment of the antibody comprising a heavy chain variable region comprising the 2nd through 119th amino acid residues of SEQ ID NO: 78 and a light chain variable region comprising the 135th through 243rd amino acid residues of SEQ ID NO: 78, an antibody or antigen-binding fragment of the antibody comprising a heavy chain variable region comprising the 2nd through 119th amino acid residues of SEQ ID NO: 80 and a light chain variable region comprising the 135th through 243rd amino acid residues of SEQ ID NO: 80, an antibody or antigen-binding fragment of the antibody comprising a heavy chain variable region comprising the 2nd through 119th amino acid residues of SEQ ID NO: 82 and a light chain variable region comprising the 135th through 243rd amino acid residues of SEQ ID NO: 82, or an antibody or antigen-binding fragment of the antibody comprising a heavy chain variable region comprising the 2nd through 119th amino acid residues of SEQ ID NO: 84 and a light chain variable region comprising the 135th through 243rd amino acid residues of SEQ ID NO: 84, according to (13).

(15) An antibody or antigen-binding fragment of an antibody according to (1), (4), (5), (8), (10), or (11), wherein the antibody or antigen-binding fragment comprises a heavy chain variable region comprising an amino acid sequence represented by SEQ ID NO: 16, a linker, and a light chain variable region comprising an amino acid sequence represented by any one of SEQ ID NOs: 17, 20, and 23.

(16) An antibody or antigen-binding fragment of an antibody according to any one of (1) to (15), wherein a heavy chain variable region binds to a light chain variable region in this order, or a light chain variable region binds to a heavy chain variable region in this order, from the amino-terminal, and optionally: i) has a linker between both variable regions, ii) has a glycine residue at amino-terminal of a variable region on the amino-terminal side, and iii) has a linker, FLAG tag and/or HIS tag at carboxyl terminal of a variable region on the carboxyl terminal side.

(17) An antibody or antigen-binding fragment of an antibody according to (16) including an amino acid sequence comprising the 2nd through 241st amino acid residues of SEQ ID NO: 64, an amino acid sequence comprising the 2nd through 243rd amino acid residues of SEQ ID NO: 66, an amino acid sequence comprising the 2nd through 243rd amino acid residues of SEQ ID NO: 68,
an amino acid sequence comprising the 2nd through 243rd amino acid residues of SEQ ID NO: 70,
an amino acid sequence comprising the 2nd through 243rd amino acid residues of SEQ ID NO: 72,
an amino acid sequence comprising the 2nd through 243rd amino acid residues of SEQ ID NO: 74,
an amino acid sequence comprising the 2nd through 243rd amino acid residues of SEQ ID NO: 75,
an amino acid sequence comprising the 2nd through 243rd amino acid residues of SEQ ID NO: 76,
an amino acid sequence comprising the 2nd through 243rd amino acid residues of SEQ ID NO: 80,
an amino acid sequence comprising the 2nd through 243rd amino acid residues of SEQ ID NO: 82, or
an amino acid sequence comprising the 2nd through 243rd amino acid residues of SEQ ID NO: 84.

(18) An antibody or antigen-binding fragment of an antibody according to (16) including
an amino acid sequence comprising the 2nd through 269th amino acid residues of SEQ ID NO: 19,
an amino acid sequence comprising the 2nd through 269th amino acid residues of SEQ ID NO: 22,
an amino acid sequence comprising the 2nd through 267th amino acid residues of SEQ ID NO: 25,
an amino acid sequence comprising the 2nd through 269th amino acid residues of SEQ ID NO: 60,
an amino acid sequence comprising the 2nd through 267th amino acid residues of SEQ ID NO: 64,
an amino acid sequence comprising the 2nd through 269th amino acid residues of SEQ ID NO: 66,
an amino acid sequence comprising the 2nd through 269th amino acid residues of SEQ ID NO: 68,
an amino acid sequence comprising the 2nd through 269th amino acid residues of SEQ ID NO: 70,
an amino acid sequence comprising the 2nd through 269th amino acid residues of SEQ ID NO: 72,
an amino acid sequence comprising the 2nd through 269th amino acid residues of SEQ ID NO: 74,
an amino acid sequence comprising the 2nd through 269th amino acid residues of SEQ ID NO: 76,
an amino acid sequence comprising the 2nd through 269th amino acid residues of SEQ ID NO: 78,
an amino acid sequence comprising the 2nd through 269th amino acid residues of SEQ ID NO: 80,
an amino acid sequence comprising the 2nd through 269th amino acid residues of SEQ ID NO: 82, or
an amino acid sequence comprising the 2nd through 269th amino acid residues of SEQ ID NO: 84.

(19) An antibody or an antigen-binding fragment of an antibody, wherein the antibody or antigen-binding fragment comprises an amino acid sequence encoded by a nucleotide sequence contained in a polynucleotide which hybridizes under stringent conditions with a complementary strand of a polynucleotide including a nucleotide sequence encoding an amino acid sequence contained in an antibody or an antigen-binding fragment of the antibody according to any one of (14) to (18), and binds to human CD3 and to cynomolgus monkey CD3.

(20) An antibody or an antigen-binding fragment of an antibody, wherein the antibody or antigen-binding fragment comprises a heavy chain including an amino acid sequence at least 90% identical to the amino acid sequence of a heavy chain contained in an antibody or an antigen-binding fragment of the antibody according to any one of (14) to (18), and a light chain including an amino acid sequence at least 70% identical to the amino acid sequence of a light chain contained in the antibody or antigen-binding fragment of the antibody according to any one of (14) to (18), and binds to human CD3 and to cynomolgus monkey CD3.

(21) An antibody or an antigen-binding fragment of an antibody, wherein the antibody or antigen-binding fragment comprises a heavy chain including an amino acid sequence derived by the substitution, deletion, or addition of 1 or more amino acid(s) from an amino acid sequence contained in a heavy chain contained in an antibody or an antigen-binding fragment of the antibody according to any one of (14) to (18), and a light chain including an amino acid sequence derived by the substitution, deletion, or addition of 1 or more amino acids from an amino acid sequence contained in a light chain contained in the antibody or antigen-binding fragment of the antibody according to any one of (14) to (18), and binds to human CD3 and to cynomolgus monkey CD3.

(22) An antibody or an antigen-binding fragment of an antibody, wherein the antibody or antigen-binding fragment binds to the same site on human CD3 as that bound by an antibody or an antigen-binding fragment of the antibody according to any one of (14) to (18), and binds to cynomolgus monkey CD3.

(23) An antibody or an antigen-binding fragment of an antibody, wherein the antibody or antigen-binding fragment competes with an antibody or an antigen-binding fragment of the antibody according to any one of (14) to (18) to bind to human CD3, and binds to cynomolgus monkey CD3.

(24) An antibody or antigen-binding fragment of the antibody according to (22), wherein the site on human CD3 bound by the antibody is constituted by 7 or more amino acids selected from the 55th serine (Ser), the 56th glutamic acid (Glu), the 58th leucine (Leu), the 59th tryptophan (Trp), the 65th asparagine (Asn), the 66th isoleucine (Ile), the 77th serine (Ser), the 78th aspartic acid (Asp), the 101st arginine (Arg), the 101nd glycine (Gly), the 103rd serine (Ser), the 104th lysine (Lys), and the 105th proline (Pro) in the amino acid sequence represented by SEQ ID NO: 1.

(25) An antibody or antigen-binding fragment of the antibody according to any one of (1) to (17) and (19) to (24), wherein the antibody is IgG.

(26) An antibody or antigen-binding fragment of an antibody according to any one of (1) to (23), wherein the antigen-binding fragment is selected from a group consisting of Fab, F(ab)', Fv, scFv, and sdAb.

(27) An antibody or antigen-binding fragment of an antibody according to any one of (1) to (17) and (19) to (25), wherein the antibody is a humanized antibody or a human antibody including a human immunoglobulin constant region.

(28) A polynucleotide comprising a nucleotide sequence encoding the amino acid sequence of an antibody or an antigen-binding fragment of the antibody according to any one of (1) to (27).

(29) A polynucleotide according to (27), wherein the polynucleotide comprises a nucleotide sequence encoding an amino acid sequence represented by
an amino acid sequence comprising the 2nd through 243rd amino acid residues of SEQ ID NO: 19,
an amino acid sequence comprising the 2nd through 243rd amino acid residues of SEQ ID NO: 22,
an amino acid sequence comprising the 2nd through 241st amino acid residues of SEQ ID NO: 25,
an amino acid sequence comprising the 2nd through 243rd amino acid residues of SEQ ID NO: 60,
an amino acid sequence comprising the 2nd through 241st amino acid residues of SEQ ID NO: 64, an amino acid sequence comprising the 2nd through 243rd amino acid residues of SEQ ID NO: 66,
an amino acid sequence comprising the 2nd through 243rd amino acid residues of SEQ ID NO: 68,
an amino acid sequence comprising the 2nd through 243rd amino acid residues of SEQ ID NO: 70,
an amino acid sequence comprising the 2nd through 243rd amino acid residues of SEQ ID NO: 72,
an amino acid sequence comprising the 2nd through 243rd amino acid residues of SEQ ID NO: 74,
an amino acid sequence comprising the 2nd through 243rd amino acid residues of SEQ ID NO: 76,
an amino acid sequence comprising the 2nd through 243rd amino acid residues of SEQ ID NO: 78,
an amino acid sequence comprising the 2nd through 243rd amino acid residues of SEQ ID NO: 80,
an amino acid sequence comprising the 2nd through 243rd amino acid residues of SEQ ID NO: 82, or an amino acid sequence comprising the 2nd through 243rd amino acid residues of SEQ ID NO: 84.

(30) A vector comprising a polynucleotide according to (28) or (29).

(31) A cell comprising a polynucleotide according to (28) or (29) or a vector according to (30), or producing an antibody or an antigen-binding fragment of the antibody according to any one of (1) to (27).

(32) A method for producing an antibody or an antigen-binding fragment of the antibody which binds to human CD3 and to cynomolgus monkey CD3, the method comprising the steps of: culturing a cell according to (31); and recovering an antibody or an antigen-binding fragment of the antibody which binds to human CD3 from the cultures.

(33) An antibody or an antigen-binding fragment of the antibody which binds to human CD3 and cynomolgus monkey CD3, the antibody or antigen-binding fragment being obtained by a method according to (32).

(34) A pharmaceutical composition comprising an antibody or an antigen-binding fragment of the antibody according to any one of (1) to (27) and (33) as an active ingredient.

(35) A molecule having antigen binding activity, comprising an antibody or an antigen-binding fragment of the antibody according to any one of (1) to (27) and (33).

(36) A molecule according to (35), wherein the molecule is multispecific.

(37) A molecule according to (35) or (36), further comprising 1 or 2 or more additional antibodies or antigen-binding fragments of the antibodies in addition to the antibody or antigen-binding fragment of the antibody according to any one of (1) to (27) and (33).

(38) A molecule according to (37), wherein the antigen-binding fragment of the additional antibody is Fab, F(ab)', Fv, scFv, or sdAb.

(39) A molecule according to (38), wherein the molecule comprises Fc.

(40) A molecule according to any one of (37) to (38), wherein the additional antibody is a humanized antibody or a human antibody comprising a human immunoglobulin constant region.

(41) A molecule according to any one of (37) to (38), wherein the additional antibody or antigen-binding fragment of the antibody is bound with the antibody or antigen-binding fragment of the antibody according to any one of (1) to (27) and (33) via a linker or without a linker.

(42) A molecule according to (41), wherein a carboxyl terminus of the amino acid sequence of the additional antibody or antigen-binding fragment of the antibody is bound with a linker, and a carboxyl terminus of the amino acid sequence of the linker is further bound with the antibody or antigen-binding fragment of the antibody according to any one of (1) to (27) and (33).

(43) A molecule according to (42), wherein the molecule comprises an amino acid sequence in which a carboxyl terminus of the amino acid sequence of the additional antibody or antigen-binding fragment of the antibody is bound with a linker, and a carboxyl terminus of the amino acid sequence of the linker is further bound with
the antibody or antigen-binding fragment of the antibody comprising the 2nd through 243rd amino acid residues of SEQ ID NO: 19,
the antibody or antigen-binding fragment of the antibody comprising of the 2nd through 243rd amino acid residues of SEQ ID NO: 22, or
the antibody or antigen-binding fragment of the antibody comprising of the 2nd through 241st amino acid residues of SEQ ID NO: 25.

(44) A molecule according to any one of (35) to (42), comprising the antibody or antigen-binding fragment of the antibody according to any one of (1) to (27) and (33), wherein the variable region comprises a heavy chain variable region and a light chain variable region in this order, or a light chain variable region and a heavy chain variable region in this order, from the amino-terminal, and optionally: i) has a linker between both variable regions, ii) has a glycine residue at amino-terminal of variable region on the amino-terminal side, and iii) has a linker, FLAG tag and/or HIS tag at carboxyl terminal of a variable region on the carxoyl terminal side. Applicable forms include Hybrid type and Dual type bispecific molecules.

(45) A molecule according to (44), wherein the additional antibody or antigen-binding fragment of the antibody is bound with
the antibody or antigen-binding fragment of the antibody comprising the 2nd through 243rd amino acid residues of SEQ ID NO: 19,
the antibody or antigen-binding fragment of the antibody comprising the 2nd through 241st amino acid residues of SEQ ID NO: 25,
the antibody or antigen-binding fragment of the antibody comprising the 2nd through 243rd amino acid residues of SEQ ID NO: 60,
the antibody or antigen-binding fragment of the antibody comprising the 2nd through 241st amino acid residues of SEQ ID NO: 64,
the antibody or antigen-binding fragment of the antibody comprising the 2nd through 243rd amino acid residues of SEQ ID NO: 66,
the antibody or antigen-binding fragment of the antibody comprising the 2nd through 243rd amino acid residues of SEQ ID NO: 68,
the antibody or antigen-binding fragment of the antibody comprising the 2nd through 243rd amino acid residues of SEQ ID NO: 70,
the antibody or antigen-binding fragment of the antibody comprising the 2nd through 243rd amino acid residues of SEQ ID NO: 72,
the antibody or antigen-binding fragment of the antibody comprising the 2nd through 243rd amino acid residues of SEQ ID NO: 74,
the antibody or antigen-binding fragment of the antibody comprising the 2nd through 243rd amino acid residues of SEQ ID NO: 76,
the antibody or antigen-binding fragment of the antibody comprising the 2nd through 243rd amino acid residues of SEQ ID NO: 78, the antibody or antigen-binding fragment of the antibody comprising the 2nd through 243rd amino acid residues of SEQ ID NO: 80, the antibody or antigen-binding fragment of the antibody comprising the 2nd through 243rd amino acid residues of SEQ ID NO: 82, or the antibody or antigen-binding fragment of the antibody comprising the 2nd through 243rd amino acid residues of SEQ ID NO: 84. Applicable forms include Hybrid type and Dual type bispecific molecules.

(46) A molecule according to any one of (36) to (45), wherein the additional antibody is anti cancer target antibody.

(47) A molecule according to any one of (36) to (46), wherein the molecule is bispecific.

(48) A molecule according to any one of (35) to (47), wherein the molecule is a polypeptide.

(49) A polynucleotide comprising a nucleotide sequence encoding the amino acid sequence of a molecule according to (48).

(50) A vector comprising a polynucleotide according to (49).

(51) A cell producing a polynucleotide according to (49) or a vector according to (50), or a molecule according to (48).

(52) A method for producing a molecule binding to human CD3 and to cynomolgus monkey CD3, the method comprising the steps of: culturing a cell according to (51); and recovering a molecule binding to human CD3 from the cultures.

(53) A molecule binding to human CD3 and cynomolgus monkey CD3, the molecule being obtained by a method according to (52).

(54) A pharmaceutical composition comprising a molecule according to any one of (35) to (48) and (53) as an active ingredient.

(55) A pharmaceutical composition according to (54), wherein the pharmaceutical composition induces cytotoxicity in target cells by the redirection of T cells to the target cells.

Effect of Invention

The present invention is able to obtain a novel anti-CD3 antibody or an antigen-binding fragment of the antibody which binds to human CD3 and binds to cynomolgus monkey CD3, and a novel molecule having antigen binding activity which includes the antibody, etc. In addition, a novel pharmaceutical composition is obtained which includes such an antibody, etc. or molecule as an active ingredient. The antibody, etc. or molecule has T cell dependent cytotoxic activity and is useful as a therapeutic or prophylactic agent for various diseases such as cancer.

BRIEF DESCRIPTION OF THE DRAWINGS

FIG. 1 is a diagram showing the amino acid sequence of human CD3ε.

FIG. 2 is a diagram showing the amino acid sequence of human CD3δ.

FIG. 3 is a diagram showing a nucleotide sequence encoding human CD3εγ single-chain antigen.

FIG. 4 is a diagram showing the amino acid sequence of human CD3εγ single-chain antigen.

FIG. 5 is a diagram showing the nucleotide sequence of a sense primer Nhe-polyC-S for heavy chain gene amplification.

FIG. 6 is a diagram showing the nucleotide sequence of a first antisense primer rIgγ-AS1 for heavy chain gene amplification.

FIG. 7 is a diagram showing the nucleotide sequence of a second antisense primer rIgγ-AS2 for heavy chain gene amplification.

FIG. 8 is a diagram showing the nucleotide sequence of a sense primer Nhe-polyC-S2 for light chain gene amplification.

FIG. 9 is a diagram showing the nucleotide sequence of a first antisense primer rIgL-AS1 for light chain gene amplification.

FIG. 10 is a diagram showing the nucleotide sequence of a second antisense primer rIgL-AS2 for light chain gene amplification.

FIG. 11 is a diagram showing the nucleotide sequence of a sense primer rIgγ-seq for heavy chain sequencing.

FIG. 12 is a diagram showing the nucleotide sequence of an antisense primer 1 rIgL-seq1 for light chain sequencing.

FIG. 13 is a diagram showing the nucleotide sequence of an antisense primer 2 rIgL-seq2 for light chain sequencing.

FIG. 14 is a diagram showing a nucleotide sequence encoding the heavy chain variable region of C3-147.

FIG. 15 is a diagram showing the amino sequence of the heavy chain variable region of C3-147.

FIG. 16 is a diagram showing a nucleotide sequence encoding the light chain variable region of C3-147.

FIG. 17 is a diagram showing the amino sequence of the light chain variable region of C3-147.

FIG. 18 is a diagram showing the oligonucleotide sequence of a G4S linker sense strand.

FIG. 19 is a diagram showing the oligonucleotide sequence of a G4S linker antisense strand.

FIG. 20 is a diagram showing a nucleotide sequence encoding C3E-7000.

FIG. 21 is a diagram showing the amino acid sequence in C3E-7000.

FIG. 22 is a diagram showing the amino acid sequence of the heavy chain variable region of C3E-7034.

FIG. 23 is a diagram showing the amino acid sequence of the light chain variable region of C3E-7034.

FIG. 24 is a diagram showing the amino acid sequence of CDR-H1 in C3E-7000.

FIG. 25 is a diagram showing the amino acid sequence of CDR-H2 in C3E-7000.

FIG. 26 is a diagram showing the amino acid sequence of CDR-H3 in C3E-7000.

FIG. 27 is a diagram showing the amino acid sequence of CDR-L1 in C3E-7000.

FIG. 28 is a diagram showing the amino acid sequence of CDR-L2 in C3E-7000.

FIG. 29 is a diagram showing the amino acid sequence of CDR-L3 in C3E-7000.

FIG. 30 is a diagram showing the amino acid sequence of the light chain variable region of C3E-7035.

FIG. 31 is a diagram showing the amino acid sequence of C3E-7035.

FIG. 32 is a diagram showing the amino acid sequence of the light chain variable region of C3E-7036.

FIG. 33 is a diagram showing the amino acid sequence of C3E-7036.

FIG. 34 is a diagram showing a nucleotide sequence encoding C3E-7034.

FIG. 35 is a diagram showing a nucleotide sequence encoding C3E-7035.

FIG. 36 is a diagram showing a nucleotide sequence encoding C3E-7036.

FIG. 37 is a diagram showing the amino acid sequence of human CD3γ.

FIG. 38 is a diagram showing the amino acid sequence of C3E-7034.

FIG. 39 is a diagram showing the complex structure of CD3εγ and C3E-7034.

FIG. 40 is a pair of diagrams showing the interaction between CD3εγ and the heavy and light chains of C3E-7034.

FIG. 40A is a diagram related to the light chain variable region of C3E-7034 and CD3ε in which the amino acid residues of CD3ε within a distance of 4 angstroms from each other are indicated by thick sticks in the model, and the other amino acids are indicated by thin sticks in the model.

FIG. 40B is a diagram related to the heavy chain variable region of C3E-7034 and CD3ε in which the amino acid residues of CD3ε within a distance of 4 angstroms from each other are indicated by thick sticks in the model, and the other amino acids are indicated by thin sticks in the model.

FIG. 41 is a diagram showing the interaction sites of human CD3ε with the sequences of the heavy and light chain variable regions in C3E-7034.

FIG. 42 is a diagram showing the amino acid sequence of the heavy chain variable region in OKT3.

FIG. 43 is a diagram showing the amino acid sequence of the heavy chain variable region in C3E-3007.

FIG. 44 is a diagram showing the amino acid sequence of the light chain variable region in OKT3.

FIG. 45 is a diagram showing the amino acid sequence of the light chain variable region in C3E-3007.

FIG. 46 is a diagram showing a nucleotide sequence encoding C3E-3007 scFv.

FIG. 47 is a diagram showing the amino acid sequence of C3E-3007 scFv.

FIG. 48 is a diagram showing the binding activity of C3E-3007, C3E-7034, C3E-7035, and C3E-7036, which are humanized anti-CD3 scFvs, to human CD3 (PBMC).

FIG. 49 is a diagram showing the binding activity of C3E-3007, C3E-7034, C3E-7035, and C3E-7036, which are humanized anti-CD3 scFvs, to cynomolgus monkey CD3 (PBMC).

FIG. 50A is a diagram showing the activating effects of C3E-7034 and C3E-3007, which are humanized anti-CD3 scFvs, on human CD8-positive cells, and FIG. 50B is a diagram showing the activating effects of C3E-7034 and C3E-3007, which are the humanized anti-CD3 scFvs, on cynomolgus monkey CD8-positive cells.

FIG. 51 is a diagram showing the amino acid sequence of HT1-11 scFv.

FIG. 52 is a diagram showing a nucleotide sequence encoding HT1-11 scFv.

FIG. 53 is a pair of diagrams showing that HT1-11 scFv binds to a human TROP2-positive cell line.

FIG. 53A is a diagram showing binding to pharyngeal squamous cell cancer cell line FaDu.

FIG. 53B is a diagram showing binding to pancreatic cancer cell line HPAF-II.

FIG. 54 is a diagram showing an ORF nucleotide sequence encoding T2C-0001.

FIG. 55 is a diagram showing an ORF nucleotide sequence encoding T2C-0003.

FIG. 56 is a diagram showing an ORF nucleotide sequence encoding T2C-0005.

FIG. 57 is a diagram showing an ORF nucleotide sequence encoding T2C-0006.

FIG. 58 is a diagram showing the amino acid sequence of T2C-0001.

FIG. 59 is a diagram showing the amino acid sequence of T2C-0003.

FIG. 60 is a diagram showing the amino acid sequence of T2C-0005.

FIG. 61 is a diagram showing the amino acid sequence of T2C-0006.

FIG. 62 is a pair of diagrams showing that anti-TROP2-CD3 bispecific molecules T2C-0001, T2C-0003, T2C-0005, and T2C-0006 bind to a TROP2-positive cell line.

FIG. 62A is a diagram showing binding to pharyngeal squamous cell cancer cell line FaDu.

FIG. 62B is a diagram showing binding to pancreatic cancer cell line HPAF-II.

FIG. 63 is a diagram showing the binding activity of anti-TROP2-CD3 bispecific molecules T2C-0001, T2C-0003, T2C-0005, and T2C-0006 to human CD3 (PBMC).

FIG. 64 is a diagram showing the binding activity of anti-TROP2-CD3 bispecific molecules T2C-0001, T2C-0003, T2C-0005, and T2C-0006 to cynomolgus monkey CD3 (PBMC).

FIG. 65A is a diagram showing TROP2 expressed in pharyngeal squamous cell cancer cell line FaDu.

FIG. 65B is a diagram showing TROP2 expressed in pancreatic cancer cell line HPAF-II.

FIG. 65C is a diagram showing that TROP2 is not expressed in lung cancer cell line Calu-6.

FIG. 66A is a diagram showing that anti-TROP2-CD3 bispecific molecules T2C-0001, T2C-0003, T2C-0005, and T2C-0006 have cytotoxic activity against a pharyngeal squamous cell cancer cell line FaDu in the presence of human PBMC.

FIG. 66B is a diagram showing that anti-TROP2-CD3 bispecific molecules T2C-0001, T2C-0003, T2C-0005, and T2C-0006 have cytotoxic activity against pancreatic cancer cell line HPAF-II in the presence of human PBMC.

FIG. 66C is a diagram showing that anti-TROP2-CD3 bispecific molecules T2C-0001, T2C-0003, T2C-0005, and T2C-0006 exhibit no cytotoxic activity against human lung cancer cell line Calu-6 in the presence of human PBMC.

FIG. 67 is a diagram showing a nucleotide sequence encoding C3E-7078.

FIG. 68 is a diagram showing the amino acid sequence of C3E-7078.

FIG. 69 is a diagram showing a nucleotide sequence encoding C3E-7079.

FIG. 70 is a diagram showing the amino acid sequence of C3E-7079.

FIG. 71 is a diagram showing a nucleotide sequence encoding C3E-7085.

FIG. 72 is a diagram showing the amino acid sequence of C3E-7085.

FIG. 73 is a diagram showing a nucleotide sequence encoding C3E-7086.

FIG. 74 is a diagram showing the amino acid sequence of C3E-7086.

FIG. 75 is a diagram showing a nucleotide sequence encoding C3E-7087.

FIG. 76 is a diagram showing the amino acid sequence of C3E-7087.

FIG. 77 is a diagram showing a nucleotide sequence encoding C3E-7088.

FIG. 78 is a diagram showing the amino acid sequence of C3E-7088.

FIG. 79 is a diagram showing a nucleotide sequence encoding C3E-7089.

FIG. 80 is a diagram showing the amino acid sequence of C3E-7089.

FIG. 81 is a diagram showing a nucleotide sequence encoding C3E-7090.

FIG. 82 is a diagram showing the amino acid sequence of C3E-7090.

FIG. 83 is a diagram showing a nucleotide sequence encoding C3E-7091.

FIG. 84 is a diagram showing the amino acid sequence of C3E-7091.

FIG. 85 is a diagram showing a nucleotide sequence encoding C3E-7092.

FIG. 86 is a diagram showing the amino acid sequence of C3E-7092.

FIG. 87 is a diagram showing a nucleotide sequence encoding C3E-7093.

FIG. 88 is a diagram showing the amino acid sequence of C3E-7093.

FIG. 89 is a diagram showing a nucleotide sequence encoding C3E-7094.

FIG. 90 is a diagram showing the amino acid sequence of C3E-7094.

FIG. 91 is a diagram showing a nucleotide sequence encoding C3E-7095.

FIG. 92 is a diagram showing the amino acid sequence of C3E-7095.

FIG. 93 is a diagram showing a nucleotide sequence encoding the primer HN53R Fw.

FIG. 94 is a diagram showing a nucleotide sequence encoding the primer HN53R Rv.

FIG. 95 is a diagram showing a nucleotide sequence encoding the primer HN53S Fw.

FIG. 96 is a diagram showing a nucleotide sequence encoding the primer HN53S Rv.

FIG. 97 is a diagram showing an ORF nucleotide sequence encoding AXC-0001.

FIG. 98 is a diagram showing the amino acid sequence of AXC-0001.

FIG. 99 is a diagram showing an ORF nucleotide sequence encoding AXC-0002.

FIG. 100 is a diagram showing the amino acid sequence of AXC-0002.

FIG. 101 is a diagram showing an ORF nucleotide sequence encoding MGC-0001.

FIG. 102 is a diagram showing the amino acid sequence of MGC-0001.

FIG. 103 is a diagram showing an ORF nucleotide sequence encoding MGC-0002.

FIG. 104 is a diagram showing the amino acid sequence of MGC-0002.

FIG. 105 shows a list of primers used in the preparation of CDR variants of anti-CD3 antibodies.

FIG. 106-1 is a diagram showing the binding activity of CDR variants of anti-CD3 antibodies to human and cynomolgus monkey CD3 (PBMC).

FIG. 106-2 is a diagram showing the binding activity of CDR variants of anti-CD3 antibodies to human and cynomolgus monkey CD3 (PBMC).

FIG. 107 is a diagram showing the expression of Axl in human lung cancer cell line A549 (A), human pancreatic cancer cell line PANC-1 (B), human pancreatic cancer cell line MIA PaCa-2 (C), human myeloma cell line U266B1 (D), and mantle cell lymphoma cell line Jeko-1 (E).

Each of FIGS. 108A, 108B, and 108C is a diagram showing that anti-Axl CD3 bispecific molecules AXC-0001 and AXC-0002 have cytotoxic activity against Axl-expressing cell lines in the presence of human PBMC. Each of FIGS. 108D and 108E is a diagram showing that anti-Axl CD3 bispecific molecules AXC-0001 and AXC-0002 have no cytotoxic activity against non-Axl-expressing cell lines in the presence of human PBMC.

FIG. 109 is a diagram showing the binding activity of MAG-032 scFv in human lymphoblast fusion cell line T2 cells supplemented with MAGEC1 peptide (A) or DMSO (B).

FIG. 110A is a diagram showing that anti-HLA-A2/MAGEC1-CD3 bispecific molecules MGC-0001 and MGC-0002 have cytotoxic activity against T2 cells supplemented with the MAGEC1 peptide in the presence of human PBMC.

FIG. 110B is a diagram showing that anti-HLA-A2/MAGEC1-CD3 bispecific molecules MGC-0001 and MGC-0002 have no cytotoxic activity against T2 supplemented with DMSO in the presence of human PBMC.

FIG. 111 is a diagram showing the amino acid sequence of MAGEC1 peptide.

FIG. 112 is a diagram showing the amino acid sequence in the CDRH2 region of a CDR variant. The first Xaa and the second Xaa each represent an arbitrary natural amino acid residue.

FIG. 113 is a diagram showing the amino acid sequence in the CDRL2 region of a CDR variant. Xaa represents an arbitrary natural amino acid residue.

FIG. 114 is a diagram showing the amino acid sequence of the variable region of the heavy chain of a CDR variant of C3E-7034. The first Xaa and the second Xaa each represent an arbitrary natural amino acid residue.

FIG. 115 is a diagram showing the amino acid sequence in the variable region of the light chain of a CDR variant of C3E-7034. Xaa represents an arbitrary natural amino acid residue.

FIG. 116 is a diagram showing the amino acid sequence in the variable region of the light chain of a CDR variant of C3E-7035. Xaa represents an arbitrary natural amino acid residue.

FIG. 117 is a diagram showing the amino acid sequence in the variable region of the light chain of a CDR variant of C3E-7036. Xaa represents an arbitrary natural amino acid residue.

EMBODIMENT OF THE INVENTION

1. Definitions

In the present invention, the term "gene" means a nucleotide comprising a nucleotide sequence encoding the amino acids of a protein, or its complementary strand. "Gene" is meant to include, for example, a polynucleotide, an oligonucleotide, DNA, mRNA, cDNA, and cRNA as the nucleotide comprising a nucleotide sequence encoding the amino acids of a protein, or its complementary strand. Such a gene is a single-stranded, double-stranded, triple-stranded, or other multi-stranded nucleotide. "Gene" is also meant to include an aggregate of DNA and RNA strands, a mixture of ribonucleotides (RNAs) and deoxyribonucleotides (DNAs) on one nucleotide strand, and a double-stranded, triple-stranded or other multi-stranded nucleotide comprising such a nucleotide strand. In the present invention, the terms "base sequence" and "nucleotide sequence" have the same meaning.

In the present invention, the term "polynucleotide" has the same meaning as "nucleic acid" and "nucleic acid molecule" and is also meant to include, for example, any DNA, RNA, probe, oligonucleotide, and primer. Such a polynucleotide is a single-stranded, double-stranded, triple-stranded or other multi-stranded polynucleotide. The "polynucleotide" is also meant to include an aggregate of DNA and RNA strands, a mixture of ribonucleotides (RNAs) and deoxyribonucleotides (DNAs) on one polynucleotide strand, and an aggregate of two strands or three or more strands comprising such a polynucleotide strand.

In the present invention, the terms "polypeptide," "peptide," and "protein" have the same meaning.

In the present invention, the term "antigen" is sometimes used to mean "immunogen."

In the present invention, the term "cell" also includes, for example, any cell derived from individual animals, subcultured cells, primary cultured cells, cell lines, recombinant cells, and microbial cells.

In the present invention, the term "antibody" has the same meaning as immunoglobulin. However, the "antibody" used for the anti-CD3 antibody of the present invention means an immunoglobulin having constant and variable regions. The antibody is not particularly limited and may be a natural immunoglobulin or may be an immunoglobulin produced by partial or complete synthesis. The anti-CD3 antibody of the present invention is included in "molecule" described below.

The basic structure of a quaternary antibody is constituted by two identical light (L) chains and two identical heavy (H) chains. Each light chain is linked to a heavy chain by one covalent disulfide bond. The two heavy chains are linked to each other by one or more disulfide bonds depending on the isotypes of the heavy chains. Each of the light and heavy chains has regularly spaced intrachain disulfide bonds. Each of the heavy and light chains contains a constant region which exhibits a very high degree of amino acid sequence similarity and a variable region which exhibits a low degree of amino acid sequence similarity. The light chain has a variable region (VL) at the amino terminus followed by a constant region (CL). The heavy chain has a variable region (VH) at the amino terminus followed by three constant regions (CH1, CH2, and CH3). VL and VH are paired, and CL is aligned with the first constant region (CH1) of the heavy chain. VL and VH are paired to form a single antigen-binding site.

The constant regions of the antibody of the present invention are not particularly limited. Preferably, constant regions derived from a human antibody are used in an antibody of the present invention for the treatment or prevention of diseases in humans. Examples of the heavy chain constant regions in the human antibody include Cγ1, Cγ2, Cγ3, Cγ4, Cμ, Cδ, Cα1, Cα2, and CS. Examples of light chain constant regions in the human antibody include Cκ and Cλ.

Fab is composed of heavy chain CH1 followed by VH, and light chain CL followed by VL. VH and VL each contain complementarity determining regions (CDRs).

Fc is constituted by the carboxyl-terminal regions of the heavy chain constant regions and is a dimer containing CH2 and CH3. The Fc of the present invention may be Fc having a natural sequence or may be a mutated form of Fc containing a mutation in the natural sequence.

The variable region is composed of regions, called hypervariable regions (HVRs), having extreme variability, and relatively invariable regions, called framework regions (FRs), interrupted by hypervariable regions. The natural heavy and light chain variable regions each contain four FRs connected by three hypervariable regions. The hypervariable regions of each chain are kept in close proximity together with the hypervariable regions of another chain by FRs and contribute to the formation of an antigen-binding site in the antibody.

The heavy and light chains of an antibody molecule are known to each have three complementarity determining regions (CDRs). The complementarity determining regions are also called hypervariable domains. These regions are located in the variable regions of the antibody heavy and light chains. These sites have a particularly highly variable primary structure and are usually separated at three positions on the respective primary structures of heavy and light chain polypeptide strands. In the present invention, the complementarity determining regions of the antibody are referred to as CDRH1, CDRH2, and CDRH3 from the amino terminus of the heavy chain amino acid sequence for the complementarity determining regions of the heavy chain and as CDRL1, CDRL2, and CDRL3 from the amino terminus of the light chain amino acid sequence for the complementarity determining regions of the light chain. These sites are close to each other in the three-dimensional structure and determine specificity for the antigen to be bound.

In the present invention, the positions and lengths of CDRs were determined according to IMGT definitions (Developmental and Comparative Immunology 27 (2003) 55-77).

The framework regions (FRs) are variable regions except for CDR residues. Each variable region usually has four FRs, namely, FR1, FR2, FR3, and FR4.

The positions of CDRs and FRs can also be determined according to other definitions well known in the art, for example, IMGT definitions as well as Kabat, Chothia, AbM, and contact definitions.

In the present invention, the term "antigen-binding fragment of the antibody" means a partial antibody fragment that has heavy and light chain variable regions and has binding activity to an antigen. Examples of the "antigen-binding fragments in the antibody" include, but are not limited to, antigen-binding fragments such as Fab, $F(ab')_2$, scFv, Fab', Fv, and single-domain antibody (sdAb). Such an antigen-binding fragment of an antibody may be obtained by treating a full-length molecule of an antibody protein with an enzyme such as papain or pepsin, or may be a recombinant protein produced in an appropriate host cell using a recombinant gene.

In the present invention, the "site" to which an antibody is bound, i.e., the "site" recognized by an antibody, means a partial peptide or partial higher-order structure on an antigen that is bound or recognized by the antibody.

In the present invention, such a site is also referred to as an epitope or an antibody binding site.

In the present invention, the term "antibody mutant" means a polypeptide that has an amino acid sequence derived from the amino acid sequence of the original antibody by substitution, deletion, and/or addition ("addition" includes insertion) (hereinafter, collectively referred to as a "mutation") of amino acid(s) and binds to the CD3 of the present invention. The number of mutated amino acids in such an antibody mutant is 1, 2, 3, 4, 5, 6, 7, 8, 9, 10, 12, 15, 20, 25, 30, 40, or 50. Such an antibody mutant can be "antibody" of the present invention.

In the present invention, the term "more" in "1 or more" refers to a number from 2 to 10.

In the present specification, the term "molecule" is a molecule comprising the aforementioned antibody or antigen-binding fragment of the antibody and also includes multispecific molecules formed by antibodies or a plurality of antigen-binding fragments derived therefrom.

In the present specification, the term "molecule which is multispecific" has the same meaning as a "multispecific molecule." Such a multispecific molecule is not particularly limited as long as the molecule is capable of binding to a plurality of epitopes different from each other on one molecule, and/or epitopes different from each other on two or more molecules. A molecule which is multispecific also includes an antibody comprising heavy chain variable (VH) and light chain variable (VL) regions. Examples of such multispecific molecules include, but are not limited to, a full-length antibody molecule having two or more types of heavy chains and two or more types of light chains, i.e., an IgG-type multispecific molecule, and a molecule consisting of two or more types of antigen-binding fragments having VLs and VHs, i.e., a molecule derived by a combination of Fab, Fab', Fv, scFv, sdAb, etc. (i.e., tandem scFv, diabodies, single chain diabodies, and triabodies). In addition, a molecule formed by genetically or chemically linking a protein having antigen binding activity without an immunoglobulin skeleton, to an antigen-binding fragment is also included in the multispecific molecule.

Examples of activities or properties realized by an anti-CD3 antibody of the present invention, an antigen-binding fragment of an antibody of the present invention, or a multispecific molecule of the present invention can include biological activities or physicochemical properties and can specifically include various biological activities, binding activity against an antigen or an epitope, stability during production or storage, and thermal stability.

In the present invention, the phrase "hybridizing under stringent conditions" means hybridization under conditions involving hybridization at 65° C. in a solution containing 5×SSC, followed by washing at 65° C. for 20 minutes in an aqueous solution containing 2×SSC-0.1% SDS, at 65° C. for 20 minutes in an aqueous solution containing 0.5×SSC-0.1% SDS, and at 65° C. for 20 minutes in an aqueous solution containing 0.2×SSC-0.1% SDS, or hybridization under equivalent conditions. SSC means an aqueous solution of 150 mM NaCl-15 mM sodium citrate, and n×SSC means SSC with n times the concentration.

In the present invention, the term "cytotoxicity" refers to some pathological change brought about in cells and means not only direct trauma but any structural or functional damage to cells, including DNA cleavage, formation of base dimers, chromosomal breaks, damage to mitotic apparatus, and reductions in the activities of various enzymes.

In the present invention, the term "cytotoxic activity" means activity that causes the cytotoxicity mentioned above.

In the present invention, the term "antibody dependent cellular cytotoxicity (ADCC) activity" means the effect or activity of damaging target cells such as tumor cells by NK cells via antibodies.

In the present invention, the term "cytotoxic activity by the redirection of T cells" means the cytotoxicity is caused by a multispecific molecule comprising an anti-tumor antigen antibody and an anti-CD3 antibody. Specifically, the term means that the anti-tumor antigen antibody binds to a target tumor cell while the anti-CD3 antibody binds to a T cell so that the target tumor cell and the T cell come closer to each other to induce T cell activation-mediated cytotoxicity. The molecule can be contained in a pharmaceutical composition.

2. Antigenic Protein CD3 (CD3 Complex)

In the present invention, the term "CD3" has the same meaning as CD3 protein.

CD3 is expressed, as a portion of a multimolecular T cell receptor complex, on T cells and is a complex of 5 types of polypeptide (γ, δ, ε, ζ, and η) chains (with molecular weights 25000 to 28000, 21000, 20000, 16000, and 22000, respectively).

The CD3 used in the present invention can be prepared by purification or isolation from animal tissues (including body fluids), cells derived from tissues, or cultures of cells, gene recombination, in vitro translation, chemical synthesis, etc.

The nucleotide sequence of a cDNA encoding human CD3ε is registered with GenBank under Accession No. NM_000733.3. The nucleotide sequence of a cDNA encoding cynomolgus monkey CD3 is registered with GenBank under Accession No. NM_001283615.1. The amino acid sequence of human CD3ε is described in SEQ ID NO: 1 of the Sequence Listing.

The CD3ε cDNA can be obtained using, for example, using the so-called PCR method in which a polymerase chain reaction (hereinafter, referred to as "PCR") (Saiki, R. K., et al., Science (1988) 239, 487-489) is performed using a cDNA library from CD3ε mRNA-expressing organs as a template and using primers capable of specifically amplifying the CD3ε cDNA.

A nucleotide sequence encoding a protein that consists of an amino acid sequence derived from the amino acids of CD3 by the substitution, deletion, or addition of 1 or more amino acids and has biological activities equivalent to CD3 is also included in the nucleotide sequence of the CD3 gene. A protein that consists of an amino acid sequence derived from the amino acid sequence of CD3 by the substitution, deletion, or addition of 1 or more amino acids and has biological activities equivalent to CD3 is also included in the CD3.

A polynucleotide hybridized under stringent conditions to a polynucleotide consisting of a nucleotide sequence complementary to the nucleotide sequence encoding human or cynomolgus monkey CD3ε, and encoding a protein having biological activities equivalent to CD3ε is also included in the CD3ε cDNA. In addition, splicing variants transcribed from human or cynomolgus monkey CD3ε gene loci, or polynucleotides hybridized thereto under stringent conditions and encoding a protein having biological activities equivalent to CD3ε are also included in the CD3ε cDNA.

3. Anti-CD3 Antibody (3-1) Classification of Antibody

An anti-CD3 antibody of the present invention and an antigen-binding fragment of the antibody (hereinafter, also referred to as the antibody, etc. of the present invention) may be either a monoclonal or a polyclonal antibody. Examples of monoclonal antibodies of the present invention include non-human animal-derived antibodies (non-human animal antibodies), human antibodies, chimeric antibodies, and humanized antibodies.

Examples of non-human animal antibodies include antibodies derived from vertebrates such as mammals and birds. Examples of the mammal-derived antibodies include rodent-derived antibodies such as mouse antibodies and rat antibodies. Examples of bird-derived antibodies include chicken antibodies. An example of an anti-human CD3 rat monoclonal antibody is C3-147 [Example 1)-7] of the present invention.

Examples of chimeric antibodies include, but are not limited to, antibodies comprising non-human animal antibody-derived variable regions bound to human antibody (human immunoglobulin) constant regions.

Examples of humanized antibodies can include, but are not limited to, human antibodies (human immunoglobulin variable regions) grafted to CDRs in variable regions of non-human animal antibodies, a human antibody grafted to CDRs as well as to partial sequences of framework regions in non-human animal antibodies, and antibodies having human antibody amino acids substituted for one or more non-human animal antibody-derived amino acids in any of these humanized antibodies. Examples of CDRs in variable regions of non-human animal antibodies include CDRH1 to CDRH3 in the heavy chain variable region and CDRL1 to CDRL3 in the light chain variable region derived from rat anti-CD3 antibody C3E-7000 of the present invention, and CDRs derived from the amino acid sequences of these CDRs by substitution of 1 or 2 amino acids by different amino acids.

The human antibody is not particularly limited as long as the antibody preferably binds to human CD3 and more preferably binds to human CD3 and to cynomolgus monkey CD3. Examples also include human antibodies binding to the same site as in the humanized antibodies of the present invention. Examples include human antibodies binding to the same site as C3E-7034.

Preferably, the antibody, etc. of the present invention binds to human CD3. More preferably, the antibody, etc. of the present invention also has binding activity to cynomolgus monkey CD3.

The antibody, etc. of the present invention may be comprised of portions derived from a plurality of different antibodies as long as the antibody binds to human CD3 and also binds to cynomolgus monkey CD3. Examples of these antibodies include antibodies comprising heavy and/or light chains exchanged among a plurality of different antibodies, antibodies comprising full-length heavy and/or light chains exchanged among themselves, antibodies comprising variable or constant regions exchanged among themselves, and antibodies comprising all or some CDRs exchanged among themselves. The heavy and light chain variable regions of a chimeric antibody may be derived from different antibodies of the present invention. CDRH1 to CDRH3 and CDRL1 to CDRL3 in the heavy and light chain variable regions of the humanized antibody may be derived from two or more different antibodies of the present invention. CDRH1 to CDRH3 and CDRL1 to CDRL3 in the heavy and light chain variable regions of the human antibody may be a combination of CDRs carried by two or more different antibodies of the present invention.

Examples of the isotype of the monoclonal antibody of the present invention can include, but are not particularly limited to, IgGs such as IgG1, IgG2, IgG3, and IgG4, IgM, IgAs such as IgA1 and IgA2, IgD, and IgE.

The isotype and subclass of the monoclonal antibody can be determined using, for example, an Ouchterlony test, an enzyme-linked immunosorbent assay (ELISA), or a radio immunoassay (RIA). A commercially available kit for identification (e.g., Rat Immunoglobulin Isotyping ELISA Kit (BD Pharmingen) may be used.

(3-2) Binding Specificity of Anti-CD3 Antibody

The antibody, etc. of the present invention recognizes CD3. In other words, the antibody, etc. of the present invention binds to CD3. The antibody, etc. of the present invention preferably binds to human CD3 and to monkey CD3, and more preferably binds to human CD3 and to cynomolgus monkey CD3.

More specifically, the antibody of the present invention and antigen-binding fragment thereof, and their variable regions, bind to an Ig-like domain present in the extracellular region of the ε chain (FIG. 1, SEQ ID NO: 1) of the human CD3 complex. Furthermore, these also bind to an Ig-like domain present in the extracellular region of the ε chain of the cynomolgus monkey CD3 complex.

Epitopes present in the extracellular region of the ε chain (FIG. 1, SEQ ID NO: 1) of the human CD3 complex bound by the antibody, etc. of the present invention contain the following amino acids:

Ser55, Glu56, Leu58, Trp59, Asn65, Ile66, Ser77, Asp78, Arg101, Gly102, Ser103, Lys104, and Pro105.

Preferably, the antibody, etc. of the present invention can maintain binding to human CD3 by binding to an epitope region containing at least 7 amino acids selected from these 13 amino acids.

When an antibody is adjacent to these amino acids within a distance of 4 angstroms, such an antibody can be confirmed to have the same epitope specificity as that of the antibody, etc. of the present invention. On the other hand, among epitope amino acids Arg101, Gly102, Ser103, Lys104, and Pro105 are present epitope residues that interact with anti-CD3 antibody OKT3 or UCHT1 as known in the art (Lars Kjer-Nielsen et al., PNAS (2004); and Kelly L Arnett et al., PNAS (2004)). However, OKT3 or UCHT1 binds to human CD3, but does not bind to cynomolgus monkey CD3.

In the present invention, "recognition," i.e., "binding," means binding which is not non-specific adsorption. Examples of criteria for determining whether recognition is achieved or not, i.e., binding is achieved or not, can include a dissociation constant (hereinafter, referred to as "KD") Preferably, the antibody, etc. of the present invention has a $K_D$ value of $1\times10^{-5}$ M or lower, $5\times10^{-6}$ M or lower, $2\times10^{-6}$ M or lower, or $1\times10^{-6}$ M or lower for CD3.

In the present invention, the binding of the antibody to the antigen can be assayed or determined using a biomolecular interaction analysis system (e.g., SPR or BLI), ELISA, or RIA. The binding of the antibody to the antigen expressed on a cell surface can be assayed by flow cytometry.

The SPR (surface plasmon resonance analysis) method is used as an analytical approach for determining a dissociation constant (KD value), etc. as an index for affinity by measuring the association rate constant (ka value) and the dissociation rate constant (kd value) by kinetic analysis. Examples of equipment used in SPR analysis include BIAcore™ (manufactured by GE Healthcare), ProteOn™ (manufactured by Bio-Rad Laboratories), SPR-Navi™ (manufactured by BioNavis), Spreeta™ (manufactured by Texas Instruments Inc.), SPRi-Plex II™ (manufactured by Horiba, Ltd.), and Autolab SPR™ (manufactured by Metrohm).

BLI (biolayer interferometry) is a method which involves measuring biomolecular interactions using biolayer interference. Examples of equipment used in BLI interaction analysis include the Octet system (manufactured by Pall ForteBio Corp.).

ELISA is a method which involves capturing an antigen or an antibody of interest contained in a sample solution using a specific antibody or antigen, while detecting and quantifying the antigen or antibody of interest through the use of enzymatic reaction. An enzyme-labeled antigen or antibody is incorporated into the reaction system, and the enzyme activity is detected. For enzyme activity detection, a substrate whose absorption spectrum is changed by the reaction is used, and the absorption spectrum is digitized by absorbance measurement.

Cell-ELISA is a method which involves capturing an analyte on the cell surface on a cell-by-cell basis, while detecting and quantifying the analyte through the use of an enzymatic reaction.

RIA (radio immunoassay) can quantify an antibody by labeling the antibody with a radioactive material and measuring radioactivity from the antibody.

Flow cytometry is an approach used to optically analyze individual cells by dispersing fine cells in a fluid and streaming a thin stream of the fluid. A fluorescent dye-labeled antibody binds to the cell surface of an antigen through an antigen-antibody reaction, and the number of cells bound to the antibody is measured using fluorescence intensity which indicates the antigen binding activity of the antibody.

As mentioned above, an antibody, etc. binding to human CD3 and to cynomolgus monkey CD3 can be subjected to various tests of efficacy or safety using primates, particularly, cynomolgus monkeys, which is essential for the nonclinical development (preclinical development) of pharmaceutical products and thus preferred. Also, an antibody, etc. binding to human CD3 and to cynomolgus monkey CD3 has cytotoxic activity and is useful, either alone or as a molecule of the present invention, in the treatment or prevention of diseases such as cancers in humans and cynomolgus monkeys. Pharmaceutical compositions are described below.

An antibody, etc. of the present invention binding to human CD3 and to cynomolgus monkey CD3 does not bind to mouse CD3. Therefore, various assays or immunohistochemical tests using human CD3 gene-transfected mouse cells, tissues, or individuals (including transgenic animals, knock-out animals, and knock-in animals) and the antibody, etc. can be carried out without being influenced by the CD3 of the host mice. Thus, the antibody, etc. is preferred for use in research and nonclinical development on mice of drugs, animal drugs, and diagnostic drugs comprising the antibody, etc.

(3-3) Monoclonal Antibody

The present invention provides monoclonal antibodies. These monoclonal antibodies include, for example, non-human animal-derived monoclonal antibodies such as rat, mouse, rabbit, chicken, and fish antibodies, chimeric antibodies, humanized antibodies, human antibodies, antigen-binding fragments thereof, antibody mutants of these antibodies or antigen-binding fragments, and variants of these antibodies or antigen-binding fragments.

For example, C3-147 obtained by the method described in Example 1 is an anti-CD3 rat monoclonal antibody.

The nucleotide sequence of a DNA encoding the heavy chain variable region of C3-147 is described in SEQ ID NO: 6 (FIG. 14) of the Sequence Listing, and its amino acid sequence is described in SEQ ID NO: 7 (FIG. 15). The nucleotide sequence of a DNA encoding the light chain variable region of C3-147 is described in SEQ ID NO: 8 (FIG. 16) of the Sequence Listing, and its amino acid sequence is described in SEQ ID NO: 9 (FIG. 17).

The antibody mutant of the present invention preferably may exhibit, for example, reduced sensitivity to protein degradation or oxidation, improved or maintained biological activities or functions, suppressed reduction or deterioration of such biological activities or functions, an improved ability to bind to antigen(s), or physicochemical or functional properties imparted thereto. It is commonly known that a side chain of a specific amino acid in a protein can be altered, thereby altering an activity or function of the protein. Examples of such alterations include deamidation of a side chain of aspartate and isomerization of a side chain of aspartate. Antibody mutants of the present invention include those in which one or more amino acids are substituted with other amino acids to prevent such alterations.

Examples of these antibody mutants of the present invention include antibodies having an amino acid sequence derived from the amino acid sequence of the original antibody by conservative amino acid substitution. Conservative amino acid substitution is substitution that occurs in an amino acid group related to amino acid side chains.

Preferred amino acid groups are as follows: an acidic group including aspartic acid and glutamic acid; a basic group including lysine, arginine, and histidine; a nonpolar group including alanine, valine, leucine, isoleucine, proline, phenylalanine, methionine, and tryptophan; and an uncharged polar family including glycine, asparagine, glutamine, cysteine, serine, threonine, and tyrosine. Other preferred amino acid groups are as follows: an aliphatic hydroxy group including serine and threonine; an amide-containing group including asparagine and glutamine; an aliphatic group including alanine, valine, leucine, and isoleucine; and an aromatic group including phenylalanine, tryptophan, and tyrosine. Amino acid substitution in an antibody mutant is preferably performed without reducing the antigen binding activity of the original antibody.

The present invention also encompasses an antibody mutant having an amino acid sequence, which is derived from the amino acid sequence composed of an antibody or antigen-binding fragment thereof according (1) mentioned above, e.g., C3-147, in which a conservative amino acid substitution and/or some other amino acid mutation occurs (or is performed); a mouse antibody, a rat antibody, a chimeric antibody, a humanized antibody, or a human antibody composed of CDRs having an amino acid sequence in which a conservative amino acid mutation and/or some other amino acid mutation occurs (or is performed) in the amino acid sequence of any of CDRH1 to CDRH3 and CDRL1 to CDRL3 derived from an antibody or antigen-binding fragment thereof according (1) mentioned above, e.g., C3-147; an antigen-binding fragment of any of these antibody mutants and mutated antibodies; and a molecule comprising such an antibody mutant, mutated antibodies or antigen-binding fragment thereof.

(3-4) Antigen-Binding Fragment of Anti-CD3 Antibody

According to one aspect, the present invention provides an antigen-binding fragment of an anti-CD3 antibody of the present invention. An antigen-binding fragment of the antibody means a fragment that maintains at least antigen binding activity among the functions of the antibody, or a variant thereof. Examples of functions of the antibody generally include antigen binding activity, antigen activity-regulating activity, antibody dependent cellular cytotoxic activity, and complement dependent cytotoxic activity. Examples of functions of an antibody, etc. of the present invention and a multispecific molecule comprising the antibody, etc. of the present invention include the redirection of T cells, the activation of T cells, and cytotoxic activity against cancer cells by the activation of T cells.

The antigen-binding fragment of the antibody is not particularly limited as long as the fragment of the antibody maintains at least antigen binding activity among the activities of the antibody. Examples include, but are not limited to, Fab, Fab', $F(ab')_2$, Fv, single chain Fv (scFv) comprising heavy and light chain Fvs linked via an appropriate linker, and single domain antibody (sdAb). The antigen-binding fragment of the antibody of the present invention is also meant to include a molecule comprising the antigen-binding fragment of the antibody of the present invention as well as other portions, such as scFv retaining a linker portion.

A molecule that is derived from an antibody protein by the deletion of 1 or more or more amino acids at its amino terminus and/or carboxyl terminus and retains at least a portion of the functions of the antibody is also encompassed in the meaning of the antigen-binding fragment of the antibody. Such a variant of an antigen-binding fragment of an antibody is also encompassed by the antibody of the present invention or antigen-binding fragment thereof, or a variant (described later) of the antibody or antigen-binding fragment.

According to one aspect, the antigen-binding fragment of the antibody of the present invention is scFv. The scFv is obtained by linking the heavy and light chain variable regions of the antibody via a polypeptide linker (Pluckthun A., The Pharmacology of Monoclonal Antibodies 113, Rosenburg and Moore, ed., Springer Verlag, New York, 269-315 (1994); and Nature Biotechnology (2005), 23, 1126-1136). Also, tandem scFv comprising two scFvs linked via a polypeptide linker can be used as a bispecific molecule. Alternatively, triabodies and such comprising three or more scFvs may be used as a multispecific molecule.

The antibody of the present invention may be an antibody that has a single heavy chain variable region and has no light chain sequence. Such an antibody, called a single domain antibody (sdAb) or a nanobody, has been reported to retain the ability to bind to an antigen (Muyldemans S. et al., Protein Eng., (1994), 7 (9), 1129-35; and Hamers-Casterman C. et al., Nature (1993), 363 (6428), 446-448). These antibodies are also encompassed in the meaning of an antigen-binding fragment of an antibody according to the present invention.

The present invention also includes a single chain immunoglobulin comprising full-length heavy and light chain sequences of the antibody linked via an appropriate linker (Lee, H-S, et al., Molecular Immunology (1999) 36, 61-71; and Shirrmann, T. et al., mAbs (2010), 2 (1), 1-4). Such a single chain immunoglobulin can be dimerized to retain a structure and activities similar to those of the antibody, which is originally a tetramer.

(3-5) Molecules Having Antigen Binding Activity

The molecule of the present invention comprises the anti-CD3 antibody of the present invention or antigen-binding fragment thereof.

The molecule of the present invention can further comprise, for example, a signal sequence, a tag for purification, amino-terminal Gly, a drug linker portion of ADC, an albumin-binding polypeptide, a polymer such as PEG, an antibody other than the anti-CD3 antibody, an antigen-binding fragment thereof, and a protein having antigen binding activity without having an immunoglobulin skeleton, which will be described below.

The molecule of the present invention binds to human CD3 and to cynomolgus monkey CD3.

The molecule of the present invention includes a multispecific molecule described below.

The molecule of the present invention may be a form of being introduced in to a cell or a form of being displayed on the cell surface, such as CAR-T, etc.

(3-6) Multispecific Molecules and Bispecific Molecules

The multispecific molecule of the present invention is a molecule having two or more antigen-binding sites. Specifically, the multispecific molecule of the present invention is a molecule capable of binding to two or more epitopes different from each other on one molecule, or epitopes different from each other on two or more molecules, and comprises a plurality of antigen-binding fragments different from each other. Examples of multispecific molecules include, but are not limited to, IgG-type multispecific molecules and multispecific molecules having two or more types of variable regions, for example, antibody fragments such as tandem scFv, single-chain diabodies, diabodies, triabodies, and antibody fragments linked by a covalent bond or a noncovalent bond. The multispecific molecule may contain Fc.

A multispecific molecule of the present invention comprises an anti-CD3 antibody of the present invention or antigen-binding fragment of the antibody. The multispecific molecule of the present invention comprises an antibody, etc. of the present invention and 1 or 2 or more additional antibodies or antigen-binding fragments of antibodies. Examples of an antigen-binding fragment of an antibody include Fab, F(ab)', Fv, scFv, and sdAb.

The multispecific molecule of the present invention specifically binds to CD3 or may further bind to a target such as an Fc receptor on effector cells.

Preferred examples of multispecific molecules of the present invention include bispecific molecules. The term "bispecific" means of the ability to bind to two epitopes different from each other on one molecule, or epitopes different from each other on two molecules. An antibody or an antigen-binding fragment having such bispecificity is encompassed by the present invention. A bispecific molecule of the present invention binds to CD3 and binds to an epitope that is absent from CD3 but present in another antigen. More specifically, such a bispecific molecule (i) binds to an epitope on CD3 (epitope 1) and (ii) binds to an epitope different from the epitope 1 on CD3 (epitope 2), or binds to an epitope on an antigen other than CD3 (epitope 3).

For example, in a tandem scFv-type bispecific molecule typified by BiTE, an antigen-binding site in the heavy chain variable region of a first antibody and an antigen-binding site in the light chain variable region of the first antibody are linked either via a linker or directly without a linker to form a first polypeptide. Also, an antigen-binding site in the heavy chain variable region of a second antibody and an antigen-binding site in the light chain variable region of the second antibody are linked either via a linker or directly without a linker to form a second polypeptide. The first polypeptide and the second polypeptide are linked either via a linker or directly without a linker. Alternatively, the first polypeptide and the second polypeptide may be linked via an additional molecule.

In a diabody-type bispecific molecule, an antigen-binding site in the heavy chain variable region of a first antibody and an antigen-binding site in the light chain variable region of a second antibody are linked either via a linker or directly without a linker. Also, an antigen-binding site in the light chain variable region of the first antibody and an antigen-binding site in the heavy chain variable region of the second antibody are linked either via a linker or directly without a linker. Also, a bispecific molecule may be prepared by the further dimerization of diabody-type bispecific molecules. In addition, the diabody-type bispecific molecule may be linked to one single chain or both chains of Fc via a linker (diabody-Fc-type bispecific molecule).

In a dual scFv-type bispecific molecule, two scFvs to be bound to different epitopes are linked to the two chains of dimeric Fc, either via linkers or directly without linkers. Alternatively, two types of scFvs to be bound to different epitopes are linked to CH and CL, respectively, via linkers and further linked to two chains of dimeric Fc, respectively, via linkers.

In an IgG-type bispecific molecule, two Fabs to be bound to different epitopes are linked to the two chains of dimeric Fc, either via linkers or directly without linkers.

Alternatively, a bispecific molecule of the present invention may be a bispecific antibody in which Fab and scFv to be bound to different epitopes are linked to the two chains of dimeric Fc, either via linkers or directly without linkers. Alternatively, a bispecific molecule of the present invention may be a bispecific molecule in which Fab in the first antibody and scFv in the second antibody are linked to the two chains of dimeric Fc via linkers.

The scFv and the Fab contained in a bispecific molecule of the present invention are preferably scFv and Fab of a humanized antibody or a human antibody, and the Fc is preferably Fc of a human antibody.

In a variable region comprised in a bispecific antibody of the present invention, a heavy chain variable region and a light chain variable region can bind in this order, or a light chain variable region and a heavy chain variable region can bind in this order, from the amino-terminal. A bispecific antibody of the present invention optionally has a linker between both variable regions, and can (optionally) have a glycine residue at the amino-termin of a variable region which is placed on the amino terminal side. A bispecific antibody of the tandem scFv type of the present invention optionally has a linker, FLAG-tag, and/or HIS-tag at the carboxyl terminus of a variable region which is placed on the carboxyl terminal side. Preferable examples of bispecific antibodies of the present invention include a bispecific antibody, in which a heavy chain variable region, a first linker, a light chain variable region, a second linker, a FLAG-tag, and His-tag bound in this order from amino terminus.

The linker also includes a single chain polypeptide or a single chain oligopeptide, or synthetic products such as PEG, nucleotides, sugar chains, and compounds. In addition, any linker known in the art may be used without particular limitations as long as the linker links two polypeptides.

The length of the linker is from 5 to 30 amino acids for, for example, a peptide linker. When the bispecific molecule contains a plurality of linkers, all the peptide linkers used may have the same length or the peptide linkers used may have different lengths.

An example of a peptide linker is a (Gly.Gly.Gly.Gly.Ser) repeating unit. One or more amino acid residues other than Gly and Ser may be added.

(3-7) Humanized Anti-CD3 Antibodies

According to one aspect, the present invention provides a humanized anti-CD3 antibody or an antigen-binding fragment thereof.

Examples of humanized antibodies of the present invention include human-derived antibodies containing only complementarity determining regions (CDRs) (Nature (1986) 321, 522-525), and human antibodies grafted to CDR sequences and to some amino acid residues of framework regions by CDR grafting (International Publication No. WO1990/07861A1).

Preferably, the heavy chain variable region contained in a humanized anti-CD3 antibody of the present invention or an antigen-binding fragment of the antibody retains CDRH1 consisting of the amino acid sequence represented by SEQ ID NO: 26 (FIG. 24) (GVTFNYYG), and CDRH2 consisting of the amino acid sequence represented by SEQ ID NO: 98 (FIG. 112) (IT Xaa Xaa GGRI) (wherein the first Xaa and the second Xaa each represent an arbitrary natural amino acid residue. Hereinafter, the first Xaa is also referred to as $X_1$, and the second Xaa is also referred to as $X_2$), and CDRH3 consisting of the amino acid sequence represented by SEQ ID NO: 28 (FIG. 26) (TLDGRDGWVAY).

Also preferably, the light chain variable region contained in a humanized anti-CD3 antibody of the present invention or an antigen-binding fragment of the antibody retains CDRL1 consisting of the amino acid sequence represented by SEQ ID NO: 29 (FIG. 27) (TGNIGSNY), CDRL2 consisting of the amino acid sequence represented by SEQ ID NO: 99 (FIG. 113) (R Xaa D) (wherein Xaa represents an arbitrary natural amino acid residue. Hereinafter, Xaa of CDRL2 is also referred to as $X_3$), and CDRL3 consisting of the amino acid sequence represented by SEQ ID NO: 31 (FIG. 29) (QSYSSGFI).

In CDRH2 (ITX$_1$X$_2$GGRI) mentioned above, preferably, $X_1$ is selected from a group consisting of A, E, G, H, I, L, T, V, R, and S, and $X_2$ is S; or $X_1$ is N, and $X_2$ is selected from a group consisting of E, R, F, Y, L, V, I, K, and T.

In CDRL2 (RX$_3$D) mentioned above, preferably, $X_3$ is selected from a group consisting of Q, A, G, S, N, and D.

In CDRH2 (ITX$_1$X$_2$GGRI) mentioned above, more preferably, $X_1$ is selected from a group consisting of R and S, and $X_2$ is S.

In CDRL2 (RX$_3$D) mentioned above, more preferably, $X_3$ is selected from a group consisting of Q, A, G, S, N, and D.

Preferred examples of heavy chain variable regions contained in such humanized anti-CD3 antibodies of the present invention or antigen-binding fragments of the antibody include a heavy chain variable region comprising the amino acid residues represented by SEQ ID NO: 100 (FIG. 114)

Also, preferred examples of light chain variable regions contained in humanized anti-CD3 antibodies of the present invention or antigen-binding fragments of the antibody include a light chain variable region comprising the amino acid residues represented by SEQ ID NO: 101 (FIG. 115), SEQ ID NO: 102 (FIG. 116), or SEQ ID NO: 103 (FIG. 117)

Specific preferred examples of heavy chain variable regions contained in humanized anti-CD3 antibodies of the present invention or antigen-binding fragments of the antibody include a heavy chain variable region which retains CDRH1 consisting of the amino acid sequence represented by SEQ ID NO: 26 (FIG. 24) (GVTFNYYG), CDRH2 consisting of the amino acid sequence represented by SEQ ID NO: 27 (FIG. 25) (ITNSGGRI), and CDRH3 consisting of the amino acid sequence represented by SEQ ID NO: 28 (FIG. 26) (TLDGRDGWVAY).

Specific preferred examples of light chain variable regions contained in humanized anti-CD3 antibodies of the present invention or antigen-binding fragments of the antibody include a light chain variable region which retains CDRL1 consisting of the amino acid sequence represented by SEQ ID NO: 29 (FIG. 27) (TGNIGSNY), CDRL2 consisting of the amino acid sequence represented by SEQ ID NO: 30 (FIG. 28) (RDD), and CDRL3 consisting of the amino acid sequence represented by SEQ ID NO: 31 (FIG. 29) (QSYSSGFI).

In the present invention, the positions and lengths of CDRs were determined according to IMGT definitions (Developmental and Comparative Immunology 27 (2003) 55-77).

Specific examples of heavy chain variable regions of the present invention include amino acid sequence comprising amino acid residues of SEQ ID NO: 16.

Specific examples of light chain variable regions of the present invention include an amino acid sequence comprising amino acid residues of SEQ ID NO: 17, 20 or 23.

Specific preferred examples of humanized anti-CD3 antibodies of the present invention or antigen-binding fragments of the antibody include an antibody or an antigen-binding fragment of the antibody comprising a heavy chain variable region comprising the 2nd through 119th amino acid residues of SEQ ID NO: 60 and a light chain variable region comprising the 135th through 241st amino acid residues of SEQ ID NO: 60, an antibody or an antigen-binding fragment of the antibody comprising a heavy chain variable region comprising the 2nd through 119th amino acid residues of SEQ ID NO: 64 and a light chain variable region comprising the 135th through 241st amino acid residues of SEQ ID NO: 64, an antibody or antigen-binding fragment of the antibody comprising a heavy chain variable region comprising the 2nd through 119th amino acid residues of SEQ ID NO: 66 and a light chain variable region comprising the 135th through 243rd amino acid residues of SEQ ID NO: 66, an antibody or antigen-binding fragment of the antibody comprising a heavy chain variable region comprising the 2nd through 119th amino acid residues of SEQ ID NO: 68 and a light chain variable region comprising the 135th through 243rd amino acid residues of SEQ ID NO: 68, an antibody or antigen-binding fragment of the antibody comprising a heavy chain variable region comprising the 2nd through 119th amino acid residues of SEQ ID NO: 70 and a light chain variable region comprising the 135th through 243rd amino acid residues of SEQ ID NO: 70, an antibody or antigen-binding fragment of the antibody comprising a heavy chain variable region comprising the 2nd through 119th amino acid residues of SEQ ID NO: 72 and a light chain variable region comprising the 135th through 243rd amino acid residues of SEQ ID NO: 72, an antibody or antigen-binding fragment of the antibody comprising a heavy chain variable region comprising the 2nd through 119th amino acid residues of SEQ ID NO: 74 and a light chain variable region comprising the 135th through 243rd amino acid residues of SEQ ID NO: 74, an antibody or antigen-binding fragment of the antibody comprising a heavy chain variable region comprising the 2nd through 119th amino acid residues of SEQ ID NO: 76 and a light chain variable region comprising the 135th through 243rd amino acid residues of SEQ ID NO: 76, an antibody or antigen-binding fragment of the antibody comprising a heavy chain variable region comprising the 2nd through 119th amino acid residues of SEQ ID NO: 78 and a light chain variable region comprising the 135th through 243rd amino acid residues of SEQ ID NO: 78, an antibody or antigen-binding fragment of the antibody comprising a heavy chain variable region comprising the 2nd through 119th amino acid residues of SEQ ID NO: 80 and a light chain variable region comprising the 135th through 243rd amino acid residues of SEQ ID NO: 80, an antibody or antigen-binding fragment of the antibody comprising a heavy chain variable region comprising the 2nd through 119th amino acid residues of SEQ ID NO: 82 and a light chain variable region comprising the 135th through 243rd amino acid residues of SEQ ID NO: 82, or an antibody or antigen-binding fragment of the antibody comprising a heavy chain variable region comprising the 2nd through 119th amino acid residues of SEQ ID NO: 84 and a light chain variable region comprising the 135th through 243rd amino acid residues of SEQ ID NO: 84.

Specific examples of humanized anti-CD3 antibodies or antigen-binding fragments of the antibody of the present invention include an antibody or antigen-binding fragment of an antibody, wherein the antibody or antigen-binding fragment comprises a heavy chain variable region including an amino acid sequence represented by SEQ ID NO: 16, a linker, and a light chain variable region including an amino acid sequence represented by any one of SEQ ID NOs: 17, 20, and 23.

In variable regions comprised in antibodies or antigen-binding fragments of the antibodies of the present invention, a heavy chain variable region and a light chain variable region can bind in this order, or a light chain variable region and a heavy chain variable region can bind in this order, from the amino-terminal. The variable regions can comprise a glycine residue at their amino-termini. A linker, FLAG-tag, and/or HIS-tag can bind at the end of carboxyl termini of the variable regions.

Specific preferred examples of humanized anti-CD3 antibodies of the present invention or antigen-binding fragments of the antibody include an antibody or an antigen-binding fragment of the antibody comprising the 2nd through 243rd amino acid residues of SEQ ID NO: 19, an antibody or an antigen-binding fragment of the antibody comprising the 2nd through 243rd amino acid residues of SEQ ID NO: 22, and an antibody or an antigen-binding fragment of the antibody comprising the 2nd through 241st amino acid residues of SEQ ID NO: 25.

More specific preferred examples of humanized anti-CD3 antibodies of the present invention or antigen-binding fragments of the antibody include an antibody (Clone ID: C3E-7078) or an antigen-binding fragment of the antibody comprising the 1st through 243rd amino acid residues of SEQ ID NO: 60 (FIG. 68), an antibody (Clone ID: C3E-7085) or an antigen-binding fragment of the antibody comprising the 1st through 241st amino acid residues of SEQ ID NO: 64 (FIG. 72), an antibody (Clone ID: C3E-7086) or an antigen-binding fragment of the antibody comprising the 1st through 243rd amino acid residues of SEQ ID NO: 66 (FIG. 74), an antibody (Clone ID: C3E-7087) or an antigen-binding fragment of the antibody comprising the 1st through 243rd amino acid residues of SEQ ID NO: 68 (FIG. 76), an antibody (Clone ID: C3E-7088) or an antigen-binding fragment of the antibody comprising the 1st through 243rd amino acid residues of SEQ ID NO: 70 (FIG. 78), an antibody (Clone ID: C3E-7089) or an antigen-binding fragment of the antibody comprising the 1st through 243rd amino acid residues of SEQ ID NO: 72 (FIG. 80), an antibody (Clone ID: C3E-7090) or an antigen-binding fragment of the antibody comprising the 1st through 243rd amino acid residues of SEQ ID NO: 74 (FIG. 82), an antibody (Clone ID: C3E-7091) or an antigen-binding fragment of the antibody comprising the 1st through 243rd amino acid residues of SEQ ID NO: 76 (FIG. 84), an antibody (Clone ID: C3E-7092) or an antigen-binding fragment of the antibody comprising the 1st through 243rd amino acid residues of SEQ ID NO: 78 (FIG. 86), an antibody (Clone ID: C3E-7093) or an antigen-binding fragment of the antibody comprising the 1st through 243rd amino acid residues of SEQ ID NO: 80 (FIG. 88), an antibody (Clone ID: C3E-7094) or an antigen-binding fragment of the antibody comprising the 1st through 243rd amino acid residues of SEQ ID NO: 82 (FIG. 90), and an antibody (Clone ID: C3E-7095) or an antigen-binding fragment of the antibody comprising the 1st through 243rd amino acid residues of SEQ ID NO: 84 (FIG. 92).

Specific preferred examples of humanized anti-CD3 antibodies of the present invention or antigen-binding fragments of the antibody, wherein a heavy chain variable region, a linker and a light chain variable region bind in this order at the end of amino terminus, and additionally, a second linker, FLAG-tag, and HIS-tag bind at the end of carboxyl terminus of the light chain variable region, include antibodies or antigen-binding fragments of the antibody written in above-mentioned (16) which comprise an amino acid sequence comprising the 2nd through 269th amino acid residues of SEQ ID NO: 22, an amino acid sequence comprising the 2nd through 267th amino acid residues of SEQ ID NO: 25, an amino acid sequence comprising the 2nd through 269th amino acid residues of SEQ ID NO: 60,
an amino acid sequence comprising the 2nd through 267th amino acid residues of SEQ ID NO: 64,
an amino acid sequence comprising the 2nd through 269th amino acid residues of SEQ ID NO: 66,
an amino acid sequence comprising the 2nd through 269th amino acid residues of SEQ ID NO: 68,
an amino acid sequence comprising the 2nd through 269th amino acid residues of SEQ ID NO: 70,
an amino acid sequence comprising the 2nd through 269th amino acid residues of SEQ ID NO: 72,
an amino acid sequence comprising the 2nd through 269th amino acid residues of SEQ ID NO: 74,
an amino acid sequence comprising the 2nd through 269th amino acid residues of SEQ ID NO: 76,
an amino acid sequence comprising the 2nd through 269th amino acid residues of SEQ ID NO: 78,
an amino acid sequence comprising the 2nd through 269th amino acid residues of SEQ ID NO: 80,
an amino acid sequence comprising the 2nd through 269th amino acid residues of SEQ ID NO: 82, or an amino acid sequence comprising the 2nd through 269th amino acid residues of SEQ ID NO: 84.

The antibody, etc. of the present invention may be a molecule including an antibody, etc. that comprises an amino acid sequence of a heavy chain variable region and/or an amino acid sequence of a light chain variable region which is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% the same as the amino acid sequence of the heavy chain variable region and/or the amino acid sequence of the light chain variable region contained in the aforementioned anti-CD3 antibody of the present invention or antigen-binding fragment of the antibody, and binds to human CD3 and to cynomolgus monkey CD3.

The antibody etc. of the present invention may be an antibody whose ability to bind to CD3 may be optimized by introducing a mutation to the aforementioned humanized anti-CD3 antibody or antigen-binding fragment of the antibody. Specific examples of the method for introducing a mutation can include random mutagenesis using error-prone PCR, site-directed amino acid mutagenesis using an NNK library, site-directed mutagenesis using structure information, and combinations thereof.

The ADCC and CDC activities of an antibody, etc. of the present invention may be reduced by the substitution of constant regions in order to decrease the effector activity of the antibody.

To avoid cytotoxicity in normal cells expressing human CD3, it is desirable that the antibody should have low effector activity. Effector activity is known to differ among antibody subclasses. For example, IgG4 has low ADCC and CDC activity, and IgG2 has CDC activity but low ADCC activity. Using these features, an antibody with reduced ADCC and CDC activity can be prepared by substituting the constant regions of IgG1 with the constant regions of IgG2 or IgG4. Also, an IgG1 antibody with reduced ADCC and CDC activity can be prepared by the substitution of a portion of the constant regions of IgG1 with reference to IgG2 or IgG4. For example, Marjan Hezareh et al., Journal of Virology, 75 (24): 12161-12168 (2001) show that ADCC and CDC activity is reduced by substituting the 234th and 235th leucine residues (the numbers are based on the EU index according to Kabat et al.) of IgG1 with alanine residues.

(3-8) Antibodies that Bind to Same Site and Also Bind to Cynomolgus Monkey CD3

An "antibody that binds to the same site" as in includes an antibody, etc. of the present invention and "binds to cynomolgus monkey CD3" also includes an antibody, etc. of the present invention. The "antibody binding to the same site" as in the case of a certain antibody means another antibody that binds to a site on an antigen molecule recognized by the antibody. If a second antibody binds to a partial peptide or a partial three-dimensional structure on an antigen molecule bound by a first antibody, the first and second antibodies are determined as binding to the same site.

Alternatively, the first and second antibodies are determined as binding to the same site by confirming that the second antibody competes with the first antibody for binding to the antigen, i.e., the second antibody interferes with the binding of the first antibody to the antigen, even if the peptide sequence or three-dimensional structure of the specific binding site is not determined.

When the first and second antibodies bind to the same site and the first antibody has an effect characteristic of one aspect of an antibody of the present invention, such as cytotoxic activity, the second antibody also has an exceedingly high probability of having the same activity.

Thus, if a second anti-CD3 antibody binds to a site bound by a first anti-CD3 antibody and the second anti-CD3 antibody binds to cynomolgus monkey CD3, the first and second antibodies can be determined as binding to the same site on the CD3 protein. An antibody or an antigen-binding fragment of the antibody that binds to the same site on human CD3 as that bound by an anti-CD3 antibody of the present invention or an antigen-binding fragment of the antibody, and binds to cynomolgus monkey CD3 is also included among the antibodies, etc. of the present invention.

Alternatively, first and second anti-CD3 antibodies can be determined as binding to the same site on the CD3 protein by confirming that the second anti-CD3 antibody competes with the first anti-CD3 antibody for binding to the CD3 protein and the second anti-CD3 antibody binds to cynomolgus monkey CD3. An antibody or an antigen-binding fragment of the antibody that competes with the anti-CD3 antibody of the present invention or antigen-binding fragment of the antibody for binding to human CD3, and binds to cynomolgus monkey CD3 is also included in the antigen, etc. of the present invention.

The antibody binding site can be determined using any method well known by those skilled in the art, such as immunoassay. For example, a series of peptides may be prepared by appropriately sequentially cleaving the amino acid sequence of the antigen from its carboxyl terminus or amino terminus, and then studying the reactivity of the antibody to roughly determine a recognition site. Then, shorter peptides are synthesized, and the reactivity of the antibody to these peptides can be studied to determine the binding site. The antigen fragment peptides can be prepared using a technique such as gene recombination or peptide synthesis.

An antibody, etc. of the present invention recognizes and binds to a region constituting the three-dimensional structure of CD3, i.e., an Ig-like domain. Such a binding site (epitope) for the antibody can be determined by identifying amino acid residues on the antigen adjacent to the antibody using X-ray structural analysis.

(3-9) Variants of Anti-CD3 Antibodies or Antigen-Binding Fragments Thereof

The present invention provides a variant of an antibody or antigen-binding fragment thereof. The variant of the antibody of the present invention or antigen-binding fragment thereof means an antibody of the present invention or an antigen-binding fragment thereof provided with chemical or biological modification. The chemically variant includes, for example, a form having an amino acid skeleton conjugated with a chemical moiety, and a form having a chemically modified N-linked or O-linked carbohydrate chain. The biological variant includes, for example, a form that has undergone post-translational modification (e.g., N-linked or O-linked glycosylation, processing of an amino-terminal or carboxyl-terminal region, deamidation, isomerization of aspartic acid, or oxidation of methionine), and a form containing a methionine residue added to the amino terminus by expression using prokaryotic host cells. Such a variant is also meant to include a form labeled to permit detection or isolation of the antibody or the antigen of the present invention, for example, an enzyme-labeled form, a fluorescently labeled form, or an affinity-labeled form. Such a variant of the antibody of the present invention or antigen-binding fragment thereof is useful for improving the stability and blood retention of the original antibody of the present invention or the original antigen-binding fragment thereof, reducing antigenicity, and detecting or isolating the antibody or the antigen, etc.

Examples of the chemical moieties contained in the chemically variants include water-soluble polymers such as polyethylene glycol, ethylene glycol/propylene glycol copolymers, carboxymethylcellulose, dextran, and polyvinyl alcohol.

Examples of biologically variants include forms modified by enzymatic treatment or cell treatment, forms fused with other peptides, such as a tag, added by gene recombination, and forms prepared from host cells expressing an endogenous or exogenous sugar chain-modifying enzyme.

Such a modification may be made at an arbitrary position or at a desired position in the antibody or antigen-binding fragment thereof. Alternatively, the same or different modifications may be made at one or two or more positions therein.

In the present invention, a "variant of an antigen-binding fragment of an antibody" is also meant to include a "fragment of a variant of an antibody."

For example, the heavy chain of an antibody produced by cultured mammalian cells is known to lack a lysine residue at the carboxy terminus (Journal of Chromatography A, 705: 129-134 (1995)). Also, the heavy chain of such an antibody is known to lack two amino acid residues (glycine and lysine) at the carboxy terminus and instead have an amidated proline residue at the carboxy terminus (Analytical Biochemistry, 360: 75-83 (2007)). Furthermore, a N (amino)-terminal glutamine or glutamic acid residue in the heavy or light chain of an antibody is known to be modified by pyroglutamylation during preparation of the antibody, and the antibody of the present invention may have such a modification (International Publication No. WO2013/147153A1).

Deletions in these heavy chain sequences or modifications in these heavy or light chain sequences, however, do not influence the ability of the antibody to bind to the antigen and its effector functions (complement activation, antibody dependent cytotoxic effects, etc.) very much. Thus, the present invention also encompasses antibodies that have been subjected to deletion or modification (hereinafter referred to as "deletion variants"). Examples include a deletion variant derived from a heavy chain by deletion of 1 or 2 amino acids at the carboxyl terminus, an amidated form of the deletion variant (e.g., a heavy chain having an amidated proline residue at the carboxyl-terminal site), and an antibody having a pyroglutamylated amino-terminal residue in its heavy or light chain. However, a deletion variant at the carboxyl terminus of the antibody heavy and light chain according to the present invention is not limited to the types described above as long as the deletion variant retains at least some ability to bind to the antigen. Two or more chains (e.g., heavy chains) present in an antibody according to the present invention may be chains (e.g., heavy chains) of any type selected from a group consisting of full-length chains (e.g., heavy chains) and the deletion variants described above, as well as any combination of two or more chains (e.g., heavy chains) of any two types selected therefrom. The quantitative or molecular ratio of each deletion variant may be influenced by the type of cultured mammalian cells producing the antibody according to the present invention, and culture conditions. Examples include the deletion of one carboxyl-terminal amino acid residue each of the two heavy chains as main components of the antibody according to the present invention.

In the present invention, a "variant of an antigen-binding fragment of an antibody" is also meant to include a "fragment of a variant of an antibody."

The antibody dependent cellular cytotoxic activity of the antibody of the present invention may be enhanced by regulating the modification (glycosylation, defucosylation, etc.) of the sugar chain bound with the antibody. For example, International Publication Nos. WO99/54342A1, WO00/61739A1, and WO02/31140A1 make known a technique for regulating the sugar chain modification of an antibody, though this technique is not limited thereto. An antibody of the present invention and antigen-binding fragment of the antibody also include an antibody and an antigen-binding fragment of an antibody that has undergone sugar chain modification thus regulated.

In the present invention, "deletions" and "modifications" of an antibody or antigen-binding fragment thereof, and mixture thereoffall within the scope of the "antibody or antigen-binding fragment thereof". And, "deletions" and "modifications" of an antibody or antigen-binding fragment thereof, and mixtures thereof fall within the scope of "an antibody or antigen-binding fragment thereof" comprised in a molecule which binds to an antigen, multispecific molecule, bispecific molecule or the like of the present invention which is disclosed in (3-5) and (3-6).

4. Production of Antibodies (4-1) Method Using Hybridoma

According to one aspect of the present invention, anti-CD3 antibody-producing cells are isolated from the spleens of animals immunized with the CD3 protein according to, for example, the method of Kohler and Milstein (Kohler and Milstein, Nature (1975) 256, p. 495-497; and Kennet, R. ed., Monoclonal Antibodies, p. 365-367, Plenum Press, N.Y. (1980)). The cells are fused with myeloma cells to establish hybridomas. Monoclonal antibodies can be obtained from cultures of these hybridomas.

(4-1-1) Preparation of Antigen

The antigen for the preparation of an anti-CD3 antibody can be obtained according to, for example, the method for preparing a native or recombinant CD3 protein (human CD3εγ single-chain antigen). Examples of antigens that may be thus prepared include the CD3 protein, CD3 protein fragments, and derivatives thereof further comprising an arbitrary amino acid sequence or carrier added (hereinafter, collectively referred to as "CD3").

The native CD3 can be purified and isolated from, for example, human tissue-derived cells or cultures of the cells.

The recombinant human CD3εγ single-chain antigen can be prepared by transfecting host cells with a gene comprising a nucleotide sequence encoding the amino acid sequence of the human CD3εγ single-chain antigen, and recovering the antigen from cultures of the cells. CD3 obtained by cell-free protein synthesis in an in vitro translation system from a gene comprising a nucleotide sequence encoding the amino acid sequence of the CD3 antigen is also included among "CD3 antigens" of the present invention.

(4-1-2) Production of Anti-CD3 Monoclonal Antibodies

A monoclonal antibody is typically produced through the following steps:

(a) preparing an antigen, (b) preparing antibody-producing cells, (c) preparing myeloma cells (hereinafter, referred to as "myelomas"), (d) fusing the antibody-producing cells with the myelomas, (e) screening for a hybridoma group producing the antibody of interest, and (f) obtaining single cell clones (cloning).

This production method further involves (g) a step of culturing the hybridomas, a step of raising hybridoma-transplanted animals, etc., and (h) a step of assaying or determining the biological activity of the monoclonal antibody, etc., if necessary.

This method for preparing monoclonal antibodies will now be described in detail with reference to these steps. However, the method for preparing the antibody is not limited to these steps. For example, antibody-producing cells other than spleen cells and myelomas may be used.

(a) Step of Preparing Antigens

A CD3 protein of the present invention can be prepared by purification or isolation from animal tissues (including body fluids), cells derived from the tissues, or cultures of the cells, gene recombination, cell-free protein synthesis, chemical synthesis, etc.

(b) Step of Preparing Antibody-Producing Cells

The antigen obtained in step (a) is mixed with an adjuvant such as a complete or incomplete Freund's adjuvant or potassium aluminum sulfate, and laboratory animals are immunized with the resulting immunogen. Any laboratory animal used in a hybridoma preparation method known in the art can be used without limitations. For example, mice, rats, goats, sheep, cattle, and horses can be used. From the viewpoint of readily available myeloma cells to be fused with isolated antibody-producing cells, etc., the animals to be immunized are preferably mice or rats.

The strain of mice or rats actually used is not particularly limited. In the case of mice, for example, A, AKR, BALB/c, BALB/cAnNCrj, BDP, BA, CE, C3H, 57BL, C57BL, C57L, DBA, FL, HTH, HT1, LP, NZB, NZW, RF, R III, SJL, SWR, WB, or 129 can be used. In the case of rats, for example, Wistar, Low, Lewis, Sprague-Dawley, ACI, BN, or Fischer can be used.

These mice and rats are available from laboratory animal breeders or distributors, for example, CLEA Japan, Inc. or Charles River Laboratories Japan, Inc.

Of those mice and rats, a BALB/c mouse strain or Wistar and Low rat strains are particularly preferred as animals to be immunized in consideration of fusion compatibility with the myeloma cells described later.

Also, in consideration of the homology between human and mouse antigens, mice whose biological mechanism to remove autoantibodies has been reduced, i.e., autoimmune disease mice, are also preferably used.

In this context, these mice or rats are preferably 5 to 12 weeks old, and more preferably 6 to 8 weeks old, at the time of immunization.

The animals can be immunized with the CD3 protein using, for example, the method of Weir, D. M., Handbook of Experimental Immunology Vol. I. II. III., Blackwell Scientific Publications, Oxford (1987), or Kabat, E. A. and Mayer, M. M., Experimental Immunochemistry, Charles C Thomas Publisher Spigfield, Ill. (1964).

Examples of methods for determining antibody titers can include, but are not limited to, immunoassays such as RIA and ELISA.

Antibody-producing cells derived from spleen cells or lymphocytes separated from the immunized animals, can be prepared according to a method known in the art, for example, Kohler et al., Nature (1975) 256, 495; Kohler et al., Eur. J. Immnol. (1977) 6, 511; Milstein et al., Nature (1977), 266, 550; or Walsh, Nature (1977) 266, 495.

In the case of spleen cells, a general method can be adopted, which involves chopping the spleens, filtering cells through a stainless-steel mesh, and then floating the resulting cells in an Eagle's minimum essential medium (MEM) to separate the antibody-producing cells.

(c) Step of Preparing Myelomas

The myeloma cells used in cell fusion are not particularly limited and can be selected for use from cell lines known in the art. For example, a hypoxanthine-guanine phosphoribosyl transferase (HGPRT)-deficient line, i.e., mouse-derived X63-Ag8 (X63), NS1-ANS/1 (NS1), P3X63-Ag8.U1 (P3U1), X63-Ag8.653 (X63.653), SP2/0-Ag14 (SP2/0), MPC11-45.6TG1.7 (45.6TG), FO, S149/5XXO, or BU.1, rat-derived 210.RSY3.Ag.1.2.3 (Y3), or human-derived U266AR (SKO-007), GM1500-GTG-A12 (GM1500), UC729-6, LICR-LOW-HMy2 (HMy2), or 8226AR/NIP4-1 (NP41), whose screening procedures have already been established, are preferably used in consideration of convenience in the selection of hybridomas from fusion cells. These HGPRT-deficient lines are available from, for example, the American Type Culture Collection (ATCC)

These cell lines are subcultured in an appropriate medium, for example, an 8-azaguanine medium [RPMI-1640 medium supplemented with glutamine, 2-mercaptoethanol, gentamicin, and fetal bovine serum (hereinafter, referred to as "FCS") and further supplemented with 8-azaguanine], an Iscove's modified Dulbecco's medium (hereinafter, referred to as "IMDM"), or a Dulbecco's modified Eagle medium (hereinafter, referred to as "DMEM") and subcultured in a normal medium [e.g., ASF104 medium (manufactured by Ajinomoto Co., Inc.) containing 10% FCS] for 3 to 4 days before cell fusion to ensure that the number of cells is equal to or greater than $2\times10^7$ cells on the day of cell fusion.

(d) Step of Fusing Antibody-Producing Cells with Myeloma Cells

The antibody-producing cells can be fused with the myeloma cells under conditions that prevent cell viability from being excessively reduced, according to any method known in the art (e.g., Weir, D. M., Handbook of Experimental Immunology Vol. I. II. III., Blackwell Scientific Publications, Oxford (1987), Kabat, E. A. and Mayer, M. M., Experimental Immunochemistry, Charles C Thomas Publisher Spigfield, Ill. (1964)). For example, a chemical method which involves mixing antibody-producing cells with myeloma cells in a high-concentration solution of a polymer such as polyethylene glycol, or a physical method using electric stimulation can be used.

(e) Step of Screening for the Hybridoma Group Producing the Antibody of Interest The method used to select hybridomas obtained by cell fusion is not particularly limited, but a hypoxanthine-aminopterin-thymidine (HAT) selection method (Kohler et al., Nature (1975) 256, 495; Milstein et al., Nature (1977) 266, 550) is typically used. This method is effective for obtaining hybridomas using an HGPRT-deficient myeloma cell line, which cannot survive in the presence of aminopterin. Specifically, unfused cells and hybridomas can be cultured in a HAT medium to allow hybridomas resistant to aminopterin to selectively live and grow.

(f) Step of Obtaining Single-Cell Clones (Cloning)

The hybridomas can be cloned using any method known in the art, for example, a methylcellulose, soft agarose, or limiting dilution method (e.g., Barbara, B. M. and Stanley, M. S.: Selected Methods in Cellular Immunology, W.H. Freeman and Company, San Francisco (1980)). The limiting dilution method is preferred.

(g) Step of Culturing Hybridomas and Step of Raising Hybridoma-Transplanted Animals The selected hybridomas can be cultured to produce monoclonal antibodies. Preferably, the desired hybridomas are cloned and then subjected to antibody production.

The monoclonal antibody produced by such a hybridoma can be recovered from cultures of the hybridoma. Also, a recombinant antibody can be recovered from cultures of cells transfected with the monoclonal antibody gene. Alternatively, the hybridoma may be injected intraperitoneally into mice of the same strain (e.g., BALB/cAnNCrj described above) or Nu/Nu mice and allowed to grow. Then, the monoclonal antibodies can be recovered from their ascites.

(h) Step of Assaying or Determining Biological Activity of Monoclonal Antibodies Various biological tests can be selected and applied depending on the purpose.

(4-2) Cell Immunization Method

Cells expressing native CD3 or cells expressing recombinant CD3 or its fragment can be used as immunogens to prepare an anti-CD3 antibody using the hybridoma method described above.

Examples of the cells expressing native CD3 include human thymus cells and T lymphocytes. These CD3-expressing cells are used in an amount of $1\times10^5$ to $1\times10^9$ cells, preferably $1\times10^6$ to $1\times10^8$ cells, more preferably 0.5 to $2\times10^7$ cells, and even more preferably $1\times10^7$ cells, per immunization shot. The number of cells used for immunization can be changed depending on the expression level of CD3. The immunogens are generally administered intraperitoneally but may be administered by an intradermal route. The hybridomas can be prepared by the application of the method described in section (4-1-2).

(4-3) DNA Immunization Method

An anti-CD3 antibody of the present invention can also be obtained by use of a DNA immunization method. This method involves transfecting an individual animal, e.g., mouse or rat, with an antigen expression plasmid and expressing the antigen in the individual to thereby induce immunity against the antigen. Examples of the transfection approach include a method of directly injecting the plasmid into the muscle, a method of injecting a transfection reagent such as a liposome or polyethylenimine into a vein, an approach using a viral vector, an approach of injecting plasmid-affixed gold particles using a gene gun, and a hydrodynamic method of rapidly injecting a large amount of plasmid solution into a vein.

An actual example of a rat anti-human CD3 antibody thus obtained is C3-147. The amino acid sequence of the light chain variable region of C3-147 is shown in SEQ ID NO: 9 of the Sequence Listing (FIG. 17). The amino acid sequence of the heavy chain variable region of C3-147 is shown in SEQ ID NO: 7 of the Sequence Listing (FIG. 15).

(4-4) Gene Recombination

In order to prepare an antibody of the present invention, a nucleotide (heavy chain nucleotide) comprising a nucleotide sequence encoding the amino acid sequence of its heavy chain and a nucleotide (light chain nucleotide) comprising a nucleotide sequence encoding the amino acid sequence of its light chain, or a vector having an insert of the heavy chain nucleotide and a vector having an insert of the light chain nucleotide, is introduced into host cells, the cells are cultured, and the antibody is recovered from the culture. The heavy chain nucleotide and the light chain nucleotide may be inserted in one vector.

Prokaryotic or eukaryotic cells can be used as the host cells. When host eukaryotic cells are used, animal cells, plant cells, or eukaryotic microbes can be used.

Examples of the animal cells include mammal-derived cells, i.e., human embryonic kidney cells HEK293F cells (Subedi G P et al., J Vis Exp. (2015) 106), monkey kidney-derived COS cells (Gluzman, Y. Cell (1981), 23, 175-182, ATCC CRL-1650), mouse fibroblast NIH3T3 (ATCC No. CRL-1658), Chinese hamster ovary cells (CHO cells, ATCC CCL-61), dihydrofolate reductase-deficient lines thereof (CHOdhfr-; Urlaub, G. and Chasin, L. A. PNAS (1980), 77, 4126-4220), cells derived from birds such as chickens, and cells derived from insects.

Also, cells modified to enhance the biological activities of antibodies by the modification of sugar chain structures can be used as the hosts. For example, CHO cells modified so that the proportion of sugar chains with fucose unbound with N-acetylglucosamine at their reducing ends is 20% or more among complex-type N-glycoside-linked sugar chains to be bound to the Fc region of the antibody, may be used to prepare an antibody having enhanced ADCC activity or CDC activity (International Publication No. WO02/31140A1).

Examples of eukaryotic microbes include yeasts. Examples of the prokaryotic cells include *E. coli* and *Bacillus subtilis.*

A signal peptide for the secretion of an antibody of the present invention (monoclonal antibodies derived from each animal, rat antibodies, mouse antibodies, chimeric antibodies, humanized antibodies, human antibodies, etc.) is not limited to the secretory signal of an antibody of the same species, the same type, or the same subtype as the antibody of the present invention or to the antibody of the present invention's own secretory signal. Any secretory signal of an antibody of a different type or subtype or any secretory signal of a protein derived from a different eukaryotic species or prokaryotic species can be selected and used.

A secreted antibody, etc. containing the signal peptide is also encompassed by the antibody, etc. of the present invention or the molecule of the present invention.

(4-5) Methods for Designing and Preparing Humanized Antibodies

Examples of humanized antibodies include, but are not limited to, human-derived antibodies having CDRs replaced with the CDRs of non-human animal antibodies (see Nature (1986), 321, p. 522-525), human antibodies grafted to CDR sequences and some amino acid residues of framework regions by CDR grafting (see WO90/07861A1 and U.S. Pat. No. 6,972,323B2), and antibodies having one or more human antibody amino acid replaced by one or more non-human animal antibody-derived amino acid in any of these humanized antibodies.

(4-6) Method for Preparing Human Antibodies

Other examples of antibodies of the present invention include human antibodies. Human anti-CD3 antibody means an anti-CD3 antibody consisting of the amino acid sequence of a human-derived antibody. A human anti-CD3 antibody can be obtained by a method using human antibody-producing mice carrying human genomic DNA fragments comprising human antibody heavy and light chain genes (see e.g., Tomizuka, K. et al., Nature Genetics (1997) 16, 133-143; Kuroiwa, Y. et. al., Nuc. Acids Res. (1998) 26, 3447-3448; Yoshida, H. et. al., Animal Cell Technology: Basic and Applied Aspects vol. 10, 69-73 (Kitagawa, Y., Matuda, T. and Iijima, S. eds.), Kluwer Academic Publishers, 1999; Tomizuka, K. et. al., Proc. Natl. Acad. Sci. USA (2000) 97, 722-727).

Specifically, human antibody-producing animals can be prepared by disrupting the endogenous immunoglobulin heavy and light chain gene loci of non-human mammals and introducing human immunoglobulin heavy and light chain gene loci via, for example, yeast artificial chromosome (YAC) vectors. Alternatively, eukaryotic cells may be transformed with cDNAs encoding the heavy and light chains, respectively, of such a human antibody, preferably with vectors comprising the cDNAs, by a gene recombination technique. The transformed cells producing a recombinant human monoclonal antibody can be cultured. This antibody can be obtained from the culture supernatant.

In this context, for example, eukaryotic cells, preferably mammalian cells such as HEK293F cells or CHO cells, can be used as the hosts.

Also, a method for obtaining a phage display-derived human antibody selected from a human antibody library is also known. For example, a phage display method can be used which involves allowing the variable regions of a human antibody to be expressed as scFv on a phage surface and selecting the phage binding to the antigen. A phage selected on the basis of its ability to bind to the antigen can be subjected to gene analysis to determine DNA sequences encoding the variable regions of the human antibody binding to the antigen. If the DNA sequence of scFv binding to the antigen is determined, an expression vector with this sequence can be prepared and introduced to a suitable host to allow them to express the human antibody (WO92/01047A1, WO92/20791 A1, WO93/06213 A1, WO93/11236 A1, WO93/19172 A1, WO95/01438 A1, WO95/15388 A1, Annu. Rev. Immunol (1994) 12, 433-455).

(4-7) Method for Preparing Antigen-Binding Fragments of Antibodies

The method for preparing scFv is well known in the art (see e.g., U.S. Pat. Nos. 4,946,778, 5,260,203, 5,091,513, and 5,455,030). In this scFv, a heavy chain variable region and a light chain variable region are linked via a linker that prevents them from forming a conjugate, preferably a polypeptide linker (Huston, J. S. et al., PNAS (1988), 85, 5879-5883). The heavy chain variable region and the light chain variable region in scFv may be derived from the same antibody or may be derived from different antibodies.

For example, an arbitrary single chain peptide consisting of 5 to 30 residues is used as the polypeptide linker that links these variable regions.

In order to obtain scFv-encoding DNA of the sequences of DNA encoding the heavy chain or heavy chain variable region of the antibody and DNA encoding the light chain or light chain variable region thereof, each DNA portion encoding the entire or desired amino acid sequence is used as a template and amplified by PCR using a primer pair flanking both ends of the template. Subsequently, DNA encoding the polypeptide linker moiety is further amplified in combination with a primer pair flanking both ends of the DNA so that the resulting fragment can be linked at its ends to the heavy and light chain DNAs. Alternatively, the DNA encoding the whole scFv region may be obtained by net synthesis.

The scFv-encoding DNA can be used to prepare, according to a routine method, an expression vector containing the DNA and host cells transformed with the expression vector. In addition, the host cells can be cultured, and the scFv can be recovered from the cultures using a routine method.

Also in order to obtain any other antigen-binding fragment of the antibody, a gene encoding the antigen-binding fragment is obtained according to the method described above and introduced to cells. The antigen-binding fragment of interest can be recovered from cultures of the cells.

The antibody, etc. of the present invention may be multimerized to enhance its affinity for the antigen. In this case, antibodies of the same type may be multimerized, or a plurality of antibodies recognizing a plurality of epitopes, respectively, of the same antigen may be multimerized. Examples of methods for multimerizing these antibodies can include the binding of two scFvs to an IgG CH3 domain, the binding of these to streptavidin, and the introduction of a helix-turn-helix motif.

The antibody, etc. of the present invention may be a mixture of plural types of anti-CD3 antibodies differing in amino acid sequence, i.e., a polyclonal antibody. Examples of the polyclonal antibody can include a mixture of multiple types of antibodies with CDR sets differing in whole or in part. Such a polyclonal antibody can be recovered from cultures of mixed-cultured different antibody-producing cells (WO2004/061104A1). Alternatively, separately prepared antibodies may be mixed. Antiserum, which is one aspect of the polyclonal antibody, can be prepared by immunizing animals with the desired antigen and recovering serum from the animals according to a standard method.

Antibodies conjugated with various molecules such as polyethylene glycol (PEG) can also be used as variants of the antibody.

The antibody, etc. of the present invention may be any conjugate formed by these antibodies with other molecules via linkers (immunoconjugates). An antibody-drug complex in which the antibody is conjugated with a radioactive material or a compound (drug) having pharmacological action can include ADC (antibody-drug conjugate) (Methods Mol Biol. (2013) 1045: 1-27).

The antibody, etc. of the present invention may further be any of antibody connected to other functional polypeptides. An example of such an antibody-peptide complex is a complex of the antibody and an albumin-binding polypeptide (Protein Eng Des Sel. (2012) (2): 81-8).

(4-8) Purification of the Antibody and Antigen-Binding Fragment of the Antibody

The resulting antibody and antigen-binding fragment of the antibody can be purified until homogeneous so as not to contain materials other than the antibody, etc. Common protein separation and purification methods can be used for the separation and purification of the antibody and antigen-binding fragment of the antibody.

The antibody can be separated and purified by appropriately selected or combined approaches, for example, chromatography columns, filters, ultrafiltration, salting out, dialysis, preparative polyacrylamide gel electrophoresis, and isoelectric focusing, though the separation and purification method is not limited.

The separation and purification method is preferably performed, for example, by preparing an expression vector using a DNA sequence encoding a His tag or a FLAG tag added to the carboxyl terminus of an antibody variable region, transforming cells with this vector, then culturing the cells to express the antibody and antigen-binding fragment of the antibody, and extracting the culture supernatant after the completion of the culture, followed by purification using metal (e.g., Ni or Co) affinity chromatography, anti-FLAG tag antibody columns, gel filtration, or ion-exchange chromatography.

The expressed antibody and antigen-binding fragments of the antibody containing an amino acid sequence encoding a tag such as a His tag or a FLAG tag is also encompassed by the antigen, etc. of the present invention or the molecule of the present invention.

(4-9) Multispecific Molecules and Bispecific Molecules

Examples of methods for preparing the bispecific molecule and the multispecific molecule of the present invention include a method which involves introducing expression plasmids to host cells to cause transient expression, a method which involves introducing plasmids to host cells and then selecting a stably expressing cell line by drug selection to cause permanent expression, a method which involves cell-free synthesis, and a method which involves preparing antibodies or antigen-binding fragments by any of the methods described above, and then chemically linking these antibodies or fragments using a synthetic peptide linker.

As for bispecific molecule preparation using antibody variable regions, examples include a method which involves connecting two single-chain antibodies (scFvs) via a peptide linker (tandem scFv), a method which involves cross-pairing domains of two antibodies differing in specificity, and forming a dimer by a noncovalent bond (diabody), a method which involves cross-pairing domains of two antibodies differing in specificity and forming a single chain (single-chain diabody), and a method which involves preparing single-chain diabodies and then forming a dimer by a noncovalent bond (TandAb, U.S. Pat. No. 7,129,330B2).

The present invention also provides a gene encoding the antibody of the present invention or antigen-binding fragment of the antibody, or a variant of the antigen, etc., a recombinant vector having an insert of the gene, a cell transfected with the gene or vector, and a cell producing the antibody of the present invention.

5. Pharmaceutical Compositions

The present invention provides a pharmaceutical composition comprising the anti-CD3 antibody or antigen-binding fragment thereof, or the variant of the antibody or antigen-binding fragment, and/or the molecule of the present invention comprising any of them, for example, the multispecific molecule.

In the present invention, the treatment and/or prevention of a disease includes, but is not limited to, the prevention of the onset of the disease, the suppression or inhibition of advancement or progress thereof, the alleviation of one or two or more symptoms exhibited by an individual affected with the disease, the suppression or remission of advancement or progress thereof, and the treatment or prevention of a secondary disease, etc. In the case of the molecule, examples of diseases include cancers.

The pharmaceutical composition of the present invention can comprise a therapeutically or prophylactically effective amount of the anti-CD3 antibody or antigen-binding fragment of the antibody and a pharmaceutically acceptable diluent, vehicle, solubilizer, emulsifier, preservative, and/or additive.

"Therapeutically or prophylactically effective amount" means an amount that has therapeutic or prophylactic effects on a particular disease by means of a particular dosage form and administration route.

The pharmaceutical composition of the present invention may comprise materials for changing, maintaining, or retaining pH, osmotic pressure, viscosity, transparency, color, tonicity, sterility, or the stability, solubility, sustained release, absorbability, permeability, dosage form, strength, properties, shape, etc., of the composition or the antibody comprised therein (hereinafter, referred to as "pharmaceutical materials"). The pharmaceutical materials are not particularly limited as long as the materials are pharmacologically acceptable. For example, non-toxic or low toxicity is a property preferably possessed by these pharmaceutical materials.

Examples of pharmaceutical materials include, but are not limited to, the following: amino acids such as glycine, alanine, glutamine, asparagine, histidine, arginine, and lysine; antimicrobial agents; antioxidants such as ascorbic acid, sodium sulfate, and sodium bisulfite; buffers such as phosphate, citrate, or borate buffers, sodium bicarbonate, and Tris-HCl solutions; fillers such as mannitol and glycine; chelating agents such as ethylenediaminetetraacetic acid (EDTA); complexing agents such as caffeine, polyvinylpyrrolidine, β-cyclodextrin, and hydroxypropyl-β-cyclodextrin; bulking agents such as glucose, mannose, and dextrin; hydrocarbons such as monosaccharides, disaccharides, glucose, mannose, and dextrin; coloring agents; corrigents; diluents; emulsifiers; hydrophilic polymers such as polyvinylpyrrolidine; low molecular weight polypeptides; salt-forming counterions; antiseptics such as benzalkonium chloride, benzoic acid, salicylic acid, thimerosal, phenethyl alcohol, methylparaben, propylparaben, chlorhexidine, sorbic acid, and hydrogen peroxide; solvents such as glycerin, propylene glycol, and polyethylene glycol; sugar alcohols such as mannitol and sorbitol; suspending agents; surfactants such as PEG, sorbitan ester, polysorbates such as polysorbate 20 and polysorbate 80, triton, tromethamine, lecithin, and cholesterol; stability enhancers such as sucrose and sorbitol; elasticity enhancers such as sodium chloride, potassium chloride, mannitol, and sorbitol; transport agents; diluents; excipients; and pharmaceutical additives.

The amount of these pharmaceutical materials added is 0.001 to 1000 times, preferably 0.01 to 100 times, and more preferably 0.1 to 10 times the weight of the anti-CD3 antibody or antigen-binding fragment thereof, or the variant of the antibody or antigen-binding fragment, or a molecule of the present invention such as a multispecific molecule.

An immunoliposome comprising an anti-CD3 antibody of the present invention or an antigen-binding fragment thereof, or a variant of the antibody or antigen-binding fragment, or a molecule of the present invention such as a multispecific molecule, encapsulated in a liposome, or a pharmaceutical composition comprising a modified antibody form comprising the antibody conjugated with a liposome (U.S. Pat. No. 6,214,388, etc.) are also included among the pharmaceutical compositions of the present invention.

The excipients or carriers are not particularly limited as long as they are liquid or solid materials usually used in injectable water, saline, artificial cerebrospinal fluids, and other preparations for oral or parenteral administration. Examples of saline can include neutral saline and serum albumin-containing saline.

Examples of buffers can include a Tris buffer adjusted to bring the final pH of the pharmaceutical composition to 7.0 to 8.5, an acetate buffer adjusted to bring the final pH to 4.0 to 5.5, a citrate buffer adjusted to bring the final pH to 5.0 to 8.0, and a histidine buffer adjusted to bring the final pH to 5.0 to 8.0.

A pharmaceutical composition of the present invention is a solid, a liquid, or a suspension. Another example of a pharmaceutical composition of the present invention is a freeze-dried preparation. Freeze-dried preparations can be formed using an excipient such as sucrose.

The administration route for a pharmaceutical composition of the present invention may be any of enteral administration, local administration, or parenteral administration, and is preferably selected depending on the targeted disease. Specific examples include intravenous administration, intraarterial administration, intramuscular administration, intradermal administration, hypodermic administration, intraperitoneal administration, transdermal administration, intraosseous administration, and intraarticular administration.

The composition of the pharmaceutical composition can be determined on the basis of the administration method, the binding affinity of the antibody for the CD3 protein, etc.

The dose of an anti-CD3 antibody of the present invention or antigen-binding fragment thereof, or a variant of the antibody or antigen-binding fragment, or a molecule of the present invention such as a multispecific molecule can be determined on the basis of the species of the individual, the type of disease, symptoms, sex, age, pre-existing conditions, the binding affinity of the antibody for the CD3 protein or its biological activity, and other factors. A dose of usually 0.01 to 1000 mg/kg, preferably 0.1 to 100 mg/kg, can be administered once daily for 180 days or twice or three or more times daily.

Examples of forms for the pharmaceutical composition include injections (including freeze-dried preparations and drops), suppositories, transnasal absorption preparations, transdermal absorption preparations, sublingual formulations, capsules, tablets, ointments, granules, aerosols, pills, powders, suspensions, emulsions, eye drops, and biological implant formulations.

An anti-CD3 antibody of the present invention or antigen-binding fragment thereof, or a variant of the antibody or antigen-binding fragment, and/or a molecule of the present invention comprising any of them such as multispecific molecule (hereinafter, referred to as the "anti-CD3 antibody, etc.") can be used in combination with another drug. The anti-CD3 antibody, etc. or the pharmaceutical composition comprising the anti-CD3 antibody, etc. as an active ingredient can be administered concurrently with or separately from the other drug, i.e., a pharmaceutical composition comprising a drug other than the anti-CD3 antibody, etc. as an active ingredient. For example, the pharmaceutical composition comprising the anti-CD3 antibody, etc. as an active ingredient may be administered after administration of the other drug, or the other drug may be administered after administration of the pharmaceutical composition comprising the anti-CD3 antibody, etc. as an active ingredient. Alternatively, the pharmaceutical composition comprising the anti-CD3 antibody, etc. as an active ingredient and the other drug may be administered concurrently. In the present invention, a case in which the anti-CD3 antibody, etc. and the other drug are both contained as active ingredients in a single pharmaceutical composition and a case in which these active ingredients are separately contained in a plurality of pharmaceutical compositions are both included in the scope of the "pharmaceutical composition comprising the anti-CD3 antibody, etc. and another drug." In the present invention, the "pharmaceutical composition" has the same meaning as a "pharmaceutical composition in which the anti-CD3 antibody, etc. is to be administered in combination with another drug."

In the present invention, the phrase "administered in combination" used for the anti-CD3 antibody, etc. and the other drug means that the anti-CD3 antibody, etc. and the other drug are introduced to the body of a recipient within a certain period. A single preparation containing the anti-CD3 antibody, etc. and the other drug may be administered, or the anti-CD3 antibody, etc. and the other drug may be separately formulated and administered as separate preparations. In the case of separate preparations, the timing of administration is not particularly limited, and the preparations may be administered concurrently or may be administered at different times or on different days in an alternating manner. In a case in which the anti-CD3 antibody, etc. and the other drug are separately administered at different times or on different days, the order of administration is not particularly limited. Since separate preparations are usually administered according to their respective administration methods, the frequency of administration may be the same or different. Further, the separate preparations may be administered by the same administration method (administration route) or may be administered by different administration methods (administration routes). It is not necessary that the anti-CD3 antibody, etc. and the other drug be present in the body concurrently, and it is sufficient that the anti-CD3 antibody, etc. and the other drug are introduced to the body for a certain period of time (e.g., for 1 month, preferably for 1 week, more preferably for several days, even more preferably for 1 day). Alternatively, when one of the active ingredients is administered, the other active ingredient may have already disappeared from the body.

Examples of dosage forms for the "pharmaceutical composition in which the anti-CD3 antibody, etc. is to be administered in combination with the other drug" can include 1) the administration of a single preparation containing the anti-CD3 antibody, etc. and the other drug, 2) the concurrent administration through the same administration route of two preparations obtained by separately formulating the anti-CD3 antibody, etc. and the other drug, 3) the administration in an alternating manner through the same administration route of two preparations obtained by separately formulating the anti-CD3 antibody, etc. and the other drug, 4) the concurrent administration through different administration routes of two preparations obtained by separately formulating the anti-CD3 antibody, etc. and the other drug, and 5) the administration in an alternating manner through different administration routes of two preparations obtained by separately formulating the anti-CD3 antibody, etc. and the other drug. The dose, dosing interval, dosage form, preparation, etc., of the "pharmaceutical composition in which the anti-CD3 antibody, etc. is to be administered in combination with the other drug" depends on the pharmaceutical composition comprising the anti-CD3 antibody, etc., but are not limited.

A pharmaceutical composition formulated in two different preparations may be in the form of a kit containing these preparations.

In the present invention, the "combination" of the anti-CD3 antibody, etc. and the other drug means that the anti-CD3 antibody, etc. and the other drug are "administered in combination."

An additional drug can also be used in the combination or the pharmaceutical composition of the present invention.

The present invention provides a method for treating or preventing CD3-related diseases, use of the antibody of the present invention for preparing a pharmaceutical composition for treatment or prevention of the diseases, and use of the antibody of the present invention for treating or preventing the diseases. The present invention also encompasses a kit for treatment or prevention comprising the antibody of the present invention.

EXAMPLES

The present invention will now be described in more detail with reference to examples. However, the present invention is not limited to these examples. Procedures related to gene manipulation in the examples below were performed according to the methods described in "Molecular Cloning" (Sambrook, J., Fritsch, E. F. and Maniatis, T., Cold Spring Harbor Laboratory Press, 1989), or using commercially available reagents or kits according to the instruction manuals, unless otherwise specified.

(Example 1) Preparation of Rat Anti-Human CD3 Antibody

1)-1 Construction of Human CD3εδ Expression Vector

A control vector pcDNA3.1-DEST engineered as a destination vector was prepared using the Gateway Vector Conversion System (Thermo Fisher Scientific Inc.). A cDNA encoding the human CD3δ protein (NCBI Reference Sequence: NP_000724.1) shown in FIG. 1 (SEQ ID NO: 1) was purchased from Sino Biological Inc. and cloned in the pcDNA3.1-DEST vector using Gateway LR Clonase Enzyme mix (Thermo Fisher Scientific Inc.) to construct hCD3δ-pcDNA3.1. A cDNA encoding the human CD3δ protein (NP_000723.1) shown in FIG. 2 (SEQ ID NO: 2) was amplified by PCR using a human T cell-derived cDNA as a template according to a method known to those skilled in the art, and cloned in pcDNA3.1(+) (Thermo Fisher Scientific Inc.) to construct an expression vector hCD3δ-pcDNA3.1. For the large-scale preparation of each expression vector, Endofree Plasmid Giga Kit (Qiagen N.V.) was used.

1)-2 Immunization

For immunization, WKY/Izm female rats (Japan SLC, Inc.) were used. First, both lower thighs of each rat were pretreated with hyaluronidase (Sigma-Aldrich Corp.). Then, the hCD3δ-pcDNA3.1 and hCD3δ-pcDNA3.1 expression vectors prepared in Example 1)-1 were intramuscularly injected at these sites. Subsequently, the in vivo electroporation of these sites was carried out using ECM830 (BTX) and a two-needle electrode. The same in vivo electroporation as above was repeated approximate once every two weeks. Then, the lymph nodes or the spleens were harvested from the rats and used in hybridoma preparation.

1)-3 Hybridoma Preparation

The lymph node cells or the spleen cells were electrically fused with mouse myeloma SP2/0-ag14 cells (ATCC, No. CRL-1 581) using LF301 Cell Fusion Unit (BEX Co., Ltd.). The fused cells were diluted with ClonaCell-HY Selection Medium D (StemCell Technologies Inc.) and cultured. Hybridoma colonies were recovered to prepare monoclonal hybridomas. Each hybridoma colony thus recovered was cultured using ClonaCell-HY Selection Medium E (StemCell Technologies Inc.), and the resulting hybridoma culture supernatant was used to screen for an anti-human CD3 antibody-producing hybridoma.

1)-4 Antibody Screening by Cell-ELISA

1)-4-1 Preparation of Antigen Gene-Expressing Cell for Cell-ELISA

HEK293α cells (stably expression HEK293-derived cell line expressing integrin αv and integrin β3) were adjusted to $7.5\times10^5$ cells/mL in a DMEM medium containing 10% FBS. hCD3ε-pcDNA3.1 and hCD3δ-pcDNA3.1, or a control pcDNA3.1-DEST was transfected thereto according to transfection procedures using Lipofectamine 2000 (Thermo Fisher Scientific Inc.). The resulting cells were dispensed in an amount of 100 μL/well to a 96-well plate (Corning Inc.) and cultured overnight at 37° C. under 5% $CO_2$ conditions in a DMEM medium containing 10% FBS. The resulting transfected cells were used in the attached state in Cell-ELISA.

1)-4-2 Cell-ELISA

After removal of the culture supernatant from the expression vector-transfected HEK293α cells prepared in Example 1)-4-1, each hybridoma culture supernatant was added to the hCD3δ-pcDNA3.1- and hCD3δ-pcDNA3.1-, or pcDNA3.1-DEST-transfected HEK293α cells, and the plate was left standing at 4° C. for 1 hour. The cells in the wells were washed once with PBS containing 5% FBS. Then, anti-Rat IgG and HRP-Linked Whole Ab Goat (GE Healthcare Bio-Sciences Corp.) diluted 500-fold with PBS containing 5% FBS was added, and the plate was left standing at 4° C. for 1 hour. The cells in the wells were washed twice with PBS containing 5% FBS. Then, an OPD chromogenic solution (OPD solution (o-phenylenediamine dihydrochloride (Wako Pure Chemicals Industries, Ltd.) and $H_2O_2$ dissolved at concentrations of 0.4 mg/mL and 0.6% (v/v), respectively, in 0.05 M trisodium citrate and 0.1 μM disodium hydrogen phosphate dodecahydrate, pH 4.5)) were added at a concentration of 100 μL/well. Color reaction was performed with occasional stirring and stopped by the addition of 1 M HCl at a concentration of 100 μL/well. Then, the absorbance was measured at 490 nm using a plate reader (ENVISION; PerkinElmer, Inc.). In order to select a hybridoma producing an antibody binding to human CD3 expressed on cell membrane surface, hybridomas that yielded a culture supernatant exhibiting higher absorbance for the hCD3δ-pcDNA3.1 and hCD3δ-pcDNA3.1 expression vector-transfected HEK293α cells compared with the control pcDNA3.1-DEST-transfected HEK293 cells were selected as anti-human CD3 antibody production-positive hybridomas.

1)-5 Antibody Screening Based on Activation of Human T Cells

The anti-CD3 antibody obtained from hybridoma was evaluated for its activation of T cells with the detection of a CD69 activation marker as an index. Human T cell line Jurkat cells (ATCC, No. TIB-152) were adjusted to a concentration of $5\times10^6$ cells/mL in an RPMI1640 medium containing FBS and added at a concentration of 100 μL/well to a 96-well plate. After removal of the supernatant by centrifugation, the culture supernatant of each anti-human CD3 antibody production-positive hybridoma selected by Cell-ELISA in Example 1)-4 or a rat IgG isotype control antibody (R&D Systems, Inc.) was added at a final concentration of 5 μg/mL to the Jurkat cells, and the plate was left standing at 37° C. for 30 minutes. Then, the cross-linker Goat Anti-rat IgG Fcγ Fragment specific (Jackson ImmunoResearch Laboratories, Inc.) was added at a final concentration of 10 μg/well, and the cells were cultured overnight at 37° C. under 5% $CO_2$ conditions. On the next day, the supernatant was removed, and the cells in the wells were washed once with PBS containing 5% FBS. Then, PE Mouse Anti-Human CD69 antibody (BD Biosciences) was added at a concentration of 20 μL/well, and the plate was left standing at 4° C. for 30 minutes. The cells in the wells were washed twice with PBS containing 5% FBS and then resuspended in PBS containing 5% FBS, followed by detection using a flow cytometer (FC500; Beckman Coulter Inc.). The data was analyzed using Flowjo (Tree Star Inc.). The PE fluorescence intensity was plotted to a histogram. Hybridomas that yielded a sample exhibiting a shift to stronger fluorescence intensity in the fluorescence intensity histogram of PE than in the fluorescence intensity histogram of the rat IgG isotype control antibody were selected as anti-human CD3 antibody-producing hybridomas positive for the ability to activate human T cells.

1)-6 Screening Based on Selective Binding Activity to Human or Monkey CD3 by Flow Cytometry 1)-6-1 Preparation of Human Antigen Gene-Expressing Cells Lenti-X293T cells (Takara Bio Inc., Cat #632180) were added at a density of $5.3\times10^4$ cells/cm$^2$ to a 225-cm$^2$ flask and cultured overnight at 37° C. under 5% $CO_2$ conditions in a DMEM medium containing 10% FBS. On the next day, hCD3ε-pcDNA3.1 and hCD3δ-pcDNA3.1 or a control pcDNA3.1-DEST was transfected to the Lenti-X293T cells using Lipofectamine 2000, and the cells were further cultured overnight at 37° C. under 5% $CO_2$ conditions. On the next day, the expression vector-transfected Lenti-X293T cells were treated with TrypLE Express (Thermo Fisher Scientific Inc.), washed with DMEM containing 10% FBS, and then adjusted to a concentration of $5\times10^6$ cells/mL in PBS containing 5% FBS. The resulting cell suspension was used in flow cytometry analysis.

1)-6-2 Flow Cytometry Analysis of Binding Activity to Human CD3

The human CD3 binding specificity of the antibody produced by each hybridoma determined to be positive for the ability to activate human T cells in Example 1)-5 was further confirmed by flow cytometry. Each Lenti-X293T cell suspension prepared in Example 1)-6-1 was added at a concentration of 100 μL/well to a 96-well U-bottomed microplate and centrifuged to remove the supernatant. The hCD3δ-pcDNA3.1- and hCD3δ-pcDNA3.1-transfected Lenti-X293T cells or the pcDNA3.1-DEST-transfected Lenti-X293T cells were suspended by the addition of the hybridoma culture supernatant and left standing at 4° C. for 1 hour. The cells were washed once with PBS containing 5% FBS, then suspended by the addition of Anti-Rat IgG FITC conjugate (Sigma-Aldrich Corp.) diluted 500-fold with PBS containing 5% FBS, and left standing at 4° C. for 30 minutes. The cells were washed twice with PBS containing 5% FBS and then resuspended in PBS containing 5% FBS and 2 μg/ml 7-aminoactinomycin D (Molecular Probes, Inc.), followed by detection using a flow cytometer. The data was analyzed using Flowjo. After removal of 7-aminoactinomycin D-positive dead cells by gating, the FITC fluorescence intensity of live cells was plotted to a histogram. Hybridomas that yielded a sample exhibiting a shift to stronger fluorescence intensity in the histogram of the hCD3ε-pcDNA3.1- and hCD3δ-pcDNA3.1-transfected Lenti-X293T cells than in the fluorescence intensity histogram of the control pcDNA3.1-DEST-transfected Lenti-X293T cells were selected as hybridomas producing antibodies binding to human CD3.

1)-6-3 Construction of Monkey CD3εδ Expression Vector cDNAs encoding the monkey CD3ε protein (NCBI Reference Sequence: NP_001270544.1) and the monkey CD3δ protein (NCBI Reference Sequence: NP_001274617.1) were amplified by PCR using a monkey T cell-derived cDNA as a template according to a method known to those skilled in the art, and cloned in pcDNA3.1(+) (Thermo Fisher Scientific Inc.) to construct expression vectors cynoCD3ε-pcDNA3.1 and cynoCD3δ-pcDNA3.1.

1)-6-4 Preparation of Monkey Antigen Gene-Expressing Cells

Lenti-X293T cells were inoculated at a density of $5.3\times10^4$ cells/cm$^2$ to a 225-cm$^2$ flask and cultured overnight at 37° C. under 5% $CO_2$ conditions in a DMEM medium containing 10% FBS. On the next day, cynoCD3δ-pcDNA3.1 and cynoCD3δ-pcDNA3.1 or a control pcDNA3.1-DEST was transfected to the Lenti-X293T cells using Lipofectamine 2000, and the cells were further cultured overnight at 37° C. under 5% $CO_2$ conditions. On the next day, the expression vector-transfected Lenti-X293T cells were treated with TrypLE Express, washed with DMEM containing 10% FBS, and then adjusted to a concentration of $5\times10^6$ cells/mL in PBS containing 5% FBS. The resulting cell suspension was used in flow cytometry analysis.

1)-6-5 Flow Cytometry Analysis of Binding Activity to Monkey CD3

The monkey CD3 binding specificity of the antibody produced by each hybridoma determined to produce the antibody binding to human CD3 in Example 1)-6-2 was further confirmed by flow cytometry. Each Lenti-X293T cell suspension prepared in Example 1)-6-4 was added at a concentration of 100 μL/well to a 96-well U-bottomed microplate and centrifuged to remove a supernatant. The cynoCD3ε-pcDNA3.1- and cynoCD3δ-pcDNA3.1-transfected Lenti-X293T cells or the pcDNA3.1-DEST-transfected Lenti-X293T cells were suspended by the addition of the hybridoma culture supernatant and left standing at 4° C. for 1 hour. The cells were washed once with PBS containing 5% FBS, then suspended by the addition of Anti-Rat IgG FITC conjugate diluted 500-fold with PBS containing 5% FBS, and left standing at 4° C. for 30 minutes. The cells were washed twice with PBS containing 5% FBS and then resuspended in PBS containing 5% FBS and 2 μg/ml 7-aminoactinomycin D, followed by detection using a flow cytometer. The data was analyzed using Flowjo. After removal of 7-aminoactinomycin D-positive dead cells by gating, the FITC fluorescence intensity of live cells was plotted to a histogram. Hybridomas that yielded a sample exhibiting a shift to stronger fluorescence intensity in the histogram of the cynoCD3δ-pcDNA3.1- and cynoCD3δ-pcDNA3.1-transfected Lenti-X293T cells than in the fluorescence intensity histogram of the control pcDNA3.1-DEST-transfected Lenti-X293T cells were selected as hybridomas producing antibodies binding to monkey CD3.

1)-6-6 Preparation of Human CD3δ Gene-Expressing Cells

Lenti-X293T cells were inoculated at a density of $5.3\times10^4$ cells/cm$^2$ to a 225-cm$^2$ flask and cultured overnight at 37° C. under 5% $CO_2$ conditions in a DMEM medium containing 10% FBS. On the next day, hCD3δ-pcDNA3.1 or a control pcDNA3.1-DEST was transfected to the Lenti-X293T cells using Lipofectamine 2000, and the cells were further cultured overnight at 37° C. under 5% $CO_2$ conditions. On the next day, the expression vector-transfected Lenti-X293T cells were treated with TrypLE Express, washed with DMEM containing 10% FBS, and then adjusted to a concentration of $5\times10^6$ cells/mL in PBS containing 5% FBS. The resulting cell suspension was used in flow cytometry analysis.

1)-6-7 Flow Cytometry Analysis of Binding Activity Against Human CD3δ

The human CD3δ binding specificity of the antibody produced by each hybridoma determined to produce the antibody binding to monkey CD3 in Example 1)-6-5 was further confirmed by flow cytometry. Each Lenti-X293T cell suspension prepared in Example 1)-6-6 was added at a concentration of 100 μL/well to a 96-well U-bottomed microplate and centrifuged to remove a supernatant. The hCD3δ-pcDNA3.1-transfected Lenti-X293T cells or the pcDNA3.1-DEST-transfected Lenti-X293T cells were suspended by the addition of the hybridoma culture supernatant and left standing at 4° C. for 1 hour. The cells were washed once with PBS containing 5% FBS, then suspended by the addition of Anti-Rat IgG FITC conjugate diluted 500-fold with PBS containing 5% FBS, and left standing at 4° C. for 30 minutes. The cells were washed twice with PBS containing 5% FBS and then resuspended in PBS containing 5% FBS and 2 μg/ml 7-aminoactinomycin D, followed by detection using a flow cytometer. The data was analyzed using Flowjo. After removal of 7-aminoactinomycin D-positive dead cells by gating, the FITC fluorescence intensity of live cells was plotted to a histogram. Hybridomas that yielded a sample exhibiting a shift to stronger fluorescence intensity in the histogram of the hCD3δ-pcDNA3.1-transfected Lenti-X293T cells than in the fluorescence intensity histogram of the control pcDNA3.1-DEST-transfected Lenti-X293T cells were excluded as hybridomas producing antibodies binding to human CD3δ.

1)-6-8 Flow Cytometry Analysis of Binding Activity to Monkey T Cell Lines

The monkey T cell line binding specificity of the antibody produced by each antibody-producing hybridoma that was not excluded in Example 1)-6-7 was further confirmed by flow cytometry. A cynomolgus monkey T cell line HSC-F (JCRB Cell Bank, No. JCRB1164) was adjusted to a concentration of $5\times10^6$ cells/mL in an RPMI1640 medium containing FBS and added at a concentration of 100 μL/well to a 96-well plate. After removal of the supernatant by centrifugation, the culture supernatant of the antibody-producing hybridoma that was not excluded in Example 1)-5-7, or a rat IgG isotype control antibody was added to the HSC-F cells, and the plate was left standing at 4° C. for 1 hour. Then, the supernatant was removed, and the cells in the wells were washed once with PBS containing 5% FBS, then suspended by the addition of Anti-Rat IgG FITC conjugate diluted 500-fold with PBS containing 5% FBS, and left standing at 4° C. for 1 hour. The cells were washed three times with PBS containing 5% FBS and then resuspended in PBS containing 5% FBS and 2 μg/ml 7-aminoactinomycin D, followed by detection using a flow cytometer. The data was analyzed using Flowjo. After removal of 7-aminoactinomycin D-positive dead cells by gating, the FITC fluorescence intensity of live cells was plotted to a histogram. Hybridomas that yielded a sample exhibiting a shift to stronger fluorescence intensity in the fluorescence intensity histogram of FITC than in the fluorescence intensity histogram of the rat IgG isotype control antibody were selected as hybridomas producing antibodies also binding to the monkey T cell line.

1)-7 Isotyping of Antibodies

C3-147 suggestive of binding to human and monkey CD3ε and also binding to a monkey T cell line, and having the high ability to activate human T cells was selected from among the rat anti-CD3 antibody-producing hybridomas obtained in Example 1)-6, and identified by antibody isotyping. The isotype was determined using Rat Immunoglobulin Isotyping ELISA Kit (BD Pharmingen). As a result, the isotype of the rat anti-CD3 monoclonal antibody C3-147 was confirmed to be IgG2b and λ chains.

(Example 2) Study of the Binding Activity of Rat Anti-CD3 Monoclonal Antibodies (C3-147) to Human CD3

2)-1 Preparation of Monoclonal Antibodies from Hybridoma Supernatant

2)-1-1 Culture of Hybridoma Producing C3-147

The rat anti-CD3 monoclonal antibody was purified from the hybridoma culture supernatant. First, the C3-147-producing hybridoma was allowed to grow to a sufficient amount in ClonaCell-HY Selection Medium E (StemCell Technologies Inc.). Then, the medium was replaced with a Hybridoma SFM (Thermo Fisher Scientific Inc.) containing 5 μg/mL gentamicin (Thermo Fisher Scientific Inc.) supplemented with 20% Ultra Low IgG FBS (Thermo Fisher Scientific Inc.), followed by culturing for 7 days. This cultured supernatant was recovered and sterilized through a 0.22 μm filter (Corning Inc.).

2)-1-2 Purification

The antibody was purified by protein G affinity chromatography from the hybridoma culture supernatant prepared in Example 2)-1-1. The antibody was adsorbed onto a protein G column (GE Healthcare Bio-Sciences Corp.), and the column was washed with PBS, followed by elution with an aqueous solution of 0.1 M glycine/hydrochloric acid (pH 2.7). The eluate was adjusted to pH 7.0 to 7.5 by the addition of 1 M Tris-HCl (pH 9.0). Then, the buffer was replaced with PBS using Centrifugal UF Filter Device VIVASPIN20 (molecular weight cutoff: UF30K, Sartorius Japan K.K.) while the antibody was concentrated and adjusted to an antibody concentration of 2 mg/mL. Finally, the concentrate was filtered through a Minisart-Plus filter (Sartorius Japan K.K.) and used as a purified sample.

2)-2 Binding of Obtained Rat Anti-CD3 Antibody (C3-147) to Human Single-Chain Antigens 2)-2-1 Preparation of Human CD3εγ Single-Chain Antigens An amino acid sequence encoding CD3ε or CD3γ was obtained from the crystal structure (PDBID: 1SY6) of an OTK3-human CD3εγ single-chain antigen complex submitted to the protein data bank. The same peptide linker composed of 26 amino acids that was reported in the reference (Kim, K. S. et al., (2000) J. Mol. Biol. 302, 899-916) was used as a linker for connecting the carboxyl terminus of CD3ε to the amino terminus of CD3γ. The gene encoding the human CD3εγ single-chain antigen shown in FIG. 3 (SEQ ID NO: 4) of the Sequence Listing was synthesized by adding restriction sites BamHI and HindIII to the 5' and 3' ends, respectively (GeneArt Gene Synthesis Service/Thermo Fisher Scientific Inc.). A fragment of approximately 4.8 kb obtained by digesting a plasmid pQE80L (Qiagen N.V.) with restriction enzymes BamHI and HindIII was ligated with a fragment of approximately 0.6 kb obtained by digesting the human CD3εγ single-chain antigen gene with BamHI and HindIII, using Ligation High (Toyobo Co., Ltd.) to prepare a plasmid pQE80L-scCD3εγ for expression in *E. coli*. The amino acid sequence of the resulting scCD3εγ is described in FIG. 4 (SEQ ID NO: 5) of the Sequence Listing. *E. coli* BL21 (DE3) for expression was transformed with the plasmid pQE80L-scCD3εγ for expression, and the resulting colony was added to 1 L MagicMedia (Invitrogen Corp.) using Ultra Yield Flasks™ (Thomson Instrument Company) and shake-cultured at 250 rpm at 30° C. for 21 hours. The bacterial cells thus cultured were recovered. Bacterial cells were disrupted using an ultrasonic homogenizer in the presence of a Tris buffer solution containing a 1% Triton solution, and the freeze-thaw cycle was repeated. Finally, inclusion bodies were recovered by centrifugation at 15000 rpm at 4° C. for 15 minutes. The procedures from refolding of the inclusion bodies to purification were performed according to the approach of the reference (Kjer-Nielsen et al. (2004) PNAS vol. 101, no. 20, 7675-7680) except that the anti-CD3 antibody used in an antibody column was a mouse anti-CD monoclonal antibody OKT3 (Sgro, Toxicology 105 (1995), 23-29, Orthoclone, Janssen-Cilag) instead of 2C11 used in the literature.

2)-2-2 SPR Measurement of Binding Activity to Human CD3εγ Single-Chain Antigens

The antibody was assayed for its binding to the antigen using BIAcore 3000 (GE Healthcare Bio-Sciences Corp.) by the capture method, which involves capturing the antibody as a ligand on an immobilized anti-mouse IgG antibody and assaying the antigen as an analyte. The antigen used was the human CD3εγ prepared in Example 2)-2-1. Approximately 11000 RU of the anti-mouse IgG antibody (Mouse Antibody Capture Kit, GE Healthcare Bio-Sciences Corp.) was covalently bound to a sensor chip CM5 (GE Healthcare Bio-Sciences Corp.) by the amine coupling method. Similarly, this antibody was immobilized onto a reference cell. The running buffer used was HBS-EP+(10 mM HEPES (pH 7.4), 0.15 M NaCl, 3 mM EDTA, and 0.05% Surfactant P20). The antibody was added onto the anti-mouse IgG antibody-immobilized chip for approximately 1 minute and then captured as a ligand. Then, 100 nM of the antigen was added at a flow rate of 30 μl/min for 120 seconds, and the binding to the antigen was monitored. 10 mM glycine-HCl (pH 1.7) was added as a regenerating solution at a flow rate of 10 μl/min for 3 minutes. As a result, the binding signal of C3-147 after 120 seconds was 34 RU.

2)-3 Confirmation of the Antigen-Binding Site in the Resulting Rat Anti-CD3 Antibody (C3-147) by SPR The method for confirming an antigen-binding site was performed in the same manner as Example 2)-2-2. As a result, the binding signal obtained for C3-147 was 34 RU. On the other hand, an antigen-binding site in SP34 (BD Pharmingen), an anti-CD3 antibody known in the art, was similarly confirmed as a comparative example. The binding signal of 34 RU was not observed in SP34. These results indicated that a binding site on the CD3εγ surface recognized by C3-147 is different from that recognized by SP34.

(Example 3) Sequencing of cDNAs Encoding Variable Regions in Rat Anti-CD3 Antibodies (C3-147)

The cDNAs encoding the variable regions of the rat anti-CD3 antibody (C3-147) were sequenced by the following method.

3)-1 cDNA Synthesis

Cell lysates (50 mM Tris-HCl (pH 7.5), 250 mM LiCl, 5 mM EDTA (pH 8), 0.5% lithium dodecyl sulfate (LiDS), and 2.5 mM dithiothreitol (DTT)) of the rat anti-CD3 antibody (C3-147)-producing hybridoma were mixed with oligo dT25-bound magnetic beads of Dynabeads mRNA DIRECT Kit (Thermo Fisher Scientific Inc.) so that the mRNA was bound to the magnetic beads. Next, the magnetic beads were washed once each with mRNA washing solution A (10 mM Tris-HCl (pH 7.5), 0.15 M LiCl, 1 mM EDTA, 0.1% LiDS, and 0.1% Triton X-100) and a solution for cDNA synthesis (50 mM Tris-HCl (pH 8.3), 75 mM KCl, 3 mM MgCl2, 5 mM DTT, 0.5 mM dNTP, 0.2% Triton X-100, and 1.2 units of RNase inhibitor (Thermo Fisher Scientific Inc.). Then, a cDNA was synthesized using a solution for cDNA synthesis supplemented with 12 units of SuperScript III Reverse Transcriptase (Thermo Fisher Scientific Inc.). Subsequently, the cDNA was washed with a 3' tailing reaction solution (50 mM potassium phosphate, 4 mM MgCl2, 0.5 mM dGTP, 0.2% Triton X-100, and 1.2 units of RNase inhibitor), followed by 3' tailing reaction with a reaction solution supplemented with 48 units of Terminal Transferase, recombinant (Roche Applied Science).

3)-2 Amplification and Sequencing of Rat Immunoglobulin Heavy and Light Chain Variable Region Gene Fragments The magnetic beads were washed with a TE solution (10 mM Tris-HCl (pH 7.5), 1 mM EDTA, and 0.1% Triton X-100). Then, the rat immunoglobulin heavy and light chain genes were amplified by 5'-RACE PCR. Specifically, the magnetic beads were transferred to a PCR reaction solution (0.2 μM primers, 0.2 mM dNTP, and 0.25 units of PrimeSTAR HS DNA Polymerase (Takara Bio Inc.)) and subjected to 35 reaction cycles each involving 94° C. for 30 seconds and 68° C. for 90 seconds. The primer sets used are described below.

PCR primer set for heavy chain gene amplification Sense primer Nhe-polyC-S 5'-GCTAGCGCTACCGGACTCAGATCCCCCCCCCCCCCCCDN-3'; Figure (SEQ ID NO: 50)

First antisense primer rIgγ-AS1 5'-TCACTGAGCTGGTGAGAGTGTAGAGCCC-3'; FIG. 6 (SEQ ID NO: 51)

Second antisense primer rIgγ-AS2 5'-TCACCGAGCTGCTGAGGGTGTAGAGCCC-3'; FIG. 7 (SEQ ID NO: 52)

PCR primer set for light chain gene amplification Sense primer Nhe-polyC-S2 5'-GCTAGCGCTACCGGACTCAGATCCCCCCCCCCCCCCCDN-3'; FIG. 8 (SEQ ID NO: 53)

First antisense primer rIgL-AS1 5'-TTCCACATCACTCGGGTAGAAATCAG-3'; FIG. 9 (SEQ ID NO: 54)

Second antisense primer rIgγ-AS2 5'-TAACACCAGGGTAGAAATCTGTCACCAT-3'; FIG. 10 (SEQ ID NO: 55)

Sequence analysis was carried out on the nucleotide sequences of the fragments amplified by the PCR reaction. The primers used are described below.

Sense primer rIgγ-seq for heavy chain sequencing 5'-CTGGCTCAGGGAAATAGCC-3'; FIG. 11 (SEQ ID NO: 56)

Antisense primer rIgL-seq1 for light chain sequencing 5'-TCCCTGGAGCTCCTCAGT-3'; FIG. 12 (SEQ ID NO: 57)

Antisense primer rIgL-seq2 for light chain sequencing 5'-GCCTTGTCAGTCTTGAGC-3'; FIG. 13 (SEQ ID NO: 58)

The sequence analysis was carried out using a gene sequence analyzer ("ABI PRISM 3700 DNA Analyzer; Applied Biosystems, Inc." or "Applied Biosystems 3730xl Analyzer; Applied Biosystems, Inc."). The Dye Terminator Cycle Sequencing System with AmpliTaq DNA polymerase (Life Technologies Corp.) and GeneAmp 9700 (Applied Biosystems, Inc.) were used in sequencing reaction.

The nucleotide sequence of the C3-147 heavy chain variable region determined by the sequence analysis is described in FIG. 14 (SEQ ID NO: 6), and its amino acid sequence is described in FIG. 15 (SEQ ID NO: 7). The nucleotide sequence of the C3-147 light chain variable region is described in FIG. 16 (SEQ ID NO: 8), and its amino acid sequence is described in FIG. 17 (SEQ ID NO: 9).

(Example 4) Preparation of Rat Anti-CD3 scFv (C3E-7000) and its Humanized Form (C3E-7034)

4)-1 Preparation of Rat Anti-CD3 Antibody (C3-147) scFv

4)-1-1 Construction of Rat Antibody CD3 scFv Expression Vector (pC3E-7000)

A sense strand oligonucleotide (FIG. 18 (SEQ ID NO: 10)) of a DNA fragment having 15-base additional sequences upstream and downstream of a DNA sequence encoding a linker to be inserted between the heavy chain variable region (VH) and the light chain variable region (VL) of C3-147, and an antisense strand oligonucleotide thereof (FIG. 19 (SEQ ID NO: 11)) were synthesized (Sigma-Aldrich Corp., Custom Oligo Synthesis Service), and adjusted to 100 pmol/μL. Then, 20 μL each of these oligonucleotides was mixed and left standing at 96° C. for 10 minutes, at 70° C. for 2 minutes, at 60° C. for 2 minutes, at 40° C. for 2 minutes, and at 30° C. for 2 minutes for annealing to prepare a DNA fragment of the linker to be inserted between VH and VL. Next, a DNA fragment amplified by PCR to add a human IgG heavy chain signal sequence, the DNA fragment (shown in FIG. 14 (SEQ ID NO: 6)) of VH of the rat anti-CD3 antibody C3-147 amplified by PCR, the DNA fragment of the linker to be inserted between VH and VL, and a DNA fragment amplified by PCR in which a DNA sequence encoding a FLAG-His tag was added to a region containing the C3-147_VL DNA sequence (shown in FIG. 16 (SEQ ID NO: 8)) such that the FLAG-His tag was located at the carboxyl terminus, were ligated with a vector backbone derived from an expression vector pcDNA-3.3TOPO for animal cells (Thermo Fisher Scientific Inc.) using In-Fusion HD cloning kit (Clontech Laboratories, Inc.) to prepare an scFv expression vector pC3E-7000 containing the nucleotide sequence of FIG. 20 (SEQ ID NO: 14) in ORF.

4)-1-2 Expression and Purification of Rat Anti-CD3 scFv (C3E-7000)

Expi293F cells (Thermo Fisher Scientific Inc.) were subcultured and cultured according to the manual. The scFv expression vector was transfected to the Expi293F cells in the logarithmic growth phase. The scFv was transiently expressed, filtered, and then used in purification. The purification was performed by two steps involving Ni affinity chromatography using His Trap Excel (GE Healthcare Bio-Sciences Corp.) and gel filtration using Superdex 200 increase (GE Healthcare Bio-Sciences Corp.). A peak corresponding to the molecular weight of the scFv monomer was recovered and used as a purified protein sample. For the purification, AKTA chromatography system was used, and all steps were performed at 4° C. HBSor (25 mM histidine/5% sorbitol, pH 5.0) was used as a buffer for the purified protein. The purified protein sample was applied to SEC for analysis to determine its purity and concentration. Then, the sample was used in various assays. The amino acid sequence in C3E-7000 is described in FIG. 21 (SEQ ID NO: 15).

4)-2 Humanization of Rat Anti-CD3 scFv (C3E-7000)

4)-2-1 Humanization Design of Anti-CD3 Antibody

The molecular modeling of the variable regions of the rat antibody was performed according to a method known in the art as homology modeling (Methods in Enzymology, 203, 121-153, (1991)) using a commercially available protein three-dimensional structure analysis program Discovery Studio 3.5 (Dassault Systems S.A.).

The humanization was performed by a method generally known as CDR grafting (Proc. Natl. Acad. Sci. USA 86, 10029-10033 (1989)). An acceptor antibody was selected from human subgroup consensus sequences specified by KABAT et al. (Sequences of Proteins of Immunological Interest, 5th Ed. Public Health Service National Institutes of Health, Bethesda, Md. (1991)) or the germline sequences on the basis of amino acid identity within framework regions, expected immunogenicity prediction scores or physical properties, etc. Also, back mutation was selected with reference to criteria, etc., provided by Queen et al. (PNAS (1989) 86, 10029-10033) through the use of the three-dimensional structure model constructed by the approach described above.

4)-2-2 Design of Humanized Amino Acid Sequence C3E-7000

On the basis of the approach described in Example 4)-2-1, the amino acid sequence of C3E-7034 serving as a humanized form of C3E-7000 was designed with human subgroup consensus sequences γ3 and λ6 as acceptors. The amino acid sequence of C3E-7034VH designed from the amino sequence of C3-147VH shown in FIG. 15 (SEQ ID NO: 7) by the replacement of arginine at amino acid position 16 with glycine, alanine at amino acid position 17 with serine, lysine at amino acid position 19 with arginine, valine at amino acid position 23 with alanine, valine at amino acid position 24 with alanine, serine at amino acid position 88 with alanine, and threonine at amino acid position 93 with valine is described in FIG. 22 (SEQ ID NO: 16).

The amino acid sequence of C3E-7034VL designed from the amino sequence of C3-147VL shown in FIG. 17 (SEQ ID NO: 9) by the replacement of glutamine at amino acid position 1 with asparagine, valine at amino acid position 3 with methionine, asparagine at amino acid position 8 with histidine, threonine at amino acid position 12 with glutamic acid, asparagine at amino acid position 13 with serine, leucine at amino acid position 14 with proline, threonine at amino acid position 16 with lysine, glutamic acid at amino acid position 19 with threonine, leucine at amino acid position 20 with isoleucine, arginine at amino acid position 43 with serine, leucine at amino acid position 75 with serine, asparagine at amino acid position 79 with serine, valine at amino acid position 81 with leucine, and glutamine at amino acid position 82 with lysine is described in FIG. 23 (SEQ ID NO: 17).

The CDR sequences of C3E-7000 and C3E-7034 based on the CDR definition of IMGT are described in FIG. 24 (SEQ ID NO: 26) for CDR-H1, FIG. 25 (SEQ ID NO: 27) for CDR-H2, FIG. 26 (SEQ ID NO: 28) for CDR-H3, FIG. 27 (SEQ ID NO: 29) for CDR-L1, FIG. 28 (SEQ ID NO: 30) for CDR-L2, and FIG. 29 (SEQ ID NO: 31) for CDR-L3.

4)-2-3 Modification of Humanized Anti-CD3 scFv C3E-7034

In order to prepare variants having distinctive binding activity and cytotoxic activity while maintaining cross-reactivity with monkey CD3δ, variants were designed, in the same way as in the approach described in Example 4)-2-1, by the replacement of amino acids in the framework regions of VL of C3E-7034 with the corresponding ones in VL of scFv (sequence containing the four mutations A2S, S8P, V13A, and F80L in IGLV1-40*01).

4)-2-3-1 Amino Acid Sequence Design of C3E-7035

The amino acid sequence of C3E-7035 serving as a variant of C3E-7034 was designed. The amino acid sequence of the C3E-7035 light chain designed from the C3E-7034 light chain variable region shown in FIG. 23 (SEQ ID NO: 17) by the replacement of asparagine at amino acid position 1 with glutamine, the replacement of phenylalanine at amino acid position 2 with alanine, the replacement of methionine at amino acid position 3 with valine, the replacement of histidine at amino acid position 8 with serine, the replacement of glutamic acid at amino acid position 12 with glycine, the replacement of serine at amino acid position 13 with valine, the replacement of lysine at amino acid position 16 with glutamine, the replacement of threonine at amino acid position 17 with arginine, the replacement of histidine at amino acid position 40 with leucine, the replacement of glutamic acid at amino acid position 41 with proline, the replacement of serine at amino acid position 43 with threonine, the replacement of serine at amino acid position 44 with alanine, the replacement of threonine at amino acid position 46 with lysine, the replacement of threonine at amino acid position 47 with leucine, the replacement of isoleucine at amino acid position 48 with leucine, the replacement of aspartic acid at amino acid position 57 with serine, the replacement of serine at amino acid position 60 with proline, the replacement of isoleucine at amino acid position 67 with lysine, the deletion of aspartic acid at amino acid position 68, the deletion of arginine at amino acid position 69, the replacement of serine at amino acid position 71 with glycine, the replacement of lysine at amino acid position 72 with threonine, the replacement of threonine at amino acid position 77 with alanine, the replacement of serine at amino acid position 79 with threonine, the replacement of asparagine at amino acid position 80 with glycine, the replacement of leucine at amino acid position 81 with phenylalanine, the replacement of lysine at amino acid position 82 with glutamine, the replacement of threonine at amino acid position 83 with alanine, and the replacement of phenylalanine at amino acid position 90 with tyrosine is described in FIG. 30 (SEQ ID NO: 20). The full-length sequence of C3E-7035 containing methionine and alanine inserted immediately before the light chain variable region is described in FIG. 31 (SEQ ID NO: 22) of the Sequence Listing.

4)-2-3-2 Amino Acid Sequence Design of C3E-7036

The amino acid sequence of C3E-7036 serving as a variant of C3E-7034 was designed. The amino acid sequence of the C3E-7036 light chain designed from the C3E-7034 light chain variable region shown in FIG. 23 (SEQ ID NO: 17) by the replacement of histidine at amino acid position 8 with serine, the replacement of glutamic acid at amino acid position 12 with glycine, the replacement of serine at amino acid position 13 with valine, the replacement of lysine at amino acid position 16 with glutamine, the replacement of threonine at amino acid position 17 with arginine, the replacement of lysine at amino acid position 23 with threonine, the replacement of arginine at amino acid position 24 with glycine, the replacement of histidine at amino acid position 40 with leucine, the replacement of glutamic acid at amino acid position 41 with proline, the replacement of serine at amino acid position 43 with threonine, the replacement of serine at amino acid position 44 with alanine, the replacement of threonine at amino acid position 46 with lysine, the replacement of threonine at amino acid position 47 with leucine, the replacement of isoleucine at amino acid position 48 with leucine, the replacement of aspartic acid at amino acid position 57 with serine, the replacement of serine at amino acid position 60 with proline, the replacement of isoleucine at amino acid position 67 with lysine, the deletion of aspartic acid at amino acid position 68, the deletion of arginine at amino acid position 69, the replacement of serine at amino acid position 71 with glycine, the replacement of lysine at amino acid position 72 with threonine, the replacement of threonine at amino acid position 77 with alanine, the replacement of serine at amino acid position 79 with threonine, the replacement of asparagine at amino acid position 80 with glycine, the replacement of leucine at amino acid position 81 with phenylalanine, the replacement of lysine at amino acid position 82 with glutamine, the replacement of threonine at amino acid position 83 with alanine, and the replacement of phenylalanine at amino acid position 90 with tyrosine is described in FIG. 32 (SEQ ID NO: 23). The full-length amino acid sequence of C3E-7036 is described in FIG. 33 (SEQ ID NO: 25).

4)-2-3-3 Amino Acid Design in CDR Variants

For the purpose of removing a deamination site present in C3E-7034 CDRH2 (FIG. 25, SEQ ID NO: 27), C3E-7078 having arginine substituted for asparagine at amino acid position 53 in the C3E-7034 heavy chain variable region shown in FIG. 22 (SEQ ID NO: 16) and C3E-7079 having serine substituted therefor were designed. Also, C3E-7085 having arginine substituted for asparagine at amino acid position 53 in the C3E-7036 heavy chain variable region was designed. The entire amino acid sequence of C3E-7078 is listed in FIG. 68 (SEQ ID NO: 60). The entire amino acid sequence of C3E-7079 is listed in FIG. 70 (SEQ ID NO: 62). The entire amino acid sequence of C3E-7085 is listed in FIG. 72 (SEQ ID NO: 64).

For the purpose of reducing the affinity of C3E-7078 for human CD3, C3E-7086 having glycine substituted for aspartic acid at amino acid position 52 in the C3E-7078 light chain variable region, C3E-7087 having glutamine substituted therefor, C3E-7088 having asparagine substituted therefor, C3E-7089 having serine substituted therefor, and C3E-7090 having alanine substituted therefor were designed. Likewise, for the purpose of reducing the affinity of C3E-7079 for human CD3, C3E-7091 having glycine substituted for aspartic acid at amino acid position 52 in the C3E-7079 light chain variable region, C3E-7092 having glutamine substituted therefor, C3E-7093 having asparagine substituted therefor, C3E-7094 having serine substituted therefor, and C3E-7095 having alanine substituted therefor were designed. The entire amino acid sequence of C3E-7086 is listed in FIG. 74 (SEQ ID NO: 66). The entire amino acid sequence of C3E-7087 is listed in FIG. 76 (SEQ ID NO: 68). The entire amino acid sequence of C3E-7088 is listed in FIG. 78 (SEQ ID NO: 70). The entire amino acid sequence of C3E-7089 is listed in FIG. 80 (SEQ ID NO: 72). The entire amino acid sequence of C3E-7090 is listed in FIG. 82 (SEQ ID NO: 74). The entire amino acid sequence of C3E-7091 is listed in FIG. 84 (SEQ ID NO: 76). The entire amino acid sequence of C3E-7092 is listed in FIG. 86 (SEQ ID NO: 78). The entire amino acid sequence of C3E-7093 is listed in FIG. 88 (SEQ ID NO: 80). The entire amino acid sequence of C3E-7094 is listed in FIG. 90 (SEQ ID NO: 82). The entire amino acid sequence of C3E-7095 is listed in FIG. 92 (SEQ ID NO: 84).

4)-3 Preparation of Humanized Anti-CD3 scFv (C3E-7034, C3E-7035, and C3E-7036)

4)-3-1 Construction of Humanized Anti-CD3 scFv (C3E-7034) Expression Vector pC3E-7034

A DNA fragment comprising a DNA sequence of scFv containing a C3E-7034 light chain (shown in FIG. 23 (SEQ ID NO: 17)) connected to the carboxyl terminus of the C3E-7034 heavy chain (shown in FIG. 22 (SEQ ID NO: 16)) via a 15-amino acid flexible linker was synthesized with 15-base additional sequences attached upstream and downstream (GeneArt Gene Synthesis Service/Thermo Fisher Scientific Inc.). A region containing the C3E-7034 DNA and additional sequences upstream and downstream was amplified by PCR using this DNA fragment as a template to obtain an insert DNA fragment. A vector region except for the scFv region was amplified by PCR using the expression vector pC3E-7000 prepared in Example 4)-1-1 as a template to obtain a vector fragment. These DNA fragments were annealed using In-Fusion HD cloning kit (Clontech Laboratories, Inc.) to prepare a humanized anti-CD3 scFv expression vector pC3E-7034 containing the nucleotide sequence of FIG. 34 (SEQ ID NO: 18) in ORF.

4)-3-2 Construction of Humanized Anti-CD3 scFv (C3E-7035) Expression Vector pC3E-7035

A DNA fragment comprising a DNA sequence of scFv containing the C3E-7035 light chain (shown in Figure (SEQ ID NO: 20)) connected to the carboxyl terminus of the C3E-7034 heavy chain (shown in FIG. 22 (SEQ ID NO: 16)) via a 17-amino acid flexible linker was synthesized with 15-base additional sequences attached upstream and downstream (GeneArt Gene Synthesis Service/Thermo Fisher Scientific Inc.). A C3E-7035 expression vector containing the nucleotide sequence of FIG. 35 (SEQ ID NO: 21) in ORF was constructed in the same way as in Example 4)-3-1. The resulting expression vector was designated as "pC3E-7035."

4)-3-3 Construction of Humanized Anti-CD3 scFv (C3E-7036) Expression Vector pC3E-7036

A DNA fragment comprising a DNA sequence of scFv containing the C3E-7036 light chain (shown in FIG. 32 (SEQ ID NO: 23)) connected to the carboxyl terminus of the C3E-7034 heavy chain (shown in FIG. 22 (SEQ ID NO: 16)) via a 15-amino acid flexible linker was synthesized with 15-base additional sequences attached to its upstream and downstream (GeneArt Gene Synthesis Service/Thermo Fisher Scientific Inc.). A C3E-7036 expression vector containing the nucleotide sequence of FIG. 36 (SEQ ID NO: 24) in ORF was constructed in the same manner as in Example 4)-3-1. The resulting expression vector was designated as "pC3E-7036."

4)-3-4 Construction of CDR Modified Humanized Antibody CD3 scFv Expression Vectors PCR-based site-directed mutagenesis was performed using pC3E-7034 containing the nucleotide sequence of C3E-7034 shown in FIG. 34 (SEQ ID NO: 18) in ORF as a template and using primers having the nucleotide sequences shown in FIGS. 93 and 94 (SEQ ID NOs: 85 and 86) to prepare a C3E-7078 expression vector containing the nucleotide sequence of C3E-7078 having arginine substituted for asparagine at amino acid position 53 in the C3E-7034 heavy chain variable region, in ORF. The resulting expression vector was designated as "pC3E-7078." Likewise, PCR-based site-directed mutagenesis was performed using pC3E-7034 as a template and using primers of FIGS. 95 and 96 (SEQ ID NOs: 87 and 88) to prepare a C3E-7079 expression vector containing the nucleotide sequence of C3E-7079 having serine substituted for asparagine at amino acid position 53 in the C3E-7034 heavy chain variable region. The resulting expression vector was designated as "pC3E-7079." Likewise, PCR-based site-directed mutagenesis was performed using pC3E-7036 as a template and using primers of FIGS. 93 and 94 (SEQ ID NOs: 85 and 86) to prepare a C3E-7085 expression vector containing the nucleotide sequence of C3E-7085 having arginine substituted for asparagine at amino acid position 53 in the C3E-7036 heavy chain variable region. The resulting expression vector was designated as "pC3E-7085."

Expression vectors containing the nucleotide sequence of C3E-7086 having glycine substituted for aspartic acid at amino acid position 52 in the C3E-7078 light chain variable region, C3E-7087 having glutamine substituted therefor, C3E-7088 having asparagine substituted therefor, C3E-7089 having serine substituted therefor, or C3E-7090 having alanine substituted therefor in ORF, and expression vectors containing the nucleotide sequence of C3E-7091 having glycine substituted for aspartic acid at amino acid position 52 in the C3E-7079 light chain variable region, C3E-7092 having glutamine substituted therefor, C3E-7093 having asparagine substituted therefor, C3E-7094 having serine substituted therefor, or C3E-7095 having alanine substituted therefor in ORF were also prepared by the same approach as above. A list of the names of the prepared vectors, templates, and primers is summarized in Table 1, and a primer list is summarized in FIG. 105.

TABLE 1

| CloneID | Template | Forward primer | Reverse primer |
|---|---|---|---|
| C3E-7086 | C3E-7078 | LD52G Fw | LD52G Rv |
| C3E-7087 | C3E-7078 | LD52Q Fw | LD52Q Rv |
| C3E-7088 | C3E-7078 | LD52N Fw | LD52N Rv |
| C3E-7089 | C3E-7078 | LD52S Fw | LD52S Rv |
| C3E-7090 | C3E-7078 | LD52A Fw | LD52A Rv |
| C3E-7091 | C3E-7079 | LD52G Fw | LD52G Rv |
| C3E-7092 | C3E-7079 | LD52Q Fw | LD52Q Rv |
| C3E-7093 | C3E-7079 | LD52N Fw | LD52N Rv |
| C3E-7094 | C3E-7079 | LD52S Fw | LD52S Rv |
| C3E-7095 | C3E-7079 | LD52A Fw | LD52A Rv |

4)-3-5 Expression and Purification of Humanized Anti-CD3 scFv

C3E-7034, C3E-7035, and C3E-7036 were expressed and purified in the same manner as in Example 4)-1-2.

4)-3-6 Expression and Purification of CDR Modified Humanized Anti-CD3 scFv

The CDR variants C3E-7078, C3E-7079, C3E-7085, C3E-7086, C3E-7087, C3E-7088, C3E-7089, C3E-7090, C3E-7091, C3E-7092, C3E-7093, C3E-7094, and C3E-7095 were expressed and purified in the same manner as in Example 4)-1-2.

(Example 5) Crystal Structure Analysis of Humanized Anti-CD3 scFv (C3E-7034)

5)-1 Preparation of a Humanized Anti-CD3 scFv (C3E-7034)-Human CD3εγ Single-Chain Antigen Complex CD3εγ prepared in Example 2)-2-1 and C3E-7034 prepared in Example 4)-3-1 were mixed at a molar ratio of 1:2. The buffer solution was replaced with 10 mM Tris HCl (pH 7.5) and 50 mM NaCl using Amicon Ultra 15 MWCO 10K (Merck Millipore), and the resulting solution was concentrated to 3.5 mg/mL. This concentrate was purified by gel filtration chromatography using Superdex 200 10/300GL (GE Healthcare Bio-Sciences Corp.). A fraction of the complex was concentrated into approximately 4.0 mg/mL using Amicon Ultra 15 MWCO 10K (Millipore).

5)-2 Crystallization

The resulting complex of CD3εγ and C3E-7034 was crystallized by the vapor diffusion method. To 0.5 μL of the protein solution, an equal amount of a precipitant solution (0.1 M MES monohydrate (pH 6.5), 1.6 M ammonium sulfate, and 10% v/v 1,4-dioxane) was added, and the resulting solution was placed in a sealed container containing 0.05 mL of a precipitant solution so that the solutions had no contact with each other. The container was left standing at 25° C. One month later, 0.1 mm×0.05 mm×0.05 mm rod-like crystals were obtained.

5)-3 X-Ray Crystal Structure Analysis and Identification of Epitope

The resulting crystal was dipped in Perfluoropolyether PFO-X175/08 (Hampton Research Corp.) and subsequently frozen in liquid nitrogen. X-ray diffraction data was collected using beamline BL41XU (SPring-8, Hyogo, Japan). The diffraction intensity was digitized from the resulting diffraction image using software imosflm (CCP4: Collaborative Computational Project No. 4) to determine crystal structure factors. The crystals were in a hexagonal system with a space group of P62 and unit cells of a=193.54 angstroms, b=193.54 angstroms, and c=43.88 angstroms.

The molecular replacement method was performed using the resulting structural factors and the three-dimensional structural coordinates of the homology models to determine phases. A software phaser (CCP4: Collaborative Computational Project No. 4) was used in calculation. The crystals contained one complex in an asymmetric unit.

Structure refinement was performed using software Refmac5 (CCP4: Collaborative Computational Project No. 4), and model correction was performed using Coot software. This operation was performed repeatedly to obtain a final R factor of 22.1% and a free R factor of 27.0% with a resolution of 3.3 angstroms. The final model contained amino acid residues 1 to 108 of the C3E-7034 light chain region (FIG. 23, SEQ ID NO: 17), amino acid residues 1 to 118 of the C3E-7034 heavy chain region (FIG. 22, SEQ ID NO: 16), amino acid residues 33 to 67 and 71 to 118 of the CD3ε region (FIG. 1, SEQ ID NO: 1), and amino acid residues 23 to 103 of the CD3γ region (FIG. 37, SEQ ID NO: 3). Amino acid residues 68 to 70 of the CD3ε region (FIG. 1, SEQ ID NO: 1), and the amino-terminal region (amino acid residue 1), the linker portion (amino acid residues 120 to 134), and the carboxyl-terminal region (amino acid residues 243 to 269) of C3E-7034 (FIG. 38, SEQ ID NO: 19) were not included in the model because of their obscure electric density. FIG. 39 shows the ribbon model of the whole complex, and the surface.

FIG. 40 shows the interaction between CD3ε and the light and heavy chains of C3E-7034. Panel A is a diagram in which the amino acids of CD3ε having a distance within 4 angstroms of the light chain variable region of C3E-7034 are indicated by thick sticks in the model, and the other amino acids are indicated by thin sticks in the model. In the diagram, Ser55, Glu56, Arg101, Gly102, Ser103, Lys104, and Pro105 denoted by residue name and residue no. inside boxes are amino acid residues of CD3ε having a distance within 4 angstroms of the light chain variable region of C3E-7034, and each amino acid position corresponds to a position in SEQ ID NO: 1 of the Sequence Listing. Panel B is a diagram in which the amino acid residues of CD3ε having a distance within 4 angstroms of the heavy chain variable region of C3E-7034 are indicated by thick sticks in the model, and the other amino acids are indicated by thin sticks in the model. In the diagram, Ser55, Glu56, Leu58, Trp59, Asn65, Ile66, Ser77, Asp78, and Arg101 denoted by residue name and residue no. inside boxes are amino acids of CD3ε, and each amino acid position corresponds to the position in SEQ ID NO: 1 of the Sequence Listing. The following amino acid residues have a distance within 4 angstroms of C3E-7034 and have been interpreted as being epitopes on CD3ε for C3E-7034: Ser55, Glu56, Leu58, Trp59, Asn65, Ile66, Ser77, Asp78, Arg101, Gly102, Ser103, Lys104, and Pro105.

Among these epitopes on CD3ε for C3E-7034, Arg101, Gly102, Ser103, Lys104, and Pro105 are common epitope residues on CD3ε for OKT3 and UCHT1 (Kjer-Nielsen et al., PNAS 101 (2004), p. 7675-80; and Arnett et al., PNAS 101 (2004), p. 16268-73). It has also been revealed that C3E-7034 does not interact with amino acid positions 22 to 48 in SEQ ID NO: 1, which correspond to epitopes for anti-CD3 antibodies such as I2C and H2C as described in WO2008/119565A2. FIG. 41 shows interacting residues on the sequence of CD3ε. The signal sequence of CD3ε is indicated by italicized letters, and amino acids having a distance within 4 angstroms of C3E-7034 are underlined.

(Example 6) Preparation of Humanized OKT3 scFv

6)-1 Construction of OKT3 scFv Expression Vector pC3E-3000 scFv of a mouse anti-CD3 monoclonal antibody OKT3 (Sgro, Toxicology 105 (1995), 23-29, Orthoclone, Janssen-Cilag) was prepared by the same approach as in Example 4)-1-1 and inserted to a pcDNA3.3-derived expression vector for animal cells. The resulting expression vector was designated as "pC3E-3000."

6)-2 Design of Humanized Amino Acid Sequence of OKT3 scFv (C3E-3000)

On the basis of the approach described in Example 4)-2-1, the amino acid sequence of C3E-3007 serving as a humanized form of OKT3 was designed with human subgroup consensus sequences gamma 1 and kappa 4 as acceptors. Kappa 1 amino acids were introduced to some sites in consideration of the influence on immunogenicity scores and on physical properties. The amino acid sequence of the C3E-3007 light chain designed from the OKT3 heavy chain variable region shown in FIG. 42 (SEQ ID NO: 36) by the replacement of glutamine at amino acid position 5 with valine, leucine at amino acid position 11 with serine, alanine at amino acid position 12 with lysine, arginine at amino acid position 13 with lysine, methionine at amino acid position 20 with valine, lysine at amino acid position 38 with arginine, arginine at amino acid position 40 with alanine, isoleucine at amino acid position 48 with methionine, lysine at amino acid position 67 with arginine, alanine at amino acid position 68 with valine, leucine at amino acid position 70 with isoleucine, threonine at amino acid position 72 with alanine, serine at amino acid position 76 with threonine, glutamine at amino acid position 82 with glutamic acid, threonine at amino acid position 87 with arginine, serine at amino acid position 91 with threonine, threonine at amino acid position 114 with leucine, and leucine at amino acid position 115 with valine is described in FIG. 43 (SEQ ID NO: 38).

The amino acid sequence of the C3E-3007 light chain designed from the OKT3 light chain variable region shown in FIG. 44 (SEQ ID NO: 37) by the replacement of valine at amino acid position 3 with glutamine, leucine at amino acid position 4 with methionine, alanine at amino acid position 9 with serine, isoleucine at amino acid position 10 with serine, methionine at amino acid position 11 with leucine, serine at amino acid position 12 with alanine, alanine at amino acid position 13 with valine, proline at amino acid position 15 with leucine, lysine at amino acid position 18 with arginine, valine at amino acid position 19 with alanine, methionine at amino acid position 21 with isoleucine, serine at amino acid position 39 with proline, threonine at amino acid position 41 with lysine, serine at amino acid position 42 with alanine, alanine at amino acid position 59 with aspartic acid, histidine at amino acid position 60 with arginine, arginine at amino acid position 62 with serine, serine at amino acid position 69 with aspartic acid, tyrosine at amino acid position 70 with phenylalanine, serine at amino acid position 71 with threonine, glycine at amino acid position 76 with serine, methionine at amino acid position 77 with leucine, glutamic acid at amino acid position 78 with glutamine, alanine at amino acid position 82 with valine, serine at amino acid position 99 with glutamine, and leucine at amino acid position 103 with valine is described in FIG. 45 (SEQ ID NO: 39).

6)-3 Construction of Humanized OKT3 scFv (C3E-3007) Expression Vector pC3E-3007

A DNA fragment comprising a DNA sequence of scFv containing the C3E-3007 light chain (shown in FIG. 45 (SEQ ID NO: 39)) region connected to the carboxyl terminus of the C3E-3007 heavy chain (shown in FIG. 43 (SEQ ID NO: 38)) via a 15-amino acid flexible linker, and 15-base additional sequences upstream and downstream thereof was synthesized (GeneArt Gene Synthesis Service/Thermo Fisher Scientific Inc.). A C3E-3007 expression vector containing the nucleotide sequence of FIG. 46 (SEQ ID NO: 34) in ORF was constructed in the same manner as in Example 4)-3-1. The resulting expression vector was designated as "pC3E-3007."

6)-4 Expression and Purification of Humanized OKT3 scFv (C3E-3007)

C3E-3007 was expressed and purified in the same manner as Example 4)-1-2. The amino acid sequence of C3E-3007 is described in FIG. 47 (SEQ ID NO: 35).

(Example 7) In Vitro Activity of Humanized Anti-CD3 scFv

7)-1 Study of Binding Activity of Humanized Anti-CD3 scFv (C3E-3007, C3E-7034, C3E-7035, and C3E-7036) Against Human CD3

7)-1-1 Study of Binding Activity of Humanized Anti-CD3 scFv (C3E-3007, C3E-7034, C3E-7035, and C3E-7036) to Human CD3 by Flow Cytometry Commercially available human PBMC (Cellular Technology Ltd. (CTL)) was adjusted to an appropriate concentration with PBS containing 5% FBS. LIVE/DEAD Fixable Near-IR Dead Cell Stain Kit (Thermo Fisher Scientific Inc.) and an anti-CD19 antibody (Beckman Coulter Inc.) were added to the cells, which were then left standing at 4° C. for 30 minutes. The cells were washed twice with PBS containing 5% FBS, then adjusted to a concentration of $1\times10^6$ cells/mL with PBS containing 5% FBS, added at a concentration of 100 μL/well to a 96-well U-bottomed microplate, and centrifuged to remove a supernatant. Each humanized anti-CD3 scFv (C3E-3007, C3E-7034, C3E-7035, and C3E-7036) diluted with PBS containing 5% FBS was added at a concentration of 100 μL/well, and the plate was left standing at 4° C. for 60 minutes. The cells were washed twice with PBS containing 5% FBS. Then, Penta-His Alexa Fluor 488 (Qiagen N.V.) diluted with PBS containing 5% FBS was added at a concentration of 30 μL/well, and the plate was left standing at 4° C. for 30 minutes. The cells were washed twice with PBS containing 5% FBS and then resuspended in PBS containing 5% FBS, followed by detection using a flow cytometer (FACSCanto™ II; Becton, Dickinson and Company). The data was analyzed using Flowjo (Tree Star Inc.). The mean fluorescence intensity (MFI) of Alexa Fluor 488 in a fraction free of dead cells and CD19-positive cells was calculated. The MFI value of the scFv-unsupplemented sample was subtracted from the MFI value of the scFv-supplemented sample to calculate a relative value of MFI (rMFI). As shown in FIG. 48, the humanized anti-CD3 scFvs were found to bind to human CD3.

7)-1-2 Study of Binding Activity of Humanized Anti-CD3 scFvs (C3E-3007, C3E-7034, C3E-7035, and C3E-7036) to Human CD3 by SPR The affinity of each humanized anti-CD3 scFv (C3E-3007, C3E-7034, C3E-7035, and C3E-7036) for CD3 was determined by the surface plasmon resonance method using BIAcore T-200 (GE Healthcare Bio-Sciences Corp.). Five different concentrations of the scFv were injected into CD3 immobilized on a sensor chip. Rmax was estimated from the resulting response, and the antibody concentration that reached 1/2 thereof was defined as the dissociation constant of the scFv for CD3. As a result, the dissociation constants of these scFvs for CD3 were 400, 4.5, 22, and 25 nM, respectively.

7)-2 A Study of the Binding Activity of Humanized Antibody CD3 scFv (C3E-3007, C3E-7034, and C3E-7036) with Cynomolgus Monkey CD3

7)-2-1 Preparation of Cynomolgus Monkey PBMC

PBMC was collected from the blood of a cynomolgus monkey according to the standard method using SepMate (StemCell Technologies Inc.) and Lymphocyte Separation Solution (Nacalai Tesque Inc.).

7)-2-2 Study of Binding Activity of Humanized Anti-CD3 scFvs (C3E-3007, C3E-7034, C3E-7035, and C3E-7036) to Cynomolgus Monkey CD3 by Flow Cytometry The cynomolgus monkey PBMC obtained in Example 7)-2-1 was adjusted to an appropriate concentration with PBS containing 5% FBS, and stained and analyzed in the same manner as Example 7)-1-1. As shown in FIG. 49, the humanized anti-CD3 scFvs (C3E-7034, C3E-7035, and C3E-7036) were found to bind to cynomolgus monkey CD3.

7)-3 T Cell Activation of Humanized Anti-CD3 scFvs (C3E-3007 and, C3E-7034)

Human peripheral blood mononuclear cells (PBMC) were isolated from the fresh buffy coats of random donors by the density gradient centrifugation method using Lympholyte-H (Cedarlane). Each humanized anti-CD3 scFv (C3E-3007 and C3E-7034) diluted to 100 nM with LR10 (RPMI1640 containing 10% ultra low IgG FBS (Thermo Fisher Scientific Inc.)) and the same concentration of Anti-His antibody (Qiagen N.V.) were mixed in the same amounts. The human or monkey PBMC was adjusted to $2\times10^5$ cells with LR10, and mixed with the mixture of the humanized anti-CD3 scFv and Anti-His antibody, in the same amounts in a 96-well U-bottomed microplate, and cultured at 37° C. for 24 hours under 5% $CO_2$ conditions. After completion of the reaction, the reaction solution was centrifuged, and a sorter buffer (HBSS(−) (Thermo Fisher Scientific Inc.), 0.1% BSA (Sigma-Aldrich Corp.), and 0.1% sodium azide (Sigma-Aldrich Corp.)) were added. After centrifugation, LIVE/DEAD Fixable Near-IR Dead Cell Stain Kit (Thermo Fisher Scientific Inc.) was added to the cells, which were then left standing at 4° C. for 20 minutes. The cells were washed with a sorter buffer. Then, a PE-labeled anti-CD69 antibody (Becton, Dickinson and Company) and an FITC-labeled anti-CD8 antibody (Becton, Dickinson and Company) diluted with a sorter buffer were added to the cells, which were then left standing at 4° C. for 20 minutes. The cells were washed with a sorter buffer and then resuspended in PBS (Wako Pure Chemicals Industries, Ltd.) containing 1% paraformaldehyde, followed by detection using a flow cytometer (FACSCanto II; Becton, Dickinson and Company). The data was analyzed using Flowjo (Tree Star Inc.). The ratio of a fraction highly expressing CD8 and highly expressing PE to a fraction free from dead cells was calculated as percentage with respect to the population (% of parents). As shown in FIG. 50, the humanized anti-CD3 scFvs were found to activate cells highly expressing human and monkey CD8.

7)-4 Comparison of the Binding Activity of CDR Modified Humanized Anti-CD3 scFv with Human and Cynomolgus Monkey CD3 by Flow Cytometry The human PBMC obtained in Example 7)-1-1 and the cynomolgus monkey PBMC obtained in Example 7)-2-1 were each adjusted to an appropriate concentration with PBS containing 5% FBS, and stained and analyzed in the same manner as Example 7)-1-1. As shown in FIG. 106, the CDR modified humanized anti-CD3 scFvs were confirmed to have binding activity with both human and monkey CD3.

(Example 8) Preparation of Humanized Anti-TROP2 scFv

8)-1 Construction of HT1-11 scFv Expression Vector pHT1-11scFv

A DNA fragment comprising a DNA sequence encoding the amino acids of HT1-11 scFv shown in FIG. 51 (SEQ ID NO: 41) was synthesized (GeneArt Gene Synthesis Service/Thermo Fisher Scientific Inc.). The synthesized DNA fragment was inserted into a vector derived from pcDNA-3.3TOPO (Thermo Fisher Scientific Inc.) using In-Fusion HD PCR cloning kit (Clontech Laboratories, Inc.) to construct a humanized anti-TROP2 scFv expression vector pHT1-11scFv containing the nucleotide sequence shown in FIG. 52 (SEQ ID NO: 40) in ORF.

8)-2 Expression and Purification of HT1-11 scFv (HT1-11 scFv)

HT1-11 scFv was expressed and purified in the same manner as Example 4)-1-2.

(Example 9) Evaluation of Binding Activity of Humanized Anti-TROP2 scFv (HT1-11 scFv) Against Human TROP2 by Flow Cytometry A pharyngeal squamous cell cancer cell line FaDu (ATCC) or a pancreatic cancer cell line HPAF-II (ATCC) was adjusted to an appropriate concentration with PBS containing 5% FBS. LIVE/DEAD Fixable Near-IR Dead Cell Stain Kit was added to the cells, which were then left standing at 4° C. for 30 minutes. The cells were washed twice with PBS containing 5% FBS, then adjusted to a concentration of $1\times10^6$ cells/mL with PBS containing 5% FBS, added at a concentration of 100 μL/well to a 96-well U-bottomed microplate, and centrifuged to remove a supernatant. The humanized anti-TROP2 scFv (HT1-11 scFv) diluted with PBS containing 5% FBS was added at a concentration of 100 μL/well, and the plate was left standing at 4° C. for 60 minutes. The cells were washed twice with PBS containing 5% FBS. Then, Penta-His Alexa Fluor 488 diluted with PBS containing 5% FBS was added at a concentration of 30 μL/well, and the plate was left standing at 4° C. for 30 minutes. The cells were washed twice with PBS containing 5% FBS and then resuspended in PBS containing 5% FBS, followed by detection using a flow cytometer (FACSCanto™ II). The data was analyzed using Flowjo. The mean fluorescence intensity (MFI) of Alexa Fluor 488 in a fraction free of dead cells was calculated. The MFI value of the antibody-unsupplemented sample was subtracted from the MFI value of the scFv-supplemented sample to calculate a relative value of MFI (rMFI). As shown in FIG. 53, the humanized anti-TROP2 scFv was found to bind to human TROP2.

(Example 10) Preparation of Anti-TROP2-CD3 Bispecific Molecules

10)-1 Construction of an Anti-TROP2-CD3 Bispecific Molecule Expression Vector

10)-1-1 Construction of HT1-11 scFv/C3E-7034 Bispecific Molecule (T2C-0001) Expression Vector An insert DNA fragment was obtained by PCR using the pHT1-11 scFv prepared in Example 8)-1 as a template and using primers designed to add the nucleotide sequences of HT1-11 scFv and a portion of a human antibody heavy chain signal sequence to the 5' side and to add the nucleotide sequence of a linker to connect scFvs to the 3' side. Also, a vector DNA fragment containing the entire vector region including anti-CD3 scFv DNA was obtained by PCR using the expression vector pC3E-7034 prepared in Example 4)-3-1 as a template and using primers encoding a signal sequence and the amino-terminal sequence of the anti-CD3 scFv. These DNA fragments were ligated using the In-Fusion HD cloning kit (Clontech Laboratories, Inc.) to prepare an anti-TROP2-anti-CD3 bispecific molecule expression vector pT2C-0001 containing the nucleotide sequence of FIG. 54 (SEQ ID NO: 42) in ORF.

10)-1-2 Construction of an HT1-11 scFv/C3E-3007 Bispecific Molecule (T2C-0003) Expression Vector An anti-TROP2-CD3 bispecific molecule expression vector containing the nucleotide sequence of FIG. 55 (SEQ ID NO: 44) in ORF was constructed in the same manner as Example 10)-1-1 except that pC3E-3007 was used as a template for preparing the vector fragment. The resulting expression vector was designated as “pT2C-0003.”

10)-1-3 Construction of an HT1-11 scFv/C3E-7035 Bispecific Molecule (T2C-0005) Expression Vector An anti-TROP2-CD3 bispecific molecule expression vector containing the nucleotide sequence of FIG. 56 (SEQ ID NO: 46) in ORF was constructed in the same manner as Example 10)-1-1 except that pC3E-7035 was used as a template for preparing the vector fragment. The resulting expression vector was designated as “pT2C-0005.”

10)-1-4 Construction of an HT1-11 scFv/C3E-7036 Bispecific Molecule (T2C-0006) Expression Vector An anti-TROP2-CD3 bispecific molecule expression vector containing the nucleotide sequence of FIG. 57 (SEQ ID NO: 48) in ORF was constructed in the same manner as Example 10)-1-1 except that pC3E-7036 was used as a template for preparing the vector fragment. The resulting expression vector was designated as “pT2C-0006.”

10)-2 Expression and Purification of Anti-TROP2-CD3 Bispecific Molecules

T2C-0001, T2C-0003, T2C-0005, and T2C-0006 were expressed and purified in the same manner as Example 4)-1-2. The amino acid sequence of T2C-0001 is described in FIG. 58 (SEQ ID NO: 43). The amino acid sequence of T2C-0003 is described in FIG. 59 (SEQ ID NO: 45). The amino acid sequence of T2C-0005 is described in FIG. 60 (SEQ ID NO: 47). The amino acid sequence of T2C-0006 is described in FIG. 61 (SEQ ID NO: 49).

(Example 11) Evaluation of In Vitro Activity of Anti-TROP2-CD3 Bispecific Molecules 11)-1 Binding Activity Evaluation by SPR 11)-1-1 Binding Activity of an Anti-TROP2-CD3 Bispecific Molecule to TROP2

The bispecific molecule was assayed for its binding to TROP2 using BIAcore 3000 (GE Healthcare Bio-Sciences Corp.) by the capture method, which involves capturing the antigen by an anti-human IgG antibody and assaying the bispecific molecule as an analyte. The antigen used was recombinant human TROP-2/human IgG Fc fused form (R&D Systems, Inc.). Approximately 2000 RU of the anti-human IgG(Fc) antibody (Human Antibody Capture Kit, GE Healthcare Bio-Sciences Corp.) was covalently bound to a sensor chip CM5 (GE Healthcare Bio-Sciences Corp.) by the amine coupling method. Similarly, this antibody was immobilized onto a reference cell. The running buffer used was HBS-P (10 mM HEPES (pH 7.4), 0.15 M NaCl, and 0.005% Surfactant P20). The bispecific molecule was prepared at a 2-fold dilution ratio from 200 nM to 1 nM. A 1 μg/ml solution of the antigen was added onto the anti-human IgG(Fc) antibody-immobilized chip for approximately 30 μseconds. Then, each concentration of the bispecific molecule was added at a flow rate of 30 μl/min for 300 seconds. Subsequently, the dissociation phase was monitored for 600 seconds. A 3 M magnesium chloride solution was added as a regenerating solution for 30 seconds. The data was analyzed using the 1:1 binding model of analytical software (BIAevaluation software, version 4.1.1) to calculate an association rate constant (ka), a dissociation rate constant (kd), and a dissociation constant (KD; KD=kd/ka).

11)-1-2 Binding Activity of an Anti-TROP2-CD3 Bispecific Molecule to a Human CD3εγ Single-Chain Antigen The bispecific molecule was assayed for its binding to the CD3εγ antigen using BIAcore 3000 (GE Healthcare Bio-Sciences Corp.) by a method which involves immobilizing the antigen and assaying the antibody as an analyte. The antigen used was the human CD3εγ single-chain antigen prepared in Example 2)-2-1. Approximately 100 RU of the antigen was covalently bound to a sensor chip CM5 (GE Healthcare Bio-Sciences Corp.) by the amine coupling method. Immobilization treatment was performed without the addition of an antigenic protein as a reference cell. The running buffer used was HBS-P (10 mM HEPES (pH 7.4), 0.15 μM NaCl, and 0.005% Surfactant P20). The bispecific molecule was prepared at a 2-fold dilution ratio from 1 μM (highest concentration) to 4 nM or at a 2-fold dilution ration from 200 nM to 1 nM. Each concentration of the bispecific molecule was added to the antigen-immobilized chip at a flow rate of 10 l/min for 25 minutes, and the amount of the bispecific molecule bound thereto was monitored. A 10 mM glycine-hydrochloric acid solution (pH 1.5) was added as a regenerating solution for 30 seconds. The data was analyzed using analytical software (BIAevaluation software, version 4.1.1) to calculate a dissociation constant KD from the amount of the bispecific molecule bound at each concentration. The results are shown in Tables 2 and 3.

TABLE 2

| | Name | $CD3_{\varepsilon\gamma}$ KD (nM) |
|---|---|---|
| 1 | T2C-0001 | 13.9 |
| 2 | T2C-0003 | 171 |
| 3 | T2C-0005 | 126 |
| 4 | T2C-0006 | 171 |

TABLE 3

| | Name | TROP2 KD (nM) |
|---|---|---|
| 1 | T2C-0001 | 12.8 |
| 2 | T2C-0003 | 6.7 |
| 3 | T2C-0005 | 11.9 |
| 4 | T2C-0006 | 9.3 |

11)-2 Binding Activity Evaluation by Flow Cytometry

11)-2-1 Binding Activity of an Anti-TROP2-CD3 Bispecific Molecule to TROP2

The same cancer cell lines as those in Example 9 were used, and stained and analyzed in the same manner as Example 9. As shown in FIG. 62, the anti-TROP2-CD3 bispecific molecules were found to bind to TROP2.

11)-2-2 Binding Activity of an Anti-TROP2-CD3 Bispecific Molecule to a Human CD3εγ Single-Chain Antigen Cells were stained and analyzed in the same manner as Example 7)-1-1. As shown in FIG. 63, the anti-TROP2-CD3 bispecific molecules were found to bind to the human CD3εγ single-chain antigen.

11)-2-3 Binding Activity of an Anti-TROP2-CD3 Bispecific Molecule to a Cynomolgus Monkey CD3 Antigen The cynomolgus monkey PBMC obtained in Example 7)-2-1 was adjusted to an appropriate concentration with PBS containing 5% FBS, and stained and analyzed in the same manner as Example 7)-1-1. As shown in FIG. 64, the anti-TROP2-CD3 bispecific molecules (T2C-0001, T2C-0005, and T2C-0006) were found to bind to the cynomolgus monkey CD3 antigen.

11)-3 Evaluation of the Cytotoxic Activity of Anti-TROP2-CD3 Bispecific Molecules 11)-3-1 Expression Analysis of TROP2 in Target Cells Pharyngeal squamous cell cancer cell line FaDu (ATCC), pancreatic cancer cell line HPAF-II (ATCC), or human lung cancer cell line Calu-6 cells were adjusted to an appropriate concentration with PBS containing 5% FBS. LIVE/DEAD Fixable Dead Cell Stain Kit (Thermo Fisher Scientific Inc.) was added to the cells, which were then left standing at 4° C. for 30 minutes. The cells were washed twice with PBS containing 5% FBS, then adjusted to a concentration of $2\times10^6$ cells/mL with PBS containing 5% FBS, inoculated at a concentration of 100 μL/well to a 96-well U-bottomed microplate, and centrifuged to remove a supernatant. Anti-TROP2 Alexa Fluor 488 antibody (Affymetrix eBioscience) and Isotype Control antibody (Affymetrix eBioscience) diluted with PBS containing 5% FBS were added at a concentration of 25 μL/well, and the plate was left standing at 4° C. for 30 minutes. The cells were washed twice with PBS containing 5% FBS and then resuspended in PBS containing 5% FBS, followed by detection using a flow cytometer (Cytomics FC500, Beckman Coulter Inc.). The data was analyzed using Flowjo (Tree Star Inc.). The geometric average fluorescence intensity (geometric MFI) of Alexa Fluor 488 in a fraction free from dead cells was calculated. As shown in FIGS. 65A, 65B, and 65C, the expression of TROP2 was observed in the FaDu and HPAF-II cells, but was not observed in the Calu-6 cells.

11)-3-2 Preparation of Target Cells

FaDu, HPAF-II, or Calu-6 cells were adjusted to a concentration of $2\times10^6$ cells/mL with an RPMI1640 medium (Thermo Fisher Scientific Inc.) containing 10% FBS. To each cell line, 100 μL of Chromium-51 Radionuclide (PerkinElmer, Inc.) was added per mL of the cell suspension, and the cells were cultured at 37° C. for 2 hours under 5% $CO_2$ conditions. The cells were washed twice with an RPMI1640 medium containing 10% FBS, then resuspended to $2\times10^5$ cells/mL in an RPMI1640 medium containing 10% FBS, and used as target cells.

11)-3-3 Preparation of Effector Cells

Commercially available frozen PBMC (Cellular Technology Limited) was thawed at 37° C., transferred to a solution of an RPMI1640 medium containing 10% FBS supplemented with Anti-aggregate Wash reagent (Cellular Technology Limited), washed twice, then adjusted to $1\times10^6$ cells/mL with an RPMI1640 medium containing 10% FBS, and used as effector cells.

11)-3-4 Cytotoxicity Assay

The FaDu cells, the HPAF-II cells, or the Calu-6 cells obtained in Example 11)-3-2 were added at a concentration of 50 μL/well to a 96-well U-bottomed microplate. Each anti-TROP2-CD3 bispecific molecule adjusted to varying concentrations was added at a concentration of 50 μL/well. The effector cells prepared in Example 11)-3-1-3 were added at a concentration of 100 μL/well. After centrifugation at room temperature at 1000 rpm for 1 minute, the cells were cultured at 37° C. for 20 to 24 hours under 5% $CO_2$ conditions. A 50 μL aliquot of the supernatant was recovered into LumaPlate (PerkinElmer, Inc.) and dried at 50° C. for approximately 2 hours, followed by measurement using a plate reader (TopCount; PerkinElmer, Inc.). The percentage of cells lysed was calculated according to the following expression:

$$\text{Percentage of cells lysed (\%)}=(A-B)/(C-B)\times100$$

A: Sample well count

B: Average background count (antibody-unsupplemented wells) (n=3). 50 μL of a medium for assay was added instead of adding the antibody. The other procedures were the same as in the case of the sample well.

C: Average of maximum release count (wells containing target cells lysed in a surfactant) (n=3). 50 μL of a medium for assay was added instead of adding the antibody. 100 μL of the surfactant was added, and the 50 μL aliquot was transferred to LumaPlate, as with the sample well, and assayed.

As shown in FIGS. 66A, 66B, and 66C, these anti-TROP2-CD3 bispecific molecules exhibited cytotoxic activity against the FaDu cells and the HPAF-II cells). On the other hand, these bispecific molecules exhibited no cytotoxic activity in the Calu-6 cells.[0282]

(Example 12) Preparation of Anti-Axl-CD3 Bispecific Molecules

12)-1 Construction of Anti-Axl-CD3 Bispecific Molecule Expression Vector

12)-1-1 Construction of 11D5-T3 scFv/C3E-7034 Bispecific Molecule (AXC-0001) Expression Vector The amino acid sequence of an anti-Axl single chain antibody 11D5-T3 scFv was designed by connecting the N-terminally glycine-added sequence of h #11D5-T3H (described in FIG. 12 in the specification of European Patent Application Publication No. 2270053) and h #11D5-T3L (described in FIG. 6 in the specification of European Patent Application Publication No. 2270053) via a polypeptide linker consisting of a sequence having 3 repeats of (GGGGS). A nucleotide sequence encoding this amino acid sequence was synthesized (GENEART, Thermo Fisher Scientific). An insert DNA fragment was obtained by PCR using this nucleotide sequence as a template and using primers designed to add the nucleotide sequence of a portion of a human antibody heavy chain signal sequence to the 5' end and to add the nucleotide sequence of a linker to connect scFvs to the 3' end. Also, a vector DNA fragment was obtained by the PCR amplification of the whole vector region including CD3 scFv DNA using the expression vector pC3E-7034 prepared in Example 4)-3-1 as a template and using primers consisting of a nucleotide sequence encoding a human antibody heavy chain signal sequence and the CD3 scFv. The DNA fragments ligated using In-Fusion HD cloning kit (Clontech Laboratories, Inc.) resulted in anti-AXL-anti-CD3 bispecific molecule expression vector pAXC-0001 containing the nucleotide sequence shown in FIG. 97 (SEQ ID NO: 89) in ORF.[0283]

12)-1-2 Construction of 11D5-T3 scFv/C3E-7036 Bispecific Molecule (AXC-0002) Expression Vector An anti-Axl-CD3 bispecific molecule expression vector containing the nucleotide sequence shown in FIG. 99 (SEQ ID NO: 91) in ORF was constructed in the same manner as Example 10)-1-1 except that pC3E-7036 was used as a template for preparing the vector fragment. The resulting expression vector was designated as "pAXC-0002."

12)-2 Expression and Purification of Anti-AxL-CD3 Bispecific Molecules

AXC-0001 and AXC-0002 were expressed and purified in the same manner as Example 4)-1-2. The amino acid sequence of AXC-0001 is described in FIG. 98 (SEQ ID NO: 90). The amino acid sequence of AXC-0002 is described in FIG. 100 (SEQ ID NO: 92).

(Example 13) Evaluation of In Vitro Activity of Anti-Axl-CD3 Bispecific Molecules 13)-1 Expression Analysis of Axl in Target Cells Human lung cancer cell line A549 (ATCC), human pancreatic cancer cell line PANC-1 (ATCC) or MIA PaCa-2 (ATCC), human myeloma cell line U266B1(ATCC), or mantle cell lymphoma cell line Jeko-1 (ATCC) was adjusted to an appropriate concentration with PBS containing 5% FBS. LIVE/DEAD Fixable Dead Cell Stain Kit (Thermo Fisher Scientific Inc.) was added to the cells, which was then left standing at 4° C. for 30 minutes. The cells were washed twice with PBS containing 5% FBS, then adjusted to a concentration of $2\times10^6$ cells/mL with PBS containing 5% FBS, inoculated at a concentration of 100 μL/well in a 96-well U-bottomed microplate, and centrifuged to remove the supernatant. Anti-Axl antibody (RD Systems, Inc.) and Isotype Control antibody (RD Systems, Inc.) diluted with PBS containing 5% FBS were added at a concentration of 25 μL/well, and the plate was left standing at 4° C. for 30 minutes. The cells were washed twice with PBS containing 5% FBS. Then, Alexa Fluor 488 anti-mouse IgG antibody (Thermo Fisher Scientific Inc.) diluted with PBS containing 5% FBS was added at a concentration of 25 μL/well, and the plate was left standing at 4° C. for 30 minutes. The cells were washed twice with PBS containing 5% FBS and then resuspended in PBS containing 5% FBS, followed by detection using a flow cytometer (Cytomics FC500, Beckman Coulter Inc.). The data was analyzed using Flowjo (Tree Star Inc.). The geometric average fluorescence intensity (geometric MFI) of Alexa Fluor 488 in a fraction free of dead cells was calculated. As shown in FIGS. 107A, 107B, 107C, 107D, and 107E, the expression of Axl was observed in A549, PANC-1, and MIA PaCa-2, but was not observed in U266B1 and Jeko-1.

13)-2 Preparation of Target Cells

A549, PANC-1, MIA PaCa-2, U266B1, and Jeko-1 were each adjusted to a concentration of $2\times10^6$ cells/mL with an RPMI1640 medium (Thermo Fisher Scientific Inc.) containing 10% FBS. To each cell line, 100 μL of Chromium-51 Radionuclide (PerkinElmer, Inc.) was added per mL of the cell suspension, and the cells were cultured at 37° C. for 2 hours under 5% $CO_2$ conditions. The cells were washed twice with an RPMI1640 medium containing 10% FBS, then resuspended to $2\times10^5$ cells/mL in an RPMI1640 medium containing 10% FBS, and used as target cells.

13)-3 Preparation of Effector Cells

Commercially available frozen PBMC (Cellular Technology Limited) was thawed at 37° C., transferred to a solution of an RPMI1640 medium containing 10% FBS supplemented with Anti-aggregate Wash reagent (Cellular Technology Limited), washed twice, then adjusted to $1\times10^6$ cells/mL with an RPMI1640 medium containing 10% FBS, and used as effector cells.

13)-4 Cytotoxicity Assay

The A549, PANC-1, MIA PaCa-2, U266B1, or Jeko-1 cells obtained in Example 13)-2 were added at a concentration of 50 μL/well to a 96-well U-bottomed microplate. Each anti-Axl CD3 bispecific molecule adjusted to varying concentrations was added at a concentration of 50 μL/well. The effector cells prepared in Example 13)-3 were added at a concentration of 100 μL/well. After centrifugation at room temperature at 1000 rpm for 1 minute, the cells were cultured at 37° C. for 20 to 24 hours under 5% $CO_2$ conditions. A 50 μL aliquot of the supernatant was transferred to a LumaPlate (PerkinElmer, Inc.) and dried at 50° C. for approximately 2 hours, followed by measurement using a plate reader (TopCount; PerkinElmer, Inc.). The percentage of cells lysed was calculated according to the following equation:

$$\text{Percentage of cells lysed (\%)}=(A-B)/(C-B)\times100$$

A: Sample well count

B: Average background count (antibody-unsupplemented wells) (n=3). 50 μL of a medium for assay was added instead of adding the antibody. The other procedures were the same as in the case of the sample well.

C: Average of maximum release count (wells containing target cells lysed in a surfactant) (n=3). 50 μL of a medium for assay was added instead of adding the antibody. 100 μL of the surfactant was added, and the 50 μL aliquot was transferred to LumaPlate, as with the sample well, and assayed.

As shown in FIGS. 108A, 108B, 108C, 108D, and 108E, these anti-Axl CD3 bispecific molecules exhibited cytotoxic activity against A549, PANC-1, and MIA PaCa-2. However, these bispecific molecules exhibited no cytotoxic activity against U266B1 or Jeko-1.

(Example 14) Preparation of Anti-HLA-A2/MAGEC1-CD3 Bispecific Molecule Expression Vector 14)-1 Construction of Anti-HLA-A2/MAGEC1-CD3 Bispecific Molecule Expression Vector 14)-1-1 Construction of MAG-032 scFv/C3E-7034 Bispecific Molecule (MGC-0001) Expression Vector MAG-032 scFv specifically binding to HLA-A2/MAGEC1 was obtained from a human antibody phage library. An insert DNA fragment containing a nucleotide sequence encoding the amino acid sequence of MAG-032 scFv was obtained by PCR using the nucleotide sequence encoding the amino acid sequence of MAG-032 scFv as a template and using primers designed to add a nucleotide sequence encoding a human antibody heavy chain signal sequence to the 5' end, and to add a nucleotide sequence encoding a linker to connect scFvs and a portion of C3E-7034 to the 3' end. Also, a vector DNA fragment was obtained by the PCR amplification of the entire vector region including anti-CD3 scFv DNA using the expression vector pC3E-7034 prepared in Example 4)-3-1 as a template and using primers consisting of a nucleotide sequence encoding a human antibody heavy chain signal sequence and the amino-terminal sequence of the anti-CD3 scFv. These DNA fragments were ligated using an In-Fusion HD cloning kit (Clontech Laboratories, Inc.) to prepare an anti-HLA-A2/MAGEC1-anti-CD3 bispecific molecule expression vector pMGC-0001 containing the nucleotide sequence shown in FIG. 101 (SEQ ID NO: 93) in ORF.

14)-1-2 Construction of MAG-032 scFv/C3E-7036 Bispecific Molecule (MGC-0002) Expression Vector An anti-HLA-A2/MAGEC1-CD3 bispecific molecule expression vector containing the nucleotide sequence shown in FIG. 103 (SEQ ID NO: 95) in ORF was constructed in the same manner as Example 14)-1-1 except that pC3E-7036 was used as a template for preparing the vector fragment. The resulting expression vector was designated as "pMGC-0002."

14)-2 Expression and Purification of Anti-HLA-A2/MAGEC1-CD3 Bispecific Molecules MGC-0001 and MGC-0002 were expressed and purified in the same manner as Example 4)-1-2. The amino acid sequence of MGC-0001 is listed in FIG. 102 (SEQ ID NO: 94). The amino acid sequence of MGC-0002 is listed in FIG. 104 (SEQ ID NO: 96).

(Example 15) Evaluation of In Vitro Activity of Anti-HLA-A2/MAGEC1-CD3 Bispecific Molecules 15)-1 Expression Analysis of HLA-A2/MAGEC1 in Target Cells Human lymphoblast fusion cell line T2 (ATCC) cells were adjusted to an appropriate concentration with an AIM-V medium (Thermo Fisher Scientific Inc.) containing 20% FBS. MAGEC1 peptide of FIG. 106 (SEQ ID NO: 97) (Sigma Genosys) or DMSO was added to the cells, which were then incubated at 37° C. for 4 hours. The cells were washed twice with an AIM-V medium containing 20% FBS and then adjusted to an appropriate concentration with PBS containing 5% FBS. LIVE/DEAD Fixable Dead Cell Stain Kit (Thermo Fisher Scientific Inc.) was added to the cells, which were then left standing at 4° C. for 30 minutes. The cells were washed twice with PBS containing 5% FBS, then adjusted to a concentration of $2\times10^6$ cells/mL with PBS containing 5% FBS, inoculated at a concentration of 100 μL/well to a 96-well U-bottomed microplate, and centrifuged to remove a supernatant. The anti-HLA-A2/MAGEC1 antibody (MAG032 scFv) diluted with PBS containing 5% FBS was added at a concentration of 25 μL/well, and the plate was left standing at 4° C. for 30 minutes. The cells were washed twice with PBS containing 5% FBS. Then, Penta-His Alexa Fluor 488 (Qiagen N.V.) diluted with PBS containing 5% FBS was added at a concentration of 25 μL/well, and the plate was left standing at 4° C. for 30 minutes. The cells were washed twice with PBS containing 5% FBS and then resuspended in PBS containing 5% FBS, followed by detection using a flow cytometer (Cytomics FC500, Beckman Coulter Inc.). The data was analyzed using Flowjo (Tree Star Inc.). The geometric average fluorescence intensity (geometric MFI) of Alexa Fluor 488 in a fraction free of dead cells was calculated. As shown in FIGS. 109A and 109B, expression of HLA-A2/MAGEC1 was observed in the T2 cells supplemented with the MAGEC1 peptide, but was not observed in the T2 cells supplemented with DMSO.

15)-2 Preparation of Target Cells

T2 cells were adjusted to an appropriate concentration with an AIM-V medium (Thermo Fisher Scientific Inc.) containing 20% FBS. MAGEC1 peptide or DMSO was added to the cells, which were then incubated at 37° C. for 4 hours. The cells were adjusted to a concentration of $2\times10^6$ cells/mL with an RPMI1640 medium (Thermo Fisher Scientific Inc.) containing 10% FBS. To this cell line, 100 μL of Chromium-51 Radionuclide (PerkinElmer, Inc.) was added per mL of the cell suspension, and the cells were cultured at 37° C. for 2 hours under 5% $CO_2$ conditions. The cells were washed twice with an RPMI1640 medium containing 10% FBS, then resuspended to $2\times10^5$ cells/mL in an RPMI1640 medium containing 10% FBS, and used as target cells.

15)-3 Preparation of Effector Cells

Commercially available frozen PBMC (Cellular Technology Limited) was thawed at 37° C., transferred to a solution of an RPMI1640 medium containing 10% FBS supplemented with Anti-aggregate Wash reagent (Cellular Technology Limited), washed twice, then adjusted to $1\times10^6$ cells/mL with an RPMI1640 medium containing 10% FBS, and used as effector cells.

15)-4 Cytotoxicity Assay

The T2 cells obtained in Example 15)-2 were added at a concentration of 50 μL/well to a 96-well U-bottomed microplate. Each anti-HLA-A2/MAGEC1-CD3 bispecific molecule adjusted to varying concentrations was added at a concentration of 50 μL/well. The effector cells prepared in Example 15)-3 were added at a concentration of 100 μL/well. After centrifugation at room temperature at 1000 rpm for 1 minute, the cells were cultured at 37° C. for 20 to 24 hours under 5% $CO_2$ conditions. A 50 μL aliquot of the supernatant was recovered in a LumaPlate (PerkinElmer, Inc.) and dried at 50° C. for approximately 2 hours, followed by measurement using a plate reader (TopCount; PerkinElmer, Inc.). The percentage of cells lysed was calculated according to the following equation:

$$\text{Percentage of Cells Lysed (\%)}=(A-B)/(C-B)\times100$$

A: Sample well count

B: Average background count (antibody-unsupplemented wells) (n=3). 50 μL of a medium for assay was added instead of adding the antibody. The other procedures were the same as in the case of the sample well.

C: Average of maximum release count (wells containing target cells lysed in a surfactant) (n=3). 50 μL of a medium for assay was added instead of adding the antibody. 100 μL of the surfactant was added, and the 50 μL aliquot was transferred to LumaPlate, as with the sample well, and assayed.

As shown in FIGS. 110A and 110B, these anti-HLA-A2/MAGEC1-CD3 bispecific molecules exhibited cytotoxic activity against the T2 cells supplemented with the MAGEC1 peptide. On the other hand, these bispecific molecules exhibited no cytotoxic activity in the T2 cells supplemented with DMSO.

INDUSTRIAL APPLICABILITY

The humanized anti-CD3 antibody of the present invention binds to human CD3 and also binds to cynomolgus monkey CD3. Therefore, the humanized anti-CD3 antibody of the present invention can be used advantageously in nonclinical trials for the development of drugs.

[Sequence Listing Free Text]

SEQ ID NO: 1: Amino acid sequence of human CD3δ

SEQ ID NO: 2: Amino acid sequence of human CD3δ

SEQ ID NO: 3: Amino acid sequence of human CD3γ

SEQ ID NO: 4: Nucleotide sequence encoding human CD3εγ single-chain antigen

SEQ ID NO: 5: Amino acid sequence of His-scCD3 antigen

SEQ ID NO: 6: Nucleotide sequence encoding the heavy chain variable region of C3-147

SEQ ID NO: 7: (C3-147_VH AA): Amino sequence of the heavy chain variable region of C3-147

SEQ ID NO: 8: (C3-147_VL DNA): Nucleotide sequence encoding the light chain variable region of C3-147

SEQ ID NO: 9: (C3-147_VL AA): Amino sequence of the light chain variable region of C3-147

SEQ ID NO: 10: (G4S linker sense):

SEQ ID NO: 11: (G4S linker antisense):

SEQ ID NO: 12: (C3E-7000_VH AA): Amino acid sequence of the heavy chain variable region in C3E-7000

SEQ ID NO: 13: (C3E-7000_VL AA): Amino acid sequence of the light chain variable region in C3E-7000

SEQ ID NO: 14: (C3E-7000 ORF): Nucleotide sequence encoding C3E-7000

SEQ ID NO: 15: (C3E-7000 AA): Amino acid sequence in C3E-7000

SEQ ID NO: 16: (C3E-7034_VH_AA): Amino acid sequence of the heavy chain variable region of C3E-7034

SEQ ID NO: 17: Amino acid sequence of the light chain variable region of C3E-7034

SEQ ID NO: 18: (C3E-7034 ORF): Nucleotide sequence encoding C3E-7034

SEQ ID NO: 19: (C3E_7034 AA): Amino acid sequence of C3E-7034

SEQ ID NO: 20: (C3E-7035_VL AA): Amino acid sequence of the light chain variable region of C3E-7035

SEQ ID NO: 21: (C3E-7035 ORF): Nucleotide sequence encoding C3E-7035

SEQ ID NO: 22: (C3E_7035 AA): Amino acid sequence of C3E-7035

SEQ ID NO: 23: (C3E-7036_VL_AA): Amino acid sequence of the light chain variable region of C3E-7036

SEQ ID NO: 24: (C3E-7036 ORF): Nucleotide sequence encoding C3E-7036

SEQ ID NO: 25: (C3E_7036 AA): Amino acid sequence of C3E-7036

SEQ ID NO: 26: (7000_CDR-H1): Amino acid sequence of CDR-H1 in C3E-7000 series

SEQ ID NO: 27: (7000_CDR-H2): Amino acid sequence of CDR-H2 in C3E-7000 series

SEQ ID NO: 28: (7000_CDR-H3): Amino acid sequence of CDR-H3 in C3E-7000 series

SEQ ID NO: 29: (7000_CDR-L1): Amino acid sequence of CDR-L1 in C3E-7000 series

SEQ ID NO: 30: (7000_CDR-L2): Amino acid sequence of CDR-L2 in C3E-7000 series

SEQ ID NO: 31: (7000_CDR-L3): Amino acid sequence of CDR-L3 in C3E-7000 series

SEQ ID NO: 32: (C3E-3000 ORF): Nucleotide sequence encoding OKT3 scFv

SEQ ID NO: 33: (C3E-3000 AA): Amino acid sequence of OKT3 scFv
SEQ ID NO: 34: (C3E-3007 ORF): Nucleotide sequence encoding C3E-3007 scFv
SEQ ID NO: 35: (C3E-3007 AA): Amino acid sequence of C3E-3007 scFv
SEQ ID NO: 36: (C3E-3000_VH AA): Amino acid sequence of the heavy chain variable region of OKT3
SEQ ID NO: 37: (C3E-3000_VL AA): Amino acid sequence of the light chain variable region of OKT3
SEQ ID NO: 38: (C3E-3007_VH AA): Amino acid sequence of the heavy chain variable region of C3E-3007
SEQ ID NO: 39: (C3E-3007_VL AA): Amino acid sequence of the light chain variable region of C3E-3007
SEQ ID NO: 40: (HT1-11 ORF): Nucleotide sequence encoding HT1-11 scFv
SEQ ID NO: 41: (HT1-11 AA): Amino acid sequence of HT1-11 scFv
SEQ ID NO: 42: (T2C-0001 ORF): ORF nucleotide sequence encoding T2C-0001
SEQ ID NO: 43: (T2C-0001 AA): Amino acid sequence of T2C-0001
SEQ ID NO: 44: (T2C-0003 ORF): ORF nucleotide sequence encoding T2C-0003
SEQ ID NO: 45: (T2C-0003 AA): Amino acid sequence of T2C-0003
SEQ ID NO: 46: (T2C-0005 ORF): ORF nucleotide sequence encoding T2C-0005
SEQ ID NO: 47: (T2C-0005 AA): Amino acid sequence of T2C-0005
SEQ ID NO: 48: (T2C-0006 ORF): ORF nucleotide sequence encoding T2C-0006
SEQ ID NO: 49: (T2C-0006 AA): Amino acid sequence of T2C-0006
SEQ ID NO: 50: Amino acid sequence of a sense primer for heavy chain gene amplification
SEQ ID NO: 51: Nucleotide sequence of a first-run antisense primer for heavy chain gene amplification
SEQ ID NO: 52: Nucleotide sequence of second-run anti-sense primer for heavy chain gene amplification
SEQ ID NO: 53: Nucleotide sequence of a sense primer for light chain gene amplification
SEQ ID NO: 54: Nucleotide sequence of a first-run antisense primer for light chain gene amplification
SEQ ID NO: 55: Nucleotide sequence of a second-run antisense primer for light chain gene amplification
SEQ ID NO: 56: Nucleotide sequence of a sense primer for heavy chain sequencing
SEQ ID NO: 57: Nucleotide sequence of antisense primer 1 for light chain sequencing
SEQ ID NO: 58: Nucleotide sequence of antisense primer 2 for light chain sequencing
SEQ ID NO: 59: ORF nucleotide sequence encoding C3E-7078
SEQ ID NO: 60: Amino acid sequence of C3E-7078
SEQ ID NO: 61: ORF nucleotide sequence encoding C3E-7079
SEQ ID NO: 62: Amino acid sequence of C3E-7079
SEQ ID NO: 63: ORF nucleotide sequence encoding C3E-7085
SEQ ID NO: 64: Amino acid sequence of C3E-7085
SEQ ID NO: 65: ORF nucleotide sequence encoding C3E-7086
SEQ ID NO: 66: Amino acid sequence of C3E-7086
SEQ ID NO: 67: ORF nucleotide sequence encoding C3E-7087
SEQ ID NO: 68: Amino acid sequence of C3E-7087
SEQ ID NO: 69: ORF nucleotide sequence encoding C3E-7088
SEQ ID NO: 70: Amino acid sequence of C3E-7088
SEQ ID NO: 71: ORF nucleotide sequence encoding C3E-7089
SEQ ID NO: 72: Amino acid sequence of C3E-7089
SEQ ID NO: 73: ORF nucleotide sequence encoding C3E-7090
SEQ ID NO: 74: Amino acid sequence of C3E-7090
SEQ ID NO: 75: ORF nucleotide sequence encoding C3E-7091
SEQ ID NO: 76: Amino acid sequence of C3E-7091
SEQ ID NO: 77: ORF nucleotide sequence encoding C3E-7092
SEQ ID NO: 78: Amino acid sequence of C3E-7092
SEQ ID NO: 79: ORF nucleotide sequence encoding C3E-7093
SEQ ID NO: 80: Amino acid sequence of C3E-7093
SEQ ID NO: 81: ORF nucleotide sequence encoding C3E-7094
SEQ ID NO: 82: Amino acid sequence of C3E-7094
SEQ ID NO: 83: ORF nucleotide sequence encoding C3E-7095
SEQ ID NO: 84: Amino acid sequence of C3E-7095
SEQ ID NO: 85: Nucleotide sequence of a sense primer for C3E-7078
SEQ ID NO: 86: Nucleotide sequence of an antisense primer for C3E-7078
SEQ ID NO: 87: Nucleotide sequence of a sense primer for C3E-7079
SEQ ID NO: 88: Nucleotide sequence of an antisense primer for C3E-7079
SEQ ID NO: 89: (AXC-0001 ORF): ORF nucleotide sequence encoding AXC-0001
SEQ ID NO: 90: (AXC-0001 AA): Amino acid sequence of AXC-0001
SEQ ID NO: 91: (AXC-0002 ORF): ORF nucleotide sequence encoding AXC-0002
SEQ ID NO: 92: (AXC-0002 AA): Amino acid sequence of AXC-0002
SEQ ID NO: 93: (MGC-0001 ORF): ORF nucleotide sequence encoding MGC-0001
SEQ ID NO: 94: (MGC-0001 AA): Amino acid sequence of MGC-0001
SEQ ID NO: 95: (MGC-0002 ORF): ORF nucleotide sequence encoding MGC-0002
SEQ ID NO: 96: (MGC-0002 AA): Amino acid sequence of MGC-0002
SEQ ID NO: 97: (MAGEC1 peptide): Amino acid sequence of MAGEC1 peptide
SEQ ID NO: 98: (CDRH2 of variants): Amino acid sequence of CDRH2 of a CDR variant
SEQ ID NO: 99: (CDRL2 of variants): Amino acid sequence of CDRL2 of a CDR variant
SEQ ID NO: 100: (VH of C3E-7034 variants): Amino acid sequence of the heavy chain variable region of the CDR variant of C3E-7034
SEQ ID NO: 101: (VL of C3E-7034 variants): Amino acid sequence of the light chain variable region of the CDR variant of C3E-7034
SEQ ID NO: 102: (VL of C3E-7035 variants): Amino acid sequence of the light chain variable region of the CDR variant of C3E-7035
SEQ ID NO: 103: (VL of C3E-7036 variants): Amino acid sequence of the light chain variable region of the CDR variant of C3E-7036

The invention claimed is:

1. An antibody or an antigen-binding fragment of the antibody, comprising:

a heavy chain sequence comprising

CDRH1 comprising SEQ ID NO: 26,

CDRH2 comprising SEQ ID NO: 98, wherein the first Xaa is selected from the group consisting of R and S, and the second Xaa is S, and CDRH3 comprising SEQ ID NO: 28; and a light chain sequence comprising CDRL1 comprising SEQ ID NO: 29, CDRL2 comprising SEQ ID NO: 99, wherein Xaa is selected from the group consisting of Q, A, G, S, N, and D, and CDRL3 comprising SEQ ID NO: 31;

wherein the antibody or antigen-binding fragment binds to human CD3 and to cynomolgus monkey CD3.

2. An antibody or antigen-binding fragment of an antibody according to claim 1, wherein the heavy chain sequence comprises a heavy chain variable region comprising SEQ ID NO: 100.

3. An antibody or antigen-binding fragment thereof according to claim 2, wherein in SEQ ID NO: 100, the first Xaa is R.

4. An antibody or antigen-binding fragment thereof according to claim 2, wherein in SEQ ID NO: 100, the first Xaa is S.

5. An antibody or antigen-binding fragment thereof according to claim 1, wherein the light chain sequence comprises a light chain variable region comprising any one of SEQ ID NOs: 101, 102, and 103.

6. An antibody or antigen-binding fragment thereof according to claim 1, wherein the antibody or antigen-binding fragment comprises a heavy chain variable region comprising SEQ ID NO: 100 and a light chain variable region comprising any one of SEQ ID NOs: 101, 102, and 103.

7. An antibody or antigen-binding fragment thereof according to claim 6, wherein in SEQ ID NO: 100 the first Xaa is R.

8. An antibody or antigen-binding fragment thereof according to claim 6, wherein the antibody or antigen-binding fragment comprises:

a heavy chain variable region comprising amino acid residues 2-119 of SEQ ID NO: 60 and a light chain variable region comprising amino acid residues 135-243 of SEQ ID NO: 60, a heavy chain variable region comprising amino acid residues 2-119 of SEQ ID NO: 62 and a light chain variable region comprising amino acid residues 135-243 of SEQ ID NO: 62, a heavy chain variable region comprising amino acid residues 2-119 of SEQ ID NO: 64 and a light chain variable region comprising amino acid residues 135-241 of SEQ ID NO: 64, a heavy chain variable region comprising amino acid residues 2-119 of SEQ ID NO: 66 and a light chain variable region comprising amino acid residues 135-243 of SEQ ID NO: 66, a heavy chain variable region comprising amino acid residues 2-119 of SEQ ID NO: 68 and a light chain variable region comprising amino acid residues 135-243 of SEQ ID NO: 68, a heavy chain variable region comprising amino acid residues 2-119 of SEQ ID NO: 70 and a light chain variable region comprising amino acid residues 135-243 of SEQ ID NO: 70, a heavy chain variable region comprising amino acid residues 2-119 of SEQ ID NO: 72 and a light chain variable region comprising amino acid residues 135-243 of SEQ ID NO: 72, a heavy chain variable region comprising amino acid residues 2-119 of SEQ ID NO: 74 and a light chain variable region comprising amino acid residues 135-243 of SEQ ID NO: 74, a heavy chain variable region comprising amino acid residues 2-119 of SEQ ID NO: 76 and a light chain variable region comprising amino acid residues 135-243 of SEQ ID NO: 76, a heavy chain variable region comprising amino acid residues 2-119 of SEQ ID NO: 78 and a light chain variable region comprising amino acid residues 135-243 of SEQ ID NO: 78, a heavy chain variable region comprising amino acid residues 2-119 of SEQ ID NO: 80 and a light chain variable region comprising amino acid residues 135-243 of SEQ ID NO: 80, a heavy chain variable region comprising amino acid residues 2-119 of SEQ ID NO: 82 and a light chain variable region comprising amino acid residues 135-243 of SEQ ID NO: 82, or a heavy chain variable region comprising amino acid residues 2-119 of SEQ ID NO: 84 and a light chain variable region comprising amino acid residues 135-243 of SEQ ID NO: 84.

9. An antibody or antigen-binding fragment thereof according to claim 1, wherein the antibody or antigen-binding fragment comprises a heavy chain variable region and a light chain variable region, and further comprising: i) a linker between the variable regions, ii) a glycine residue at the amino-terminal of the variable region on the amino-terminal side, and iii) a linker, FLAG tag and/or HIS tag at the carboxyl terminal of the variable region on the carboxyl terminal side.

10. An antibody or antigen-binding fragment thereof according to claim 1, wherein the antibody is IgG.

11. An antibody or antigen-binding fragment thereof according to claim 1, wherein the antigen-binding fragment is selected from a group consisting of Fab, F(ab)', Fv, scFv, and sdAb.

12. An antibody or antigen-binding fragment thereof according to claim 1, wherein the antibody is a humanized antibody or a human antibody including a human immunoglobulin constant region.

13. A polynucleotide comprising a nucleotide sequence encoding an antibody or an antigen-binding fragment thereof according to claim 1.

14. A vector comprising a polynucleotide according to claim 13.

15. A cell comprising a polynucleotide according to claim 13.

16. A method for producing an antibody or an antigen-binding fragment of the antibody which binds to human CD3 and to cynomolgus monkey CD3, the method comprising the steps of: culturing a cell according to claim 15; and recovering an antibody or an antigen-binding fragment of the antibody which binds to human CD3 from the cultures.

17. A pharmaceutical composition comprising an antibody or an antigen-binding fragment thereof according to claim 1 as an active ingredient.

18. A molecule having antigen binding activity, comprising an antibody or an antigen-binding fragment of the antibody according to claim 1.

19. A molecule according to claim 18, wherein the molecule is multispecific.

20. A molecule according to claim 18, further comprising 1 or 2 or more additional antibodies or antigen-binding fragments of the antibodies in addition to the antibody or antigen-binding fragment.

21. A molecule according to claim 20, wherein the antigen-binding fragment of the additional antibody is Fab, F(ab)', Fv, scFv, or sdAb.

22. A molecule according to claim 20, wherein the molecule comprises Fc.

23. A molecule according to claim 20, wherein the additional antibody is a humanized antibody or a human antibody comprising a human immunoglobulin constant region.

24. A molecule according to claim 20, wherein the antibody or antigen-binding fragment and the 1 or 2 or more additional antibodies or antigen-binding fragments are bound via a linker or without a linker.

25. A molecule according to claim 24, wherein a carboxyl terminus of the amino acid sequence of the additional antibody or antigen-binding fragment is bound with a linker, and a carboxyl terminus of the amino acid sequence of the linker is further bound with the antibody or antigen-binding fragment.

26. A molecule according to claim 18, wherein the antibody or antigen-binding fragment comprises a heavy chain variable region and a light chain variable region, and further comprising: i) a linker between the variable regions, ii) a glycine residue at the amino-terminal of the variable region on the amino-terminal side, and iii) a linker, FLAG tag and/or HIS tag at the carboxyl terminal of the variable region on the carboxyl terminal side.

27. A molecule according to claim 20, wherein the additional antibody is an anti cancer target antibody.

28. A molecule according to claim 19, wherein the molecule is bispecific.

29. A molecule according to claim 18, wherein the molecule is a protein.

30. A polynucleotide comprising a nucleotide sequence encoding the amino acid sequence of a molecule according to claim 29.

31. A vector comprising a polynucleotide according to claim 30.

32. A cell comprising a polynucleotide according to claim 30.

33. A method for producing a molecule binding to human CD3 and to cynomolgus monkey CD3, the method comprising the steps of: culturing a cell according to claim 32; and recovering a molecule binding to human CD3 from the cultures.

34. A pharmaceutical composition comprising a molecule according to claim 18 as an active ingredient.

35. A pharmaceutical composition according to claim 34, wherein the pharmaceutical composition induces cytotoxicity in target cells by the redirection of T cells to the target cells.

36. An antibody or antigen-binding fragment thereof according to claim 6, wherein in SEQ ID NO: 100 the first Xaa is S.

37. An antibody or an antigen-binding fragment of the antibody, wherein the antibody or an antigen-binding fragment of the antibody comprising:

a heavy chain sequence comprising

CDRH1 comprising SEQ ID NO: 26,

CDRH2 comprising SEQ ID NO: 98, wherein the first Xaa is selected from the group consisting of R and S, and the second Xaa is S, and CDRH3 comprising SEQ ID NO: 28; and a light chain sequence comprising CDRL1 comprising SEQ ID NO: 29, CDRL2 comprising SEQ ID NO: 99, wherein Xaa is selected from the group consisting of Q, A, G, S, N, and D, and CDRL3 comprising SEQ ID NO: 31;

wherein the antibody or antigen-binding fragment binds to human CD3 and to cynomolgus monkey CD3, wherein the antibody or antigen-binding fragment comprises a heavy chain variable region comprising SEQ ID NO: 100 and a light chain variable region comprising any one of SEQ ID NOs: 101, 102, and 103.

38. An antibody or antigen binding fragment of the antibody according to claim 37, wherein the antibody or antigen-binding fragment comprises:

a heavy chain variable region comprising amino acid residues 2-119 of SEQ ID NO: 60 and a light chain variable region comprising amino acid residues 135-243 of SEQ ID NO: 60, a heavy chain variable region comprising amino acid residues 2-119 of SEQ ID NO: 62and a light chain variable region comprising amino acid residues 135-243 of SEQ ID NO: 62, a heavy chain variable region comprising amino acid residues 2-119 of SEQ ID NO: 64 and a light chain variable region comprising amino acid residues 135-241 of SEQ ID NO: 64, a heavy chain variable region comprising amino acid residues 2-119 of SEQ ID NO: 66 and a light chain variable region comprising amino acid residues 135-243 of SEQ ID NO: 66, a heavy chain variable region comprising amino acid residues 2-119 of SEQ ID NO: 68 and a light chain variable region comprising amino acid residues 135-243 of SEQ ID NO: 68, a heavy chain variable region comprising amino acid residues 2-119 of SEQ ID NO: 70 and a light chain variable region comprising amino acid residues 135-243 of SEQ ID NO: 70, a heavy chain variable region comprising amino acid residues 2-119 of SEQ ID NO: 72 and a light chain variable region comprising amino acid residues 135-243 of SEQ ID NO: 72, a heavy chain variable region comprising amino acid residues 2-119 of SEQ ID NO: 74 and a light chain variable region comprising amino acid residues 135-243 of SEQ ID NO: 74, a heavy chain variable region comprising amino acid residues 2-119 of SEQ ID NO: 76 and a light chain variable region comprising amino acid residues 135-243 of SEQ ID NO: 76, a heavy chain variable region comprising amino acid residues 2-119 of SEQ ID NO: 78 and a light chain variable region comprising amino acid residues 135-243 of SEQ ID NO: 78, a heavy chain variable region comprising amino acid residues 2-119 of SEQ ID NO: 80 and a light chain variable region comprising amino acid residues 135-243 of SEQ ID NO: 80, a heavy chain variable region comprising amino acid residues 2-119 of SEQ ID NO: 82 and a light chain variable region comprising amino acid residues 135-243 of SEQ ID NO: 82, or a heavy chain variable region comprising amino acid residues 2-119 of SEQ ID NO: 84 and a light chain variable region comprising amino acid residues 135-243 of SEQ ID NO: 84.

39. A molecule comprising an antibody or an antigen-binding fragment of the antibody, wherein the antibody or an antigen-binding fragment of the antibody comprises:

a heavy chain sequence comprising

CDRH1 comprising SEQ ID NO: 26,

CDRH2 comprising SEQ ID NO: 98, wherein the first Xaa is selected from the group consisting of R and S, and the second Xaa is S, and CDRH3 comprising SEQ ID NO: 28; and a light chain sequence comprising CDRL1 comprising SEQ ID NO: 29, CDRL2 comprising SEQ ID NO: 99, wherein Xaa is selected from the group consisting of Q, A, G, S, N, and D, and CDRL3 comprising SEQ ID NO: 31;

wherein the antibody or antigen-binding fragment binds to human CD3 and to cynomolgus monkey CD3, wherein the antibody or antigen-binding fragment comprises a heavy chain variable region comprising SEQ ID NO: 100 and a light chain variable region comprising any one of the Seq ID NOs: 101, 102, and 103.

40. A molecule according to claim 39, wherein the antibody or antigen-binding fragment of the antibody comprises:

a heavy chain variable region comprising amino acid residues 2-119 of SEQ ID NO: 60 and a light chain variable region comprising amino acid residues 135-243 of SEQ ID NO: 60, a heavy chain variable region comprising amino acid residues 2-119 of SEQ ID NO: 62 and a light chain variable region comprising amino acid residues 135-243 of SEQ ID NO: 62, a heavy chain variable region comprising amino acid residues 2-119 of SEQ ID NO: 64 and a light chain variable region comprising amino acid residues 135-241 of SEQ ID NO: 64, a heavy chain variable region comprising amino acid residues 2-119 of SEQ ID NO: 66 and a light chain variable region comprising amino acid residues 135-243 of SEQ ID NO: 66, a heavy chain variable region comprising amino acid residues 2-119 of SEQ ID NO: 68 and a light chain variable region comprising amino acid residues 135-243 of SEQ ID NO: 68, a heavy chain variable region comprising amino acid residues 2-119 of SEQ ID NO: 70 and a light chain variable region comprising amino acid residues 135-243 of SEQ ID NO: 70, a heavy chain variable region comprising amino acid residues 2-119 of SEQ ID NO: 72 and a light chain variable region comprising amino acid residues 135-243 of SEQ ID NO: 72, a heavy chain variable region comprising amino acid residues 2-119 of SEQ ID NO: 74 and a light chain variable region comprising amino acid residues 135-243 of SEQ ID NO: 74, a heavy chain variable region comprising amino acid residues 2-119 of SEQ ID NO: 76 and a light chain variable region comprising amino acid residues 135-243 of SEQ ID NO: 76, a heavy chain variable region comprising amino acid residues 2-119 of SEQ ID NO: 78 and a light chain variable region comprising amino acid residues 135-243 of SEQ ID NO: 78, a heavy chain variable region comprising amino acid residues 2-119 of SEQ ID NO: 80 and a light chain variable region comprising amino acid residues 135-243 of SEQ ID NO: 80, a heavy chain variable region comprising amino acid residues 2-119 of SEQ ID NO: 82 and a light chain variable region comprising amino acid residues 135-243 of SEQ ID NO: 82, or a heavy chain variable region comprising amino acid residues 2-119 of SEQ ID NO: 84 and a light chain variable region comprising amino acid residues 135-243 of SEQ ID NO: 84.

41. A pharmaceutical composition comprising a molecule according to claim 40 as an active ingredient.

* * * * *

SEQUENCE LISTING

<160> NUMBER OF SEQ ID NOS: 103

<210> SEQ ID NO 1
<211> LENGTH: 207
<212> TYPE: PRT
<213> ORGANISM: Homo sapiens

<400> SEQUENCE: 1

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205
```

<210> SEQ ID NO 2
<211> LENGTH: 171
<212> TYPE: PRT
<213> ORGANISM: Homo sapiens

<400> SEQUENCE: 2

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
```

```
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170
```

<210> SEQ ID NO 3
<211> LENGTH: 182
<212> TYPE: PRT
<213> ORGANISM: Homo sapiens

<400> SEQUENCE: 3

```
Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180
```

<210> SEQ ID NO 4
<211> LENGTH: 657
<212> TYPE: DNA
<213> ORGANISM: Artificial Sequence
<220> FEATURE:
<223> OTHER INFORMATION: CD3 epsilon gamma DNA

<400> SEQUENCE: 4

```
atgagaggat cgcatcacca tcaccatcac ggatcccaga gcattaaagg taatcacctg      60

gtgaaagtgt atgactatca agaagatggt agcgttctgc tgacctgtga tgcagaagca     120

aaaaacatta cctggttcaa agacggcaaa atgattggtt ttctgaccga agataaaaaa     180

aaatggaatc tgggcagcaa tgcaaaagat ccgcgtggta tgtatcagtg taaaggtagc     240

cagaataaaa gcaaaccgct gcaggtttat tatcgtatgg gtagcgcaga tgatgcaaaa     300

aaagatgcag ccaaaaaaga cgacgcgaaa aaagatgatg ctaaaaaaga cggttccgat     360

ggcaatgaag aaatgggtgg tattacccag accccgtata aagttagcat tagcggcacc     420
```

```
accgttattc tgacctgtcc gcagtatccg ggtagcgaaa ttctgtggca gcataacgat    480

aaaaacattg gcggtgatga ggacgacaaa aatatcggta gtgatgaaga tcatctgagc    540

ctgaaagaat tcagcgaact ggaacagagc ggttattatg tttgttatcc tcgtggtagc    600

aaaccggaag atgcaaactt ttatctgtat ctgcgtgcac gtgttgggaa gcttaat       657


<210> SEQ ID NO 5
<211> LENGTH: 219
<212> TYPE: PRT
<213> ORGANISM: Artificial Sequence
<220> FEATURE:
<223> OTHER INFORMATION: His-scCD3 AA

<400> SEQUENCE: 5

Met Arg Gly Ser His His His His His His Gly Ser Gln Ser Ile Lys
1               5                   10                  15

Gly Asn His Leu Val Lys Val Tyr Asp Tyr Gln Glu Asp Gly Ser Val
            20                  25                  30

Leu Leu Thr Cys Asp Ala Glu Ala Lys Asn Ile Thr Trp Phe Lys Asp
        35                  40                  45

Gly Lys Met Ile Gly Phe Leu Thr Glu Asp Lys Lys Lys Trp Asn Leu
    50                  55                  60

Gly Ser Asn Ala Lys Asp Pro Arg Gly Met Tyr Gln Cys Lys Gly Ser
65                  70                  75                  80

Gln Asn Lys Ser Lys Pro Leu Gln Val Tyr Tyr Arg Met Gly Ser Ala
                85                  90                  95

Asp Asp Ala Lys Lys Asp Ala Ala Lys Lys Asp Asp Ala Lys Lys Asp
            100                 105                 110

Asp Ala Lys Lys Asp Gly Ser Asp Gly Asn Glu Glu Met Gly Gly Ile
        115                 120                 125

Thr Gln Thr Pro Tyr Lys Val Ser Ile Ser Gly Thr Thr Val Ile Leu
    130                 135                 140

Thr Cys Pro Gln Tyr Pro Gly Ser Glu Ile Leu Trp Gln His Asn Asp
145                 150                 155                 160

Lys Asn Ile Gly Gly Asp Glu Asp Asp Lys Asn Ile Gly Ser Asp Glu
                165                 170                 175

Asp His Leu Ser Leu Lys Glu Phe Ser Glu Leu Glu Gln Ser Gly Tyr
            180                 185                 190

Tyr Val Cys Tyr Pro Arg Gly Ser Lys Pro Glu Asp Ala Asn Phe Tyr
        195                 200                 205

Leu Tyr Leu Arg Ala Arg Val Gly Lys Leu Asn
    210                 215


<210> SEQ ID NO 6
<211> LENGTH: 354
<212> TYPE: DNA
<213> ORGANISM: Rutilus rutilus

<400> SEQUENCE: 6

gaggtgcagt tggtggagtc tgggggaggc ctggtgcagc ctggaagggc cctgaaactc     60

tcctgtgtag tctctggagt cacattcaat tactacggga tgagctggat ccgccaggct    120

ccagggaagg ggctggagtg ggttgcatcc attactaatt ctggtggtag aatttactat    180

ccagactctg tgaagggccg attcactatc tccagagaaa atacacaaaa gaccctatac    240

ctacaaatga acagtctgag gtctgaggac acggccactt attactgtac tctcgatggt    300

cgcgatggtt gggttgctta ctggggccaa ggcactctgg tcactgtctc ttca          354
```

```
<210> SEQ ID NO 7
<211> LENGTH: 118
<212> TYPE: PRT
<213> ORGANISM: Rutilus rutilus

<400> SEQUENCE: 7

Glu Val Gln Leu Val Glu Ser Gly Gly Gly Leu Val Gln Pro Gly Arg
1               5                   10                  15

Ala Leu Lys Leu Ser Cys Val Val Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Asn Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ser Glu Asp Thr Ala Thr Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
        115


<210> SEQ ID NO 8
<211> LENGTH: 327
<212> TYPE: DNA
<213> ORGANISM: Rutilus rutilus

<400> SEQUENCE: 8

cagtttgtgc ttactcagcc aaactctgtg tctacgaatc tcggaaccac agtcgaactg     60

tcttgcaagc gcaacactgg gaacattgga agcaattatg tgaactggta ccagcagcat    120

gagggaagat ctcccaccac tattatttat agggatgata agagaccaga tggagtttct    180

gacaggttct ctgggtccat tgacagatct tccaagtcag ccctcctgac aatcaataat    240

gtgcagactg aagatgaagc tgactacttc tgtcagtctt acagtagtgg ttttattttc    300

ggcggtggaa ccaagctcac tgtccta                                        327


<210> SEQ ID NO 9
<211> LENGTH: 109
<212> TYPE: PRT
<213> ORGANISM: Artificial Sequence
<220> FEATURE:
<223> OTHER INFORMATION: C3-147_VL AA

<400> SEQUENCE: 9

Gln Phe Val Leu Thr Gln Pro Asn Ser Val Ser Thr Asn Leu Gly Thr
1               5                   10                  15

Thr Val Glu Leu Ser Cys Lys Arg Asn Thr Gly Asn Ile Gly Ser Asn
            20                  25                  30

Tyr Val Asn Trp Tyr Gln Gln His Glu Gly Arg Ser Pro Thr Thr Ile
        35                  40                  45

Ile Tyr Arg Asp Asp Lys Arg Pro Asp Gly Val Ser Asp Arg Phe Ser
    50                  55                  60

Gly Ser Ile Asp Arg Ser Ser Lys Ser Ala Leu Leu Thr Ile Asn Asn
65                  70                  75                  80

Val Gln Thr Glu Asp Glu Ala Asp Tyr Phe Cys Gln Ser Tyr Ser Ser
```

```
                85                  90                  95

Gly Phe Ile Phe Gly Gly Gly Thr Lys Leu Thr Val Leu
            100                 105


<210> SEQ ID NO 10
<211> LENGTH: 75
<212> TYPE: DNA
<213> ORGANISM: Artificial Sequence
<220> FEATURE:
<223> OTHER INFORMATION: G4S linker sense

<400> SEQUENCE: 10

gtcactgtct cttcaggtgg aggcggttca ggcggaggtg gcagcggcgg tggcgggagt      60

cagtttgtgc ttact                                                       75


<210> SEQ ID NO 11
<211> LENGTH: 75
<212> TYPE: DNA
<213> ORGANISM: Artificial Sequence
<220> FEATURE:
<223> OTHER INFORMATION: G4sS linker antisense

<400> SEQUENCE: 11

agtaagcaca aactgactcc cgccaccgcc gctgccacct ccgcctgaac cgcctccacc      60

tgaagagaca gtgac                                                       75


<210> SEQ ID NO 12
<211> LENGTH: 118
<212> TYPE: PRT
<213> ORGANISM: Rutilus rutilus

<400> SEQUENCE: 12

Glu Val Gln Leu Val Glu Ser Gly Gly Gly Leu Val Gln Pro Gly Arg
1               5                   10                  15

Ala Leu Lys Leu Ser Cys Val Val Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Asn Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ser Glu Asp Thr Ala Thr Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
        115


<210> SEQ ID NO 13
<211> LENGTH: 109
<212> TYPE: PRT
<213> ORGANISM: Rutilus rutilus

<400> SEQUENCE: 13

Gln Phe Val Leu Thr Gln Pro Asn Ser Val Ser Thr Asn Leu Gly Thr
1               5                   10                  15

Thr Val Glu Leu Ser Cys Lys Arg Asn Thr Gly Asn Ile Gly Ser Asn
            20                  25                  30
```

```
Tyr Val Asn Trp Tyr Gln Gln His Glu Gly Arg Ser Pro Thr Thr Ile
        35                  40                  45

Ile Tyr Arg Asp Asp Lys Arg Pro Asp Gly Val Ser Asp Arg Phe Ser
    50                  55                  60

Gly Ser Ile Asp Arg Ser Ser Lys Ser Ala Leu Leu Thr Ile Asn Asn
65                  70                  75                  80

Val Gln Thr Glu Asp Glu Ala Asp Tyr Phe Cys Gln Ser Tyr Ser Ser
                85                  90                  95

Gly Phe Ile Phe Gly Gly Gly Thr Lys Leu Thr Val Leu
            100                 105
```

<210> SEQ ID NO 14
<211> LENGTH: 867
<212> TYPE: DNA
<213> ORGANISM: Artificial Sequence
<220> FEATURE:
<223> OTHER INFORMATION: C3E-7000 ORF

<400> SEQUENCE: 14

```
atgaaacacc tgtggttctt cctcctgctg gtggcagctc ccagatgggt gctgagcgag     60

gtgcagttgg tggagtctgg gggaggcctg gtgcagcctg gaagggccct gaaactctcc    120

tgtgtagtct ctggagtcac attcaattac tacgggatga gctggatccg ccaggctcca    180

gggaaggggc tggagtgggt tgcatccatt actaattctg gtggtagaat ttactatcca    240

gactctgtga agggccgatt cactatctcc agagaaaata cacaaaagac cctataccta    300

caaatgaaca gtctgaggtc tgaggacacg gccacttatt actgtactct cgatggtcgc    360

gatggttggg ttgcttactg gggccaaggc actctggtca ctgtctcttc aggtggaggc    420

ggttcaggcg gaggtggcag cggcggtggc gggagtcagt ttgtgcttac tcagccaaac    480

tctgtgtcta cgaatctcgg aaccacagtc gaactgtctt gcaagcgcaa cactgggaac    540

attggaagca attatgtgaa ctggtaccag cagcatgagg gaagatctcc caccactatt    600

atttataggg atgataagag accagatgga gtttctgaca ggttctctgg gtccattgac    660

agatcttcca agtcagccct cctgacaatc aataatgtgc agactgaaga tgaagctgac    720

tacttctgtc agtcttacag tagtggtttt attttcggcg gtggaaccaa gctcactgtc    780

ctaggcgcgt ctgcggccgc aggatccggt ggtgattaca aagatgatga cgataaaggt    840

gcagcggcgc atcaccatca tcaccac                                        867
```

<210> SEQ ID NO 15
<211> LENGTH: 270
<212> TYPE: PRT
<213> ORGANISM: Artificial Sequence
<220> FEATURE:
<223> OTHER INFORMATION: C3E-7000 AA

<400> SEQUENCE: 15

```
Glu Val Gln Leu Val Glu Ser Gly Gly Gly Leu Val Gln Pro Gly Arg
1               5                   10                  15

Ala Leu Lys Leu Ser Cys Val Val Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Asn Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80
```

```
Leu Gln Met Asn Ser Leu Arg Ser Glu Asp Thr Ala Thr Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Phe Val Leu Thr Gln Pro Asn Ser Val Ser
    130                 135                 140

Thr Asn Leu Gly Thr Thr Val Glu Leu Ser Cys Lys Arg Asn Thr Gly
145                 150                 155                 160

Asn Ile Gly Ser Asn Tyr Val Asn Trp Tyr Gln Gln His Glu Gly Arg
                165                 170                 175

Ser Pro Thr Thr Ile Ile Tyr Arg Asp Asp Lys Arg Pro Asp Gly Val
            180                 185                 190

Ser Asp Arg Phe Ser Gly Ser Ile Asp Arg Ser Ser Lys Ser Ala Leu
        195                 200                 205

Leu Thr Ile Asn Asn Val Gln Thr Glu Asp Glu Ala Asp Tyr Phe Cys
    210                 215                 220

Gln Ser Tyr Ser Ser Gly Phe Ile Phe Gly Gly Gly Thr Lys Leu Thr
225                 230                 235                 240

Val Leu Gly Ala Ser Ala Ala Ala Gly Ser Gly Gly Asp Tyr Lys Asp
                245                 250                 255

Asp Asp Asp Lys Gly Ala Ala Ala His His His His His His
            260                 265                 270


<210> SEQ ID NO 16
<211> LENGTH: 118
<212> TYPE: PRT
<213> ORGANISM: Artificial Sequence
<220> FEATURE:
<223> OTHER INFORMATION: C3E-7034_VH AA

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Asn Ser Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
        115


<210> SEQ ID NO 17
<211> LENGTH: 109
<212> TYPE: PRT
<213> ORGANISM: Artificial Sequence
<220> FEATURE:
<223> OTHER INFORMATION: C3E-7034_VL AA
```

<400> SEQUENCE: 17

```
Asn Phe Met Leu Thr Gln Pro His Ser Val Ser Glu Ser Pro Gly Lys
1               5                   10                  15

Thr Val Thr Ile Ser Cys Lys Arg Asn Thr Gly Asn Ile Gly Ser Asn
            20                  25                  30

Tyr Val Asn Trp Tyr Gln Gln His Glu Gly Ser Ser Pro Thr Thr Ile
        35                  40                  45

Ile Tyr Arg Asp Asp Lys Arg Pro Asp Gly Val Ser Asp Arg Phe Ser
    50                  55                  60

Gly Ser Ile Asp Arg Ser Ser Lys Ser Ala Ser Leu Thr Ile Ser Asn
65                  70                  75                  80

Leu Lys Thr Glu Asp Glu Ala Asp Tyr Phe Cys Gln Ser Tyr Ser Ser
                85                  90                  95

Gly Phe Ile Phe Gly Gly Gly Thr Lys Leu Thr Val Leu
            100                 105
```

<210> SEQ ID NO 18
<211> LENGTH: 864
<212> TYPE: DNA
<213> ORGANISM: Artificial Sequence
<220> FEATURE:
<223> OTHER INFORMATION: C3E-7034 ORF

<400> SEQUENCE: 18

```
atgaaacacc tgtggttctt cctcctgctg gtggcagctc ccagatgggt gctgagcgga     60

gaagtgcagc tggtggaatc cgggggggc ctggtgcagc ctgggggag cctgagactg    120

agttgtgccg cctctggggt gacatttaac tactatggca tgtcttggat ccgccaggca    180

cctggaaagg gcctggagtg ggtggccagc atcactaatt ccggcgggcg aatctactat    240

cccgacagcg tcaagggcag gttcacaatt tcccgcgaga acacacagaa aactctgtac    300

ctgcagatga atagcctgag agccgaagat acagctgtgt actattgcac tctggacggc    360

agggatgggt gggtcgccta ttgggggcag ggaaccctgg tgacagtcag ctccggagga    420

ggaggatctg gcggaggagg cagtgggga ggcgggtcaa actttatgct gacccagccc    480

cacagtgtgt cagagagccc tggcaagact gtcaccatct cttgtaaaag gaacaccgga    540

aatattggca gtaactacgt gaattggtat cagcagcatg aagggtctag tccaaccaca    600

atcatctacc gggacgataa gagacccgac ggggtgtccg atcgattctc cggatctatc    660

gaccggtcaa gcaagagtgc ttcactgacc attagcaatc tgaaaacaga ggacgaagca    720

gattactttt gccagtccta ttcctctggc ttcatctttg gaggcgggac taaactgacc    780

gtgctgggcg cggccgcagg tgcaggtggt gattacaaag atgatgacga taaaggtgca    840

gcggcgcatc accatcatca ccac                                           864
```

<210> SEQ ID NO 19
<211> LENGTH: 269
<212> TYPE: PRT
<213> ORGANISM: Artificial Sequence
<220> FEATURE:
<223> OTHER INFORMATION: C3E-7034 AA

<400> SEQUENCE: 19

```
Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30
```

```
Tyr Gly Met Ser Trp Ile Arg Gln Ala Pro Gly Lys Gly Leu Glu Trp
        35                  40                  45

Val Ala Ser Ile Thr Asn Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175

Ser Ser Pro Thr Thr Ile Ile Tyr Arg Asp Asp Lys Arg Pro Asp Gly
            180                 185                 190

Val Ser Asp Arg Phe Ser Gly Ser Ile Asp Arg Ser Ser Lys Ser Ala
        195                 200                 205

Ser Leu Thr Ile Ser Asn Leu Lys Thr Glu Asp Glu Ala Asp Tyr Phe
    210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
            260                 265


<210> SEQ ID NO 20
<211> LENGTH: 107
<212> TYPE: PRT
<213> ORGANISM: Artificial Sequence
<220> FEATURE:
<223> OTHER INFORMATION: C3E-7035_VL AA

<400> SEQUENCE: 20

Gln Ala Val Leu Thr Gln Pro Ser Ser Val Ser Gly Val Pro Gly Gln
1               5                   10                  15

Arg Val Thr Ile Ser Cys Lys Arg Asn Thr Gly Asn Ile Gly Ser Asn
            20                  25                  30

Tyr Val Asn Trp Tyr Gln Gln Leu Pro Gly Thr Ala Pro Lys Leu Leu
        35                  40                  45

Ile Tyr Arg Asp Asp Lys Arg Pro Ser Gly Val Pro Asp Arg Phe Ser
    50                  55                  60

Gly Ser Lys Ser Gly Thr Ser Ala Ser Leu Ala Ile Thr Gly Phe Gln
65                  70                  75                  80

Ala Glu Asp Glu Ala Asp Tyr Tyr Cys Gln Ser Tyr Ser Ser Gly Phe
                85                  90                  95

Ile Phe Gly Gly Gly Thr Lys Leu Thr Val Leu
            100                 105


<210> SEQ ID NO 21
<211> LENGTH: 864
```

<212> TYPE: DNA
<213> ORGANISM: Artificial Sequence
<220> FEATURE:
<223> OTHER INFORMATION: C3E-7035 ORF

<400> SEQUENCE: 21

```
atgaaacacc tgtggttctt cctcctgctg gtggcagctc ccagatgggt gctgagcgga     60

gaagtgcagc tggtggaatc cggggggggc ctggtgcagc ctggggggag cctgagactg    120

agttgtgccg cctctggggt gacatttaac tactatggca tgtcttggat ccgccaggca    180

cctggaaagg gcctggagtg ggtggccagc atcactaatt ccggcgggcg aatctactat    240

cccgacagcg tcaagggcag gttcacaatt tcccgcgaga acacacagaa aactctgtac    300

ctgcagatga atagcctgag agccgaagat acagctgtgt actattgcac tctggacggc    360

agggatgggt gggtcgccta ttgggggcag ggaaccctgg tgacagtcag ctccggagga    420

ggaggatctg gcggaggagg cagtggggga ggcgggtcaa tggcccaggc tgtgctcact    480

cagccgtcct ctgtttctgg cgtacctggc caacgggtga ccattagctg taaaaggaat    540

accgggaata tcgggtctaa ctacgtgaac tggtatcagc agcttccagg gacagctccc    600

aagttgctga tctatcgcga cgacaaaaga ccctcagggg tccctgaccg atttagtggc    660

agcaaaagcg gtacttccgc ttccctggcg ataaccggct ttcaggccga agatgaggca    720

gactactatt gccagtcata ttccagcggc ttcatcttcg gaggcggaac taagctgaca    780

gtgctgggcg cggccgcagg tgcaggtggt gattacaaag atgatgacga taaaggtgca    840

gcggcgcatc accatcatca ccac                                           864
```

<210> SEQ ID NO 22
<211> LENGTH: 269
<212> TYPE: PRT
<213> ORGANISM: Artificial Sequence
<220> FEATURE:
<223> OTHER INFORMATION: C3E-7035 AA

<400> SEQUENCE: 22

```
Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Asn Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Met Ala Gln Ala Val Leu Thr Gln Pro Ser
    130                 135                 140

Ser Val Ser Gly Val Pro Gly Gln Arg Val Thr Ile Ser Cys Lys Arg
145                 150                 155                 160

Asn Thr Gly Asn Ile Gly Ser Asn Tyr Val Asn Trp Tyr Gln Gln Leu
                165                 170                 175
```

```
Pro Gly Thr Ala Pro Lys Leu Leu Ile Tyr Arg Asp Asp Lys Arg Pro
            180                 185                 190

Ser Gly Val Pro Asp Arg Phe Ser Gly Ser Lys Ser Gly Thr Ser Ala
        195                 200                 205

Ser Leu Ala Ile Thr Gly Phe Gln Ala Glu Asp Glu Ala Asp Tyr Tyr
    210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
            260                 265
```

<210> SEQ ID NO 23
<211> LENGTH: 107
<212> TYPE: PRT
<213> ORGANISM: Artificial Sequence
<220> FEATURE:
<223> OTHER INFORMATION: C3E-7036_VL AA

<400> SEQUENCE: 23

```
Asn Phe Met Leu Thr Gln Pro Ser Ser Val Ser Gly Val Pro Gly Gln
1               5                   10                  15

Arg Val Thr Ile Ser Cys Thr Gly Asn Thr Gly Asn Ile Gly Ser Asn
            20                  25                  30

Tyr Val Asn Trp Tyr Gln Gln Leu Pro Gly Thr Ala Pro Lys Leu Leu
        35                  40                  45

Ile Tyr Arg Asp Asp Lys Arg Pro Ser Gly Val Pro Asp Arg Phe Ser
    50                  55                  60

Gly Ser Lys Ser Gly Thr Ser Ala Ser Leu Ala Ile Thr Gly Phe Gln
65                  70                  75                  80

Ala Glu Asp Glu Ala Asp Tyr Tyr Cys Gln Ser Tyr Ser Ser Gly Phe
                85                  90                  95

Ile Phe Gly Gly Gly Thr Lys Leu Thr Val Leu
            100                 105
```

<210> SEQ ID NO 24
<211> LENGTH: 858
<212> TYPE: DNA
<213> ORGANISM: Artificial Sequence
<220> FEATURE:
<223> OTHER INFORMATION: C3E-7036 ORF

<400> SEQUENCE: 24

```
atgaaacacc tgtggttctt cctcctgctg gtggcagctc ccagatgggt gctgagcgga      60

gaagtgcagc tggtggaatc cggggggggc ctggtgcagc ctggggggag cctgagactg     120

agttgtgccg cctctggggt gacatttaac tactatggca tgtcttggat ccgccaggca     180

cctggaaagg gcctggagtg ggtggccagc atcactaatt ccggcgggcg aatctactat     240

cccgacagcg tcaagggcag gttcacaatt tcccgcgaga acacacagaa aactctgtac     300

ctgcagatga atagcctgag agccgaagat acagctgtgt actattgcac tctggacggc     360

agggatgggt gggtcgccta ttgggggcag ggaaccctgg tgacagtcag ctccggagga     420

ggaggatctg gcggaggagg cagtggggga ggcgggtcaa actttatgct cactcagccg     480

tcctctgttt ctggcgtacc tggccaacgg gtgaccatta gctgtacggg taataccggg     540

aatatcgggt ctaactacgt gaactggtat cagcagcttc cagggacagc tcccaagttg     600
```

```
ctgatctatc gcgacgacaa aagaccctca ggggtccctg accgatttag tggcagcaaa    660

agcggtactt ccgcttccct ggcgataacc ggctttcagg ccgaagatga ggcagactac    720

tattgccagt catattccag cggcttcatc ttcggaggcg gaactaagct gacagtgttg    780

ggtgcggccg caggtgcagg tggtgattac aaagatgatg acgataaagg tgcagcggcg    840

catcaccatc atcaccac                                                  858
```

<210> SEQ ID NO 25
<211> LENGTH: 267
<212> TYPE: PRT
<213> ORGANISM: Artificial Sequence
<220> FEATURE:
<223> OTHER INFORMATION: C3E-7036 AA

<400> SEQUENCE: 25

```
Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Asn Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro Ser Ser Val
    130                 135                 140

Ser Gly Val Pro Gly Gln Arg Val Thr Ile Ser Cys Thr Gly Asn Thr
145                 150                 155                 160

Gly Asn Ile Gly Ser Asn Tyr Val Asn Trp Tyr Gln Gln Leu Pro Gly
                165                 170                 175

Thr Ala Pro Lys Leu Leu Ile Tyr Arg Asp Asp Lys Arg Pro Ser Gly
            180                 185                 190

Val Pro Asp Arg Phe Ser Gly Ser Lys Ser Gly Thr Ser Ala Ser Leu
        195                 200                 205

Ala Ile Thr Gly Phe Gln Ala Glu Asp Glu Ala Asp Tyr Tyr Cys Gln
    210                 215                 220

Ser Tyr Ser Ser Gly Phe Ile Phe Gly Gly Gly Thr Lys Leu Thr Val
225                 230                 235                 240

Leu Gly Ala Ala Ala Gly Ala Gly Gly Asp Tyr Lys Asp Asp Asp Asp
                245                 250                 255

Lys Gly Ala Ala Ala His His His His His His
            260                 265
```

<210> SEQ ID NO 26
<211> LENGTH: 8
<212> TYPE: PRT
<213> ORGANISM: Artificial Sequence
<220> FEATURE:
<223> OTHER INFORMATION: 7000_CDR-H1

<400> SEQUENCE: 26

Gly Val Thr Phe Asn Tyr Tyr Gly
1               5

<210> SEQ ID NO 27
<211> LENGTH: 8
<212> TYPE: PRT
<213> ORGANISM: Artificial Sequence
<220> FEATURE:
<223> OTHER INFORMATION: 7000_CDR-H2

<400> SEQUENCE: 27

Ile Thr Asn Ser Gly Gly Arg Ile
1               5

<210> SEQ ID NO 28
<211> LENGTH: 11
<212> TYPE: PRT
<213> ORGANISM: Artificial Sequence
<220> FEATURE:
<223> OTHER INFORMATION: 7000_CDR-H3

<400> SEQUENCE: 28

Thr Leu Asp Gly Arg Asp Gly Trp Val Ala Tyr
1               5                   10

<210> SEQ ID NO 29
<211> LENGTH: 8
<212> TYPE: PRT
<213> ORGANISM: Artificial Sequence
<220> FEATURE:
<223> OTHER INFORMATION: 7000_CDR-L1

<400> SEQUENCE: 29

Thr Gly Asn Ile Gly Ser Asn Tyr
1               5

<210> SEQ ID NO 30
<211> LENGTH: 3
<212> TYPE: PRT
<213> ORGANISM: Artificial Sequence
<220> FEATURE:
<223> OTHER INFORMATION: 7000_CDR-L2

<400> SEQUENCE: 30

Arg Asp Asp
1

<210> SEQ ID NO 31
<211> LENGTH: 8
<212> TYPE: PRT
<213> ORGANISM: Artificial Sequence
<220> FEATURE:
<223> OTHER INFORMATION: 7000_CDR-L3

<400> SEQUENCE: 31

Gln Ser Tyr Ser Ser Gly Phe Ile
1               5

<210> SEQ ID NO 32
<211> LENGTH: 864
<212> TYPE: DNA
<213> ORGANISM: Artificial Sequence
<220> FEATURE:
<223> OTHER INFORMATION: C3E-3000 ORF

<400> SEQUENCE: 32

```
atgaagcacc tgtggttctt tctgctgctg gtggccgctc ccagatgggt gctgtctcag     60
gtgcagctgc agcagtctgg cgccgaactg gctagacctg gcgcctccgt gaagatgagc    120
tgcaaggcca gcggctacac cttcacccgg tacaccatgc actgggtcaa gcagaggcct    180
ggacagggcc tggaatggat cggctacatc aaccccagcc ggggctacac caactacaac    240
cagaagttca aggacaaggc caccctgacc accgacaaga gcagcagcac cgcctacatg    300
cagctgtcca gcctgaccag cgaggacagc gccgtgtact actgcgcccg gtactacgac    360
gaccactact gcctggacta ctggggccag ggcaccacac tgaccgtgtc tagtggtgga    420
ggcggttcag gcggaggtgg cagcggcggt ggcgggagtc agatcgtgct gacacagagc    480
cccgccatca tgtctgccag ccctggcgag aaagtgacca tgacctgtag cgccagcagc    540
agcgtgtcct acatgaactg gtatcagcag aagtccggca ccagccccaa gcggtggatc    600
tacgacacaa gcaagctggc ctctggcgtg cccgcccact ttagaggctc tggcagcggc    660
acaagctaca gcctgaccat cagcggcatg gaagccgagg atgccgccac ctactactgc    720
cagcagtggt ccagcaaccc cttcaccttt ggctccggca caaagctgga aatcaagcgg    780
ggcgcgtctg cggccgcagg tagcggtggt gattacaaag atgatgacga taaaggtgca    840
gcggcgcatc accatcatca ccac                                           864
```

<210> SEQ ID NO 33
<211> LENGTH: 269
<212> TYPE: PRT
<213> ORGANISM: Artificial Sequence
<220> FEATURE:
<223> OTHER INFORMATION: C3E-3000 AA

<400> SEQUENCE: 33

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly Gly
        115                 120                 125

Ser Gly Gly Gly Gly Ser Gln Ile Val Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
```

```
        195                 200                 205

Ser Gly Met Glu Ala Glu Asp Ala Ala Thr Tyr Tyr Cys Gln Gln Trp
    210                 215                 220

Ser Ser Asn Pro Phe Thr Phe Gly Ser Gly Thr Lys Leu Glu Ile Lys
225                 230                 235                 240

Arg Gly Ala Ser Ala Ala Ala Gly Ser Gly Gly Asp Tyr Lys Asp Asp
                245                 250                 255

Asp Asp Lys Gly Ala Ala Ala His His His His His His
            260                 265


<210> SEQ ID NO 34
<211> LENGTH: 864
<212> TYPE: DNA
<213> ORGANISM: Artificial Sequence
<220> FEATURE:
<223> OTHER INFORMATION: C3E-3007 ORF

<400> SEQUENCE: 34

atgaagcacc tgtggttctt tctgctgctg gtggccgctc ccagatgggt gctgtctcag      60

gtgcagctgg tgcagtctgg cgccgagagc aaaaagcctg gcgcctccgt gaaggtgtcc     120

tgcaaggcca gcggctacac ctttacccgg tacaccatgc actgggtgcg ccaggcacct     180

ggacagggcc tggaatggat gggctacatc aaccccagcc ggggctacac caactacaac     240

cagaaattca aggaccgcgt gaccatcacc gccgacaaga gcaccagcac cgcctacatg     300

gaactgagca gcctgcggag cgaggacacc gccgtgtact actgtgcccg gtactacgac     360

gaccactact gcctggacta ctggggccag ggcacactcg tgaccgtgtc tagtggtgga     420

ggcggttcag gcggaggtgg cagcggcggt ggcgggagtc agatccagat gacccagagc     480

cctagcagcc tggccgtgtc tctgggagag agagccacca tcacctgtag cgccagcagc     540

agcgtgtcct acatgaactg gtatcagcag aagcccggca aggcccccaa gcggtggatc     600

tacgatacca gcaagctggc ctccggcgtg cccgatagat tttctggcag cggctccggc     660

accgacttca ccctgacaat cagctccctg caggccgagg acgtggccac ctactactgt     720

cagcagtggt ccagcaaccc cttcaccttc ggccagggca ccaaggtgga aatcaagcgg     780

ggcgcgtctg cggccgcagg tagcggtggt gattacaaag atgatgacga taaaggtgca     840

gcggcgcatc accatcatca ccac                                            864


<210> SEQ ID NO 35
<211> LENGTH: 269
<212> TYPE: PRT
<213> ORGANISM: Artificial Sequence
<220> FEATURE:
<223> OTHER INFORMATION: C3E-3007 AA

<400> SEQUENCE: 35

Gln Val Gln Leu Val Gln Ser Gly Ala Glu Ser Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Met
        35                  40                  45

Gly Tyr Ile Asn Pro Ser Arg Gly Tyr Thr Asn Tyr Asn Gln Lys Phe
    50                  55                  60

Lys Asp Arg Val Thr Ile Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gln Ile Gln Met Thr Gln Ser Pro Ser Ser
    130                 135                 140

Leu Ala Val Ser Leu Gly Glu Arg Ala Thr Ile Thr Cys Ser Ala Ser
145                 150                 155                 160

Ser Ser Val Ser Tyr Met Asn Trp Tyr Gln Gln Lys Pro Gly Lys Ala
                165                 170                 175

Pro Lys Arg Trp Ile Tyr Asp Thr Ser Lys Leu Ala Ser Gly Val Pro
            180                 185                 190

Asp Arg Phe Ser Gly Ser Gly Ser Gly Thr Asp Phe Thr Leu Thr Ile
        195                 200                 205

Ser Ser Leu Gln Ala Glu Asp Val Ala Thr Tyr Tyr Cys Gln Gln Trp
    210                 215                 220

Ser Ser Asn Pro Phe Thr Phe Gly Gln Gly Thr Lys Val Glu Ile Lys
225                 230                 235                 240

Arg Gly Ala Ser Ala Ala Ala Gly Ser Gly Gly Asp Tyr Lys Asp Asp
                245                 250                 255

Asp Asp Lys Gly Ala Ala Ala His His His His His His
            260                 265


<210> SEQ ID NO 36
<211> LENGTH: 119
<212> TYPE: PRT
<213> ORGANISM: Artificial Sequence
<220> FEATURE:
<223> OTHER INFORMATION: C3E-3000_VH AA

<400> SEQUENCE: 36

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115


<210> SEQ ID NO 37
<211> LENGTH: 106
<212> TYPE: PRT
<213> ORGANISM: Artificial Sequence
<220> FEATURE:
<223> OTHER INFORMATION: C3E-3000_VL AA

<400> SEQUENCE: 37
```

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Lys
            100                 105


<210> SEQ ID NO 38
<211> LENGTH: 119
<212> TYPE: PRT
<213> ORGANISM: Artificial Sequence
<220> FEATURE:
<223> OTHER INFORMATION: C3E-3007_VH AA

<400> SEQUENCE: 38

Gln Val Gln Leu Val Gln Ser Gly Ala Glu Ser Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Met
        35                  40                  45

Gly Tyr Ile Asn Pro Ser Arg Gly Tyr Thr Asn Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser
        115


<210> SEQ ID NO 39
<211> LENGTH: 106
<212> TYPE: PRT
<213> ORGANISM: Artificial Sequence
<220> FEATURE:
<223> OTHER INFORMATION: C3E-3007_VL AA

<400> SEQUENCE: 39

Gln Ile Gln Met Thr Gln Ser Pro Ser Ser Leu Ala Val Ser Leu Gly
1               5                   10                  15

Glu Arg Ala Thr Ile Thr Cys Ser Ala Ser Ser Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Leu Ala Ser Gly Val Pro Asp Arg Phe Ser Gly Ser
    50                  55                  60

Gly Ser Gly Thr Asp Phe Thr Leu Thr Ile Ser Ser Leu Gln Ala Glu
```

```
65                  70                  75                  80

Asp Val Ala Thr Tyr Tyr Cys Gln Gln Trp Ser Ser Asn Pro Phe Thr
                85                  90                  95

Phe Gly Gln Gly Thr Lys Val Glu Ile Lys
            100                 105
```

<210> SEQ ID NO 40
<211> LENGTH: 822
<212> TYPE: DNA
<213> ORGANISM: Artificial Sequence
<220> FEATURE:
<223> OTHER INFORMATION: HT1-11 scFv ORF

<400> SEQUENCE: 40

```
atgaagcacc tgtggttctt tctgctgctg gtggccgctc ccagatgggt gctgtctcag      60

gtgcagctgg tgcagtctgg cgccgaagtg aagaaaccag gcgccagcgt gaaggtgtcc     120

tgcaaggcca gcggctacac ctttaccacc gccggcatgc agtgggtgcg ccaggctcct     180

ggacagggcc tggaatggat gggctggatc aacacccaca gcggcgtgcc caaatacgcc     240

gaggacttca agggcagagt gaccatcagc gccgacacca gcacctccac agcctacctg     300

cagctgagca gcctgaagtc cgaggacacc gccgtgtact actgcgccag aagcggcttc     360

ggcagcagct actggtactt cgacgtgtgg ggccagggca ccctcgtgac agtgtctagc     420

ggaggcggag gatctggcgg cggaggaagt ggcggagggg gatccgatat ccagatgacc     480

cagagcccca gcagcctgtc tgccagcgtg ggcgacagag tgacaattac atgcaaggcc     540

tcccaggacg tgtccacagc cgtggcctgg tatcagcaga agcctggcaa ggcccccaag     600

ctgctgatct acagcgccag ctaccggtac accggcgtgc caagcagatt ttccggcagc     660

ggctccggca ccgacttcac cctgacaatc agctccctgc agcccgagga tttcgccgtg     720

tattattgcc agcagcacta catcaccccc ctgaccttcg gccaggggac caagctggaa     780

atcaagagaa caggcgccgc tgcccaccac caccatcacc at                        822
```

<210> SEQ ID NO 41
<211> LENGTH: 255
<212> TYPE: PRT
<213> ORGANISM: Artificial Sequence
<220> FEATURE:
<223> OTHER INFORMATION: HT1-11 scFv AA

<400> SEQUENCE: 41

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Arg Gln Ala Pro Gly Gln Gly Leu Glu Trp Met
        35                  40                  45

Gly Trp Ile Asn Thr His Ser Gly Val Pro Lys Tyr Ala Glu Asp Phe
    50                  55                  60

Lys Gly Arg Val Thr Ile Ser Ala Asp Thr Ser Thr Ser Thr Ala Tyr
65                  70                  75                  80

Leu Gln Leu Ser Ser Leu Lys Ser Glu Asp Thr Ala Val Tyr Tyr Cys
                85                  90                  95

Ala Arg Ser Gly Phe Gly Ser Ser Tyr Trp Tyr Phe Asp Val Trp Gly
            100                 105                 110

Gln Gly Thr Leu Val Thr Val Ser Ser Gly Gly Gly Gly Ser Gly Gly
        115                 120                 125
```

```
Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asp Val Ser Thr Ala Val Ala Trp Tyr Gln Gln Lys Pro
                165                 170                 175

Gly Lys Ala Pro Lys Leu Leu Ile Tyr Ser Ala Ser Tyr Arg Tyr Thr
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Val Tyr Tyr Cys
    210                 215                 220

Gln Gln His Tyr Ile Thr Pro Leu Thr Phe Gly Gln Gly Thr Lys Leu
225                 230                 235                 240

Glu Ile Lys Arg Thr Gly Ala Ala Ala His His His His His His
                245                 250                 255


<210> SEQ ID NO 42
<211> LENGTH: 1614
<212> TYPE: DNA
<213> ORGANISM: Artificial Sequence
<220> FEATURE:
<223> OTHER INFORMATION: T2C-0001 ORF

<400> SEQUENCE: 42

atgaaacacc tgtggttctt cctcctgctg gtggcagctc ccagatgggt gctgagcgga     60

caggtgcagc tggtgcagtc tggcgccgaa gtgaagaaac caggcgccag cgtgaaggtg    120

tcctgcaagg ccagcggcta cacctttacc accgccggca tgcagtgggt gcgccaggct    180

cctggacagg gcctggaatg gatgggctgg atcaacaccc acagcggcgt gcccaaatac    240

gccgaggact tcaagggcag agtgaccatc agcgccgaca ccagcacctc cacagcctac    300

ctgcagctga gcagcctgaa gtccgaggac accgccgtgt actactgcgc cagaagcggc    360

ttcggcagca gctactggta cttcgacgtg tggggccagg gcaccctcgt gacagtgtct    420

agcggaggcg gaggatctgg cggcggagga agtggcggag ggggatccga tatccagatg    480

acccagagcc ccagcagcct gtctgccagc gtgggcgaca gagtgacaat tacatgcaag    540

gcctcccagg acgtgtccac agccgtggcc tggtatcagc agaagcctgg caaggccccc    600

aagctgctga tctacagcgc cagctaccgg tacaccggcg tgccaagcag attttccggc    660

agcggctccg gcaccgactt caccctgaca atcagctccc tgcagcccga ggatttcgcc    720

gtgtattatt gccagcagca ctacatcacc cccctgacct tcggccaggg gaccaagctg    780

gaaatcaaga gaacaggggg aggcggttca gaagtgcagc tggtggaatc cggggggggc    840

ctggtgcagc ctggggggag cctgagactg agttgtgccg cctctggggt gacatttaac    900

tactatggca tgtcttggat ccgccaggca cctggaaagg gcctggagtg ggtggccagc    960

atcactaatt ccggcgggcg aatctactat cccgacagcg tcaagggcag gttcacaatt   1020

tcccgcgaga acacacagaa aactctgtac ctgcagatga atagcctgag agccgaagat   1080

acagctgtgt actattgcac tctggacggc agggatgggt gggtcgccta ttgggggcag   1140

ggaaccctgg tgacagtcag ctccggagga ggaggatctg gcggaggagg cagtggggga   1200

ggcgggtcaa actttatgct gacccagccc cacagtgtgt cagagagccc tggcaagact   1260

gtcaccatct cttgtaaaag gaacaccgga aatattggca gtaactacgt gaattggtat   1320
```

```
cagcagcatg aagggtctag tccaaccaca atcatctacc gggacgataa gagacccgac   1380

ggggtgtccg atcgattctc cggatctatc gaccggtcaa gcaagagtgc ttcactgacc   1440

attagcaatc tgaaaacaga ggacgaagca gattactttt gccagtccta ttcctctggc   1500

ttcatctttg gaggcgggac taaactgacc gtgctgggcg cggccgcagg tgcaggtggt   1560

gattacaaag atgatgacga taaaggtgca gcggcgcatc accatcatca ccac         1614
```

```
<210> SEQ ID NO 43
<211> LENGTH: 519
<212> TYPE: PRT
<213> ORGANISM: Artificial Sequence
<220> FEATURE:
<223> OTHER INFORMATION: T2C-0001 AA

<400> SEQUENCE: 43

Gly Gln Val Gln Leu Val Gln Ser Gly Ala Glu Val Lys Lys Pro Gly
1               5                   10                  15

Ala Ser Val Lys Val Ser Cys Lys Ala Ser Gly Tyr Thr Phe Thr Thr
            20                  25                  30

Ala Gly Met Gln Trp Val Arg Gln Ala Pro Gly Gln Gly Leu Glu Trp
        35                  40                  45

Met Gly Trp Ile Asn Thr His Ser Gly Val Pro Lys Tyr Ala Glu Asp
    50                  55                  60

Phe Lys Gly Arg Val Thr Ile Ser Ala Asp Thr Ser Thr Ser Thr Ala
65                  70                  75                  80

Tyr Leu Gln Leu Ser Ser Leu Lys Ser Glu Asp Thr Ala Val Tyr Tyr
                85                  90                  95

Cys Ala Arg Ser Gly Phe Gly Ser Ser Tyr Trp Tyr Phe Asp Val Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Gln Asp Val Ser Thr Ala Val Ala Trp Tyr Gln Gln Lys
                165                 170                 175

Pro Gly Lys Ala Pro Lys Leu Leu Ile Tyr Ser Ala Ser Tyr Arg Tyr
            180                 185                 190

Thr Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Val Tyr Tyr
    210                 215                 220

Cys Gln Gln His Tyr Ile Thr Pro Leu Thr Phe Gly Gln Gly Thr Lys
225                 230                 235                 240

Leu Glu Ile Lys Arg Thr Gly Gly Gly Gly Ser Glu Val Gln Leu Val
                245                 250                 255

Glu Ser Gly Gly Gly Leu Val Gln Pro Gly Gly Ser Leu Arg Leu Ser
            260                 265                 270

Cys Ala Ala Ser Gly Val Thr Phe Asn Tyr Tyr Gly Met Ser Trp Ile
        275                 280                 285

Arg Gln Ala Pro Gly Lys Gly Leu Glu Trp Val Ala Ser Ile Thr Asn
    290                 295                 300

Ser Gly Gly Arg Ile Tyr Tyr Pro Asp Ser Val Lys Gly Arg Phe Thr
305                 310                 315                 320
```

```
Ile Ser Arg Glu Asn Thr Gln Lys Thr Leu Tyr Leu Gln Met Asn Ser
                325                 330                 335

Leu Arg Ala Glu Asp Thr Ala Val Tyr Tyr Cys Thr Leu Asp Gly Arg
            340                 345                 350

Asp Gly Trp Val Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
    370                 375                 380

Asn Phe Met Leu Thr Gln Pro His Ser Val Ser Glu Ser Pro Gly Lys
385                 390                 395                 400

Thr Val Thr Ile Ser Cys Lys Arg Asn Thr Gly Asn Ile Gly Ser Asn
                405                 410                 415

Tyr Val Asn Trp Tyr Gln Gln His Glu Gly Ser Ser Pro Thr Thr Ile
            420                 425                 430

Ile Tyr Arg Asp Asp Lys Arg Pro Asp Gly Val Ser Asp Arg Phe Ser
        435                 440                 445

Gly Ser Ile Asp Arg Ser Ser Lys Ser Ala Ser Leu Thr Ile Ser Asn
    450                 455                 460

Leu Lys Thr Glu Asp Glu Ala Asp Tyr Phe Cys Gln Ser Tyr Ser Ser
465                 470                 475                 480

Gly Phe Ile Phe Gly Gly Gly Thr Lys Leu Thr Val Leu Gly Ala Ala
                485                 490                 495

Ala Gly Ala Gly Gly Asp Tyr Lys Asp Asp Asp Asp Lys Gly Ala Ala
            500                 505                 510

Ala His His His His His His
        515
```

<210> SEQ ID NO 44
<211> LENGTH: 1647
<212> TYPE: DNA
<213> ORGANISM: Artificial Sequence
<220> FEATURE:
<223> OTHER INFORMATION: T2C-0003 ORF

<400> SEQUENCE: 44

```
atgaaacacc tgtggttctt cctcctgctg gtggcagctc ccagatgggt gctgagcgga     60

caggtgcagc tggtgcagtc tggcgccgaa gtgaagaaac caggcgccag cgtgaaggtg    120

tcctgcaagg ccagcggcta cacctttacc accgccggca tgcagtgggt gcgccaggct    180

cctggacagg gcctggaatg gatgggctgg atcaacaccc acagcggcgt gcccaaatac    240

gccgaggact tcaagggcag agtgaccatc agcgccgaca ccagcacctc cacagcctac    300

ctgcagctga gcagcctgaa gtccgaggac accgccgtgt actactgcgc cagaagcggc    360

ttcggcagca gctactggta cttcgacgtg tggggccagg gcaccctcgt gacagtgtct    420

agcggaggcg gaggatctgg cggcggagga agtggcggag ggggatccga tatccagatg    480

acccagagcc ccagcagcct gtctgccagc gtgggcgaca gagtgacaat tacatgcaag    540

gcctcccagg acgtgtccac agccgtggcc tggtatcagc agaagcctgg caaggccccc    600

aagctgctga tctacagcgc cagctaccgg tacaccggcg tgccaagcag attttccggc    660

agcggctccg gcaccgactt caccctgaca atcagctccc tgcagcccga ggatttcgcc    720

gtgtattatt gccagcagca ctacatcacc cccctgacct tcggccaggg gaccaagctg    780

gaaatcaaga gaacaggggg aggcggttca gaagtgcagc tggtggaatc cggcggaggc    840

ctggtccagc ctggcggcag cctgaaactg agctgcgccg ccagcggctt caccttcaac    900
```

```
aaatacgcca tgaactgggt ccgccaggct cctggaaagg gactcgagtg ggtggcccgg    960

atcagaagca agtacaacaa ctacgccacc tactacgccg acagcgtgaa ggaccggttc   1020

accatcagcc gggacgacag caagaacacc gcctacctgc agatgaacaa cctgaaaacc   1080

gaggacacag ccgtgtacta ctgcgtgcgg cacggcaact tcggcaacag ctacatcagc   1140

tactgggcct attggggaca gggaacactc gtgacagtgt ccagtggcgg aggcggcagt   1200

ggtgggggag gaagcggagg tggcggatct cagaccgtgg tcacccagga acccagcctg   1260

acagtcagcc ctggaggcac cgtgaccctg acctgtggaa gcagcacagg cgccgtgacc   1320

agcggctact accccaactg ggtgcagcag aagcccggcc aggctcctag aggcctgatc   1380

ggcggcacca agtttctggc ccctggcacc cctgcccggt tctctggatc tctgctgggc   1440

ggcaaggccg ccctgacact gagcggagtg cagcccgagg acgaggccga gtactactgt   1500

gccctgtggt acagcaacag atgggtgttc ggcggaggga ccaagctgac cgtgctgggc   1560

agcggcgcgt ctgcggccgc aggtagcggt ggtgattaca aagatgatga cgataaaggt   1620

gcagcggcgc atcaccatca tcaccac                                       1647
```

```
<210> SEQ ID NO 45
<211> LENGTH: 530
<212> TYPE: PRT
<213> ORGANISM: Artificial Sequence
<220> FEATURE:
<223> OTHER INFORMATION: T2C-0003 AA

<400> SEQUENCE: 45

Gly Gln Val Gln Leu Val Gln Ser Gly Ala Glu Val Lys Lys Pro Gly
1               5                   10                  15

Ala Ser Val Lys Val Ser Cys Lys Ala Ser Gly Tyr Thr Phe Thr Thr
            20                  25                  30

Ala Gly Met Gln Trp Val Arg Gln Ala Pro Gly Gln Gly Leu Glu Trp
        35                  40                  45

Met Gly Trp Ile Asn Thr His Ser Gly Val Pro Lys Tyr Ala Glu Asp
    50                  55                  60

Phe Lys Gly Arg Val Thr Ile Ser Ala Asp Thr Ser Thr Ser Thr Ala
65                  70                  75                  80

Tyr Leu Gln Leu Ser Ser Leu Lys Ser Glu Asp Thr Ala Val Tyr Tyr
                85                  90                  95

Cys Ala Arg Ser Gly Phe Gly Ser Ser Tyr Trp Tyr Phe Asp Val Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Gln Asp Val Ser Thr Ala Val Ala Trp Tyr Gln Gln Lys
                165                 170                 175

Pro Gly Lys Ala Pro Lys Leu Leu Ile Tyr Ser Ala Ser Tyr Arg Tyr
            180                 185                 190

Thr Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Val Tyr Tyr
    210                 215                 220
```

```
Cys Gln Gln His Tyr Ile Thr Pro Leu Thr Phe Gly Gln Gly Thr Lys
225                 230                 235                 240

Leu Glu Ile Lys Arg Thr Gly Gly Gly Gly Ser Glu Val Gln Leu Val
                245                 250                 255

Glu Ser Gly Gly Gly Leu Val Gln Pro Gly Gly Ser Leu Lys Leu Ser
            260                 265                 270

Cys Ala Ala Ser Gly Phe Thr Phe Asn Lys Tyr Ala Met Asn Trp Val
        275                 280                 285

Arg Gln Ala Pro Gly Lys Gly Leu Glu Trp Val Ala Arg Ile Arg Ser
    290                 295                 300

Lys Tyr Asn Asn Tyr Ala Thr Tyr Tyr Ala Asp Ser Val Lys Asp Arg
305                 310                 315                 320

Phe Thr Ile Ser Arg Asp Asp Ser Lys Asn Thr Ala Tyr Leu Gln Met
                325                 330                 335

Asn Asn Leu Lys Thr Glu Asp Thr Ala Val Tyr Tyr Cys Val Arg His
            340                 345                 350

Gly Asn Phe Gly Asn Ser Tyr Ile Ser Tyr Trp Ala Tyr Trp Gly Gln
        355                 360                 365

Gly Thr Leu Val Thr Val Ser Ser Gly Gly Gly Gly Ser Gly Gly Gly
    370                 375                 380

Gly Ser Gly Gly Gly Gly Ser Gln Thr Val Val Thr Gln Glu Pro Ser
385                 390                 395                 400

Leu Thr Val Ser Pro Gly Gly Thr Val Thr Leu Thr Cys Gly Ser Ser
                405                 410                 415

Thr Gly Ala Val Thr Ser Gly Tyr Tyr Pro Asn Trp Val Gln Gln Lys
            420                 425                 430

Pro Gly Gln Ala Pro Arg Gly Leu Ile Gly Gly Thr Lys Phe Leu Ala
        435                 440                 445

Pro Gly Thr Pro Ala Arg Phe Ser Gly Ser Leu Leu Gly Gly Lys Ala
    450                 455                 460

Ala Leu Thr Leu Ser Gly Val Gln Pro Glu Asp Glu Ala Glu Tyr Tyr
465                 470                 475                 480

Cys Ala Leu Trp Tyr Ser Asn Arg Trp Val Phe Gly Gly Gly Thr Lys
                485                 490                 495

Leu Thr Val Leu Gly Ser Gly Ala Ser Ala Ala Ala Gly Ser Gly Gly
            500                 505                 510

Asp Tyr Lys Asp Asp Asp Asp Lys Gly Ala Ala Ala His His His His
        515                 520                 525

His His
    530
```

<210> SEQ ID NO 46
<211> LENGTH: 1614
<212> TYPE: DNA
<213> ORGANISM: Artificial Sequence
<220> FEATURE:
<223> OTHER INFORMATION: T2C-0005 ORF

<400> SEQUENCE: 46

```
atgaagcacc tgtggttctt cctcctgctg gtggcagctc ccagatgggt gctgagcgga      60

caggtgcagc tggtgcagtc tggcgccgaa gtgaagaaac caggcgccag cgtgaaggtg     120

tcctgcaagg ccagcggcta cacctttacc accgccggca tgcagtgggt gcgccaggct     180

cctggacagg gcctggaatg gatgggctgg atcaacaccc acagcggcgt gcccaaatac     240

gccgaggact tcaagggcag agtgaccatc agcgccgaca ccagcacctc cacagcctac     300
```

```
ctgcagctga gcagcctgaa gtccgaggac accgccgtgt actactgcgc cagaagcggc    360

ttcggcagca gctactggta cttcgacgtg tggggccagg gcaccctcgt gacagtgtct    420

agcggaggcg gaggatctgg cggcggagga agtggcggag gggatccga tatccagatg    480

acccagagcc ccagcagcct gtctgccagc gtgggcgaca gagtgacaat tacatgcaag    540

gcctcccagg acgtgtccac agccgtggcc tggtatcagc agaagcctgg caaggccccc    600

aagctgctga tctacagcgc cagctaccgg tacaccggcg tgccaagcag attttccggc    660

agcggctccg gcaccgactt caccctgaca atcagctccc tgcagcccga ggatttcgcc    720

gtgtattatt gccagcagca ctacatcacc cccctgacct tcggccaggg gaccaagctg    780

gaaatcaaga gaacaggggg aggcggttca gaagtgcagc tggtggaatc cgggggggc    840

ctggtgcagc ctgggggag cctgagactg agttgtgccg cctctggggt gacatttaac    900

tactatggca tgtcttggat ccgccaggca cctggaaagg gcctggagtg ggtggccagc    960

atcactaatt ccggcgggcg aatctactat cccgacagcg tcaagggcag gttcacaatt   1020

tcccgcgaga acacacagaa aactctgtac ctgcagatga atagcctgag agccgaagat   1080

acagctgtgt actattgcac tctggacggc agggatgggt gggtcgccta ttgggggcag   1140

ggaaccctgg tgacagtcag ctccggagga ggaggatctg gcggaggagg cagtgggga   1200

ggcgggtcaa tggcccaggc tgtgctcact cagccgtcct ctgtttctgg cgtacctggc   1260

caacgggtga ccattagctg taaaaggaat accgggaata tcgggtctaa ctacgtgaac   1320

tggtatcagc agcttccagg gacagctccc aagttgctga tctatcgcga cgacaaaaga   1380

ccctcagggg tccctgaccg atttagtggc agcaaaagcg gtacttccgc ttccctggcg   1440

ataaccggct ttcaggccga agatgaggca gactactatt gccagtcata ttccagcggc   1500

ttcatcttcg gaggcggaac taagctgaca gtgttgggcg cggccgcagg tgcaggtggt   1560

gattacaaag atgatgacga taaaggtgca gcggcgcatc accatcatca ccac         1614
```

<210> SEQ ID NO 47
<211> LENGTH: 519
<212> TYPE: PRT
<213> ORGANISM: Artificial Sequence
<220> FEATURE:
<223> OTHER INFORMATION: T2C-0005 AA

<400> SEQUENCE: 47

```
Gly Gln Val Gln Leu Val Gln Ser Gly Ala Glu Val Lys Lys Pro Gly
1               5                   10                  15

Ala Ser Val Lys Val Ser Cys Lys Ala Ser Gly Tyr Thr Phe Thr Thr
            20                  25                  30

Ala Gly Met Gln Trp Val Arg Gln Ala Pro Gly Gln Gly Leu Glu Trp
        35                  40                  45

Met Gly Trp Ile Asn Thr His Ser Gly Val Pro Lys Tyr Ala Glu Asp
    50                  55                  60

Phe Lys Gly Arg Val Thr Ile Ser Ala Asp Thr Ser Thr Ser Thr Ala
65                  70                  75                  80

Tyr Leu Gln Leu Ser Ser Leu Lys Ser Glu Asp Thr Ala Val Tyr Tyr
                85                  90                  95

Cys Ala Arg Ser Gly Phe Gly Ser Ser Tyr Trp Tyr Phe Asp Val Trp
            100                 105                 110

Gly Gln Gly Thr Leu Val Thr Val Ser Ser Gly Gly Gly Gly Ser Gly
        115                 120                 125
```

```
Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Gln Asp Val Ser Thr Ala Val Ala Trp Tyr Gln Gln Lys
                165                 170                 175

Pro Gly Lys Ala Pro Lys Leu Leu Ile Tyr Ser Ala Ser Tyr Arg Tyr
            180                 185                 190

Thr Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Val Tyr Tyr
    210                 215                 220

Cys Gln Gln His Tyr Ile Thr Pro Leu Thr Phe Gly Gln Gly Thr Lys
225                 230                 235                 240

Leu Glu Ile Lys Arg Thr Gly Gly Gly Gly Ser Glu Val Gln Leu Val
                245                 250                 255

Glu Ser Gly Gly Gly Leu Val Gln Pro Gly Gly Ser Leu Arg Leu Ser
            260                 265                 270

Cys Ala Ala Ser Gly Val Thr Phe Asn Tyr Tyr Gly Met Ser Trp Ile
        275                 280                 285

Arg Gln Ala Pro Gly Lys Gly Leu Glu Trp Val Ala Ser Ile Thr Asn
    290                 295                 300

Ser Gly Gly Arg Ile Tyr Tyr Pro Asp Ser Val Lys Gly Arg Phe Thr
305                 310                 315                 320

Ile Ser Arg Glu Asn Thr Gln Lys Thr Leu Tyr Leu Gln Met Asn Ser
                325                 330                 335

Leu Arg Ala Glu Asp Thr Ala Val Tyr Tyr Cys Thr Leu Asp Gly Arg
            340                 345                 350

Asp Gly Trp Val Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
    370                 375                 380

Met Ala Gln Ala Val Leu Thr Gln Pro Ser Ser Val Ser Gly Val Pro
385                 390                 395                 400

Gly Gln Arg Val Thr Ile Ser Cys Lys Arg Asn Thr Gly Asn Ile Gly
                405                 410                 415

Ser Asn Tyr Val Asn Trp Tyr Gln Gln Leu Pro Gly Thr Ala Pro Lys
            420                 425                 430

Leu Leu Ile Tyr Arg Asp Asp Lys Arg Pro Ser Gly Val Pro Asp Arg
        435                 440                 445

Phe Ser Gly Ser Lys Ser Gly Thr Ser Ala Ser Leu Ala Ile Thr Gly
    450                 455                 460

Phe Gln Ala Glu Asp Glu Ala Asp Tyr Tyr Cys Gln Ser Tyr Ser Ser
465                 470                 475                 480

Gly Phe Ile Phe Gly Gly Gly Thr Lys Leu Thr Val Leu Gly Ala Ala
                485                 490                 495

Ala Gly Ala Gly Gly Asp Tyr Lys Asp Asp Asp Asp Lys Gly Ala Ala
            500                 505                 510

Ala His His His His His His
        515
```

<210> SEQ ID NO 48
<211> LENGTH: 1608
<212> TYPE: DNA

<213> ORGANISM: Artificial Sequence
<220> FEATURE:
<223> OTHER INFORMATION: T2C-0006 ORF

<400> SEQUENCE: 48

```
atgaagcacc tgtggttctt cctcctgctg gtggcagctc ccagatgggt gctgagcgga     60
caggtgcagc tggtgcagtc tggcgccgaa gtgaagaaac caggcgccag cgtgaaggtg    120
tcctgcaagg ccagcggcta cacctttacc accgccggca tgcagtgggt gcgccaggct    180
cctggacagg gcctggaatg gatgggctgg atcaacaccc acagcggcgt gcccaaatac    240
gccgaggact tcaagggcag agtgaccatc agcgccgaca ccagcacctc cacagcctac    300
ctgcagctga gcagcctgaa gtccgaggac accgccgtgt actactgcgc cagaagcggc    360
ttcggcagca gctactggta cttcgacgtg tggggccagg gcaccctcgt gacagtgtct    420
agcggaggcg gaggatctgg cggcggagga agtggcggag gggatccga tatccagatg    480
acccagagcc ccagcagcct gtctgccagc gtgggcgaca gagtgacaat tacatgcaag    540
gcctcccagg acgtgtccac agccgtggcc tggtatcagc agaagcctgg caaggccccc    600
aagctgctga tctacagcgc cagctaccgg tacaccggcg tgccaagcag attttccggc    660
agcggctccg gcaccgactt caccctgaca atcagctccc tgcagcccga ggatttcgcc    720
gtgtattatt gccagcagca ctacatcacc cccctgacct tcggccaggg gaccaagctg    780
gaaatcaaga gaacaggggg aggcggttca gaagtgcagc tggtggaatc cgggggggc    840
ctggtgcagc ctgggggag cctgagactg agttgtgccg cctctggggt gacatttaac    900
tactatggca tgtcttggat ccgccaggca cctggaaagg gcctggagtg ggtggccagc    960
atcactaatt ccggcgggcg aatctactat cccgacagcg tcaagggcag gttcacaatt   1020
tcccgcgaga acacacagaa aactctgtac ctgcagatga atagcctgag agccgaagat   1080
acagctgtgt actattgcac tctggacggc agggatgggt gggtcgccta ttgggggcag   1140
ggaaccctgg tgacagtcag ctccggagga ggaggatctg gcggaggagg cagtggggga   1200
ggcgggtcaa actttatgct cactcagccg tcctctgttt ctggcgtacc tggccaacgg   1260
gtgaccatta gctgtacggg taataccggg aatatcgggt ctaactacgt gaactggtat   1320
cagcagcttc cagggacagc tcccaagttg ctgatctatc gcgacgacaa aagaccctca   1380
ggggtccctg accgatttag tggcagcaaa agcggtactt ccgcttccct ggcgataacc   1440
ggctttcagg ccgaagatga ggcagactac tattgccagt catattccag cggcttcatc   1500
ttcggaggcg gaactaagct gacagtgttg ggcgcggccg caggtgcagg tggtgattac   1560
aaagatgatg acgataaagg tgcagcggcg catcaccatc atcaccac                1608
```

<210> SEQ ID NO 49
<211> LENGTH: 517
<212> TYPE: PRT
<213> ORGANISM: Artificial Sequence
<220> FEATURE:
<223> OTHER INFORMATION: T2C-0006 AA

<400> SEQUENCE: 49

```
Gly Gln Val Gln Leu Val Gln Ser Gly Ala Glu Val Lys Lys Pro Gly
1               5                   10                  15

Ala Ser Val Lys Val Ser Cys Lys Ala Ser Gly Tyr Thr Phe Thr Thr
            20                  25                  30

Ala Gly Met Gln Trp Val Arg Gln Ala Pro Gly Gln Gly Leu Glu Trp
        35                  40                  45
```

```
Met Gly Trp Ile Asn Thr His Ser Gly Val Pro Lys Tyr Ala Glu Asp
    50                  55                  60

Phe Lys Gly Arg Val Thr Ile Ser Ala Asp Thr Ser Thr Ser Thr Ala
65                  70                  75                  80

Tyr Leu Gln Leu Ser Ser Leu Lys Ser Glu Asp Thr Ala Val Tyr Tyr
                85                  90                  95

Cys Ala Arg Ser Gly Phe Gly Ser Ser Tyr Trp Tyr Phe Asp Val Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Gln Asp Val Ser Thr Ala Val Ala Trp Tyr Gln Gln Lys
                165                 170                 175

Pro Gly Lys Ala Pro Lys Leu Leu Ile Tyr Ser Ala Ser Tyr Arg Tyr
            180                 185                 190

Thr Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Val Tyr Tyr
    210                 215                 220

Cys Gln Gln His Tyr Ile Thr Pro Leu Thr Phe Gly Gln Gly Thr Lys
225                 230                 235                 240

Leu Glu Ile Lys Arg Thr Gly Gly Gly Gly Ser Glu Val Gln Leu Val
                245                 250                 255

Glu Ser Gly Gly Gly Leu Val Gln Pro Gly Gly Ser Leu Arg Leu Ser
            260                 265                 270

Cys Ala Ala Ser Gly Val Thr Phe Asn Tyr Tyr Gly Met Ser Trp Ile
        275                 280                 285

Arg Gln Ala Pro Gly Lys Gly Leu Glu Trp Val Ala Ser Ile Thr Asn
    290                 295                 300

Ser Gly Gly Arg Ile Tyr Tyr Pro Asp Ser Val Lys Gly Arg Phe Thr
305                 310                 315                 320

Ile Ser Arg Glu Asn Thr Gln Lys Thr Leu Tyr Leu Gln Met Asn Ser
                325                 330                 335

Leu Arg Ala Glu Asp Thr Ala Val Tyr Tyr Cys Thr Leu Asp Gly Arg
            340                 345                 350

Asp Gly Trp Val Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
    370                 375                 380

Asn Phe Met Leu Thr Gln Pro Ser Ser Val Ser Gly Val Pro Gly Gln
385                 390                 395                 400

Arg Val Thr Ile Ser Cys Thr Gly Asn Thr Gly Asn Ile Gly Ser Asn
                405                 410                 415

Tyr Val Asn Trp Tyr Gln Gln Leu Pro Gly Thr Ala Pro Lys Leu Leu
            420                 425                 430

Ile Tyr Arg Asp Asp Lys Arg Pro Ser Gly Val Pro Asp Arg Phe Ser
        435                 440                 445

Gly Ser Lys Ser Gly Thr Ser Ala Ser Leu Ala Ile Thr Gly Phe Gln
    450                 455                 460

Ala Glu Asp Glu Ala Asp Tyr Tyr Cys Gln Ser Tyr Ser Ser Gly Phe
```

```
465                 470                 475                 480

Ile Phe Gly Gly Gly Thr Lys Leu Thr Val Leu Gly Ala Ala Ala Gly
                485                 490                 495

Ala Gly Gly Asp Tyr Lys Asp Asp Asp Asp Lys Gly Ala Ala Ala His
            500                 505                 510

His His His His His
        515


<210> SEQ ID NO 50
<211> LENGTH: 37
<212> TYPE: DNA
<213> ORGANISM: Artificial Sequence
<220> FEATURE:
<223> OTHER INFORMATION: Nhe-polyC-S
<220> FEATURE:
<221> NAME/KEY: misc_feature
<222> LOCATION: (37)..(37)
<223> OTHER INFORMATION: n is a, c, g or t

<400> SEQUENCE: 50

gctagcgcta ccggactcag atcccccccc cccccdn                              37


<210> SEQ ID NO 51
<211> LENGTH: 28
<212> TYPE: DNA
<213> ORGANISM: Artificial Sequence
<220> FEATURE:
<223> OTHER INFORMATION: rIg gamma-AS1

<400> SEQUENCE: 51

tcactgagct ggtgagagtg tagagccc                                        28


<210> SEQ ID NO 52
<211> LENGTH: 28
<212> TYPE: DNA
<213> ORGANISM: Artificial Sequence
<220> FEATURE:
<223> OTHER INFORMATION: rIg gamma-AS2

<400> SEQUENCE: 52

tcaccgagct gctgagggtg tagagccc                                        28


<210> SEQ ID NO 53
<211> LENGTH: 37
<212> TYPE: DNA
<213> ORGANISM: Artificial Sequence
<220> FEATURE:
<223> OTHER INFORMATION: Nhe-polyC-S2
<220> FEATURE:
<221> NAME/KEY: misc_feature
<222> LOCATION: (37)..(37)
<223> OTHER INFORMATION: n is a, c, g or t

<400> SEQUENCE: 53

gctagcgcta ccggactcag atcccccccc cccccdn                              37


<210> SEQ ID NO 54
<211> LENGTH: 26
<212> TYPE: DNA
<213> ORGANISM: Artificial Sequence
<220> FEATURE:
<223> OTHER INFORMATION: rIgL-AS1

<400> SEQUENCE: 54

ttccacatca ctcgggtaga aatcag                                          26
```

<210> SEQ ID NO 55
<211> LENGTH: 28
<212> TYPE: DNA
<213> ORGANISM: Artificial Sequence
<220> FEATURE:
<223> OTHER INFORMATION: rIgL-AS2

<400> SEQUENCE: 55
taacaccagg gtagaaatct gtcaccat 28

<210> SEQ ID NO 56
<211> LENGTH: 19
<212> TYPE: DNA
<213> ORGANISM: Artificial Sequence
<220> FEATURE:
<223> OTHER INFORMATION: rIg gamma-seq

<400> SEQUENCE: 56
ctggctcagg gaaatagcc 19

<210> SEQ ID NO 57
<211> LENGTH: 18
<212> TYPE: DNA
<213> ORGANISM: Artificial Sequence
<220> FEATURE:
<223> OTHER INFORMATION: rIgL-seq1

<400> SEQUENCE: 57
tccctggagc tcctcagt 18

<210> SEQ ID NO 58
<211> LENGTH: 18
<212> TYPE: DNA
<213> ORGANISM: Artificial Sequence
<220> FEATURE:
<223> OTHER INFORMATION: rIgL-seq2

<400> SEQUENCE: 58
gccttgtcag tcttgagc 18

<210> SEQ ID NO 59
<211> LENGTH: 864
<212> TYPE: DNA
<213> ORGANISM: Artificial Sequence
<220> FEATURE:
<223> OTHER INFORMATION: C3E-7078 ORF

<400> SEQUENCE: 59
atgaaacacc tgtggttctt cctcctgctg gtggcagctc ccagatgggt gctgagcgga 60
gaagtgcagc tggtggaatc cggggggggc ctggtgcagc ctggggggag cctgagactg 120
agttgtgccg cctctggggt gacatttaac tactatggca tgtcttggat ccgccaggca 180
cctggaaagg gcctggagtg ggtggccagc atcactaggt ccggcgggcg aatctactat 240
cccgacagcg tcaagggcag gttcacaatt tcccgcgaga acacacagaa aactctgtac 300
ctgcagatga atagcctgag agccgaagat acagctgtgt actattgcac tctggacggc 360
agggatgggt gggtcgccta ttgggggcag ggaaccctgg tgacagtcag ctccggagga 420
ggaggatctg gcggaggagg cagtggggga ggcgggtcaa actttatgct gacccagccc 480
cacagtgtgt cagagagccc tggcaagact gtcaccatct cttgtaaaag gaacaccgga 540
aatattggca gtaactacgt gaattggtat cagcagcatg aagggtctag tccaaccaca 600
atcatctacc gggacgataa gagacccgac ggggtgtccg atcgattctc cggatctatc 660

```
gaccggtcaa gcaagagtgc ttcactgacc attagcaatc tgaaaacaga ggacgaagca    720

gattactttt gccagtccta ttcctctggc ttcatctttg gaggcgggac taaactgacc    780

gtgctgggcg cggccgcagg tgcaggtggt gattacaaag atgatgacga taaaggtgca    840

gcggcgcatc accatcatca ccac                                           864
```

<210> SEQ ID NO 60
<211> LENGTH: 269
<212> TYPE: PRT
<213> ORGANISM: Artificial Sequence
<220> FEATURE:
<223> OTHER INFORMATION: C3E-7078 AA

<400> SEQUENCE: 60

```
Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Arg Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175

Ser Ser Pro Thr Thr Ile Ile Tyr Arg Asp Asp Lys Arg Pro Asp Gly
            180                 185                 190

Val Ser Asp Arg Phe Ser Gly Ser Ile Asp Arg Ser Ser Lys Ser Ala
        195                 200                 205

Ser Leu Thr Ile Ser Asn Leu Lys Thr Glu Asp Glu Ala Asp Tyr Phe
    210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
            260                 265
```

<210> SEQ ID NO 61
<211> LENGTH: 864
<212> TYPE: DNA
<213> ORGANISM: Artificial Sequence
<220> FEATURE:
<223> OTHER INFORMATION: C3E-7079 ORF

<400> SEQUENCE: 61

```
atgaaacacc tgtggttctt cctcctgctg gtggcagctc ccagatgggt gctgagcgga     60

gaagtgcagc tggtggaatc cggggggggc ctggtgcagc ctgggggggag cctgagactg    120

agttgtgccg cctctggggt gacatttaac tactatggca tgtcttggat ccgccaggca    180

cctggaaagg gcctggagtg ggtggccagc atcacttctt ccggcgggcg aatctactat    240

cccgacagcg tcaagggcag gttcacaatt tcccgcgaga acacacagaa aactctgtac    300

ctgcagatga atagcctgag agccgaagat acagctgtgt actattgcac tctggacggc    360

agggatgggt gggtcgccta ttgggggcag ggaaccctgg tgacagtcag ctccggagga    420

ggaggatctg gcggaggagg cagtggggga ggcgggtcaa actttatgct gacccagccc    480

cacagtgtgt cagagagccc tggcaagact gtcaccatct cttgtaaaag gaacaccgga    540

aatattggca gtaactacgt gaattggtat cagcagcatg aagggtctag tccaaccaca    600

atcatctacc gggacgataa gagacccgac ggggtgtccg atcgattctc cggatctatc    660

gaccggtcaa gcaagagtgc ttcactgacc attagcaatc tgaaaacaga ggacgaagca    720

gattactttt gccagtccta ttcctctggc ttcatctttg gaggcgggac taaactgacc    780

gtgctgggcg cggccgcagg tgcaggtggt gattacaaag atgatgacga taaaggtgca    840

gcggcgcatc accatcatca ccac                                           864
```

```
<210> SEQ ID NO 62
<211> LENGTH: 269
<212> TYPE: PRT
<213> ORGANISM: Artificial Sequence
<220> FEATURE:
<223> OTHER INFORMATION: C3E-7079 AA

<400> SEQUENCE: 62

Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Ser Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175

Ser Ser Pro Thr Thr Ile Ile Tyr Arg Asp Asp Lys Arg Pro Asp Gly
            180                 185                 190

Val Ser Asp Arg Phe Ser Gly Ser Ile Asp Arg Ser Ser Lys Ser Ala
        195                 200                 205
```

```
Ser Leu Thr Ile Ser Asn Leu Lys Thr Glu Asp Glu Ala Asp Tyr Phe
    210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
            260                 265
```

<210> SEQ ID NO 63
<211> LENGTH: 858
<212> TYPE: DNA
<213> ORGANISM: Artificial Sequence
<220> FEATURE:
<223> OTHER INFORMATION: C3E-7085 ORF

<400> SEQUENCE: 63

```
atgaaacacc tgtggttctt cctcctgctg gtggcagctc ccagatgggt gctgagcgga     60

gaagtgcagc tggtggaatc cggggggggc ctggtgcagc ctggggggag cctgagactg    120

agttgtgccg cctctggggt gacatttaac tactatggca tgtcttggat ccgccaggca    180

cctggaaagg gcctggagtg ggtggccagc atcactaggt ccggcgggcg aatctactat    240

cccgacagcg tcaagggcag gttcacaatt tcccgcgaga acacacagaa aactctgtac    300

ctgcagatga atagcctgag agccgaagat acagctgtgt actattgcac tctggacggc    360

agggatgggt gggtcgccta ttgggggcag ggaaccctgg tgacagtcag ctccggagga    420

ggaggatctg gcggaggagg cagtggggga ggcgggtcaa actttatgct cactcagccg    480

tcctctgttt ctggcgtacc tggccaacgg gtgaccatta gctgtacggg taataccggg    540

aatatcgggt ctaactacgt gaactggtat cagcagcttc cagggacagc tcccaagttg    600

ctgatctatc gcgacgacaa aagaccctca ggggtccctg accgatttag tggcagcaaa    660

agcggtactt ccgcttccct ggcgataacc ggctttcagg ccgaagatga ggcagactac    720

tattgccagt catattccag cggcttcatc ttcggaggcg gaactaagct gacagtgttg    780

ggcgcggccg caggtgcagg tggtgattac aaagatgatg acgataaagg tgcagcggcg    840

catcaccatc atcaccac                                                  858
```

<210> SEQ ID NO 64
<211> LENGTH: 267
<212> TYPE: PRT
<213> ORGANISM: Artificial Sequence
<220> FEATURE:
<223> OTHER INFORMATION: C3E-7085 AA

<400> SEQUENCE: 64

```
Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Arg Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
```

```
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro Ser Ser Val
    130                 135                 140

Ser Gly Val Pro Gly Gln Arg Val Thr Ile Ser Cys Thr Gly Asn Thr
145                 150                 155                 160

Gly Asn Ile Gly Ser Asn Tyr Val Asn Trp Tyr Gln Gln Leu Pro Gly
                165                 170                 175

Thr Ala Pro Lys Leu Leu Ile Tyr Arg Asp Asp Lys Arg Pro Ser Gly
            180                 185                 190

Val Pro Asp Arg Phe Ser Gly Ser Lys Ser Gly Thr Ser Ala Ser Leu
        195                 200                 205

Ala Ile Thr Gly Phe Gln Ala Glu Asp Glu Ala Asp Tyr Tyr Cys Gln
    210                 215                 220

Ser Tyr Ser Ser Gly Phe Ile Phe Gly Gly Gly Thr Lys Leu Thr Val
225                 230                 235                 240

Leu Gly Ala Ala Ala Gly Ala Gly Gly Asp Tyr Lys Asp Asp Asp Asp
                245                 250                 255

Lys Gly Ala Ala Ala His His His His His His
            260                 265
```

<210> SEQ ID NO 65
<211> LENGTH: 864
<212> TYPE: DNA
<213> ORGANISM: Artificial Sequence
<220> FEATURE:
<223> OTHER INFORMATION: C3E-7086 ORF

<400> SEQUENCE: 65

```
atgaaacacc tgtggttctt cctcctgctg gtggcagctc ccagatgggt gctgagcgga     60

gaagtgcagc tggtggaatc cggggggggc ctggtgcagc ctggggggag cctgagactg    120

agttgtgccg cctctggggt gacatttaac tactatggca tgtcttggat ccgccaggca    180

cctggaaagg gcctggagtg ggtggccagc atcactaggt ccggcgggcg aatctactat    240

cccgacagcg tcaagggcag gttcacaatt tcccgcgaga acacacagaa aactctgtac    300

ctgcagatga atagcctgag agccgaagat acagctgtgt actattgcac tctggacggc    360

agggatgggt gggtcgccta ttgggggcag ggaaccctgg tgacagtcag ctccggagga    420

ggaggatctg gcggaggagg cagtggggga ggcgggtcaa actttatgct gacccagccc    480

cacagtgtgt cagagagccc tggcaagact gtcaccatct cttgtaaaag gaacaccgga    540

aatattggca gtaactacgt gaattggtat cagcagcatg aagggtctag tccaaccaca    600

atcatctacc ggggcgataa gagacccgac ggggtgtccg atcgattctc cggatctatc    660

gaccggtcaa gcaagagtgc ttcactgacc attagcaatc tgaaaacaga ggacgaagca    720

gattactttt gccagtccta ttcctctggc ttcatctttg gaggcgggac taaactgacc    780

gtgctgggcg cggccgcagg tgcaggtggt gattacaaag atgatgacga taaaggtgca    840

gcggcgcatc accatcatca ccac                                           864
```

<210> SEQ ID NO 66
<211> LENGTH: 269
<212> TYPE: PRT

<213> ORGANISM: Artificial Sequence
<220> FEATURE:
<223> OTHER INFORMATION: C3E-7086 AA

<400> SEQUENCE: 66

```
Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Arg Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175

Ser Ser Pro Thr Thr Ile Ile Tyr Arg Gly Asp Lys Arg Pro Asp Gly
            180                 185                 190

Val Ser Asp Arg Phe Ser Gly Ser Ile Asp Arg Ser Ser Lys Ser Ala
        195                 200                 205

Ser Leu Thr Ile Ser Asn Leu Lys Thr Glu Asp Glu Ala Asp Tyr Phe
    210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
            260                 265
```

<210> SEQ ID NO 67
<211> LENGTH: 864
<212> TYPE: DNA
<213> ORGANISM: Artificial Sequence
<220> FEATURE:
<223> OTHER INFORMATION: C3E-7087 ORF

<400> SEQUENCE: 67

```
atgaaacacc tgtggttctt cctcctgctg gtggcagctc ccagatgggt gctgagcgga     60

gaagtgcagc tggtggaatc cggggggggc ctggtgcagc ctggggggag cctgagactg    120

agttgtgccg cctctggggt gacatttaac tactatggca tgtcttggat ccgccaggca    180

cctggaaagg gcctggagtg ggtggccagc atcactaggt ccggcgggcg aatctactat    240

cccgacagcg tcaagggcag gttcacaatt tcccgcgaga acacacagaa aactctgtac    300

ctgcagatga atagcctgag agccgaagat acagctgtgt actattgcac tctggacggc    360
```

```
agggatgggt gggtcgccta ttgggggcag ggaaccctgg tgacagtcag ctccggagga    420

ggaggatctg gcggaggagg cagtggggga ggcgggtcaa actttatgct gacccagccc    480

cacagtgtgt cagagagccc tggcaagact gtcaccatct cttgtaaaag gaacaccgga    540

aatattggca gtaactacgt gaattggtat cagcagcatg aagggtctag tccaaccaca    600

atcatctacc ggcaggataa gagacccgac ggggtgtccg atcgattctc cggatctatc    660

gaccggtcaa gcaagagtgc ttcactgacc attagcaatc tgaaaacaga ggacgaagca    720

gattactttt gccagtccta ttcctctggc ttcatctttg gaggcgggac taaactgacc    780

gtgctgggcg cggccgcagg tgcaggtggt gattacaaag atgatgacga taaaggtgca    840

gcggcgcatc accatcatca ccac                                           864


<210> SEQ ID NO 68
<211> LENGTH: 269
<212> TYPE: PRT
<213> ORGANISM: Artificial Sequence
<220> FEATURE:
<223> OTHER INFORMATION: C3E-7087 AA

<400> SEQUENCE: 68

Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Arg Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175

Ser Ser Pro Thr Thr Ile Ile Tyr Arg Gln Asp Lys Arg Pro Asp Gly
            180                 185                 190

Val Ser Asp Arg Phe Ser Gly Ser Ile Asp Arg Ser Ser Lys Ser Ala
        195                 200                 205

Ser Leu Thr Ile Ser Asn Leu Lys Thr Glu Asp Glu Ala Asp Tyr Phe
    210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
            260                 265
```

<210> SEQ ID NO 69
<211> LENGTH: 864
<212> TYPE: DNA
<213> ORGANISM: Artificial Sequence
<220> FEATURE:
<223> OTHER INFORMATION: C3E-7088 ORF

<400> SEQUENCE: 69

```
atgaaacacc tgtggttctt cctcctgctg gtggcagctc ccagatgggt gctgagcgga     60

gaagtgcagc tggtggaatc cggggggggc ctggtgcagc ctgggggggag cctgagactg    120

agttgtgccg cctctggggt gacatttaac tactatggca tgtcttggat ccgccaggca    180

cctggaaagg gcctggagtg ggtggccagc atcactaggt ccggcgggcg aatctactat    240

cccgacagcg tcaagggcag gttcacaatt tcccgcgaga acacacagaa aactctgtac    300

ctgcagatga atagcctgag agccgaagat acagctgtgt actattgcac tctggacggc    360

agggatgggt gggtcgccta ttgggggcag ggaaccctgg tgacagtcag ctccggagga    420

ggaggatctg gcggaggagg cagtggggga ggcgggtcaa actttatgct gacccagccc    480

cacagtgtgt cagagagccc tggcaagact gtcaccatct cttgtaaaag gaacaccgga    540

aatattggca gtaactacgt gaattggtat cagcagcatg aagggtctag tccaaccaca    600

atcatctacc ggaacgataa gagacccgac ggggtgtccg atcgattctc cggatctatc    660

gaccggtcaa gcaagagtgc ttcactgacc attagcaatc tgaaaacaga ggacgaagca    720

gattactttt gccagtccta ttcctctggc ttcatctttg gaggcgggac taaactgacc    780

gtgctgggcg cggccgcagg tgcaggtggt gattacaaag atgatgacga taaaggtgca    840

gcggcgcatc accatcatca ccac                                           864
```

<210> SEQ ID NO 70
<211> LENGTH: 269
<212> TYPE: PRT
<213> ORGANISM: Artificial Sequence
<220> FEATURE:
<223> OTHER INFORMATION: C3E-7088 AA

<400> SEQUENCE: 70

```
Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Arg Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Lys Arg Asn Thr
145                 150                 155                 160
```

```
Gly Asn Ile Gly Ser Asn Tyr Val Asn Trp Tyr Gln Gln His Glu Gly
                165                 170                 175

Ser Ser Pro Thr Thr Ile Ile Tyr Arg Asn Asp Lys Arg Pro Asp Gly
            180                 185                 190

Val Ser Asp Arg Phe Ser Gly Ser Ile Asp Arg Ser Ser Lys Ser Ala
        195                 200                 205

Ser Leu Thr Ile Ser Asn Leu Lys Thr Glu Asp Glu Ala Asp Tyr Phe
    210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
            260                 265
```

<210> SEQ ID NO 71
<211> LENGTH: 864
<212> TYPE: DNA
<213> ORGANISM: Artificial Sequence
<220> FEATURE:
<223> OTHER INFORMATION: C3E-7089 ORF

<400> SEQUENCE: 71

```
atgaaacacc tgtggttctt cctcctgctg gtggcagctc ccagatgggt gctgagcgga      60

gaagtgcagc tggtggaatc cggggggggc ctggtgcagc ctggggggag cctgagactg     120

agttgtgccg cctctggggt gacatttaac tactatggca tgtcttggat ccgccaggca     180

cctggaaagg gcctggagtg ggtggccagc atcactaggt ccggcgggcg aatctactat     240

cccgacagcg tcaagggcag gttcacaatt tcccgcgaga acacacagaa aactctgtac     300

ctgcagatga atagcctgag agccgaagat acagctgtgt actattgcac tctggacggc     360

agggatgggt gggtcgccta ttgggggcag ggaaccctgg tgacagtcag ctccggagga     420

ggaggatctg gcggaggagg cagtggggga ggcgggtcaa actttatgct gacccagccc     480

cacagtgtgt cagagagccc tggcaagact gtcaccatct cttgtaaaag gaacaccgga     540

aatattggca gtaactacgt gaattggtat cagcagcatg aagggtctag tccaaccaca     600

atcatctacc ggagcgataa gagacccgac ggggtgtccg atcgattctc cggatctatc     660

gaccggtcaa gcaagagtgc ttcactgacc attagcaatc tgaaaacaga ggacgaagca     720

gattactttt gccagtccta ttcctctggc ttcatctttg gaggcgggac taaactgacc     780

gtgctgggcg cggccgcagg tgcaggtggt gattacaaag atgatgacga taaaggtgca     840

gcggcgcatc accatcatca ccac                                            864
```

<210> SEQ ID NO 72
<211> LENGTH: 269
<212> TYPE: PRT
<213> ORGANISM: Artificial Sequence
<220> FEATURE:
<223> OTHER INFORMATION: C3E-7089 AA

<400> SEQUENCE: 72

```
Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
```

```
        35                  40                  45

Val Ala Ser Ile Thr Arg Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175

Ser Ser Pro Thr Thr Ile Ile Tyr Arg Ser Asp Lys Arg Pro Asp Gly
            180                 185                 190

Val Ser Asp Arg Phe Ser Gly Ser Ile Asp Arg Ser Ser Lys Ser Ala
        195                 200                 205

Ser Leu Thr Ile Ser Asn Leu Lys Thr Glu Asp Glu Ala Asp Tyr Phe
    210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
            260                 265
```

<210> SEQ ID NO 73
<211> LENGTH: 864
<212> TYPE: DNA
<213> ORGANISM: Artificial Sequence
<220> FEATURE:
<223> OTHER INFORMATION: C3E-7090 ORF

<400> SEQUENCE: 73

```
atgaaacacc tgtggttctt cctcctgctg gtggcagctc ccagatgggt gctgagcgga     60

gaagtgcagc tggtggaatc cggggggggc ctggtgcagc ctgggggggag cctgagactg    120

agttgtgccg cctctggggt gacatttaac tactatggca tgtcttggat ccgccaggca    180

cctggaaagg gcctggagtg ggtggccagc atcactaggt ccggcgggcg aatctactat    240

cccgacagcg tcaagggcag gttcacaatt tcccgcgaga acacacagaa aactctgtac    300

ctgcagatga atagcctgag agccgaagat acagctgtgt actattgcac tctggacggc    360

agggatgggt gggtcgccta ttgggggcag ggaaccctgg tgacagtcag ctccggagga    420

ggaggatctg gcggaggagg cagtggggga ggcgggtcaa actttatgct gacccagccc    480

cacagtgtgt cagagagccc tggcaagact gtcaccatct cttgtaaaag gaacaccgga    540

aatattggca gtaactacgt gaattggtat cagcagcatg aagggtctag tccaaccaca    600

atcatctacc gggccgataa gagacccgac ggggtgtccg atcgattctc cggatctatc    660

gaccggtcaa gcaagagtgc ttcactgacc attagcaatc tgaaaacaga ggacgaagca    720

gattactttt gccagtccta ttcctctggc ttcatctttg gaggcgggac taaactgacc    780
```

```
gtgctgggcg cggccgcagg tgcaggtggt gattacaaag atgatgacga taaaggtgca    840

gcggcgcatc accatcatca ccac                                           864


<210> SEQ ID NO 74
<211> LENGTH: 269
<212> TYPE: PRT
<213> ORGANISM: Artificial Sequence
<220> FEATURE:
<223> OTHER INFORMATION: C3E-7090 AA

<400> SEQUENCE: 74

Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Arg Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175

Ser Ser Pro Thr Thr Ile Ile Tyr Arg Ala Asp Lys Arg Pro Asp Gly
            180                 185                 190

Val Ser Asp Arg Phe Ser Gly Ser Ile Asp Arg Ser Ser Lys Ser Ala
        195                 200                 205

Ser Leu Thr Ile Ser Asn Leu Lys Thr Glu Asp Glu Ala Asp Tyr Phe
    210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
            260                 265


<210> SEQ ID NO 75
<211> LENGTH: 864
<212> TYPE: DNA
<213> ORGANISM: Artificial Sequence
<220> FEATURE:
<223> OTHER INFORMATION: C3E-7091 ORF

<400> SEQUENCE: 75

atgaaacacc tgtggttctt cctcctgctg gtggcagctc ccagatgggt gctgagcgga     60

gaagtgcagc tggtggaatc cggggggggc ctggtgcagc ctgggggggag cctgagactg    120
```

```
agttgtgccg cctctggggt gacatttaac tactatggca tgtcttggat ccgccaggca    180

cctggaaagg gcctggagtg ggtggccagc atcacttctt ccggcgggcg aatctactat    240

cccgacagcg tcaagggcag gttcacaatt tcccgcgaga acacacagaa aactctgtac    300

ctgcagatga atagcctgag agccgaagat acagctgtgt actattgcac tctggacggc    360

agggatgggt gggtcgccta ttgggggcag ggaaccctgg tgacagtcag ctccggagga    420

ggaggatctg gcggaggagg cagtggggga ggcgggtcaa actttatgct gacccagccc    480

cacagtgtgt cagagagccc tggcaagact gtcaccatct cttgtaaaag gaacaccgga    540

aatattggca gtaactacgt gaattggtat cagcagcatg aagggtctag tccaaccaca    600

atcatctacc ggggcgataa gagacccgac ggggtgtccg atcgattctc cggatctatc    660

gaccggtcaa gcaagagtgc ttcactgacc attagcaatc tgaaaacaga ggacgaagca    720

gattactttt gccagtccta ttcctctggc ttcatctttg gaggcgggac taaactgacc    780

gtgctgggcg cggccgcagg tgcaggtggt gattacaaag atgatgacga taaaggtgca    840

gcggcgcatc accatcatca ccac                                           864
```

```
<210> SEQ ID NO 76
<211> LENGTH: 269
<212> TYPE: PRT
<213> ORGANISM: Artificial Sequence
<220> FEATURE:
<223> OTHER INFORMATION: C3E-7091 AA

<400> SEQUENCE: 76

Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Ser Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175

Ser Ser Pro Thr Thr Ile Ile Tyr Arg Gly Asp Lys Arg Pro Asp Gly
            180                 185                 190

Val Ser Asp Arg Phe Ser Gly Ser Ile Asp Arg Ser Ser Lys Ser Ala
        195                 200                 205

Ser Leu Thr Ile Ser Asn Leu Lys Thr Glu Asp Glu Ala Asp Tyr Phe
    210                 215                 220
```

```
Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
            260                 265


<210> SEQ ID NO 77
<211> LENGTH: 864
<212> TYPE: DNA
<213> ORGANISM: Artificial Sequence
<220> FEATURE:
<223> OTHER INFORMATION: C3E-7092 ORF

<400> SEQUENCE: 77

atgaaacacc tgtggttctt cctcctgctg gtggcagctc ccagatgggt gctgagcgga     60

gaagtgcagc tggtggaatc cggggggggc ctggtgcagc ctggggggag cctgagactg    120

agttgtgccg cctctggggt gacatttaac tactatggca tgtcttggat ccgccaggca    180

cctggaaagg gcctggagtg ggtggccagc atcacttctt ccggcgggcg aatctactat    240

cccgacagcg tcaagggcag gttcacaatt tcccgcgaga acacacagaa aactctgtac    300

ctgcagatga atagcctgag agccgaagat acagctgtgt actattgcac tctggacggc    360

agggatgggt gggtcgccta ttgggggcag ggaaccctgg tgacagtcag ctccggagga    420

ggaggatctg gcggaggagg cagtggggga ggcgggtcaa actttatgct gacccagccc    480

cacagtgtgt cagagagccc tggcaagact gtcaccatct cttgtaaaag gaacaccgga    540

aatattggca gtaactacgt gaattggtat cagcagcatg aagggtctag tccaaccaca    600

atcatctacc ggcaggataa gagacccgac ggggtgtccg atcgattctc cggatctatc    660

gaccggtcaa gcaagagtgc ttcactgacc attagcaatc tgaaaacaga ggacgaagca    720

gattactttt gccagtccta ttcctctggc ttcatctttg gaggcgggac taaactgacc    780

gtgctgggcg cggccgcagg tgcaggtggt gattacaaag atgatgacga taaaggtgca    840

gcggcgcatc accatcatca ccac                                           864


<210> SEQ ID NO 78
<211> LENGTH: 269
<212> TYPE: PRT
<213> ORGANISM: Artificial Sequence
<220> FEATURE:
<223> OTHER INFORMATION: C3E-7092 AA

<400> SEQUENCE: 78

Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Ser Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110
```

```
Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175

Ser Ser Pro Thr Thr Ile Ile Tyr Arg Gln Asp Lys Arg Pro Asp Gly
            180                 185                 190

Val Ser Asp Arg Phe Ser Gly Ser Ile Asp Arg Ser Ser Lys Ser Ala
        195                 200                 205

Ser Leu Thr Ile Ser Asn Leu Lys Thr Glu Asp Glu Ala Asp Tyr Phe
    210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
            260                 265
```

<210> SEQ ID NO 79
<211> LENGTH: 864
<212> TYPE: DNA
<213> ORGANISM: Artificial Sequence
<220> FEATURE:
<223> OTHER INFORMATION: C3E-7093 ORF

<400> SEQUENCE: 79

```
atgaaacacc tgtggttctt cctcctgctg gtggcagctc ccagatgggt gctgagcgga     60

gaagtgcagc tggtggaatc cgggggggc ctggtgcagc ctgggggag cctgagactg     120

agttgtgccg cctctggggt gacatttaac tactatggca tgtcttggat ccgccaggca    180

cctggaaagg gcctggagtg ggtggccagc atcacttctt ccggcgggcg aatctactat    240

cccgacagcg tcaagggcag gttcacaatt tcccgcgaga acacacagaa aactctgtac    300

ctgcagatga atagcctgag agccgaagat acagctgtgt actattgcac tctggacggc    360

agggatgggt gggtcgccta ttgggggcag ggaaccctgg tgacagtcag ctccggagga    420

ggaggatctg gcggaggagg cagtgggggga ggcgggtcaa actttatgct gacccagccc    480

cacagtgtgt cagagagccc tggcaagact gtcaccatct cttgtaaaag gaacaccgga    540

aatattggca gtaactacgt gaattggtat cagcagcatg aagggtctag tccaaccaca    600

atcatctacc ggaacgataa gagacccgac ggggtgtccg atcgattctc cggatctatc    660

gaccggtcaa gcaagagtgc ttcactgacc attagcaatc tgaaaacaga ggacgaagca    720

gattactttt gccagtccta ttcctctggc ttcatctttg gaggcgggac taaactgacc    780

gtgctgggcg cggccgcagg tgcaggtggt gattacaaag atgatgacga taaaggtgca    840

gcggcgcatc accatcatca ccac                                           864
```

<210> SEQ ID NO 80
<211> LENGTH: 269
<212> TYPE: PRT
<213> ORGANISM: Artificial Sequence
<220> FEATURE:
<223> OTHER INFORMATION: C3E-7093 AA

<400> SEQUENCE: 80

```
Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Ser Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175

Ser Ser Pro Thr Thr Ile Ile Tyr Arg Asn Asp Lys Arg Pro Asp Gly
            180                 185                 190

Val Ser Asp Arg Phe Ser Gly Ser Ile Asp Arg Ser Ser Lys Ser Ala
        195                 200                 205

Ser Leu Thr Ile Ser Asn Leu Lys Thr Glu Asp Glu Ala Asp Tyr Phe
    210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
            260                 265
```

<210> SEQ ID NO 81
<211> LENGTH: 864
<212> TYPE: DNA
<213> ORGANISM: Artificial Sequence
<220> FEATURE:
<223> OTHER INFORMATION: C3E-7094 ORF

<400> SEQUENCE: 81

```
atgaaacacc tgtggttctt cctcctgctg gtggcagctc ccagatgggt gctgagcgga     60

gaagtgcagc tggtggaatc cgggggggc ctggtgcagc ctgggggag cctgagactg    120

agttgtgccg cctctggggt gacatttaac tactatggca tgtcttggat ccgccaggca    180

cctggaaagg gcctggagtg ggtggccagc atcacttctt ccggcgggcg aatctactat    240

cccgacagcg tcaagggcag gttcacaatt tcccgcgaga acacacagaa aactctgtac    300

ctgcagatga atagcctgag agccgaagat acagctgtgt actattgcac tctggacggc    360

agggatgggt gggtcgccta ttgggggcag ggaaccctgg tgacagtcag ctccggagga    420

ggaggatctg gcggaggagg cagtggggga ggcgggtcaa actttatgct gacccagccc    480
```

```
cacagtgtgt cagagagccc tggcaagact gtcaccatct cttgtaaaag gaacaccgga    540

aatattggca gtaactacgt gaattggtat cagcagcatg aagggtctag tccaaccaca    600

atcatctacc ggagcgataa gagacccgac ggggtgtccg atcgattctc cggatctatc    660

gaccggtcaa gcaagagtgc ttcactgacc attagcaatc tgaaaacaga ggacgaagca    720

gattactttt gccagtccta ttcctctggc ttcatctttg gaggcgggac taaactgacc    780

gtgctgggcg cggccgcagg tgcaggtggt gattacaaag atgatgacga taaaggtgca    840

gcggcgcatc accatcatca ccac                                            864
```

```
<210> SEQ ID NO 82
<211> LENGTH: 269
<212> TYPE: PRT
<213> ORGANISM: Artificial Sequence
<220> FEATURE:
<223> OTHER INFORMATION: C3E-7094 AA

<400> SEQUENCE: 82

Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Ser Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175

Ser Ser Pro Thr Thr Ile Ile Tyr Arg Ser Asp Lys Arg Pro Asp Gly
            180                 185                 190

Val Ser Asp Arg Phe Ser Gly Ser Ile Asp Arg Ser Ser Lys Ser Ala
        195                 200                 205

Ser Leu Thr Ile Ser Asn Leu Lys Thr Glu Asp Glu Ala Asp Tyr Phe
    210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
            260                 265

<210> SEQ ID NO 83
<211> LENGTH: 864
<212> TYPE: DNA
```

<213> ORGANISM: Artificial Sequence
<220> FEATURE:
<223> OTHER INFORMATION: C3E-7095 ORF

<400> SEQUENCE: 83

```
atgaaacacc tgtggttctt cctcctgctg gtggcagctc ccagatgggt gctgagcgga     60

gaagtgcagc tggtggaatc cggggggggc ctggtgcagc ctgggggggag cctgagactg    120

agttgtgccg cctctggggt gacatttaac tactatggca tgtcttggat ccgccaggca    180

cctggaaagg gcctggagtg ggtggccagc atcacttctt ccggcgggcg aatctactat    240

cccgacagcg tcaagggcag gttcacaatt tcccgcgaga acacacagaa aactctgtac    300

ctgcagatga atagcctgag agccgaagat acagctgtgt actattgcac tctggacggc    360

agggatgggt gggtcgccta ttgggggcag ggaaccctgg tgacagtcag ctccggagga    420

ggaggatctg gcggaggagg cagtggggga ggcgggtcaa actttatgct gacccagccc    480

cacagtgtgt cagagagccc tggcaagact gtcaccatct cttgtaaaag gaacaccgga    540

aatattggca gtaactacgt gaattggtat cagcagcatg aagggtctag tccaaccaca    600

atcatctacc gggccgataa gagacccgac ggggtgtccg atcgattctc cggatctatc    660

gaccggtcaa gcaagagtgc ttcactgacc attagcaatc tgaaaacaga ggacgaagca    720

gattactttt gccagtccta ttcctctggc ttcatctttg gaggcgggac taaactgacc    780

gtgctgggcg cggccgcagg tgcaggtggt gattacaaag atgatgacga taaaggtgca    840

gcggcgcatc accatcatca ccac                                            864
```

<210> SEQ ID NO 84
<211> LENGTH: 269
<212> TYPE: PRT
<213> ORGANISM: Artificial Sequence
<220> FEATURE:
<223> OTHER INFORMATION: C3E-7095 AA

<400> SEQUENCE: 84

```
Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Ser Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175
```

```
Ser Ser Pro Thr Thr Ile Ile Tyr Arg Ala Asp Lys Arg Pro Asp Gly
            180                 185                 190

Val Ser Asp Arg Phe Ser Gly Ser Ile Asp Arg Ser Ser Lys Ser Ala
        195                 200                 205

Ser Leu Thr Ile Ser Asn Leu Lys Thr Glu Asp Glu Ala Asp Tyr Phe
    210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
            260                 265


<210> SEQ ID NO 85
<211> LENGTH: 33
<212> TYPE: DNA
<213> ORGANISM: Artificial Sequence
<220> FEATURE:
<223> OTHER INFORMATION: HN53R Fw

<400> SEQUENCE: 85

gtggccagca tcactaggtc cggcgggcga atc                                   33


<210> SEQ ID NO 86
<211> LENGTH: 33
<212> TYPE: DNA
<213> ORGANISM: Artificial Sequence
<220> FEATURE:
<223> OTHER INFORMATION: HN53R Rv

<400> SEQUENCE: 86

gattcgcccg ccggacctag tgatgctggc cac                                   33


<210> SEQ ID NO 87
<211> LENGTH: 33
<212> TYPE: DNA
<213> ORGANISM: Artificial Sequence
<220> FEATURE:
<223> OTHER INFORMATION: HN53S Fw

<400> SEQUENCE: 87

gtggccagca tcacttcttc cggcgggcga atc                                   33


<210> SEQ ID NO 88
<211> LENGTH: 33
<212> TYPE: DNA
<213> ORGANISM: Artificial Sequence
<220> FEATURE:
<223> OTHER INFORMATION: HN53S Rv

<400> SEQUENCE: 88

gattcgcccg ccggaagaag tgatgctggc cac                                   33


<210> SEQ ID NO 89
<211> LENGTH: 1590
<212> TYPE: DNA
<213> ORGANISM: Artificial Sequence
<220> FEATURE:
<223> OTHER INFORMATION: AXC-0001 ORF

<400> SEQUENCE: 89

atgaaacacc tgtggttctt cctcctgctg gtggcagctc ccagatgggt gctgagcgga      60

gaagtgcagc tgcaggaatc tggccctggc ctcgtgaagc ctagccagac cctgagcctg     120
```

```
acctgtaccg tgtccggcta cagcatcacc agcaactact ggggctggat cagaaagttc    180
cccggcaaca agatggaatg gatcggccac atcaccaaca gcggcaacac cacctacaac    240
cccagcctga agtcccggat cagcatcagc cgggacacca gcaagaacca gttctccctg    300
aagctgtcca gcgtgacccc tgccgatacc gccgtgtact actgtgccaa gggcgccttc    360
gattactggg gccagggaac cctcgtgacc gtgtctagcg gaggcggagg atctggcggc    420
ggaggaagtg gcggaggggg atctgatatc cagatgaccc agagccccag cagcctgtct    480
gccagcgtgg gcgacagagt gaccatcacc tgtagagcca gccaggacat cggcaactac    540
ctgagctggt tccagcagaa agtgggcaag tcccccagac ggatgatcta cggcgccatc    600
aagctggccg tgggcgtgcc aagcagattc agcggcagca gaagcggcag cgactacacc    660
ctgaccatca gctccctgca gcccgaggac ttcgccatct actactgcct gcagtacatc    720
cagttccctc tgaccttcgg cagcggcacc aagctggaaa tcaagagaac cgggggaggc    780
ggttcagaag tgcagctggt ggaatccggg gggggcctgg tgcagcctgg ggggagcctg    840
agactgagtt gtgccgcctc tggggtgaca tttaactact atggcatgtc ttggatccgc    900
caggcacctg gaaagggcct ggagtgggtg gccagcatca ctaattccgg cgggcgaatc    960
tactatcccg acagcgtcaa gggcaggttc acaatttccc gcgagaacac acagaaaact   1020
ctgtacctgc agatgaatag cctgagagcc gaagatacag ctgtgtacta ttgcactctg   1080
gacggcaggg atgggtgggt cgcctattgg gggcagggaa ccctggtgac agtcagctcc   1140
ggaggaggag gatctggcgg aggaggcagt gggggaggcg ggtcaaactt tatgctgacc   1200
cagccccaca gtgtgtcaga gagccctggc aagactgtca ccatctcttg taaaaggaac   1260
accggaaata ttggcagtaa ctacgtgaat tggtatcagc agcatgaagg gtctagtcca   1320
accacaatca tctaccggga cgataagaga cccgacgggg tgtccgatcg attctccgga   1380
tctatcgacc ggtcaagcaa gagtgcttca ctgaccatta gcaatctgaa aacagaggac   1440
gaagcagatt acttttgcca gtcctattcc tctggcttca tctttggagg cgggactaaa   1500
ctgaccgtgc tgggcgcggc cgcaggtgca ggtggtgatt acaaagatga tgacgataaa   1560
ggtgcagcgg cgcatcacca tcatcaccac                                    1590
```

<210> SEQ ID NO 90
<211> LENGTH: 511
<212> TYPE: PRT
<213> ORGANISM: Artificial Sequence
<220> FEATURE:
<223> OTHER INFORMATION: AXC-0001 AA

<400> SEQUENCE: 90

```
Gly Glu Val Gln Leu Gln Glu Ser Gly Pro Gly Leu Val Lys Pro Ser
1               5                   10                  15

Gln Thr Leu Ser Leu Thr Cys Thr Val Ser Gly Tyr Ser Ile Thr Ser
            20                  25                  30

Asn Tyr Trp Gly Trp Ile Arg Lys Phe Pro Gly Asn Lys Met Glu Trp
        35                  40                  45

Ile Gly His Ile Thr Asn Ser Gly Asn Thr Thr Tyr Asn Pro Ser Leu
    50                  55                  60

Lys Ser Arg Ile Ser Ile Ser Arg Asp Thr Ser Lys Asn Gln Phe Ser
65                  70                  75                  80

Leu Lys Leu Ser Ser Val Thr Pro Ala Asp Thr Ala Val Tyr Tyr Cys
                85                  90                  95
```

-continued

```
Ala Lys Gly Ala Phe Asp Tyr Trp Gly Gln Gly Thr Leu Val Thr Val
            100                 105                 110

Ser Ser Gly Gly Gly Gly Ser Gly Gly Gly Gly Ser Gly Gly Gly Gly
        115                 120                 125

Ser Asp Ile Gln Met Thr Gln Ser Pro Ser Ser Leu Ser Ala Ser Val
    130                 135                 140

Gly Asp Arg Val Thr Ile Thr Cys Arg Ala Ser Gln Asp Ile Gly Asn
145                 150                 155                 160

Tyr Leu Ser Trp Phe Gln Gln Lys Val Gly Lys Ser Pro Arg Arg Met
                165                 170                 175

Ile Tyr Gly Ala Ile Lys Leu Ala Val Gly Val Pro Ser Arg Phe Ser
            180                 185                 190

Gly Ser Arg Ser Gly Ser Asp Tyr Thr Leu Thr Ile Ser Ser Leu Gln
        195                 200                 205

Pro Glu Asp Phe Ala Ile Tyr Tyr Cys Leu Gln Tyr Ile Gln Phe Pro
    210                 215                 220

Leu Thr Phe Gly Ser Gly Thr Lys Leu Glu Ile Lys Arg Thr Gly Gly
225                 230                 235                 240

Gly Gly Ser Glu Val Gln Leu Val Glu Ser Gly Gly Gly Leu Val Gln
                245                 250                 255

Pro Gly Gly Ser Leu Arg Leu Ser Cys Ala Ala Ser Gly Val Thr Phe
            260                 265                 270

Asn Tyr Tyr Gly Met Ser Trp Ile Arg Gln Ala Pro Gly Lys Gly Leu
        275                 280                 285

Glu Trp Val Ala Ser Ile Thr Asn Ser Gly Gly Arg Ile Tyr Tyr Pro
    290                 295                 300

Asp Ser Val Lys Gly Arg Phe Thr Ile Ser Arg Glu Asn Thr Gln Lys
305                 310                 315                 320

Thr Leu Tyr Leu Gln Met Asn Ser Leu Arg Ala Glu Asp Thr Ala Val
                325                 330                 335

Tyr Tyr Cys Thr Leu Asp Gly Arg Asp Gly Trp Val Ala Tyr Trp Gly
            340                 345                 350

Gln Gly Thr Leu Val Thr Val Ser Ser Gly Gly Gly Gly Ser Gly Gly
        355                 360                 365

Gly Gly Ser Gly Gly Gly Gly Ser Asn Phe Met Leu Thr Gln Pro His
    370                 375                 380

Ser Val Ser Glu Ser Pro Gly Lys Thr Val Thr Ile Ser Cys Lys Arg
385                 390                 395                 400

Asn Thr Gly Asn Ile Gly Ser Asn Tyr Val Asn Trp Tyr Gln Gln His
                405                 410                 415

Glu Gly Ser Ser Pro Thr Thr Ile Ile Tyr Arg Asp Asp Lys Arg Pro
            420                 425                 430

Asp Gly Val Ser Asp Arg Phe Ser Gly Ser Ile Asp Arg Ser Ser Lys
        435                 440                 445

Ser Ala Ser Leu Thr Ile Ser Asn Leu Lys Thr Glu Asp Glu Ala Asp
    450                 455                 460

Tyr Phe Cys Gln Ser Tyr Ser Ser Gly Phe Ile Phe Gly Gly Gly Thr
465                 470                 475                 480

Lys Leu Thr Val Leu Gly Ala Ala Ala Gly Ala Gly Gly Asp Tyr Lys
                485                 490                 495

Asp Asp Asp Asp Lys Gly Ala Ala Ala His His His His His His
            500                 505                 510
```

<210> SEQ ID NO 91
<211> LENGTH: 1584
<212> TYPE: DNA
<213> ORGANISM: Artificial Sequence
<220> FEATURE:
<223> OTHER INFORMATION: AXC-0002 ORF

<400> SEQUENCE: 91

```
atgaaacacc tgtggttctt cctcctgctg gtggcagctc ccagatgggt gctgagcgga      60

gaagtgcagc tgcaggaatc tggccctggc ctcgtgaagc ctagccagac cctgagcctg     120

acctgtaccg tgtccggcta cagcatcacc agcaactact ggggctggat cagaaagttc     180

cccggcaaca agatggaatg gatcggccac atcaccaaca gcggcaacac cacctacaac     240

cccagcctga agtcccggat cagcatcagc cgggacacca gcaagaacca gttctccctg     300

aagctgtcca gcgtgacccc tgccgatacc gccgtgtact actgtgccaa gggcgccttc     360

gattactggg gccagggaac cctcgtgacc gtgtctagcg gaggcggagg atctggcggc     420

ggaggaagtg gcggaggggg atctgatatc cagatgaccc agagccccag cagcctgtct     480

gccagcgtgg gcgacagagt gaccatcacc tgtagagcca gccaggacat cggcaactac     540

ctgagctggt tccagcagaa agtgggcaag tcccccagac ggatgatcta cggcgccatc     600

aagctggccg tgggcgtgcc aagcagattc agcggcagca gaagcggcag cgactacacc     660

ctgaccatca gctccctgca gcccgaggac ttcgccatct actactgcct gcagtacatc     720

cagttccctc tgaccttcgg cagcggcacc aagctggaaa tcaagagaac cgggggaggc     780

ggttcagaag tgcagctggt ggaatccggg gggggcctgg tgcagcctgg ggggagcctg     840

agactgagtt gtgccgcctc tggggtgaca tttaactact atggcatgtc ttggatccgc     900

caggcacctg gaaagggcct ggagtgggtg gccagcatca ctaattccgg cgggcgaatc     960

tactatcccg acagcgtcaa gggcaggttc acaatttccc gcgagaacac acagaaaact    1020

ctgtacctgc agatgaatag cctgagagcc gaagatacag ctgtgtacta ttgcactctg    1080

gacggcaggg atgggtgggt cgcctattgg gggcagggaa ccctggtgac agtcagctcc    1140

ggaggaggag gatctggcgg aggaggcagt gggggaggcg ggtcaaactt tatgctcact    1200

cagccgtcct ctgtttctgg cgtacctggc caacgggtga ccattagctg tacgggtaat    1260

accgggaata tcgggtctaa ctacgtgaac tggtatcagc agcttccagg gacagctccc    1320

aagttgctga tctatcgcga cgacaaaaga ccctcagggg tccctgaccg atttagtggc    1380

agcaaaagcg gtacttccgc ttccctggcg ataaccggct ttcaggccga agatgaggca    1440

gactactatt gccagtcata ttccagcggc ttcatcttcg gaggcggaac taagctgaca    1500

gtgttgggcg cggccgcagg tgcaggtggt gattacaaag atgatgacga taaaggtgca    1560

gcggcgcatc accatcatca ccac                                           1584
```

<210> SEQ ID NO 92
<211> LENGTH: 509
<212> TYPE: PRT
<213> ORGANISM: Artificial Sequence
<220> FEATURE:
<223> OTHER INFORMATION: AXC-0002 AA

<400> SEQUENCE: 92

```
Gly Glu Val Gln Leu Gln Glu Ser Gly Pro Gly Leu Val Lys Pro Ser
1               5                   10                  15

Gln Thr Leu Ser Leu Thr Cys Thr Val Ser Gly Tyr Ser Ile Thr Ser
            20                  25                  30
```

```
Asn Tyr Trp Gly Trp Ile Arg Lys Phe Pro Gly Asn Lys Met Glu Trp
        35                  40                  45

Ile Gly His Ile Thr Asn Ser Gly Asn Thr Thr Tyr Asn Pro Ser Leu
    50                  55                  60

Lys Ser Arg Ile Ser Ile Ser Arg Asp Thr Ser Lys Asn Gln Phe Ser
65                  70                  75                  80

Leu Lys Leu Ser Ser Val Thr Pro Ala Asp Thr Ala Val Tyr Tyr Cys
                85                  90                  95

Ala Lys Gly Ala Phe Asp Tyr Trp Gly Gln Gly Thr Leu Val Thr Val
            100                 105                 110

Ser Ser Gly Gly Gly Gly Ser Gly Gly Gly Gly Ser Gly Gly Gly Gly
        115                 120                 125

Ser Asp Ile Gln Met Thr Gln Ser Pro Ser Ser Leu Ser Ala Ser Val
    130                 135                 140

Gly Asp Arg Val Thr Ile Thr Cys Arg Ala Ser Gln Asp Ile Gly Asn
145                 150                 155                 160

Tyr Leu Ser Trp Phe Gln Gln Lys Val Gly Lys Ser Pro Arg Arg Met
                165                 170                 175

Ile Tyr Gly Ala Ile Lys Leu Ala Val Gly Val Pro Ser Arg Phe Ser
            180                 185                 190

Gly Ser Arg Ser Gly Ser Asp Tyr Thr Leu Thr Ile Ser Ser Leu Gln
        195                 200                 205

Pro Glu Asp Phe Ala Ile Tyr Tyr Cys Leu Gln Tyr Ile Gln Phe Pro
    210                 215                 220

Leu Thr Phe Gly Ser Gly Thr Lys Leu Glu Ile Lys Arg Thr Gly Gly
225                 230                 235                 240

Gly Gly Ser Glu Val Gln Leu Val Glu Ser Gly Gly Gly Leu Val Gln
                245                 250                 255

Pro Gly Gly Ser Leu Arg Leu Ser Cys Ala Ala Ser Gly Val Thr Phe
            260                 265                 270

Asn Tyr Tyr Gly Met Ser Trp Ile Arg Gln Ala Pro Gly Lys Gly Leu
        275                 280                 285

Glu Trp Val Ala Ser Ile Thr Asn Ser Gly Gly Arg Ile Tyr Tyr Pro
    290                 295                 300

Asp Ser Val Lys Gly Arg Phe Thr Ile Ser Arg Glu Asn Thr Gln Lys
305                 310                 315                 320

Thr Leu Tyr Leu Gln Met Asn Ser Leu Arg Ala Glu Asp Thr Ala Val
                325                 330                 335

Tyr Tyr Cys Thr Leu Asp Gly Arg Asp Gly Trp Val Ala Tyr Trp Gly
            340                 345                 350

Gln Gly Thr Leu Val Thr Val Ser Ser Gly Gly Gly Gly Ser Gly Gly
        355                 360                 365

Gly Gly Ser Gly Gly Gly Gly Ser Asn Phe Met Leu Thr Gln Pro Ser
    370                 375                 380

Ser Val Ser Gly Val Pro Gly Gln Arg Val Thr Ile Ser Cys Thr Gly
385                 390                 395                 400

Asn Thr Gly Asn Ile Gly Ser Asn Tyr Val Asn Trp Tyr Gln Gln Leu
                405                 410                 415

Pro Gly Thr Ala Pro Lys Leu Leu Ile Tyr Arg Asp Asp Lys Arg Pro
            420                 425                 430

Ser Gly Val Pro Asp Arg Phe Ser Gly Ser Lys Ser Gly Thr Ser Ala
        435                 440                 445

Ser Leu Ala Ile Thr Gly Phe Gln Ala Glu Asp Glu Ala Asp Tyr Tyr
```

```
    450                 455                 460

Cys Gln Ser Tyr Ser Ser Gly Phe Ile Phe Gly Gly Gly Thr Lys Leu
465                 470                 475                 480

Thr Val Leu Gly Ala Ala Ala Gly Ala Gly Gly Asp Tyr Lys Asp Asp
                485                 490                 495

Asp Asp Lys Gly Ala Ala Ala His His His His His His
            500                 505


<210> SEQ ID NO 93
<211> LENGTH: 1620
<212> TYPE: DNA
<213> ORGANISM: Artificial Sequence
<220> FEATURE:
<223> OTHER INFORMATION: MGC-0001 ORF

<400> SEQUENCE: 93

atgaaacacc tgtggttctt cctcctgctg gtggcagctc ccagatgggt gctgagcgga     60

caggtgcagc tggtgcagtc tggggggaggc ttggtccagc ctggagggtc cctgagactc    120

tcctgtgcag cctctggatt caccttcagt gactacgaca tggactgggt ccgccaggct    180

ccagggaagg ggctggagtg ggtggcagtt atatcatctg atgaaaacac taaatactac    240

gcagactccg tgaagggccg attcaccatc tccagagaca attccaagaa cacgctgtat    300

ctgcaaatga acagcctgag agccgaggac acggctgtgt attactgtgc aacctatacc    360

agcacctggt atgccgttga ctcctggggc cagggaaccc tggtcaccgt ctcctcaggt    420

ggaggcggtt caggcggagg tggcagcggc ggtggcggga gtgatgttgt gatgactcag    480

tctccactct ccctgcccgt cacccctgga gagccggcct ccatctcctg caggtctagt    540

cagagcctcc tgcatagtaa cggaaagaac tatttggatt ggtacctgca gaagccaggg    600

cagtctccac agctcctgat ctatttgggt tctaatcggg cctccggggt ccctgacagg    660

ttcagtggca gtggatcagg cacagatttt acactgaaga tcagcagagt ggaggctgag    720

gatgttgggg tttattactg catgcaaact cttcaaaccc cctacacttt tggccagggg    780

accaaggtgg aaatcaaacg tgggggaggc ggttcagaag tgcagctggt ggaatccggg    840

gggggcctgg tgcagcctgg ggggagcctg agactgagtt gtgccgcctc tggggtgaca    900

tttaactact atggcatgtc ttggatccgc caggcacctg gaaagggcct ggagtgggtg    960

gccagcatca ctaattccgg cgggcgaatc tactatcccg acagcgtcaa gggcaggttc   1020

acaatttccc gcgagaacac acagaaaact ctgtacctgc agatgaatag cctgagagcc   1080

gaagatacag ctgtgtacta ttgcactctg gacggcaggg atgggtgggt cgcctattgg   1140

gggcagggaa ccctggtgac agtcagctcc ggaggaggag gatctggcgg aggaggcagt   1200

gggggaggcg ggtcaaactt tatgctgacc cagccccaca gtgtgtcaga gagccctggc   1260

aagactgtca ccatctcttg taaaaggaac accggaaata ttggcagtaa ctacgtgaat   1320

tggtatcagc agcatgaagg gtctagtcca accacaatca tctaccggga cgataagaga   1380

cccgacgggg tgtccgatcg attctccgga tctatcgacc ggtcaagcaa gagtgcttca   1440

ctgaccatta gcaatctgaa aacagaggac gaagcagatt acttttgcca gtcctattcc   1500

tctggcttca tctttggagg cgggactaaa ctgaccgtgc tgggcgcggc cgcaggtgca   1560

ggtggtgatt acaaagatga tgacgataaa ggtgcagcgg cgcatcacca tcatcaccac   1620


<210> SEQ ID NO 94
<211> LENGTH: 521
<212> TYPE: PRT
```

```
<213> ORGANISM: Artificial Sequence
<220> FEATURE:
<223> OTHER INFORMATION: MGC-0001 AA

<400> SEQUENCE: 94

Gly Gln Val Gln Leu Val Gln Ser Gly Gly Gly Leu Val Gln Pro Gly
1               5                   10                  15

Gly Ser Leu Arg Leu Ser Cys Ala Ala Ser Gly Phe Thr Phe Ser Asp
            20                  25                  30

Tyr Asp Met Asp Trp Val Arg Gln Ala Pro Gly Lys Gly Leu Glu Trp
        35                  40                  45

Val Ala Val Ile Ser Ser Asp Glu Asn Thr Lys Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Thr Tyr Thr Ser Thr Trp Tyr Ala Val Asp Ser Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Val Met Thr Gln Ser Pro Leu
    130                 135                 140

Ser Leu Pro Val Thr Pro Gly Glu Pro Ala Ser Ile Ser Cys Arg Ser
145                 150                 155                 160

Ser Gln Ser Leu Leu His Ser Asn Gly Lys Asn Tyr Leu Asp Trp Tyr
                165                 170                 175

Leu Gln Lys Pro Gly Gln Ser Pro Gln Leu Leu Ile Tyr Leu Gly Ser
            180                 185                 190

Asn Arg Ala Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Met Gln Thr Leu Gln Thr Pro Tyr Thr Phe Gly Gln
225                 230                 235                 240

Gly Thr Lys Val Glu Ile Lys Arg Gly Gly Gly Gly Ser Glu Val Gln
                245                 250                 255

Leu Val Glu Ser Gly Gly Gly Leu Val Gln Pro Gly Gly Ser Leu Arg
            260                 265                 270

Leu Ser Cys Ala Ala Ser Gly Val Thr Phe Asn Tyr Tyr Gly Met Ser
        275                 280                 285

Trp Ile Arg Gln Ala Pro Gly Lys Gly Leu Glu Trp Val Ala Ser Ile
    290                 295                 300

Thr Asn Ser Gly Gly Arg Ile Tyr Tyr Pro Asp Ser Val Lys Gly Arg
305                 310                 315                 320

Phe Thr Ile Ser Arg Glu Asn Thr Gln Lys Thr Leu Tyr Leu Gln Met
                325                 330                 335

Asn Ser Leu Arg Ala Glu Asp Thr Ala Val Tyr Tyr Cys Thr Leu Asp
            340                 345                 350

Gly Arg Asp Gly Trp Val Ala Tyr Trp Gly Gln Gly Thr Leu Val Thr
        355                 360                 365

Val Ser Ser Gly Gly Gly Gly Ser Gly Gly Gly Gly Ser Gly Gly Gly
    370                 375                 380

Gly Ser Asn Phe Met Leu Thr Gln Pro His Ser Val Ser Glu Ser Pro
```

```
385                 390                 395                 400

Gly Lys Thr Val Thr Ile Ser Cys Lys Arg Asn Thr Gly Asn Ile Gly
                405                 410                 415

Ser Asn Tyr Val Asn Trp Tyr Gln Gln His Glu Gly Ser Ser Pro Thr
            420                 425                 430

Thr Ile Ile Tyr Arg Asp Asp Lys Arg Pro Asp Gly Val Ser Asp Arg
        435                 440                 445

Phe Ser Gly Ser Ile Asp Arg Ser Ser Lys Ser Ala Ser Leu Thr Ile
    450                 455                 460

Ser Asn Leu Lys Thr Glu Asp Glu Ala Asp Tyr Phe Cys Gln Ser Tyr
465                 470                 475                 480

Ser Ser Gly Phe Ile Phe Gly Gly Gly Thr Lys Leu Thr Val Leu Gly
                485                 490                 495

Ala Ala Ala Gly Ala Gly Gly Asp Tyr Lys Asp Asp Asp Asp Lys Gly
            500                 505                 510

Ala Ala Ala His His His His His His
        515                 520
```

<210> SEQ ID NO 95
<211> LENGTH: 1614
<212> TYPE: DNA
<213> ORGANISM: Artificial Sequence
<220> FEATURE:
<223> OTHER INFORMATION: MGC-0002 ORF

<400> SEQUENCE: 95

```
atgaaacacc tgtggttctt cctcctgctg gtggcagctc ccagatgggt gctgagcgga      60

caggtgcagc tggtgcagtc tgggggaggc ttggtccagc ctggagggtc cctgagactc     120

tcctgtgcag cctctggatt caccttcagt gactacgaca tggactgggt ccgccaggct     180

ccagggaagg ggctggagtg ggtggcagtt atatcatctg atgaaaacac taaatactac     240

gcagactccg tgaagggccg attcaccatc tccagagaca attccaagaa cacgctgtat     300

ctgcaaatga acagcctgag agccgaggac acggctgtgt attactgtgc aacctatacc     360

agcacctggt atgccgttga ctcctggggc cagggaaccc tggtcaccgt ctcctcaggt     420

ggaggcggtt caggcggagg tggcagcggc ggtggcggga gtgatgttgt gatgactcag     480

tctccactct ccctgcccgt cacccctgga gagccggcct ccatctcctg caggtctagt     540

cagagcctcc tgcatagtaa cggaaagaac tatttggatt ggtacctgca gaagccaggg     600

cagtctccac agctcctgat ctatttgggt tctaatcggg cctccggggt ccctgacagg     660

ttcagtggca gtggatcagg cacagatttt acactgaaga tcagcagagt ggaggctgag     720

gatgttgggg tttattactg catgcaaact cttcaaaccc cctacacttt tggccagggg     780

accaaggtgg aaatcaaacg tgggggaggc ggttcagaag tgcagctggt ggaatccggg     840

gggggcctgg tgcagcctgg ggggagcctg agactgagtt gtgccgcctc tggggtgaca     900

tttaactact atggcatgtc ttggatccgc caggcacctg gaaagggcct ggagtgggtg     960

gccagcatca ctaattccgg cgggcgaatc tactatcccg acagcgtcaa gggcaggttc    1020

acaatttccc gcgagaacac acagaaaact ctgtacctgc agatgaatag cctgagagcc    1080

gaagatacag ctgtgtacta ttgcactctg gacggcaggg atgggtgggt cgcctattgg    1140

gggcagggaa ccctggtgac agtcagctcc ggaggaggag gatctggcgg aggaggcagt    1200

gggggaggcg ggtcaaactt tatgctcact cagccgtcct ctgtttctgg cgtacctggc    1260

caacgggtga ccattagctg tacgggtaat accgggaata tcgggtctaa ctacgtgaac    1320
```

```
tggtatcagc agcttccagg gacagctccc aagttgctga tctatcgcga cgacaaaaga   1380

ccctcagggg tccctgaccg atttagtggc agcaaaagcg gtacttccgc ttccctggcg   1440

ataaccggct ttcaggccga agatgaggca gactactatt gccagtcata ttccagcggc   1500

ttcatcttcg gaggcggaac taagctgaca gtgttgggcg cggccgcagg tgcaggtggt   1560

gattacaaag atgatgacga taaaggtgca gcggcgcatc accatcatca ccac         1614


<210> SEQ ID NO 96
<211> LENGTH: 519
<212> TYPE: PRT
<213> ORGANISM: Artificial Sequence
<220> FEATURE:
<223> OTHER INFORMATION: MGC-0002 AA

<400> SEQUENCE: 96

Gly Gln Val Gln Leu Val Gln Ser Gly Gly Gly Leu Val Gln Pro Gly
1               5                   10                  15

Gly Ser Leu Arg Leu Ser Cys Ala Ala Ser Gly Phe Thr Phe Ser Asp
            20                  25                  30

Tyr Asp Met Asp Trp Val Arg Gln Ala Pro Gly Lys Gly Leu Glu Trp
        35                  40                  45

Val Ala Val Ile Ser Ser Asp Glu Asn Thr Lys Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Thr Tyr Thr Ser Thr Trp Tyr Ala Val Asp Ser Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Val Met Thr Gln Ser Pro Leu
    130                 135                 140

Ser Leu Pro Val Thr Pro Gly Glu Pro Ala Ser Ile Ser Cys Arg Ser
145                 150                 155                 160

Ser Gln Ser Leu Leu His Ser Asn Gly Lys Asn Tyr Leu Asp Trp Tyr
                165                 170                 175

Leu Gln Lys Pro Gly Gln Ser Pro Gln Leu Leu Ile Tyr Leu Gly Ser
            180                 185                 190

Asn Arg Ala Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Met Gln Thr Leu Gln Thr Pro Tyr Thr Phe Gly Gln
225                 230                 235                 240

Gly Thr Lys Val Glu Ile Lys Arg Gly Gly Gly Gly Ser Glu Val Gln
                245                 250                 255

Leu Val Glu Ser Gly Gly Gly Leu Val Gln Pro Gly Gly Ser Leu Arg
            260                 265                 270

Leu Ser Cys Ala Ala Ser Gly Val Thr Phe Asn Tyr Tyr Gly Met Ser
        275                 280                 285

Trp Ile Arg Gln Ala Pro Gly Lys Gly Leu Glu Trp Val Ala Ser Ile
    290                 295                 300

Thr Asn Ser Gly Gly Arg Ile Tyr Tyr Pro Asp Ser Val Lys Gly Arg
```

```
305                 310                 315                 320

Phe Thr Ile Ser Arg Glu Asn Thr Gln Lys Thr Leu Tyr Leu Gln Met
                325                 330                 335

Asn Ser Leu Arg Ala Glu Asp Thr Ala Val Tyr Tyr Cys Thr Leu Asp
            340                 345                 350

Gly Arg Asp Gly Trp Val Ala Tyr Trp Gly Gln Gly Thr Leu Val Thr
        355                 360                 365

Val Ser Ser Gly Gly Gly Gly Ser Gly Gly Gly Gly Ser Gly Gly Gly
    370                 375                 380

Gly Ser Asn Phe Met Leu Thr Gln Pro Ser Ser Val Ser Gly Val Pro
385                 390                 395                 400

Gly Gln Arg Val Thr Ile Ser Cys Thr Gly Asn Thr Gly Asn Ile Gly
                405                 410                 415

Ser Asn Tyr Val Asn Trp Tyr Gln Gln Leu Pro Gly Thr Ala Pro Lys
            420                 425                 430

Leu Leu Ile Tyr Arg Asp Asp Lys Arg Pro Ser Gly Val Pro Asp Arg
        435                 440                 445

Phe Ser Gly Ser Lys Ser Gly Thr Ser Ala Ser Leu Ala Ile Thr Gly
    450                 455                 460

Phe Gln Ala Glu Asp Glu Ala Asp Tyr Tyr Cys Gln Ser Tyr Ser Ser
465                 470                 475                 480

Gly Phe Ile Phe Gly Gly Gly Thr Lys Leu Thr Val Leu Gly Ala Ala
                485                 490                 495

Ala Gly Ala Gly Gly Asp Tyr Lys Asp Asp Asp Asp Lys Gly Ala Ala
            500                 505                 510

Ala His His His His His His
        515


<210> SEQ ID NO 97
<211> LENGTH: 10
<212> TYPE: PRT
<213> ORGANISM: Homo sapiens

<400> SEQUENCE: 97

Ile Leu Phe Gly Ile Ser Leu Arg Glu Val
1               5                   10


<210> SEQ ID NO 98
<211> LENGTH: 8
<212> TYPE: PRT
<213> ORGANISM: Artificial Sequence
<220> FEATURE:
<223> OTHER INFORMATION: CDRH2 of variants
<220> FEATURE:
<221> NAME/KEY: Xaa
<222> LOCATION: (3)..(3)
<223> OTHER INFORMATION: the first Xaa is any naturally occurring amino
      acid
<220> FEATURE:
<221> NAME/KEY: Xaa
<222> LOCATION: (4)..(4)
<223> OTHER INFORMATION: the second Xaa is any naturally occurring amino
      acid

<400> SEQUENCE: 98

Ile Thr Xaa Xaa Gly Gly Arg Ile
1               5


<210> SEQ ID NO 99
<211> LENGTH: 3
<212> TYPE: PRT
```

```
<213> ORGANISM: Artificial Sequence
<220> FEATURE:
<223> OTHER INFORMATION: CDRL2 of variants
<220> FEATURE:
<221> NAME/KEY: X
<222> LOCATION: (2)..(2)
<223> OTHER INFORMATION: Xaa is any naturally occurring amino acid

<400> SEQUENCE: 99

Arg Xaa Asp
1


<210> SEQ ID NO 100
<211> LENGTH: 118
<212> TYPE: PRT
<213> ORGANISM: Artificial Sequence
<220> FEATURE:
<223> OTHER INFORMATION: VH of C3E-7034 variants
<220> FEATURE:
<221> NAME/KEY: MISC_FEATURE
<222> LOCATION: (53)..(53)
<223> OTHER INFORMATION: The first Xaa is any naturally occurring amino
      acid
<220> FEATURE:
<221> NAME/KEY: MISC_FEATURE
<222> LOCATION: (54)..(54)
<223> OTHER INFORMATION: The second Xaa is any naturally occurring amino
      acid

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Asn Tyr Tyr
            20                  25                  30

Gly Met Ser Trp Ile Arg Gln Ala Pro Gly Lys Gly Leu Glu Trp Val
        35                  40                  45

Ala Ser Ile Thr Xaa Xaa Gly Gly Arg Ile Tyr Tyr Pro Asp Ser Val
    50                  55                  60

Lys Gly Arg Phe Thr Ile Ser Arg Glu Asn Thr Gln Lys Thr Leu Tyr
65                  70                  75                  80

Leu Gln Met Asn Ser Leu Arg Ala Glu Asp Thr Ala Val Tyr Tyr Cys
                85                  90                  95

Thr Leu Asp Gly Arg Asp Gly Trp Val Ala Tyr Trp Gly Gln Gly Thr
            100                 105                 110

Leu Val Thr Val Ser Ser
        115


<210> SEQ ID NO 101
<211> LENGTH: 109
<212> TYPE: PRT
<213> ORGANISM: Artificial Sequence
<220> FEATURE:
<223> OTHER INFORMATION: VL of C3E-7034 variants
<220> FEATURE:
<221> NAME/KEY: MISC_FEATURE
<222> LOCATION: (52)..(52)
<223> OTHER INFORMATION: Xaa is any naturally occurring amino acid

<400> SEQUENCE: 101

Asn Phe Met Leu Thr Gln Pro His Ser Val Ser Glu Ser Pro Gly Lys
1               5                   10                  15

Thr Val Thr Ile Ser Cys Lys Arg Asn Thr Gly Asn Ile Gly Ser Asn
            20                  25                  30

Tyr Val Asn Trp Tyr Gln Gln His Glu Gly Ser Ser Pro Thr Thr Ile
        35                  40                  45
```

```
Ile Tyr Arg Xaa Asp Lys Arg Pro Asp Gly Val Ser Asp Arg Phe Ser
    50                  55                  60

Gly Ser Ile Asp Arg Ser Ser Lys Ser Ala Ser Leu Thr Ile Ser Asn
65                  70                  75                  80

Leu Lys Thr Glu Asp Glu Ala Asp Tyr Phe Cys Gln Ser Tyr Ser Ser
                85                  90                  95

Gly Phe Ile Phe Gly Gly Gly Thr Lys Leu Thr Val Leu
            100                 105
```

<210> SEQ ID NO 102
<211> LENGTH: 107
<212> TYPE: PRT
<213> ORGANISM: Artificial Sequence
<220> FEATURE:
<223> OTHER INFORMATION: VL of C3E-7035 variants
<220> FEATURE:
<221> NAME/KEY: MISC_FEATURE
<222> LOCATION: (52)..(52)
<223> OTHER INFORMATION: Xaa is any naturally occurring amino acid

<400> SEQUENCE: 102

```
Gln Ala Val Leu Thr Gln Pro Ser Ser Val Ser Gly Val Pro Gly Gln
1               5                   10                  15

Arg Val Thr Ile Ser Cys Lys Arg Asn Thr Gly Asn Ile Gly Ser Asn
            20                  25                  30

Tyr Val Asn Trp Tyr Gln Gln Leu Pro Gly Thr Ala Pro Lys Leu Leu
        35                  40                  45

Ile Tyr Arg Xaa Asp Lys Arg Pro Ser Gly Val Pro Asp Arg Phe Ser
    50                  55                  60

Gly Ser Lys Ser Gly Thr Ser Ala Ser Leu Ala Ile Thr Gly Phe Gln
65                  70                  75                  80

Ala Glu Asp Glu Ala Asp Tyr Tyr Cys Gln Ser Tyr Ser Ser Gly Phe
                85                  90                  95

Ile Phe Gly Gly Gly Thr Lys Leu Thr Val Leu
            100                 105
```

<210> SEQ ID NO 103
<211> LENGTH: 107
<212> TYPE: PRT
<213> ORGANISM: Artificial Sequence
<220> FEATURE:
<223> OTHER INFORMATION: VL of C3E-7036 variants
<220> FEATURE:
<221> NAME/KEY: MISC_FEATURE
<222> LOCATION: (52)..(52)
<223> OTHER INFORMATION: Xaa is any naturally occurring amino acid

<400> SEQUENCE: 103

```
Asn Phe Met Leu Thr Gln Pro Ser Ser Val Ser Gly Val Pro Gly Gln
1               5                   10                  15

Arg Val Thr Ile Ser Cys Thr Gly Asn Thr Gly Asn Ile Gly Ser Asn
            20                  25                  30

Tyr Val Asn Trp Tyr Gln Gln Leu Pro Gly Thr Ala Pro Lys Leu Leu
        35                  40                  45

Ile Tyr Arg Xaa Asp Lys Arg Pro Ser Gly Val Pro Asp Arg Phe Ser
    50                  55                  60

Gly Ser Lys Ser Gly Thr Ser Ala Ser Leu Ala Ile Thr Gly Phe Gln
65                  70                  75                  80
```

-continued

```
Ala Glu Asp Glu Ala Asp Tyr Tyr Cys Gln Ser Tyr Ser Ser Gly Phe
                85                  90                  95

Ile Phe Gly Gly Gly Thr Lys Leu Thr Val Leu
            100                 105
```